US012240840B2

(12) United States Patent
Spergel et al.

(10) Patent No.: US 12,240,840 B2
(45) Date of Patent: Mar. 4, 2025

(54) AMIDE-SUBSTITUTED HETEROCYCLIC COMPOUNDS FOR THE TREATMENT OF CONDITIONS RELATED TO THE MODULATION OF IL-12, IL-23 AND/OR IFN-ALPHA

(71) Applicant: BRISTOL-MYERS SQUIBB COMPANY, Princeton, NJ (US)

(72) Inventors: Steven H. Spergel, Warrington, PA (US); William J. Pitts, Newtown, PA (US); Michael E. Mertzman, New Hope, PA (US); Ryan M. Moslin, Princeton, NJ (US); Trevor C. Sherwood, West Windsor, NJ (US); John L. Gilmore, Yardley, PA (US); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 902 days.

(21) Appl. No.: 17/289,269

(22) PCT Filed: Oct. 28, 2019

(86) PCT No.: PCT/US2019/058268
§ 371 (c)(1),
(2) Date: Apr. 28, 2021

(87) PCT Pub. No.: WO2020/092196
PCT Pub. Date: May 7, 2020

(65) Prior Publication Data
US 2023/0020273 A1    Jan. 19, 2023

Related U.S. Application Data

(60) Provisional application No. 62/752,414, filed on Oct. 30, 2018.

(51) Int. Cl.
| C07D 413/14 | (2006.01) |
| C07B 59/00 | (2006.01) |
| C07D 401/14 | (2006.01) |
| C07D 403/12 | (2006.01) |
| C07D 403/14 | (2006.01) |
| C07D 413/12 | (2006.01) |
| C07D 417/12 | (2006.01) |
| C07D 417/14 | (2006.01) |

(52) U.S. Cl.
CPC .......... *C07D 413/14* (2013.01); *C07B 59/002* (2013.01); *C07D 401/14* (2013.01); *C07D 403/12* (2013.01); *C07D 403/14* (2013.01); *C07D 413/12* (2013.01); *C07D 417/12* (2013.01); *C07D 417/14* (2013.01); *C07B 2200/05* (2013.01)

(58) Field of Classification Search
CPC .. C07D 413/14; C07D 401/14; C07D 403/12; C07D 403/14; C07D 413/12; C07D 417/12; C07D 417/14; C07B 2200/05; C07B 59/002
See application file for complete search history.

(56) References Cited

U.S. PATENT DOCUMENTS

| 9,315,494 | B2 * | 4/2016 | Moslin | A61P 37/02 |
| 9,663,467 | B2 * | 5/2017 | Moslin | A61P 37/00 |
| 9,987,266 | B2 * | 6/2018 | Moslin | A61P 29/00 |
| 10,000,480 | B2 * | 6/2018 | Moslin | A61P 7/00 |
| RE47,929 | E * | 4/2020 | Moslin | A61P 13/12 |
| 11,021,475 | B2 * | 6/2021 | Moslin | A61P 7/00 |
| 11,866,414 | B2 * | 1/2024 | Spergel | A61P 37/00 |

FOREIGN PATENT DOCUMENTS

| WO | 14074660 A1 | 5/2014 | |
| WO | 14074661 A1 | 5/2014 | |
| WO | WO-2014074660 A1 * | 5/2014 | .............. A61P 29/00 |
| WO | WO-2014074661 A1 * | 5/2014 | ................ A61P 1/00 |
| WO | 15069310 A1 | 5/2015 | |
| WO | WO-2019183186 A1 * | 9/2019 | ........... A61K 31/444 |

OTHER PUBLICATIONS

U.S. Appl. No. 14/441,193, filed May 7, 2015, now U.S. Pat. No. 9,315,494.
PCT/US2013/068842, Nov. 7, 2013, WO2014/074660.
U.S. Appl. No. 14/441,213, filed May 7, 2015, now U.S. Pat. No. 9,540,333.
PCT/US2013/068866, Nov. 7, 2013, WO2014/074670.
U.S. Appl. No. 14/441,183, filed May 7, 2015, now U.S. Pat. No. 9,505,748.
U.S. Appl. No. 15/289,437, filed Oct. 10, 2016, now U.S. Pat. No. 10,000,480.
U.S. Appl. No. 15/979,770, filed May 15, 2018, now U.S. Pat. No. 10,526,321.

(Continued)

*Primary Examiner* — Matthew P Coughlin
*Assistant Examiner* — Ashli Ariana Chicks
(74) *Attorney, Agent, or Firm* — Jing G. Sun

(57) ABSTRACT

Compounds having the following formula I: or a stereoisomer or pharmaceutically-acceptable salt thereof, where $R^1$, $R^2$, $R^3$, $R^4$, and $R^5$ are as defined herein, are useful in the modulation of IL-12, IL-23 and/or IFNα, by acting on Tyk-2 to cause signal transduction inhibition.

2 Claims, No Drawings

(56) References Cited

OTHER PUBLICATIONS

U.S. Appl. No. 16/687,279, filed Nov. 18, 2019, US20200071315A1.
U.S. Appl. No. 16/201,653, filed Nov. 27, 2018, RE47929.
PCT/US2013/068846, Nov. 7, 2013, WO2014/074661.
U.S. Appl. No. 15/034,915, filed May 5, 2016, now U.S. Pat. No. 9,663,467
U.S. Appl. No. 15/480,787, filed Apr. 6, 2017, now U.S. Pat. No. 9,987,266.
PCT/US2014/011769, Jan. 31, 2020, WO2015/069310.
U.S. Appl. No. 15/838,434, filed Dec. 12, 2017, now U.S. Pat. No. 10,294,256.
PCT/US2017/065665, Dec. 12, 2017, WO2018/111787.
U.S. Appl. No. 16/195,951, filed Nov. 20, 2018.
PCT/US2018/061726, Nov. 19, 2018, WO2019/103952.
U.S. Appl. No. 16/982,937, filed Sep. 21, 2020, US-2021-0032220-A1
PCT/US2019/023111, Mar. 20, 2019, WO2019/183186.
U.S. Appl. No. 17/425,336, filed Jul. 23, 2021.
PCT/US2020/015291, Jan. 28, 2020, WO2020/159904.
U.S. Appl. No. 63/016,539, filed Apr. 28, 2020.

\* cited by examiner

AMIDE-SUBSTITUTED HETEROCYCLIC COMPOUNDS FOR THE TREATMENT OF CONDITIONS RELATED TO THE MODULATION OF IL-12, IL-23 AND/OR IFN-ALPHA

CROSS-REFERENCE TO RELATED APPLICATIONS

This application is a national phase application under 35 U.S.C. § 371 of International Patent Application No. PCT/US2019/058268, filed Oct. 28, 2019, which claims priority to U.S. Provisional Application Ser. 62/752,414, filed Oct. 30, 2018, the contents of which are specifically incorporated fully herein by reference.

FIELD OF THE INVENTION

This invention relates to compounds useful in the modulation of IL-12, IL-23 and/or IFNα by acting on Tyk-2 to cause signal transduction inhibition. Provided herein are amide-substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.*, 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", *Eur. J. Immunol.*, 26:1217-1221 (1996); Schroder, K. et al., "Interferon-gamma: an overview of signals, mechanisms and functions", *J. Leukoc. Biol.*, 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.*, 184:4605-4609 (2010); Hong, K. et al., "IL-12, independently of IFN-gamma, plays a crucial role in the pathogenesis of a murine psoriasis like skin disorder", *J. Immunol.*, 162:7480-7491 (1999); Hue, S. et al., "Interleukin-23 drives innate and T cell-mediated intestinal inflammation", *J. Exp. Med.*, 203:2473-2483 (2006); Cua, D. J. et al., "Interleukin-23 rather than interleukin-12 is the critical cytokine for autoimmune inflammation of the brain", *Nature*, 421:744-748 (2003); Murphy, C. A. et al., "Divergent pro- and anti-inflammatory roles for IL-23 and IL-12 in joint autoimmune inflammation", *J. Exp. Med.*, 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.*, 199:125-130 (2004); Tzartos, J. S. et al., "Interleukin-17 production in central nervous system infiltrating T cells and glial cells is associated with active disease in multiple sclerosis", *Am. J. Pathol.*, 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.*, 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.*, 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut*, 60:1739-1753 (2011); Tao, J. H. et al., "Meta-analysis of TYK2 gene polymorphisms association with susceptibility to autoimmune and inflammatory diseases", *Mol. Biol. Rep.*, 38:4663-4672 (2011); Cho, J. H. et al., "Recent insights into the genetics of inflammatory bowel disease", *Gastroenterology*, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet*, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology*, 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet*, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

In a first aspect of the present invention, there is provided a compound of formula (I)

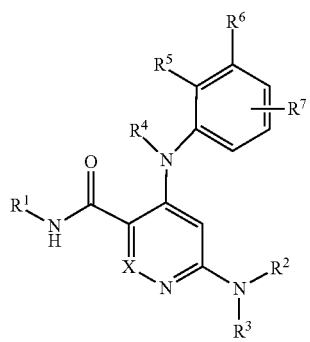

I wherein
X is N or CH;
$R^1$ is H, $CD_3$, $C_{1-3}$ alkyl or $C_{3-6}$ cycloalkyl;
$R^2$ is H, —C(O)$R^{2a}$; $C_{1-6}$ alkyl, —(CH$_2$)$_r$-3-14 membered carbocycle substituted with 0-1 $R^{2a}$ or a 5-12 membered heterocycle substituted with 0-4 $R^{2a}$;
$R^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^d$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle substituted with 0-2 $R^a$;
$R^3$ is H, $C_{1-3}$ alkyl or $C_{3-6}$ cycloalkyl;
$R^4$ is H, $C_{1-3}$ alkyl or $C_{3-6}$ cycloalkyl;
$R^5$ is $C_{1-4}$ alkyl substituted with 0-1 $R^{5a}$, $C_{1-4}$ alkoxy substituted with 0-1 $R^{5a}$, (CH$_2$)$_r$-phenyl substituted with 0-3 $R^{5a}$ or a —(CH$_2$)-5-7 membered heterocycle;
$R^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-3}$ alkyl or (CH$_2$)$_r$-phenyl;
$R^6$ is a —(CH$_2$)-5-7 membered heterocycle substituted with 0-3 $R^{6a}$;
$R^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^d$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle substituted with 0-2 $R^a$;

$R^7$ is H, halogen or $C_{1-3}$ alkyl;
$R^{11}$ at each occurrence is independently H, $C_{1-4}$ alkyl substituted with 0-3 $R^f$, CF$_3$, $C_{3-10}$ cycloalkyl substituted with 0-1 $R^f$, (CH$_2$)$_r$-phenyl substituted with 0-3 $R^d$ or —(CH$_2$)$_r$-5-7 membered heterocycle substituted with 0-3 $R^d$;
$R^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-3 $R^f$, $C_{1-6}$ haloalkyl, —(CH$_2$)$_r$-3-14 membered carbocycle or —(CH$_2$)$_r$-5-7 membered heterocycle substituted with 0-3 $R^f$;
$R^b$ is H, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle substituted with 0-3 $R^f$ or (CH$_2$)$_r$-phenyl substituted with 0-3 $R^d$;
$R^c$ is $C_{1-6}$ alkyl substituted with 0-3 $R^f$, (CH$_2$)$_r$—C$_{3-6}$ cycloalkyl substituted with 0-3 $R^f$ or (CH$_2$)$_r$-phenyl substituted with 0-3 $R^f$;
$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^e$, $C_{1-6}$ alkyl or (CH$_2$)$_r$-phenyl substituted with 0-3 $R^f$;
$R^e$ is independently at each occurrence, hydrogen, $C_{1-6}$ alkyl, $C_{3-6}$ cycloalkyl or (CH$_2$)$_r$-phenyl substituted with 0-3 $R^f$;
$R^f$ is independently at each occurrence, hydrogen, halo, CN, NH$_2$, OH, $C_{3-6}$ cycloalkyl, CF$_3$, O(C$_{1-6}$ alkyl) or a —(CH$_2$)$_r$-5-7 membered heterocycle;
p is 0, 1, or 2;
r is 0, 1, 2, 3, 4 or 5;
or a stereoisomer or pharmaceutically acceptable salt thereof.

In a second aspect of the present invention, there is provided a compound of the formula

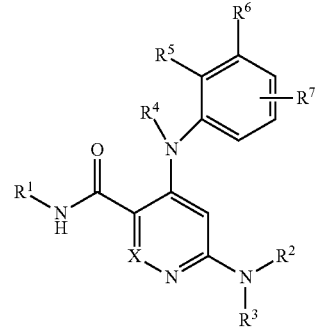

I wherein
X is N or CH;
$R^1$ is H, CD$_3$, $C_{1-3}$ alkyl or $C_{3-6}$ cycloalkyl;
$R^2$ is H, —C(O)$R^{2a}$; $C_{1-6}$ alkyl, —(CH$_2$)$_r$-3-14 membered carbocycle substituted with 0-1 $R^{2a}$ or a 5-12 membered heterocycle substituted with 0-4 $R^{2a}$;
$R^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^3$ is H, C$_{1-3}$ alkyl or C$_{3-6}$ cycloalkyl;

R$^4$ is H or C$_{1-3}$ alkyl;

R$^5$ is C$_{1-4}$ alkyl substituted with 0-1 R$^{5a}$, C$_{1-4}$ alkoxy substituted with 0-1 R$^{5a}$, (CH$_2$)$_r$-phenyl substituted with 0-3 R$^{5a}$ or a —(CH$_2$)-5-7 membered heterocycle;

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-3}$ alkyl or (CH$_2$)$_r$-phenyl;

R$^6$ is a —(CH$_2$)-5-7 membered heterocycle substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a third aspect of the present invention, there is provided a compound of the formula

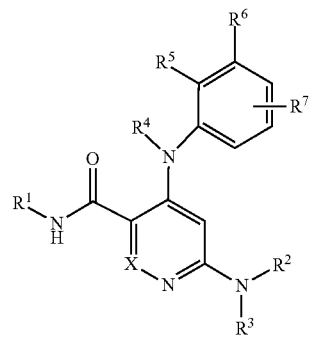

I wherein
X is N or CH;
R$^1$ is H, CD$_3$, C$_{1-3}$ alkyl or C$_{3-6}$ cycloalkyl;
R$^2$ is H, —C(O)R$^{2a}$; C$_{1-6}$ alkyl, —(CH$_2$)$_r$-3-14 membered carbocycle substituted with 0-1 R$^{2a}$ or a 5-12 membered heterocycle substituted with 0-4 R$^{2a}$;
R$^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^3$ is H, C$_{1-3}$ alkyl or C$_{3-6}$ cycloalkyl;
R$^4$ is H or C$_{1-3}$ alkyl;
R$^5$ is C$_{1-4}$ alkyl or C$_{1-4}$ alkoxy;
R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-3}$ alkyl or (CH$_2$)$_r$-phenyl;
R$^6$ is a —(CH$_2$)-5-7 membered heterocycle substituted with 0-3 R$^{6a}$;
R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;
R$^7$ is H, halogen or C$_{1-3}$ alkyl;
R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;
R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—C$_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 4th aspect of the present invention, there is provided a compound of the formula

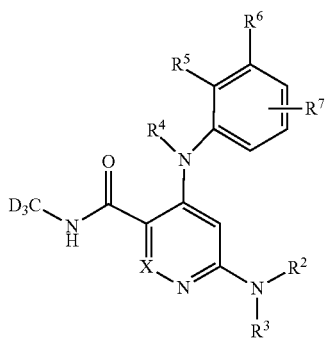

wherein

X is N or CH;

$R^2$ is H, —C(O)R$^{2a}$; $C_{1-6}$ alkyl, —(CH$_2$)$_r$-3-14 membered carbocycle substituted with 0-1 $R^{2a}$ or a 5-12 membered heterocycle substituted with 0-4 $R^{2a}$;

$R^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle substituted with 0-2 $R^a$;

$R^3$ is H, $C_{1-3}$ alkyl or $C_{3-6}$ cycloalkyl;

$R^4$ is H or $C_{1-3}$ alkyl;

$R^5$ is $C_{1-4}$ alkyl or $C_{1-4}$ alkoxy, $R^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-3}$ alkyl or (CH$_2$)$_r$-phenyl;

$R^6$ is a —(CH$_2$)-5-7 membered heterocycle substituted with 0-3 $R^{6a}$;

$R^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle substituted with 0-2 $R^a$;

$R^7$ is H, halogen or $C_{1-3}$ alkyl;

$R^{11}$ at each occurrence is independently H, $C_{1-4}$ alkyl substituted with 0-3 $R^f$, CF$_3$, $C_{3-10}$ cycloalkyl substituted with 0-1 $R^f$, (CH$_2$)$_r$-phenyl substituted with 0-3 $R^d$ or —(CH$_2$)$_r$-5-7 membered heterocycle substituted with 0-3 $R^d$;

$R^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O) R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-3 $R^f$, $C_{1-6}$ haloalkyl, —(CH$_2$)$_r$-3-14 membered carbocycle or —(CH$_2$)$_r$-5-7 membered heterocycle substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—C$_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 5th aspect of the present invention, there is provided a compound of the formula

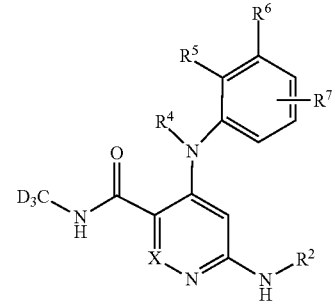

wherein

X is N or CH;

$R^2$ is H, —C(O)R$^{2a}$; $C_{1-6}$ alkyl, —(CH$_2$)$_r$-3-14 membered carbocycle substituted with 0-1 $R^{2a}$ or a 5-12 membered heterocycle substituted with 0-4 $R^{2a}$;

$R^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^4$ is H or C$_{1-3}$ alkyl;

R$^5$ is C$_{1-4}$ alkyl or C$_{1-4}$ alkoxy,

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-3}$ alkyl or (CH$_2$)$_r$-phenyl;

R$^6$ is a —(CH$_2$)-5-7 membered heterocycle substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 6th aspect of the present invention, there is provided a compound of the formula

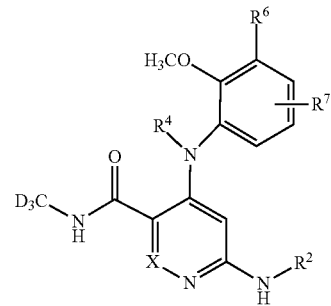

wherein
X is N or CH;
R$^2$ is H, —C(O)R$^{2a}$; C$_{1-6}$ alkyl, —(CH$_2$)$_r$-3-14 membered carbocycle substituted with 0-1 R$^{2a}$ or a 5-12 membered heterocycle substituted with 0-4 R$^{2a}$;

R$^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^4$ is H or C$_{1-3}$ alkyl;

R$^6$ is a —(CH$_2$)-5-7 membered heterocycle substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$ C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 7th aspect of the present invention, there is provided a compound of the formula

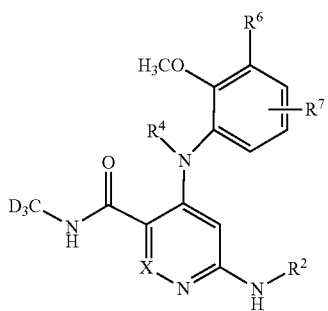

wherein

X is N or CH;

R$^2$ is H, —C(O)R$^{2a}$; C$_{1-6}$ alkyl, —(CH$_2$)$_r$-3-14 membered carbocycle substituted with 0-1 R$^{2a}$ or a 5-12 membered heterocycle substituted with 0-4 R$^{2a}$;

R$^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^4$ is H or C$_{1-3}$ alkyl;

R$^6$ is a triazole, oxadiazole, thiazole, oxazole or pyrazole substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$ C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In an 8th aspect of the present invention, there is provided a compound of the formula

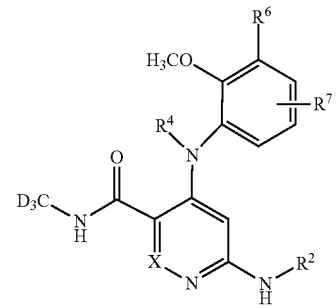

wherein

X is N or CH;

R$^2$ is H, —C(O)-cyclopropyl, —C(O)—CH$_2$-cyclopropyl, pyridine, pyridazine, pyrazole, triazole or piperazine, all of which, except the H group, may be substituted with 0-3 R$^{2a}$;

R$^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^4$ is H or C$_{1-3}$ alkyl;

R$^6$ is a triazole, oxadiazole, thiazole, oxazole or pyrazole substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)

R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 9th aspect of the present invention, there is provided a compound of the formula

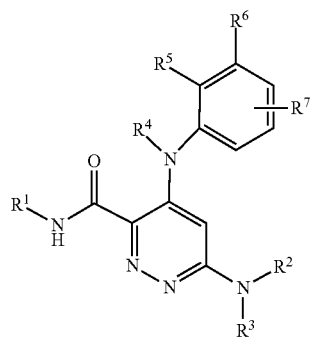

wherein

R$^1$ is H, CD$_3$, C$_{1-3}$ alkyl or C$_{3-6}$ cycloalkyl;

R$^2$ is H, —C(O)R$^{2a}$; C$_{1-6}$ alkyl, —(CH$_2$)$_r$-3-14 membered carbocycle substituted with 0-1 R$^{2a}$ or a 5-12 membered heterocycle substituted with 0-4 R$^{2a}$;

R$^{2a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^3$ is H, C$_{1-3}$ alkyl or C$_{3-6}$ cycloalkyl;

R$^4$ is H, C$_{1-3}$ alkyl or C$_{3-6}$ cycloalkyl;

R$^5$ is C$_{1-4}$ alkyl substituted with 0-1 R$^{5a}$, C$_{1-4}$ alkoxy substituted with 0-1 R$^{5a}$, (CH$_2$)$_r$-phenyl substituted with 0-3 R$^{5a}$ or a —(CH$_2$)-5-7 membered heterocycle;

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-3}$ alkyl or (CH$_2$)$_r$-phenyl;

R$^6$ is a —(CH$_2$)-5-7 membered heterocycle substituted with 0-3 R$^{6a}$;

R$^{6a}$ is independently at each occurrence, H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle substituted with 0-2 R$^a$;

R$^7$ is H, halogen or C$_{1-3}$ alkyl;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle or —(CH$_2$)$_r$-5-7 membered heterocycle substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle;

p is 0, 1, or 2;

r is 0, 1, 2, 3, 4 or 5;

or a stereoisomer or pharmaceutically acceptable salt thereof.

In a 10th aspect of the present invention, there is provided a compound of the formula

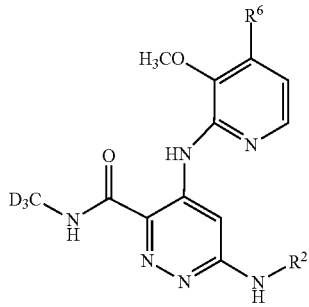

wherein
- R² is H, —C(O)-cyclopropyl, —C(O)—CH₂-cyclopropyl, pyridine, pyridazine, pyrazole, triazole or piperazine, all of which, except the H group, may be substituted with 0-3 R²ᵃ;
- R²ᵃ is independently at each occurrence, H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle substituted with 0-2 Rᵃ;
- R⁴ is H or C₁₋₃ alkyl;
- R⁶ is a triazole, oxadiazole, thiazole, oxazole or pyrazole substituted with 0-3 R⁶ᵃ;
- R⁶ᵃ is independently at each occurrence, H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle substituted with 0-2 Rᵃ;
- R⁷ is H, halogen or C₁₋₃ alkyl;
- R¹¹ at each occurrence is independently H, C₁₋₄ alkyl substituted with 0-3 Rᶠ, CF₃, C₃₋₁₀ cycloalkyl substituted with 0-1 Rᶠ, (CH₂)ᵣ-phenyl substituted with 0-3 Rᵈ or —(CH₂)ᵣ-5-7 membered heterocycle substituted with 0-3 Rᵈ;
- Rᵃ at each occurrence is independently H, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇ C(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, —(CH₂)ᵣ-3-14 membered carbocycle or —(CH₂)ᵣ-5-7 membered heterocycle substituted with 0-3 Rᶠ;
- Rᵇ is H, C₁₋₆ alkyl substituted with 0-3 Rᵈ, C₁₋₆ haloalkyl, C₃₋₆ cycloalkyl substituted with 0-2 Rᵈ, or —(CH₂)ᵣ-5-7 membered heterocycle substituted with 0-3 Rᶠ or (CH₂)ᵣ-phenyl substituted with 0-3 Rᵈ;
- Rᶜ is C₁₋₆ alkyl substituted with 0-3 Rᶠ, (CH₂)ᵣ—C₃₋₆ cycloalkyl substituted with 0-3 Rᶠ or (CH₂)ᵣ-phenyl substituted with 0-3 Rᶠ;
- Rᵈ is independently at each occurrence, hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl or (CH₂)ᵣ-phenyl substituted with 0-3 Rᶠ;
- Rᵉ is independently at each occurrence, hydrogen, C₁₋₆ alkyl, C₃₋₆ cycloalkyl or (CH₂)ᵣ-phenyl substituted with 0-3 Rᶠ;
- Rᶠ is independently at each occurrence, hydrogen, halo, CN, NH₂, OH, C₃₋₆ cycloalkyl, CF₃, O(C₁₋₆ alkyl) or a —(CH₂)ᵣ-5-7 membered heterocycle;
- p is 0, 1, or 2;
- r is 0, 1, 2, 3, 4 or 5;
- or a stereoisomer or pharmaceutically acceptable salt thereof.

In an 11th aspect of the present invention, there is provided a compound of the formula

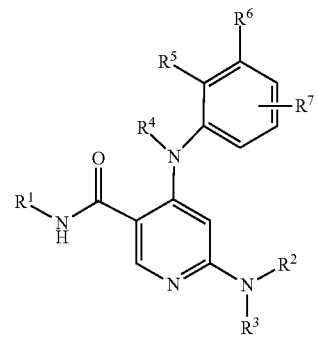

wherein
- R¹ is H, CD₃, C₁₋₃ alkyl or C₃₋₆ cycloalkyl;
- R² is H, —C(O)R²ᵃ; C₁₋₆ alkyl, —(CH₂)ᵣ-3-14 membered carbocycle substituted with 0-1 R²ᵃ or a 5-12 membered heterocycle substituted with 0-4 R²ᵃ;
- R²ᵃ is independently at each occurrence, H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle substituted with 0-2 Rᵃ;
- R³ is H, C₁₋₃ alkyl or C₃₋₆ cycloalkyl;
- R⁴ is H, C₁₋₃ alkyl or C₃₋₆ cycloalkyl;
- R⁵ is C₁₋₄ alkyl substituted with 0-1 R⁵ᵃ, C₁₋₄ alkoxy substituted with 0-1 R⁵ᵃ, (CH₂)ᵣ-phenyl substituted with 0-3 R⁵ᵃ or a —(CH₂)-5-7 membered heterocycle;
- R⁵ᵃ is independently at each occurrence, H, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₃ alkyl or (CH₂)ᵣ-phenyl;
- R⁶ is a —(CH₂)-5-7 membered heterocycle substituted with 0-3 R⁶ᵃ;
- R⁶ᵃ is independently at each occurrence, H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, (CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle substituted with 0-2 $R^a$;

$R^7$ is H, halogen or $C_{1-3}$ alkyl;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle substituted with 0-3 $R^d$;

$R^a$ at each occurrence is independently H, F, Cl, Br, $OCF_3$, $CF_3$, $CHF_2$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-3 $R^f$, $C_{1-6}$ haloalkyl, —$(CH_2)_r$-3-14 membered carbocycle or —$(CH_2)_r$-5-7 membered heterocycle substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_r C(O)R^c$, —$NR^e R^e$, —$NR^e C(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle;

p is 0, 1, or 2;

r is 0, 1, 2, 3, 4 or 5;

or a stereoisomer or pharmaceutically acceptable salt thereof.

In a 12th aspect of the present invention, there is provided a compound of the formula

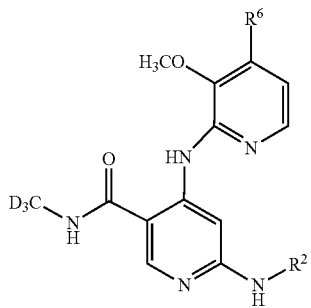

wherein $R^2$ is H, —C(O)-cyclopropyl, —C(O)—$CH_2$-cyclopropyl, pyridine, pyridazine, pyrazole, triazole or piperazine, all of which, except the H group, may be substituted with 0-3 $R^{2a}$;

$R^{2a}$ is independently at each occurrence, H, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)_p R^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle substituted with 0-2 $R^a$;

$R^4$ is H or $C_{1-3}$ alkyl;

$R^6$ is a triazole, oxadiazole, thiazole, oxazole or pyrazole substituted with 0-3 $R^{6a}$;

$R^{6a}$ is independently at each occurrence, H, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, $(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)_p R^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle substituted with 0-2 $R^a$;

$R^7$ is H, halogen or $C_{1-3}$ alkyl;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle substituted with 0-3 $R^d$;

$R^a$ at each occurrence is independently H, F, Cl, Br, $OCF_3$, $CF_3$, $CHF_2$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)R^c$, —$S(O)_2 R^c$, $C_{1-6}$ alkyl substituted with 0-3 $R^f$, $C_{1-6}$ haloalkyl, —$(CH_2)_r$-3-14 membered carbocycle or —$(CH_2)_r$-5-7 membered heterocycle substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_r C(O)R^c$, —$NR^e R^e$, —$NR^e C(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle;

p is 0, 1, or 2;

r is 0, 1, 2, 3, 4 or 5;

or a stereoisomer or pharmaceutically acceptable salt thereof.

In another aspect, there is provided a compound selected from the exemplified examples within the scope of the first aspect, or a pharmaceutically acceptable salt or stereoisomer thereof.

In another aspect, there is provided a compound selected from any subset list of compounds within the scope of any of the above aspects.

In another aspect, there is provided a compound (IUPAC naming convention) selected from 6-cyclopropaneamido-4-{[2-methoxy-3-(5-{1-[(2-methoxyethyl)carbamoyl]propyl}-1,2,4-oxadiazol-3-yl)phenyl]amino}-N-(2H3)methylpyridazine-3-carboxamide, 6-cyclopropaneamido-4-[(2-methoxy-3-{5-[1-(morpholin-4-yl)-1-oxopentan-2-yl]-1,2,4-oxadiazol-3-yl}phenyl)amino]-N-(2H3)methylpyridazine-3-carboxamide, 6-cyclopropaneamido-4-{[2-methoxy-3-(5-{1-[(2-methoxyethyl) carbamoyl]butyl}-1,2,4-oxadiazol-3-yl)phenyl]amino}-N-(2H3)methylpyridazine-3-carboxamide, tert-butyl N-[(1R,2R)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}propyl]carbamate, 6-cyclopropaneamido-4-[(3-{3-[(1R,2R)-1-acetamido-2-hydroxypropyl]-1,2,4-oxadiazol-5-yl}-2-methoxyphenyl)amino]-N-(2H3)methylpyridazine-3-carboxamide, methyl N-[(1R,2R)-1-{5-[3-({6-cyclopropaneamido-3-[(2H3)methylcarbamoyl]pyridazin-4-yl}amino)-2-methoxyphenyl]-1,2,4-oxadiazol-3-yl}-2-hydroxypropyl]carbamate, 6-cyclopropaneamido-4-[(3-{3-[(1R,2R)-2-hydroxy-1-propanamidopropyl]-1,2,4-oxadiazol-5-yl}-2-methoxyphenyl)amino]-N-(2H3)methylpyridazine-3-carboxamide, tert-butyl N-[(1R)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}ethyl]carbamate, 6-cyclopropaneamido-4-[(3-{3-[(1R)-2-hydroxy-1-propanamidoethyl]-1,2,4-oxadiazol-5-yl}-2-methoxyphenyl)amino]-N-(2H3)methylpyridazine-3-carboxamide, 6-cyclopropaneamido-4-[(3-{3-[(1R)-1-acetamido-2-hydroxyethyl]-1,2,4-oxadiazol-5-yl}-2-methoxyphenyl)amino]-N-(2H3)methylpyridazine-3-carboxamide, (2R)-2-{5-[3-({6-cyclopropaneamido-3-[(2H3)methylcarbamoyl]pyridazin-4-yl}amino)-2-methoxyphenyl]-1,2,4-oxadiazol-3-yl}-2-acetamidoethyl acetate, 6-cyclopropaneamido-4-[(3-{3-[(1R)-2-hydroxy-1-(2-methoxyacetamido)ethyl]-1,2,4-oxadiazol-5-yl}-2-methoxyphenyl)amino]-N-(2H3)methylpyridazine-3-carboxamide, 6-cyclopropaneamido-4-[(3-{3-[(1S,2S)-1-acetamido-2-hydroxypropyl]-1,2,4-oxadiazol-5-yl}-2-methoxyphenyl)amino]-N-(2H3)methylpyridazine-3-carboxamide, 6-cyclopropaneamido-4-[(3-{3-[(1S,2S)-2-hydroxy-1-(2-methoxyacetamido)propyl]-1,2,4-oxadiazol-5-yl}-2-methoxyphenyl)amino]-N-(2H3)methylpyridazine-3-carboxamide, tert-butyl N-[(1S,2S)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}propyl]carbamate, 6-cyclopropaneamido-4-[(3-{3-[(1S,2S)-2-hydroxy-1-propanamidopropyl]-1,2,4-oxadiazol-5-yl}-2-methoxyphenyl)amino]-N-(2H3)methylpyridazine-3-carboxamide, tert-butyl N-[(1S)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}ethyl]carbamate, or 6-cyclopropaneamido-4-[(3-{3-[(1S)-1-acetamido-2-hydroxyethyl]-1,2,4-oxadiazol-5-yl}-2-methoxyphenyl)amino]-N-(2H3)methylpyridazine-3-carboxamide, or a pharmaceutically acceptable salt thereof.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating rheumatoid arthritis or the use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (FTP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an IC$_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

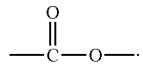

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

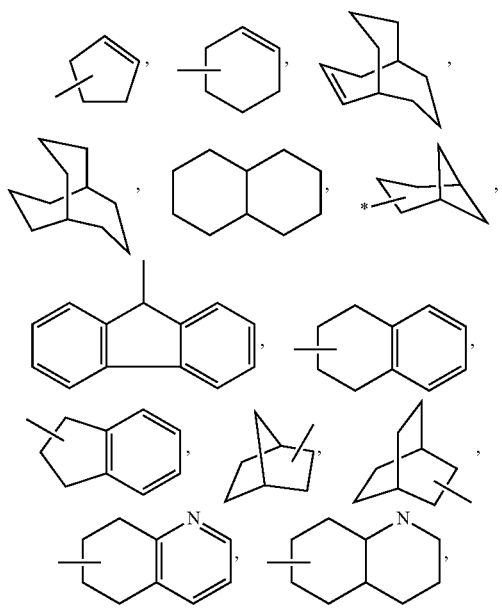

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

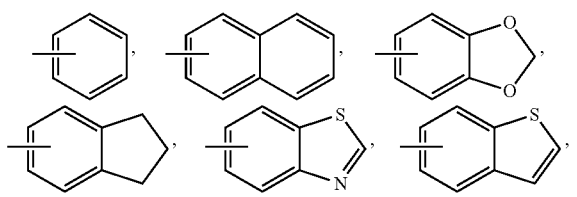

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

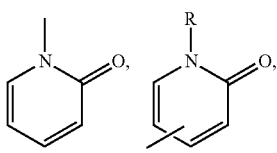

-continued

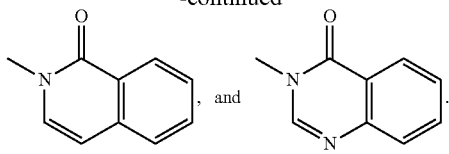, and

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

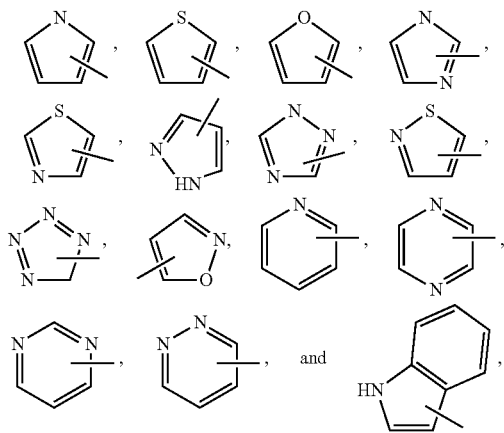

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

UTILITY

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PRO-GRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. The following abbreviations are used:

| Abbreviations | |
|---|---|
| Abbreviation | Meaning |
| Ac | acetyl |
| ACN | acetonitrile |
| AcOH | acetic acid |
| anhyd. | anhydrous |
| aq. | aqueous |
| Bn | benzyl |
| Bu | butyl |
| Boc | tert-butoxycarbonyl |
| BOP | benzotriazol-1-yloxytris-(dimethylamino)-phosphonium hexafluorophosphate |
| CV | Column Volumes |
| DCE | dichloroethane |
| DCM | dichloromethane |
| DIC | N,N'-Diisopropylcarbodiimide |
| DMF | dimethylformamide |
| DMSO | dimethylsulfoxide |
| EtOAc | ethyl acetate |
| Et | ethyl |
| H or $H_2$ | hydrogen |
| h, hr or hrs | hour(s) |
| hex | hexane |
| i | iso |
| ISCO | automated chromatography |
| HOAc or AcOH | acetic acid |
| HCl | hydrochloric acid |
| HPLC | high pressure liquid chromatography |
| LC | liquid chromatography |
| LiHMDS | Lithium bis(trimethylsilyl)amide |
| M | molar |
| mM | millimolar |
| Me | methyl |
| MeOH | methanol |
| MHz | megahertz |
| min. | minute(s) |
| mins | minute(s) |
| M + 1 | (M + H)+ |
| MS | mass spectrometry |
| n or N | normal |
| nm | nanometer |
| nM | nanomolar |
| Pd/C | palladium on carbon |
| Ph | phenyl |
| Pr | propyl |
| PSI | pounds per square inch |
| rb | round bottle |
| rt | room temperature |
| Ret Time | retention time |
| sat. | saturated |
| SFC | supercritical fluid chromatography |
| TBAF | Tetra-n-butylammonium fluoride |
| TEA | triethylamine |
| TFA | trifluoroacetic acid |
| THF | tetrahydrofuran |
| Xantphos | 4,5-Bis(diphenylphosphino)-9,9-dimethylxanthene |

Preparations

The preparations set out below are for the synthesis of reagents that were not obtained from commercial sources and were employed for the preparation of compounds of formula I of the invention. All chiral compounds in the Tables and Schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

HPLC Methods

Method A

Column: Waters Acquity BEH $C_{18}$ 2.0×50 mm, 1.7 µm; mobile phase A: water with 0.1% TFA; mobile phase B: MeCN with 0.1% TFA; temperature: 40° C.; flow rate 1 mL/min; gradient: 0-100% B over 1.5 min, then 0.5 min isocratic at 100% B.

QC-ACN-AA-XB: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method E

Phenominex Kinetics C18, 2.1×50 mm, 2.1-µm particles; Mobile Phase A: 5:95 acetonitrile:water with 10 mM ammonium acetate; mobile phase A: 10% acetonitrile in water with 0.1% TFA; mobile phase B: 90% acetonitrile in water with 0.1% TFA; Temperature: 40° C.; Gradient: 0-100% B over 2 minutes: UV at 220 nm.

Method F

Column: YMC Combiscreen ODS-A 4.6×50 mm S-5; 5:95 acetonitrile:water with 10 mM ammonium acetate; mobile phase A: 10% methanol in water with 0.1% TFA; mobile phase B: 90% methanol in water with 0.1% TFA; temperature: RT; flow rate 1 mL/min; gradient: 0-100% B over 4 min, then 1 min isocratic at 100% B; UV at 254 nm.

Method OC-ACN-AA-XB

Waters Acquity UPLC BEH C18, 2.1×50 mm, 1.7-µm particles; Mobile Phase A: 5:95 acetonitrile: water with 10 mM ammonium acetate; Mobile Phase B: 95:5 acetonitrile: water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method OC-ACN-TFA-XB

Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method I

Column: Sunfire C18 (4.6×150) mm, 3.5 µm; Mobile Phase A: 5:95 acetonitrile: water with 0.05% TFA; Mobile Phase B: 95:5 acetonitrile: water with 0.05% TFA; Temperature: 50° C.; Gradient: 10-100% B over 12 minutes; Flow: 1 ml/min.

Method TS1

Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5 minute hold at 98% B; Flow rate: 0.8 mL/min;

Example 1

6-(cyclopropanecarboxamido)-4-((3-(4-((1,1-dioxidothiomorpholino)methyl)-1H-1,2,3-triazol-1-yl)-2-methoxyphenyl)amino)-N-(trideuteromethyl)pyridazine-3-carboxamide

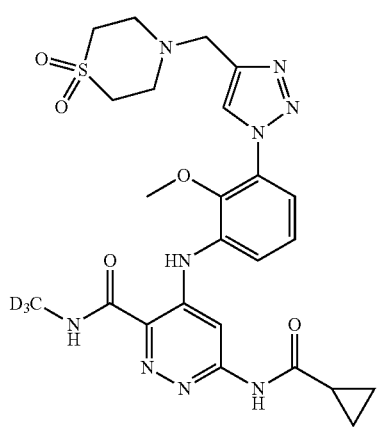

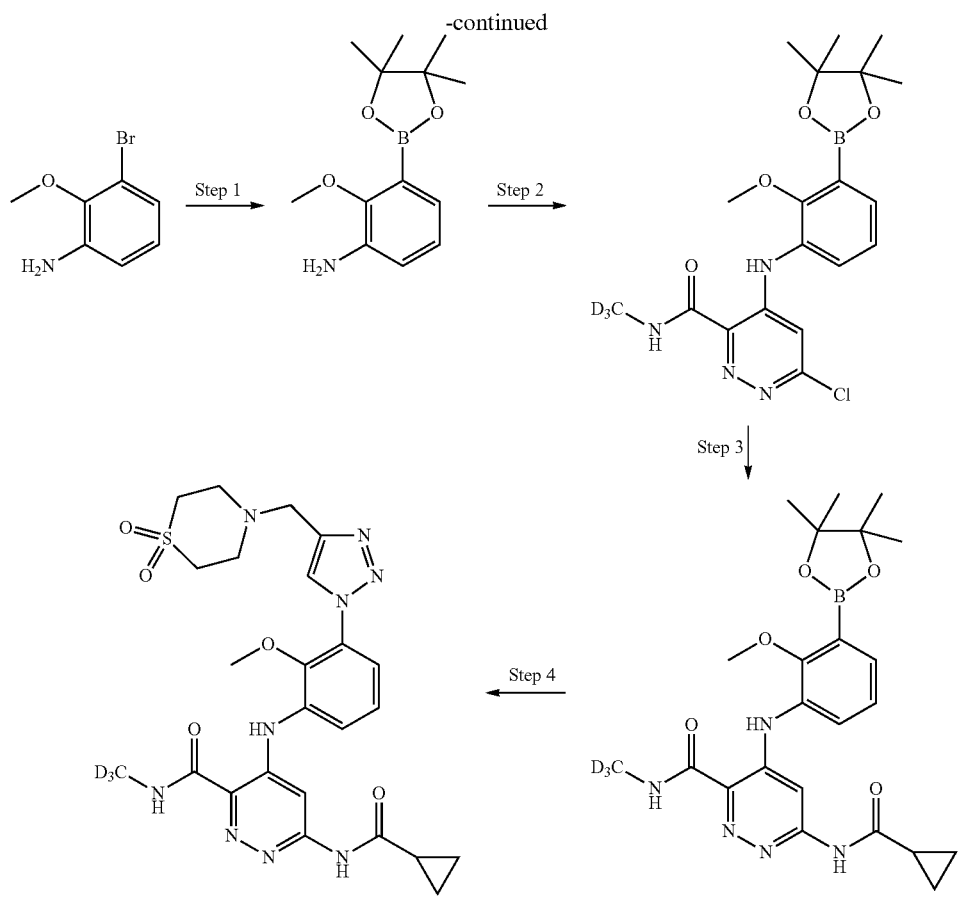

Step 1

A mixture of 3-bromo-2-methoxyaniline (500 mg, 2.48 mmol), 4,4,4',4',5,5,5',5'-octamethyl-2,2'-bi(1,3,2-dioxaborolane) (943 mg, 3.71 mmol), KOAc (729 mg, 7.42 mmol) and PdCl$_2$(dppf) (91 mg, 0.124 mmol) in 1,4-dioxane (10 mL) was degassed by bubbling with nitrogen gas for 10 minutes. The reaction mixture was sealed and heated to 100° C. for 4.5 hours. Upon completion, the reaction was cooled to room temperature and loaded directly onto silica gel plug for purification by column chromatography eluting in Hexanes/EtOAc 0-100%. The desired fractions were concentrated and the material was further purified by silica gel column chromatography eluting with DCM/MeOH 0-10% to give 2-methoxy-3-(4,4,5,5-tetramethyl-1,3,2-dioxaborolan-2-yl)aniline. LCMS m/z 250.0 (M+H)$^+$; HPLC $t_R$ 0.73 min (analytical HPLC Method TS1). $^1$H NMR (400 MHz, CHLOROFORM-d) δ 7.12 (dd, J=7.3, 1.7 Hz, 1H), 6.96-6.91 (m, 1H), 6.89-6.84 (m, 1H), 3.82 (s, 5H), 1.37 (s, 12H).

Step 2

To a solution of 4,6-dichloro-N-trideuteromethylpyridazine-3-carboxamide (295 mg, 1.41 mmol) and 2-methoxy-3-(4,4,5,5-tetramethyl-1,3,2-dioxaborolan-2-yl)aniline (387 mg, 1.55 mmol) in THF (6 mL) was added LiHMDS (1M in THF, 3.53 mL, 3.53 mmol). The reaction vial was stirred at 25° C. for 20 minutes. Upon completion, the reaction was quenched with saturated aqueous ammonium chloride solution and diluted with DCM and water. The aqueous layer was extracted with DCM. The combined organic layer was dried over sodium sulfate, filtered, and concentrated to give crude material that was assumed quantitative of 6-chloro-4-((2-methoxy-3-(4,4,5,5-tetramethyl-1,3,2-dioxaborolan-2-yl)phenyl)amino)-N-trideuteromethylpyridazine-3-carboxamide (1.41 mmol) and used as such. LCMS m/z 422.1 (M+H)$^+$; HPLC $t_R$ 1.07 min (analytical HPLC Method TS1).

Step 3

A mixture of 6-chloro-4-((2-methoxy-3-(4,4,5,5-tetramethyl-1,3,2-dioxaborolan-2-yl)phenyl)amino)-N-trideuteromethylpyridazine-3-carboxamide (0.11 mmol, crude from Step 2), cyclopropanecarboxamide (50.5 mg, 0.593 mmol), Pd$_2$(dba)$_3$ (10.9 mg, 0.012 mmol), Xantphos (13.7 mg, 0.024 mmol) and Cs$_2$CO$_3$ (97 mg, 0.296 mmol) in 1,4-dioxane (1 mL) was degassed by bubbling nitrogen gas through the mixture for 5 minutes. The reaction vessel was sealed and heated to 130° C. for 30 minutes. Upon completion, the reaction was cooled to room temperature and loaded directly onto silica gel for purification by column chromatography eluting with DCM/MeOH 0-10% to give the desired product mixed with water soluble impurities. The collected fractions were dissolved in DCM and washed with water three times, dried over sodium sulfate, filtered, and concentrated to afford 6-(cyclopropanecarboxamido)-4-((2-methoxy-3-(4,4,5,5-tetramethyl-1,3,2-dioxaborolan-2-yl)phenyl)amino)-N-trideuteromethylpyridazine-3-carboxamide (27 mg, 0.057 mmol, 52% yield) as a yellow solid. LCMS m/z 471.2 (M+H)+; HPLC tR 0.95 min (analytical HPLC Method TS1). 1H NMR (400 MHz, CHLORO- FORM-d) ☐ 10.90 (s, 1H), 9.53 (br. s., 1H), 8.20-8.14 (m, 1H), 8.03 (s, 1H), 7.56-7.50 (m, 2H), 7.17 (t, J=7.6 Hz, 1H), 3.82 (s, 3H), 1.79 (ddd, J=12.3, 7.9, 4.4 Hz, 1H), 1.36 (s, 12H), 1.12-1.07 (m, 2H), 0.92-0.86 (m, 2H)

Step 4

6-(cyclopropanecarboxamido)-4-((2-methoxy-3-(4,4,5,5-tetramethyl-1,3,2-dioxaborolan-2-yl)phenyl)amino)-N-trideuteromethylpyridazine-3-carboxamide (20 mg, 0.043 mmol) was suspended in MeOH (0.3 mL), and sodium azide (5.5 mg, 0.085 mmol) and copper(II) acetate (1.9 mg, 0.011 mmol) were added. The reaction was stirred under an atmosphere of air at 65° C. for 2.5 hours. Upon completion, the reaction was cooled to room temperature and sodium ascorbate (2.1 mg, 0.011 mmol) and 4-(prop-2-yn-1-yl)thiomorpholine 1,1-dioxide (29.5 mg, 0.170 mmol) were added sequentially. The reaction was stirred for 2 hours. Upon completion, the reaction was concentrated, taken up in DMF, filtered through a 0.45 micron syringe filter, and purified by preparative LC/MS with the following conditions: Column: Waters XBridge C18, 19×200 mm, 5-m particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 20 minutes, then a 5-minute hold at 100% B; Flow: 20 mL/min. The fractions containing the desired product were combined and dried via centrifugal evaporation to give 6-(cyclopropanecarboxamido)-4-((3-(4-(((1,1-dioxidothiomorpholino)methyl)-1H-1,2,3-triazol-1-yl)-2-methoxyphenyl)amino)-N-trideuteromethylpyridazine-3-carboxamide, TFA (11.4 mg, 0.017 mmol, 38% yield). LCMS m/z 559.3 (M+H)+; HPLC $t_R$ 1.18 min (analytical HPLC Method QC-ACN-AA-XB). Select NMR peaks: $^1$H NMR (500 MHz, DMSO-d$_6$) δ 11.40 (s, 1H), 11.08 (s, 1H), 9.17 (s, 1H), 8.56 (s, 1H), 8.18 (s, 1H), 7.66 (d, J=7.7 Hz, 1H), 7.51 (d, J=7.4 Hz, 1H), 7.46-7.39 (m, 1H), 4.24 (s, 2H), 2.12-2.02 (m, 1H), 0.91-0.77 (m, 4H).

The Examples in Table 1 were prepared using a similar procedure used to prepare Example 1.

TABLE 1

| Ex. No. | Structure | MW | Obs. MS Ion | RT | QC Method |
|---|---|---|---|---|---|
| 2 | | 510.6 | 511.4 | 1.19 | QC-ACN-AA-XB |
| 3 | 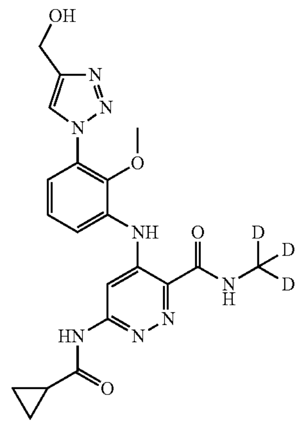 [SMILES: [2H]C([2H])([2H])NC(=O)c1nnc(NC(=O)C2CC2)cc1Nc1cccc(-n2cc(CO)nn2)c1OC] | 441.5 | 442.3 | 0.92 | QC-ACN-TFA-XB |
| 4 | 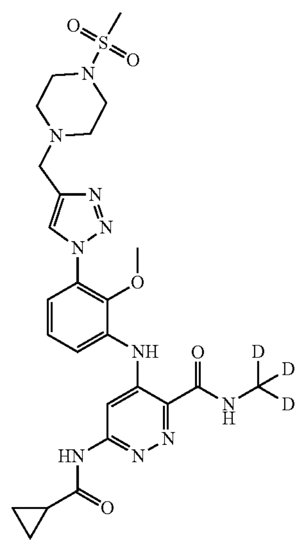 [SMILES: [2H]C([2H])([2H])NC(=O)c1nnc(NC(=O)C2CC2)cc1Nc1cccc(-n2cc(CN3CCN(S(C)(=O)=O)CC3)nn2)c1OC] | 587.7 | 588.4 | 0.96 | QC-ACN-TFA-XB |
| 5 | 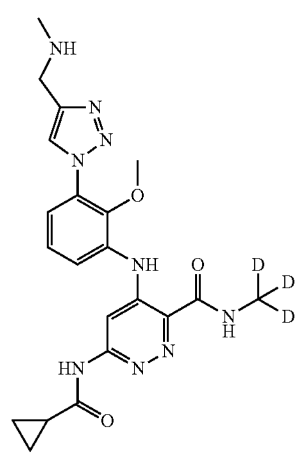 [SMILES: [2H]C([2H])([2H])NC(=O)c1nnc(NC(=O)C2CC2)cc1Nc1cccc(-n2cc(CNC)nn2)c1OC] | 454.5 | 455.2 | 0.96 | QC-ACN-AA-XB |

Example 6
4-((3-(5-(aminomethyl)-1,2,4-oxadiazol-3-yl)-2-methoxyphenyl)amino)-6-(cyclopropanecarboxamido)-N-trideuteromethylpyridazine-3-carboxamide
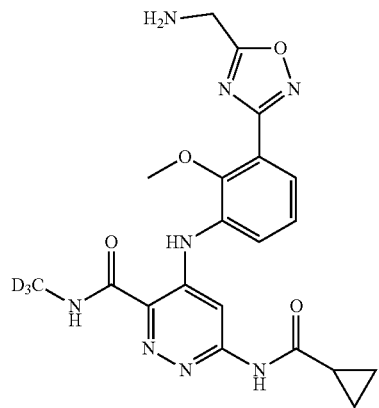 [SMILES: [2H]C([2H])([2H])NC(=O)c1nnc(NC(=O)C2CC2)cc1Nc1cccc(-c2noc(CN)n2)c1OC]
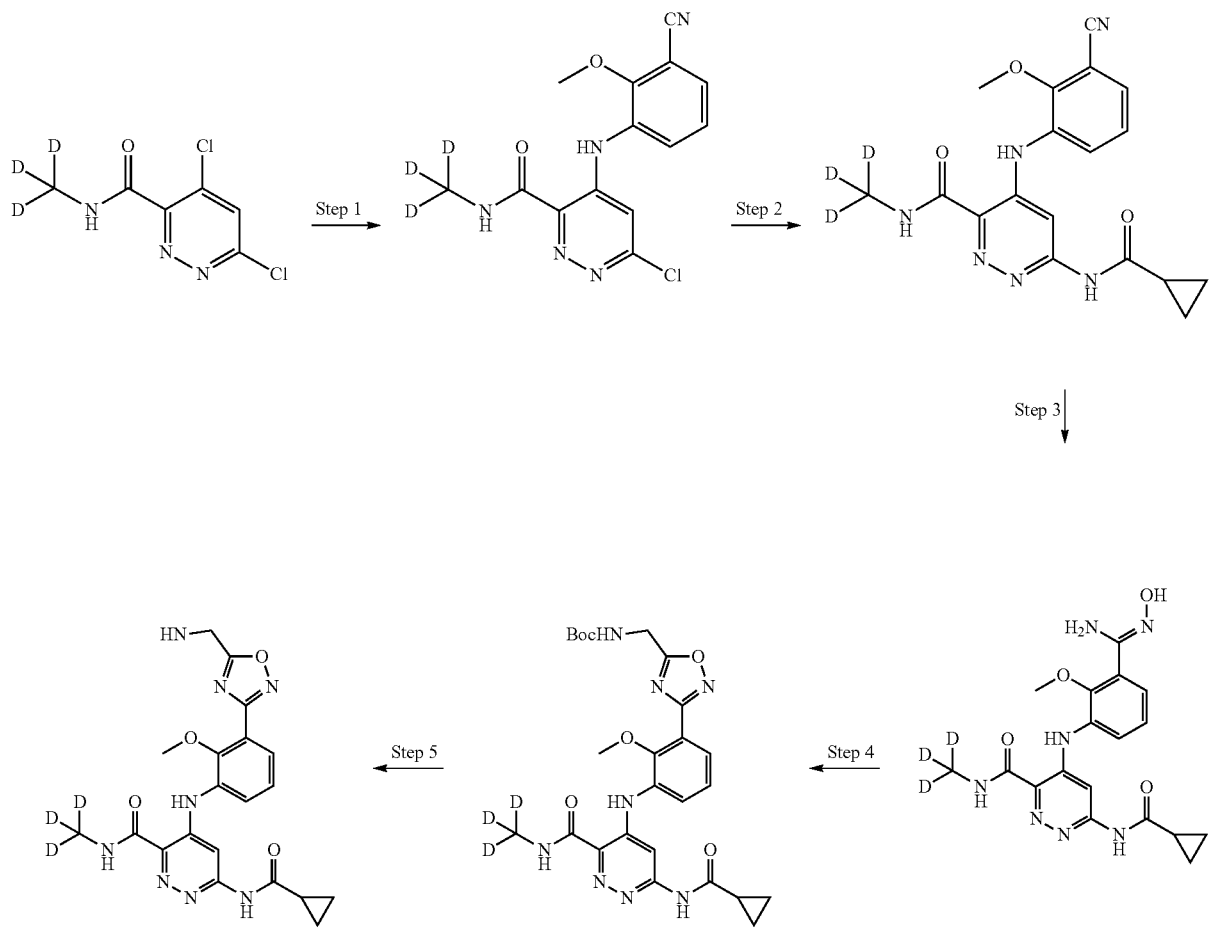

Step 1

To a solution of 4,6-dichloro-N-trideuteromethylpyridazine-3-carboxamide (605 mg, 2.89 mmol) and 3-amino-2-methoxybenzonitrile (472 mg, 3.18 mmol) in THF (15 mL) was added LiHMDS (0.5M in 2-MeTHF, 18.52 mL, 9.26 mmol). The reaction vial was stirred at 25° C. for 35 minutes. Upon completion, the reaction was quenched via addition of saturated aqueous ammonium chloride solution, water, and DCM. The aqueous layer was extracted with DCM. The combined organic layer was dried over sodium sulfate, filtered, and concentrated to give material assumed to be quantitative yield of 6-chloro-4-((3-cyano-2-methoxyphenyl)amino)-N-trideuteromethylpyridazine-3-carboxamide (2.89 mmol). Carried forward as such. LCMS m/z 321.0 (M+H)$^+$; HPLC $t_R$ 0.84 min (analytical HPLC Method TS1).

Step 2

The material from Step 1 (6-chloro-4-((3-cyano-2-methoxyphenyl)amino)-N-trideuteromethylpyridazine-3-carboxamide (2.89 mmol)), cyclopropanecarboxamide (1.23 g, 14.5 mmol), Pd$_2$(dba)$_3$ (0.265 g, 0.289 mmol), Xantphos (0.334 g, 0.578 mmol) and Cs$_2$CO$_3$ (2.354 g, 7.23 mmol) in 1,4-dioxane (15 mL) was degassed by bubbling nitrogen gas through the mixture for 5 minutes. The reaction vessel was sealed and heated to 130° C. for 45 minutes. Upon completion, the reaction mixture was diluted with DCM, filtered through a celite pad, and concentrated. The crude isolate was then purified by column chromatography on silica gel loading in DMF and eluting with DCM/MeOH 0-10% to give fractions containing water-soluble impurities. The desired fractions were combined and washed with water five times, dried over sodium sulfate, and concentrated to afford 4-((3-cyano-2-methoxyphenyl)amino)-6-(cyclopropanecarboxamido)-N-trideuteromethylpyridazine-3-carboxamide in assumed quantitative yield (2.76 mmol). Material was carried forward as such. LCMS m/z 370.1 (M+H)$^+$; HPLC $t_R$ 0.78 min (analytical HPLC Method TS1). $^1$H NMR (400 MHz, DMSO-d$_6$) δ 11.37 (s, 1H), 10.99 (s, 1H), 9.17 (s, 1H), 8.05 (s, 1H), 7.78 (dd, J=8.0, 1.4 Hz, 1H), 7.61 (dd, J=7.9, 1.5 Hz, 1H), 7.36 (t, J=7.9 Hz, 1H), 3.91 (s, 3H), 2.13-2.01 (m, 1H), 0.90-0.75 (m, 4H)

Step 3

To a mixture of 4-((3-cyano-2-methoxyphenyl)amino)-6-(cyclopropanecarboxamido)-N-trideuteromethylpyridazine-3-carboxamide (0.541 mmol) and hydroxylamine hydrochloride (192 mg, 2.76 mmol) in EtOH (15 mL) was added potassium hydroxide (149 mg, 2.65 mmol). The mixture was sealed and heated to 80° C. After 24 hours, another aliquot of hydroxylamine hydrochloride (192 mg, 2.76 mmol) and potassium hydroxide (149 mg, 2.65 mmol) were each added and the reaction was heated for 90 minutes more at 80° C. Upon completion, the reaction was cooled to room temperature, concentrated, taken up in DCM with a small amount of MeOH and filtered through a pad of celite. The filtrate was concentrated to give material in assumed quantitative yield of (Z)-6-(cyclopropanecarboxamido)-4-((3-(N'-hydroxycarbamimidoyl)-2-methoxyphenyl)amino)-N-trideuteromethylpyridazine-3-carboxamide (0.541 mmol). Material was used as such. LCMS m/z 403.1 (M+H)$^+$; HPLC $t_R$ 0.55 min (analytical HPLC Method TS1).

Step 4

A portion of the material (1/10) from Step 3 ((Z)-6-(cyclopropanecarboxamido)-4-((3-(N'-hydroxycarbamimidoyl)-2-methoxyphenyl)amino)-N-trideuteromethylpyridazine-3-carboxamide (0.0541 mmol)) was suspended in DMF (0.5 mL) with 2-((tert-butoxycarbonyl)amino)acetic acid (19 mg, 0.108 mmol). To this mixture was added DIC (0.020 mL, 0.130 mmol) at room temperature, and the reaction was stirred for 90 minutes. Then, TBAF (1M in THF, 0.249 mL, 0.249 mmol) was added in a single portion. After 4 hours, another aliquot of TBAF (1M in THF, 0.12 mL, 0.12 mmol) was added. After 16 hours, the reaction was quenched via the addition of a few drops of saturated aqueous ammonium chloride solution, water and DCM. The aqueous layer was extracted four times with 4/1 CHCl$_3$/iPrOH, and the combined organic layer was washed with water, dried over sodium sulfate, filtered and concentrated to afford material in assumed quantitative yield of tert-butyl ((3-(3-((6-(cyclopropanecarboxamido)-3-(trideuteromethylcarbamoyl)pyridazin-4-yl)amino)-2-methoxyphenyl)-1,2,4-oxadiazol-5-yl)methyl)carbamate (0.0541 mmol). Used as such. LCMS m/z 542.3 (M+H)$^+$; HPLC $t_R$ 1.71 min (analytical HPLC Method QC-ACN-AA-XB).

Step 5

Half of the material from Step 4 (tert-butyl ((3-(3-((6-(cyclopropanecarboxamido)-3-(trideuteromethylcarbamoyl)pyridazin-4-yl)amino)-2-methoxyphenyl)-1,2,4-oxadiazol-5-yl)methyl)carbamate (0.0270 mmol) was suspended in DCM (0.5 mL) and TFA (0.5 mL) and stirred at room temperature for 1 hour. Upon completion, the reaction was concentrated. The crude residue was taken up in DMF with a few drops of Et$_3$N to quench residual TFA. The material was purified via preparative LC/MS with the following conditions: Column: Waters XBridge C18, 19×200 mm, 5-m particles; Mobile Phase A: 5:95 acetonitrile: water with 10-mM ammonium acetate; Mobile Phase B: 95:5 acetonitrile: water with 10-mM ammonium acetate; Gradient: 5-55% B over 20 minutes, then a 5-minute hold at 100% B; Flow: 20 mL/min. The fractions containing the desired product were combined and dried via centrifugal evaporation to give 4-((3-(5-(aminomethyl)-1,2,4-oxadiazol-3-yl)-2-methoxyphenyl)amino)-6-(cyclopropanecarboxamido)-N-trideuteromethylpyridazine-3-carboxamide (1.2 mg, 2.61 µmol, 9.66% yield). LCMS m/z 442.3 (M+H)$^+$; HPLC $t_R$ 1.11 min (analytical HPLC Method QC-ACN-AA-XB). $^1$H NMR (500 MHz, DMSO-d$_6$) δ 11.34 (s, 1H), 11.00 (s, 1H), 9.13 (s, 1H), 8.12 (s, 1H), 7.69 (m, 2H), 7.39 (t, J=8.0 Hz, 1H), 4.20 (s, 2H), 3.73 (s, 3H), 2.11-1.98 (m, 1H), 0.89-0.71 (m, 4H).

The Examples in Table 2 were prepared using a similar procedure used to prepare Example 6.

TABLE 2

| Ex. No. | Structure | MW | Obs. MS Ion | RT | QC Method |
|---|---|---|---|---|---|
| 7 | 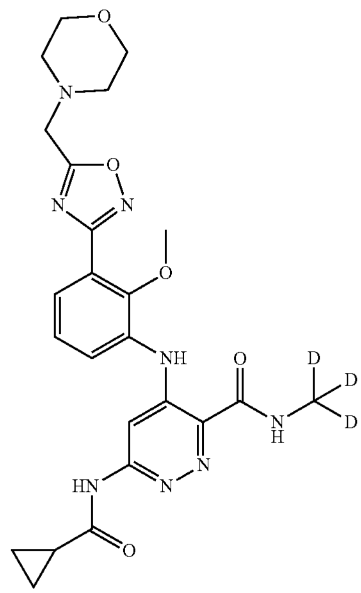 [SMILES: [2H]C([2H])([2H])NC(=O)c1nnc(NC(=O)C2CC2)cc1Nc1cccc(-c2noc(CN3CCOCC3)n2)c1OC] | 511.6 | 512.1 | 0.86 | QC-ACN-TFA-XB |
| 8 | 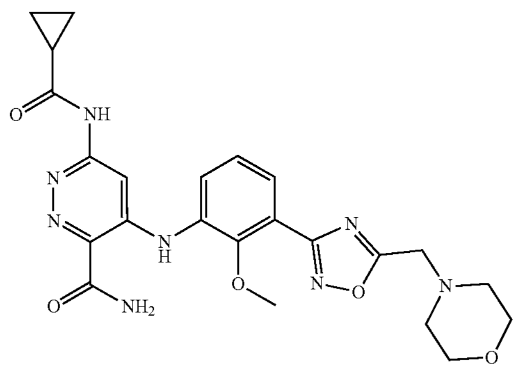 [SMILES: COc1c(Nc2cc(NC(=O)C3CC3)nnc2C(N)=O)cccc1-c1noc(CN2CCOCC2)n1] | 494.5 | 495.1 | 1.33 | QC-ACN-AA-XB |
| 9 | 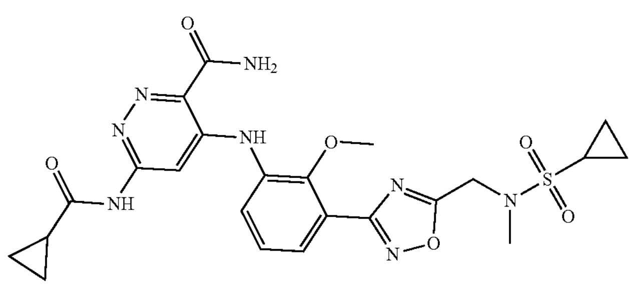 [SMILES: COc1c(Nc2cc(NC(=O)C3CC3)nnc2C(N)=O)cccc1-c1noc(CN(C)S(=O)(=O)C2CC2)n1] | 542.6 | 543.1 | 1.45 | QC-ACN-AA-XB |
| 10 | 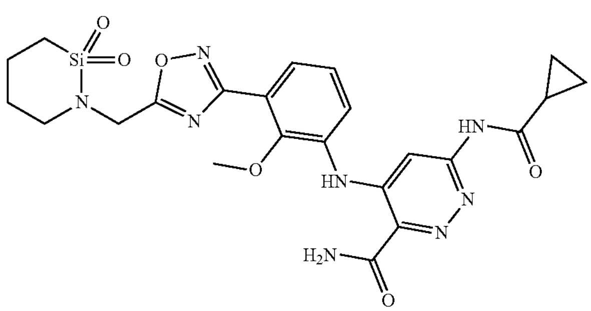 | 542.6 | 543.3 | 1.12 | QC-ACN-TFA-XB |

TABLE 2-continued

| Ex. No. | Structure | MW | Obs. MS Ion | RT | QC Method |
|---|---|---|---|---|---|
| 11 | 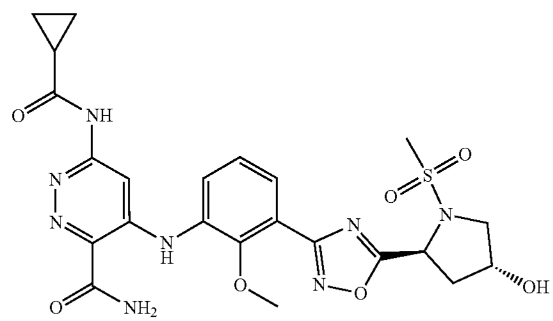 [SMILES: COc1c(Nc2cc(NC(=O)C3CC3)nnc2C(N)=O)cccc1-c1noc([C@@H]2C[C@@H](O)CN2S(C)(=O)=O)n1] | 558.6 | 559 | 0.98 | QC-ACN-TFA-XB |
| 12 | 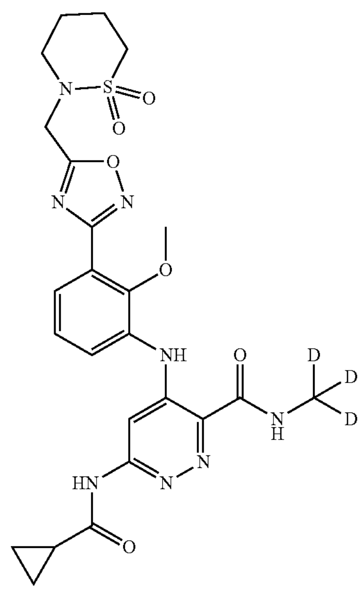 [SMILES: [2H]C([2H])([2H])NC(=O)c1nnc(NC(=O)C2CC2)cc1Nc1cccc(-c2noc(CN3CCCCS3(=O)=O)n2)c1OC] | 559.6 | 560.3 | 1.48 | QC-ACN-AA-XB |
| 13 | 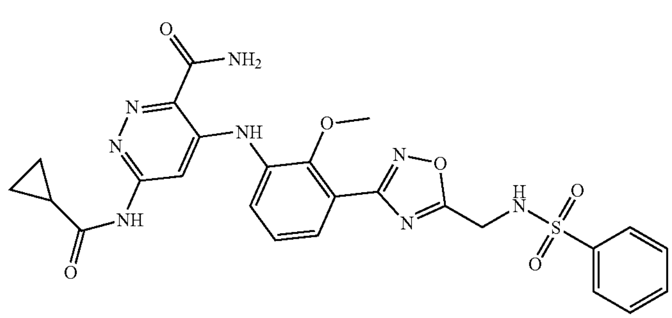 [SMILES: COc1c(Nc2cc(NC(=O)C3CC3)nnc2C(N)=O)cccc1-c1noc(CNS(=O)(=O)c2ccccc2)n1] | 564.6 | 565.3 | 1.26 | QC-ACN-TFA-XB |

TABLE 2-continued

| Ex. No. | Structure | MW | Obs. MS Ion | RT | QC Method |
|---|---|---|---|---|---|
| 14 | 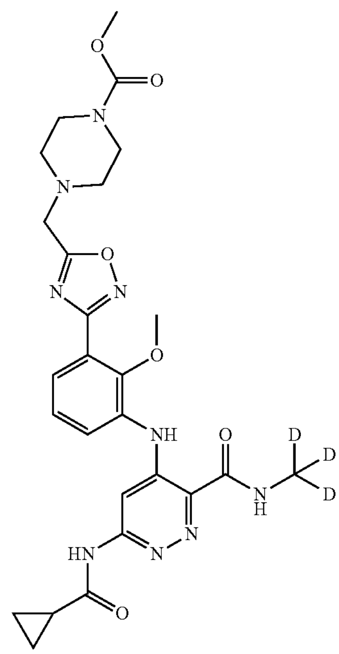 [SMILES: [2H]C([2H])([2H])NC(=O)c1nnc(NC(=O)C2CC2)cc1Nc1cccc(-c2noc(CN3CCN(C(=O)OC)CC3)n2)c1OC] | 568.6 | 569.3 | 1.52 | QC-ACN-AA-XB |
| 15 | 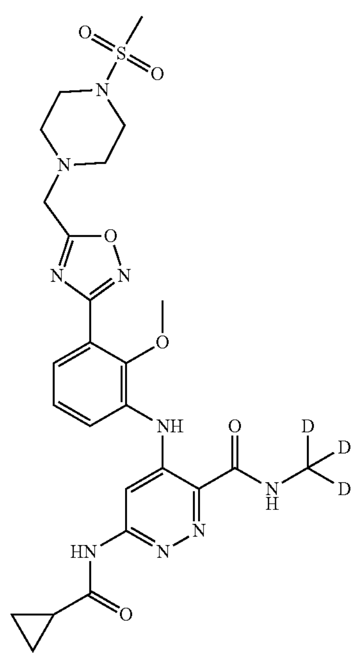 [SMILES: [2H]C([2H])([2H])NC(=O)c1nnc(NC(=O)C2CC2)cc1Nc1cccc(-c2noc(CN3CCN(S(C)(=O)=O)CC3)n2)c1OC] | 588.7 | 589.5 | 1.42 | QC-ACN-AA-XB |

TABLE 2-continued

| Ex. No. | Structure | MW | Obs. MS Ion | RT | QC Method |
|---|---|---|---|---|---|
| 16 | 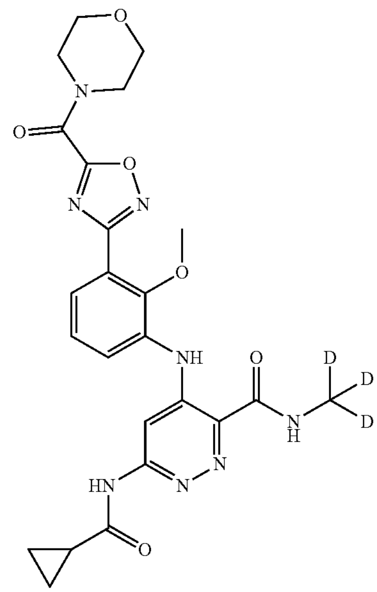 [SMILES: [2H]C([2H])([2H])NC(=O)c1nnc(NC(=O)C2CC2)cc1Nc1cccc(-c2noc(C(=O)N3CCOCC3)n2)c1OC] | 525.5 | 526.2 | 1.45 | QC-ACN-AA-XB |
| 17 | 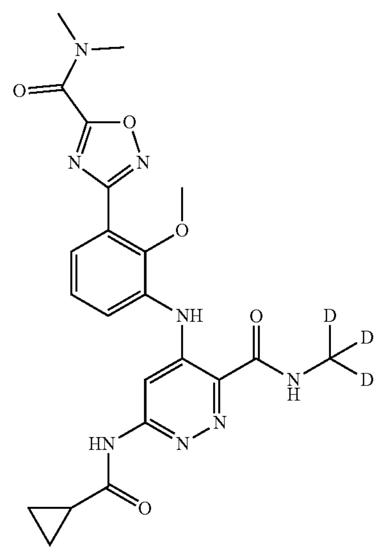 [SMILES: [2H]C([2H])([2H])NC(=O)c1nnc(NC(=O)C2CC2)cc1Nc1cccc(-c2noc(C(=O)N(C)C)n2)c1OC] | 483.5 | 484.3 | 1.16 | QC-ACN-TFA-XB |
| 18 | 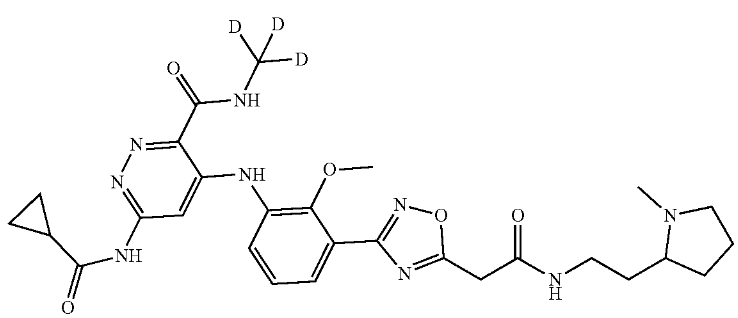 [SMILES: [2H]C([2H])([2H])NC(=O)c1nnc(NC(=O)C2CC2)cc1Nc1cccc(-c2noc(CC(=O)NCCC3CCCN3C)n2)c1OC] | 580.7 | 581.3 | 1.05 | QC-ACN-AA-XB |

TABLE 2-continued
| Ex. No. | Structure | MW | Obs. MS Ion | RT | QC Method |
|---|---|---|---|---|---|
| 19 | 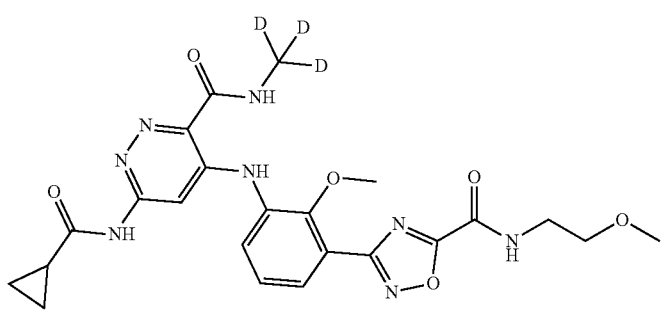 [SMILES: [2H]C([2H])([2H])NC(=O)c1nnc(NC(=O)C2CC2)cc1Nc1cccc(-c2noc(C(=O)NCCOC)n2)c1OC] | 513.5 | 514.3 | 1.37 | QC-ACN-AA-XB |
| 20 | 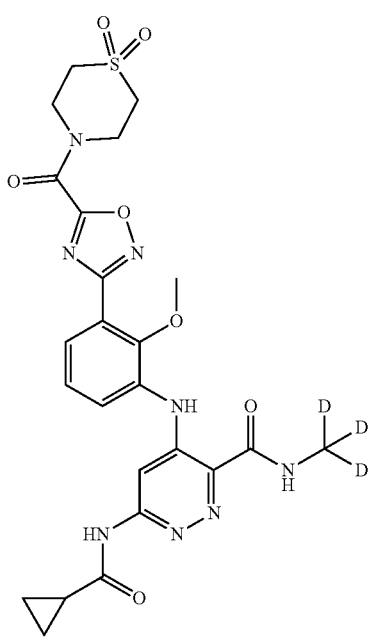 [SMILES: [2H]C([2H])([2H])NC(=O)c1nnc(NC(=O)C2CC2)cc1Nc1cccc(-c2noc(C(=O)N3CCS(=O)(=O)CC3)n2)c1OC] | 573.6 | 574.3 | 1.11 | QC-ACN-TFA-XB |
| 21 | 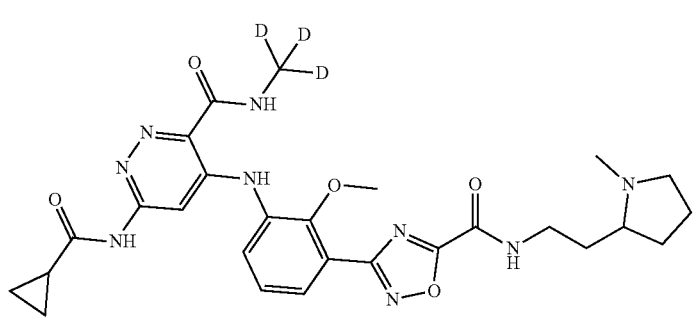 [SMILES: [2H]C([2H])([2H])NC(=O)c1nnc(NC(=O)C2CC2)cc1Nc1cccc(-c2noc(C(=O)NCCC3CCCN3C)n2)c1OC] | 566.6 | 567.4 | 1.1 | QC-ACN-AA-XB |

TABLE 2-continued
| Ex. No. | Structure | MW | Obs. MS Ion | RT | QC Method |
|---|---|---|---|---|---|
| 22 | 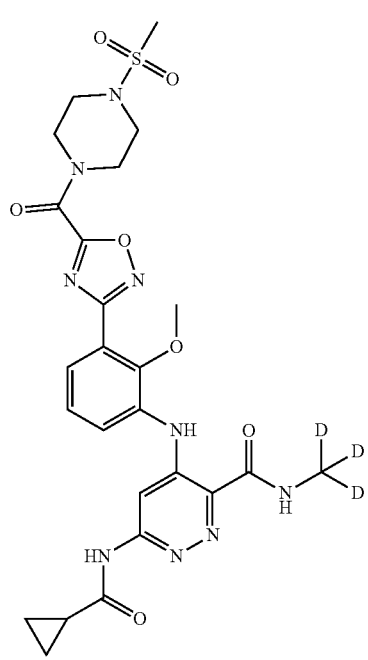 [SMILES: [2H]C([2H])([2H])NC(=O)c1nnc(NC(=O)C2CC2)cc1Nc1cccc(-c2noc(C(=O)N3CCN(S(C)(=O)=O)CC3)n2)c1OC] | 602.6 | 603.2 | 1.43 | QC-ACN-AA-XB |
| 23 | 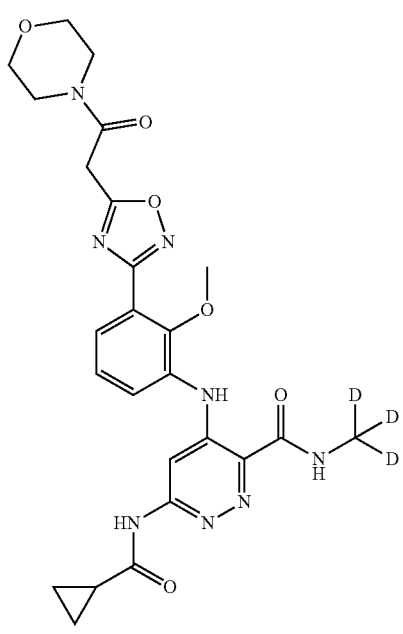 [SMILES: [2H]C([2H])([2H])NC(=O)c1nnc(NC(=O)C2CC2)cc1Nc1cccc(-c2noc(CC(=O)N3CCOCC3)n2)c1OC] | 539.6 | 540.4 | 1.27 | QC-ACN-AA-XB |

TABLE 2-continued
| Ex. No. | Structure | MW | Obs. MS Ion | RT | QC Method |
|---|---|---|---|---|---|
| 24 | 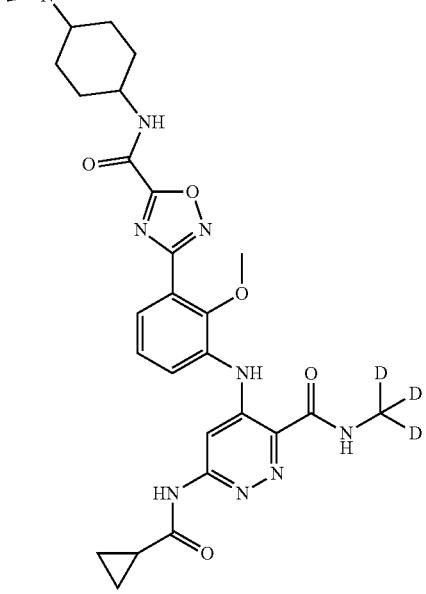 | 580.7 | 581.3 | 1.16 | QC-ACN-AA-XB |
| 25 | 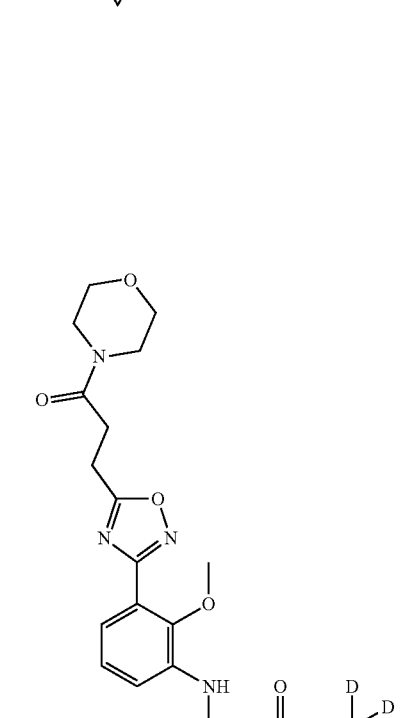 | 553.6 | 554.3 | 1.33 | QC-ACN-AA-XB |

TABLE 2-continued

| Ex. No. | Structure | MW | Obs. MS Ion | RT | QC Method |
|---|---|---|---|---|---|
| 26 | 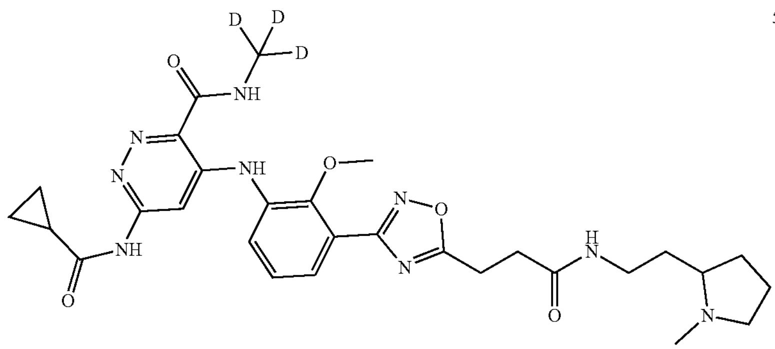 [SMILES: [2H]C([2H])([2H])NC(=O)c1nnc(NC(=O)C2CC2)cc1Nc1cccc(-c2noc(CCC(=O)NCCC3CCCN3C)n2)c1OC] | 594.7 | 595.4 | 0.86 | QC-ACN-TFA-XB |
| 27 | 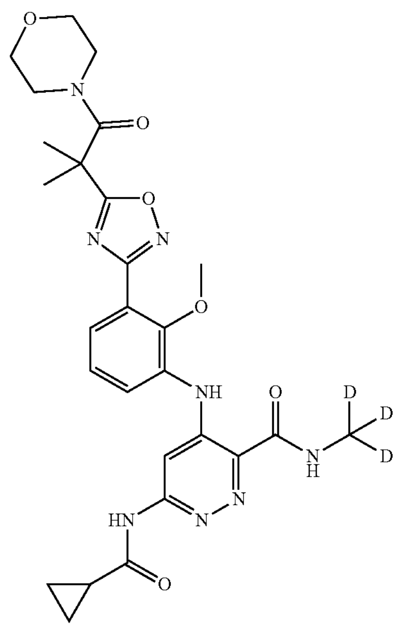 [SMILES: [2H]C([2H])([2H])NC(=O)c1nnc(NC(=O)C2CC2)cc1Nc1cccc(-c2noc(C(C)(C)C(=O)N3CCOCC3)n2)c1OC] | 567.6 | 568.3 | 1.38 | QC-ACN-TFA-XB |
| 28 | 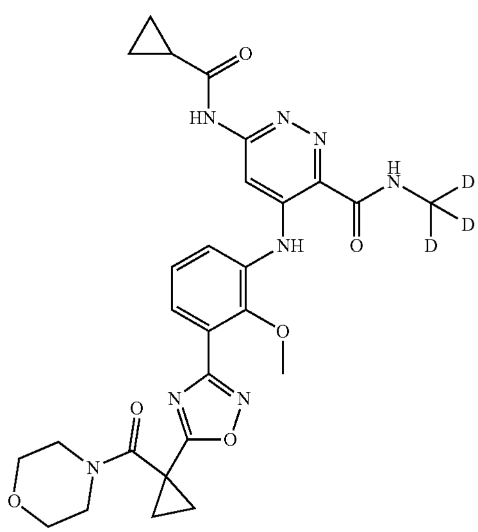 [SMILES: [2H]C([2H])([2H])NC(=O)c1nnc(NC(=O)C2CC2)cc1Nc1cccc(-c2noc(C3(C(=O)N4CCOCC4)CC3)n2)c1OC] | 565.6 | 566.5 | 1.16 | QC-ACN-TFA-XB |

TABLE 2-continued

| Ex. No. | Structure | MW | Obs. MS Ion | RT | QC Method |
|---|---|---|---|---|---|
| 29 | 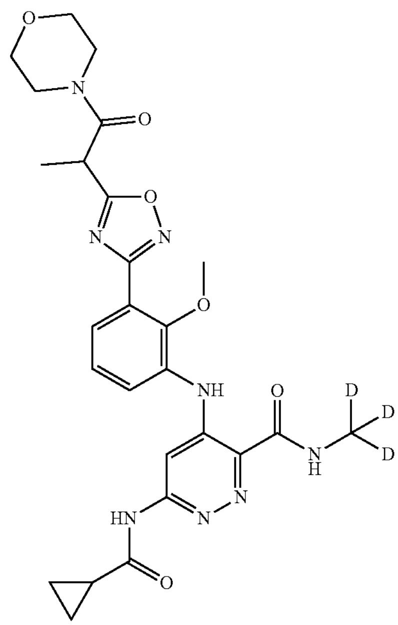 [SMILES: [2H]C([2H])([2H])NC(=O)c1nnc(NC(=O)C2CC2)cc1Nc1cccc(-c2noc(C(C)C(=O)N3CCOCC3)n2)c1OC] | 553.6 | 554.3 | 1.42 | QC-ACN-AA-XB |
| 30 | 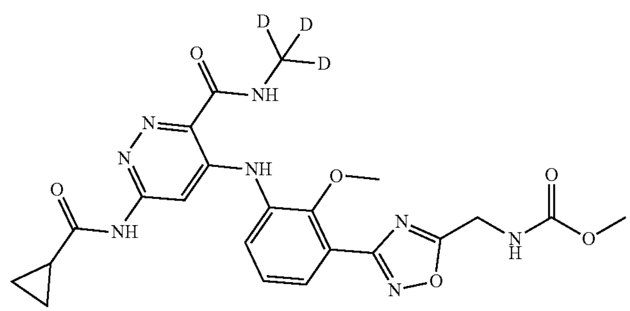 [SMILES: [2H]C([2H])([2H])NC(=O)c1nnc(NC(=O)C2CC2)cc1Nc1cccc(-c2noc(CNC(=O)OC)n2)c1OC] | 499.5 | 500.1 | 1.14 | QC-ACN-TFA-XB |
| 31 | 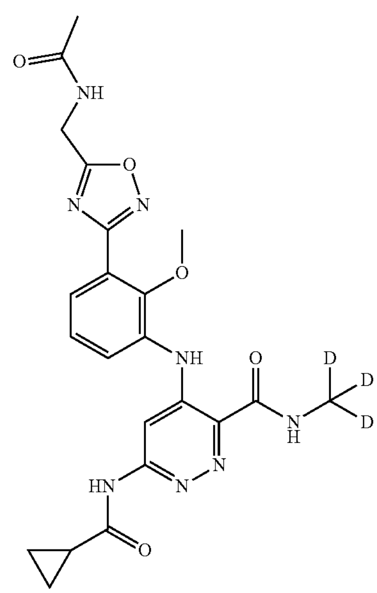 [SMILES: [2H]C([2H])([2H])NC(=O)c1nnc(NC(=O)C2CC2)cc1Nc1cccc(-c2noc(CNC(C)=O)n2)c1OC] | 483.5 | 484.1 | 0.99 | QC-ACN-TFA-XB |

TABLE 2-continued

| Ex. No. | Structure | MW | Obs. MS Ion | RT | QC Method |
|---|---|---|---|---|---|
| 32 | 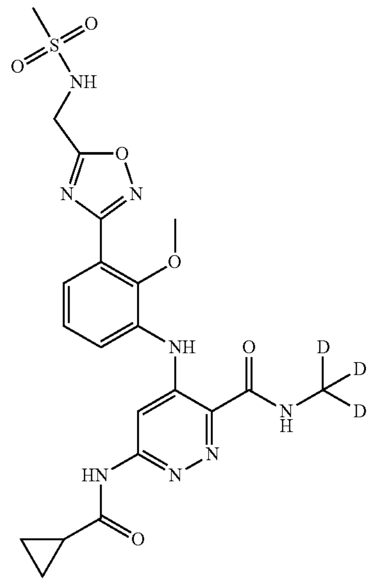 [SMILES: [2H]C([2H])([2H])NC(=O)c1nnc(NC(=O)C2CC2)cc1Nc1cccc(-c2noc(CNS(C)(=O)=O)n2)c1OC] | 519.6 | 520.1 | 1.08 | QC-ACN-TFA-XB |
| 33 | 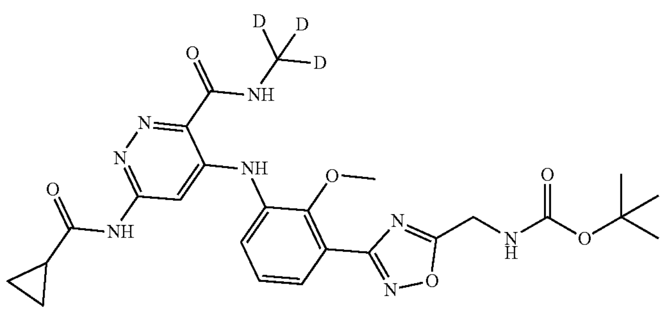 [SMILES: [2H]C([2H])([2H])NC(=O)c1nnc(NC(=O)C2CC2)cc1Nc1cccc(-c2noc(CNC(=O)OC(C)(C)C)n2)c1OC] | 541.6 | 542.2 | 1.49 | QC-ACN-TFA-XB |
| 34 | 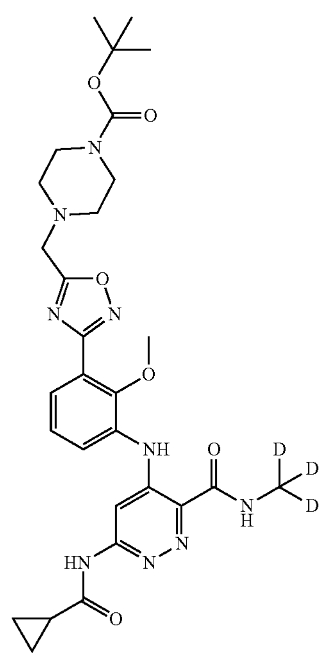 [SMILES: [2H]C([2H])([2H])NC(=O)c1nnc(NC(=O)C2CC2)cc1Nc1cccc(-c2noc(CN3CCN(C(=O)OC(C)(C)C)CC3)n2)c1OC] | 610.7 | 611.4 | 1.85 | QC-ACN-AA-XB |

TABLE 2-continued
| Ex. No. | Structure | MW | Obs. MS Ion | RT | QC Method |
|---|---|---|---|---|---|
| 35 | 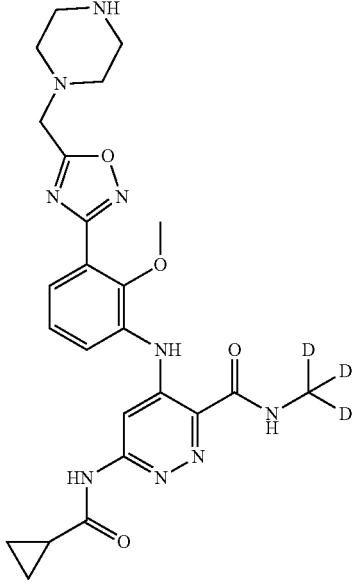 [SMILES: [2H]C([2H])([2H])NC(=O)c1nnc(NC(=O)C2CC2)cc1Nc1cccc(-c2noc(CN3CCNCC3)n2)c1OC] | 510.6 | 511.2 | 0.94 | QC-ACN-TFA-XB |
| 36 | 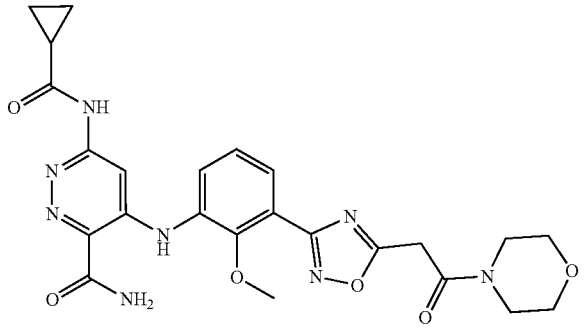 [SMILES: COc1c(Nc2cc(NC(=O)C3CC3)nnc2C(N)=O)cccc1-c1noc(CC(=O)N2CCOCC2)n1] | 522.5 | 523.3 | 0.94 | QC-ACN-TFA-XB |
| 37 | 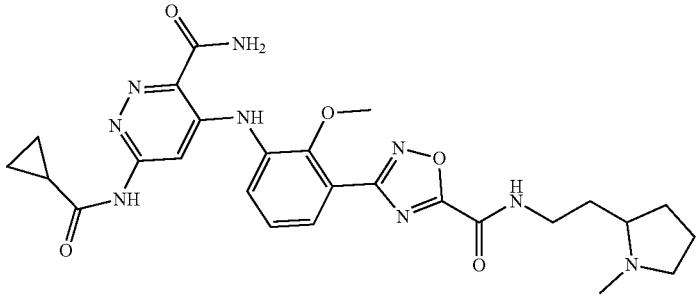 [SMILES: COc1c(Nc2cc(NC(=O)C3CC3)nnc2C(N)=O)cccc1-c1noc(C(=O)NCCC2CCCN2C)n1] | 549.6 | 550.3 | 0.96 | QC-ACN-AA-XB |
| 38 | 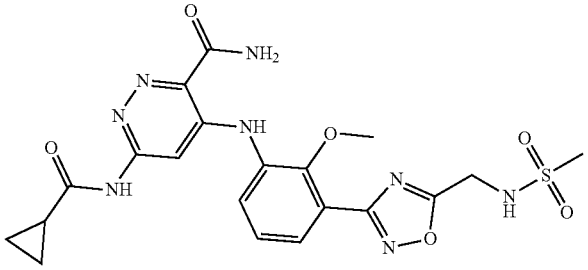 [SMILES: COc1c(Nc2cc(NC(=O)C3CC3)nnc2C(N)=O)cccc1-c1noc(CNS(C)(=O)=O)n1] | 502.5 | 503.2 | 1.1 | QC-ACN-AA-XB |

TABLE 2-continued
| Ex. No. | Structure | MW | Obs. MS Ion | RT | QC Method |
|---|---|---|---|---|---|
| 39 | 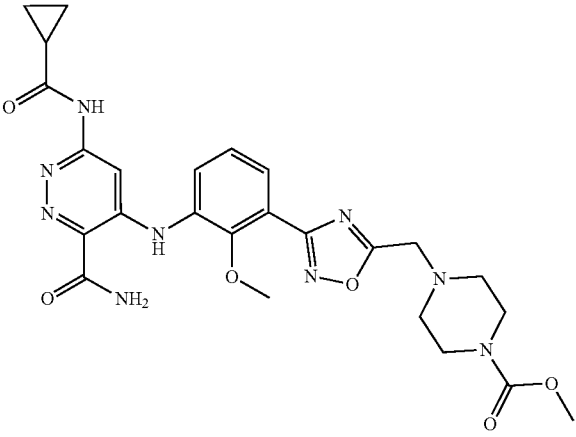 [SMILES: COC(=O)N1CCN(Cc2nc(-c3cccc(Nc4cc(NC(=O)C5CC5)nnc4C(N)=O)c3OC)no2)CC1] | 551.6 | 552.4 | 0.95 | QC-ACN-TFA-XB |
| 40 | 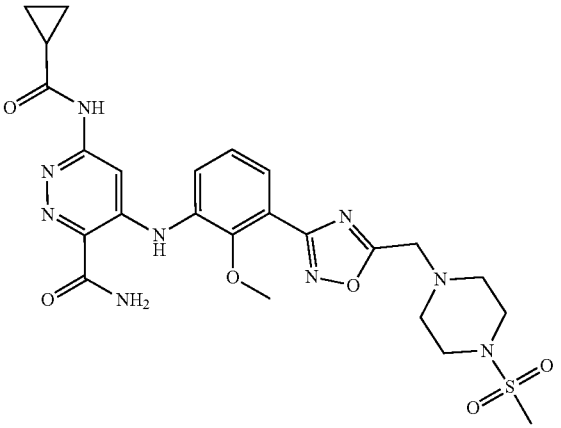 [SMILES: COc1c(Nc2cc(NC(=O)C3CC3)nnc2C(N)=O)cccc1-c1noc(CN2CCN(S(C)(=O)=O)CC2)n1] | 571.6 | 572.2 | 1.35 | QC-ACN-AA-XB |
| 41 | 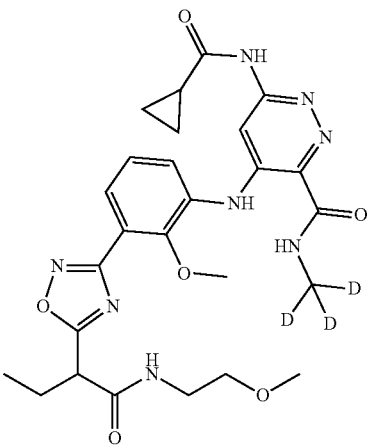 [SMILES: [2H]C([2H])([2H])NC(=O)c1nnc(NC(=O)C2CC2)cc1Nc1cccc(-c2noc(C(CC)C(=O)NCCOC)n2)c1OC] | 555.6 | 556.2 | 1.46 | QC-ACN-AA-XB |

TABLE 2-continued
| Ex. No. | Structure | MW | Obs. MS Ion | RT | QC Method |
|---|---|---|---|---|---|
| 42 | 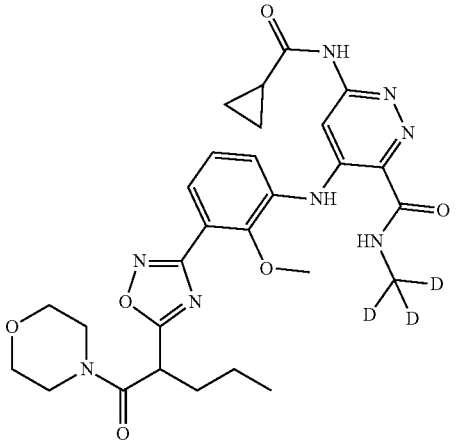 [SMILES: [2H]C([2H])([2H])NC(=O)c1nnc(NC(=O)C2CC2)cc1Nc1cccc(-c2noc(C(CCC)C(=O)N3CCOCC3)n2)c1OC] | 581.6 | 582.3 | 1.64 | QC-ACN-AA-XB |
| 43 | 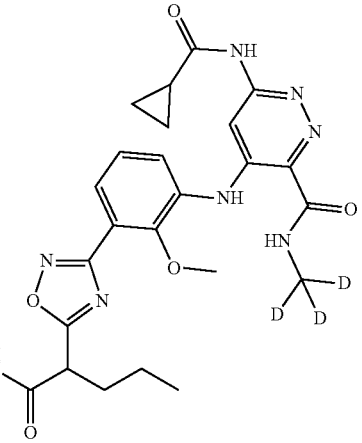 | 569.6 | 570.3 | 1.37 | QC-ACN-TFA-XB |
| 44 | 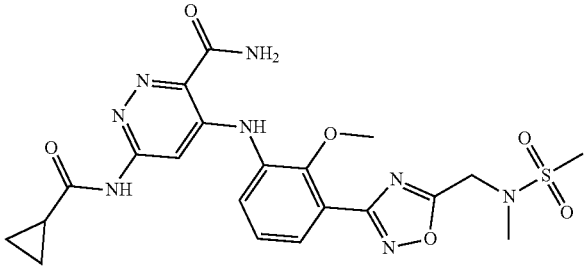 [SMILES: COc1c(Nc2cc(NC(=O)C3CC3)nnc2C(N)=O)cccc1-c1noc(CN(C)S(C)(=O)=O)n1] | 516.5 | 517.1 | 1.32 | QC-ACN-AA-XB |

TABLE 2-continued
| Ex. No. | Structure | MW | Obs. MS Ion | RT | QC Method |
|---|---|---|---|---|---|
| 45 | 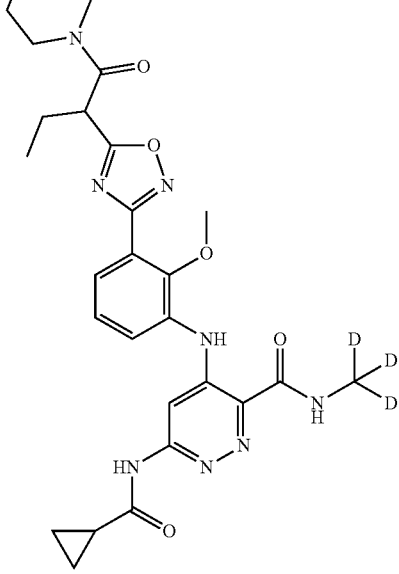 | 567.6 | 568.4 | 1.32 | QC-ACN-TFA-XB |
| 46 | 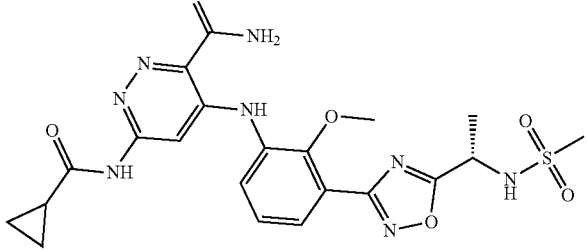 | 516.5 | 517.2 | 1.21 | QC-ACN-AA-XB |
| 47 | 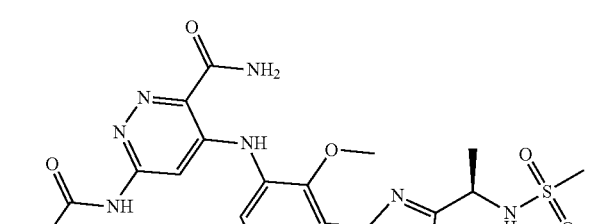 | 516.5 | 517.1 | 1.21 | QC-ACN-AA-XB |
| 48 | 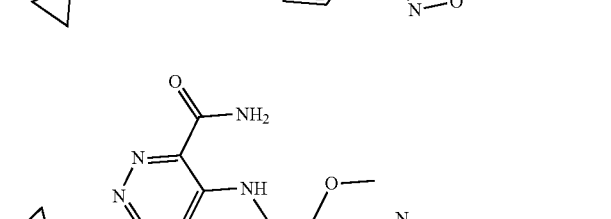 | 516.5 | 517.2 | 1.2 | QC-ACN-AA-XB |

TABLE 2-continued

| Ex. No. | Structure | MW | Obs. MS Ion | RT | QC Method |
|---|---|---|---|---|---|
| 49 | 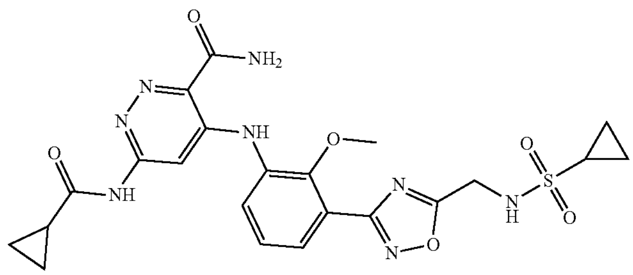 [SMILES: COc1c(Nc2cc(NC(=O)C3CC3)nnc2C(N)=O)cccc1-c1noc(CNS(=O)(=O)C2CC2)n1] | 528.5 | 529.2 | 1.25 | QC-ACN-AA-XB |
| 50 | 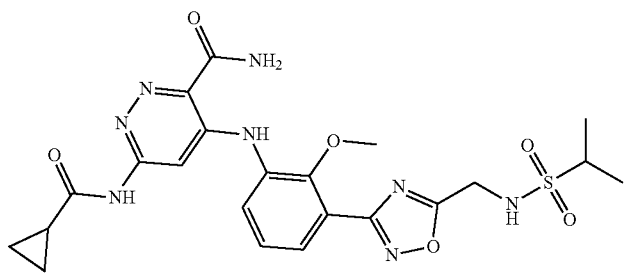 [SMILES: COc1c(Nc2cc(NC(=O)C3CC3)nnc2C(N)=O)cccc1-c1noc(CNS(=O)(=O)C(C)C)n1] | 530.6 | 531.1 | 1.14 | QC-ACN-TFA-XB |
| 51 | 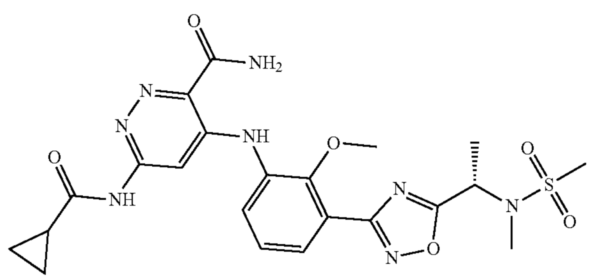 [SMILES: COc1c(Nc2cc(NC(=O)C3CC3)nnc2C(N)=O)cccc1-c1noc([C@H](C)N(C)S(C)(=O)=O)n1] | 530.6 | 531.2 | 1.41 | QC-ACN-AA-XB |
| 52 | 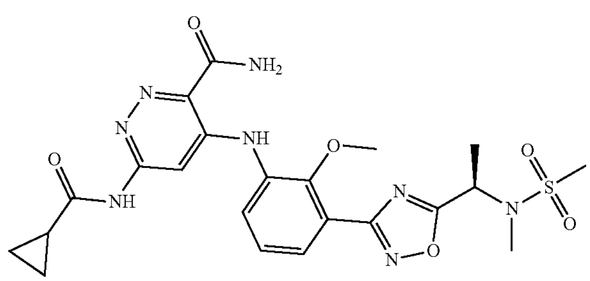 [SMILES: COc1c(Nc2cc(NC(=O)C3CC3)nnc2C(N)=O)cccc1-c1noc([C@@H](C)N(C)S(C)(=O)=O)n1] | 530.6 | 531.1 | 1.22 | QC-ACN-TFA-XB |
| 53 | 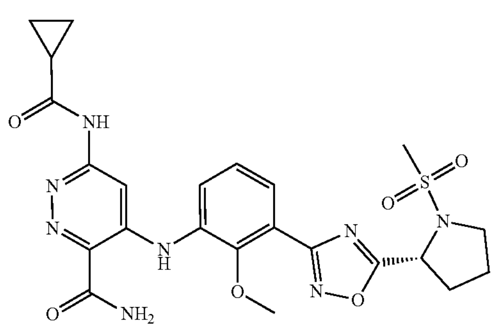 [SMILES: COc1c(Nc2cc(NC(=O)C3CC3)nnc2C(N)=O)cccc1-c1noc([C@H]2CCCN2S(C)(=O)=O)n1] | 542.6 | 543.1 | 1.37 | QC-ACN-AA-XB |

TABLE 2-continued

| Ex. No. | Structure | MW | Obs. MS Ion | RT | QC Method |
|---|---|---|---|---|---|
| 54 | 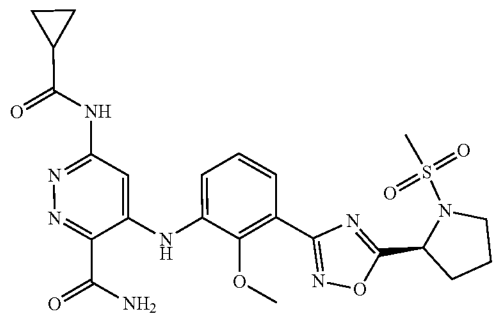 [SMILES: COc1c(Nc2cc(NC(=O)C3CC3)nnc2C(N)=O)cccc1-c1noc([C@@H]2CCCN2S(C)(=O)=O)n1] | 542.6 | 542.9 | 1.28 | QC-ACN-TFA-XB |
| 55 | 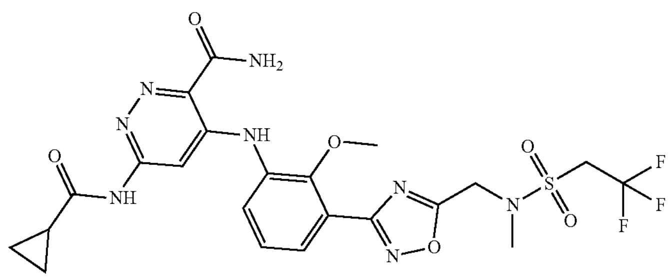 [SMILES: COc1c(Nc2cc(NC(=O)C3CC3)nnc2C(N)=O)cccc1-c1noc(CN(C)S(=O)(=O)CC(F)(F)F)n1] | 584.5 | 585 | 1.56 | QC-ACN-AA-XB |
| 56 | 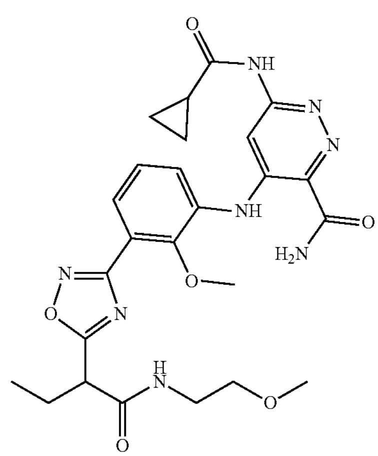 [SMILES: CCC(C(=O)NCCOC)c1nc(-c2cccc(Nc3cc(NC(=O)C4CC4)nnc3C(N)=O)c2OC)no1] | 538.6 | 539.2 | 1.36 | QC-ACN-AA-XB |
| 57 | 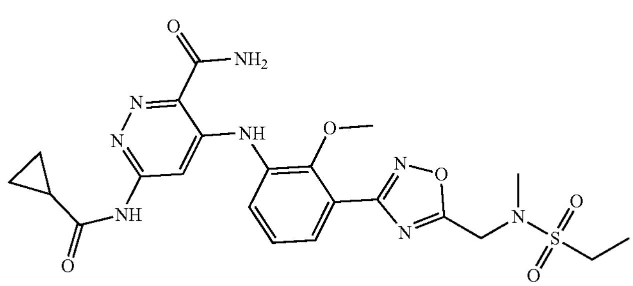 [SMILES: CCS(=O)(=O)N(C)Cc1nc(-c2cccc(Nc3cc(NC(=O)C4CC4)nnc3C(N)=O)c2OC)no1] | 530.6 | 531.2 | 1.37 | QC-ACN-AA-XB |

TABLE 2-continued

| Ex. No. | Structure | MW | Obs. MS Ion | RT | QC Method |
|---|---|---|---|---|---|
| 58 | 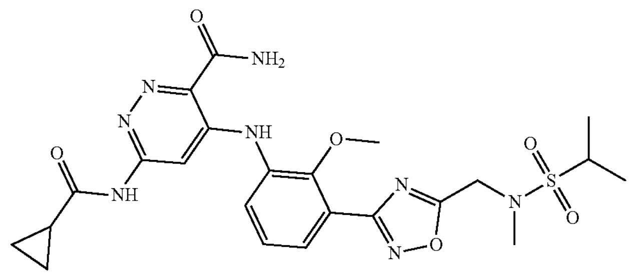 [SMILES: COc1c(Nc2cc(NC(=O)C3CC3)nnc2C(N)=O)cccc1-c1noc(CN(C)S(=O)(=O)C(C)C)n1] | 544.6 | 545.2 | 1.27 | QC-ACN-TFA-XB |
| 59 | 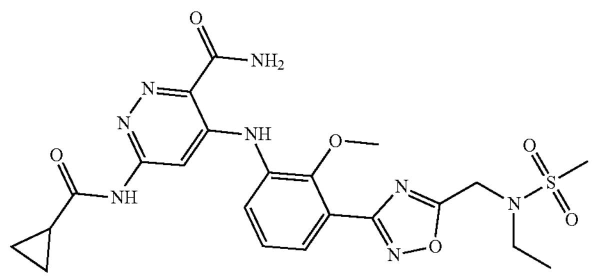 [SMILES: CCN(Cc1nc(-c2cccc(Nc3cc(NC(=O)C4CC4)nnc3C(N)=O)c2OC)no1)S(C)(=O)=O] | 530.6 | 531.2 | 1.38 | QC-ACN-AA-XB |
| 60 | 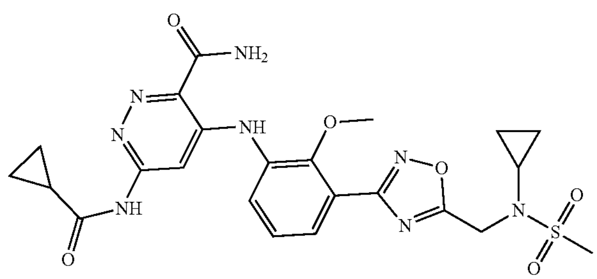 [SMILES: COc1c(Nc2cc(NC(=O)C3CC3)nnc2C(N)=O)cccc1-c1noc(CN(C2CC2)S(C)(=O)=O)n1] | 542.6 | 543.2 | 1.22 | QC-ACN-TFA-XB |
| 61 | 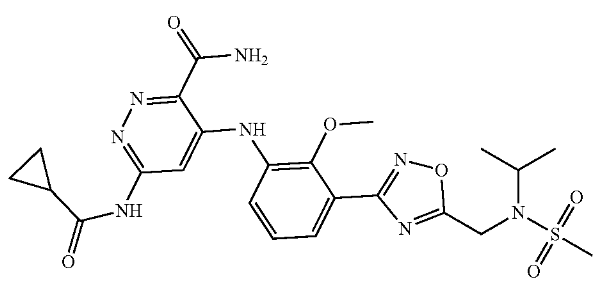 [SMILES: COc1c(Nc2cc(NC(=O)C3CC3)nnc2C(N)=O)cccc1-c1noc(CN(C(C)C)S(C)(=O)=O)n1] | 544.6 | 545.4 | 1.23 | QC-ACN-TFA-XB |
| 62 | 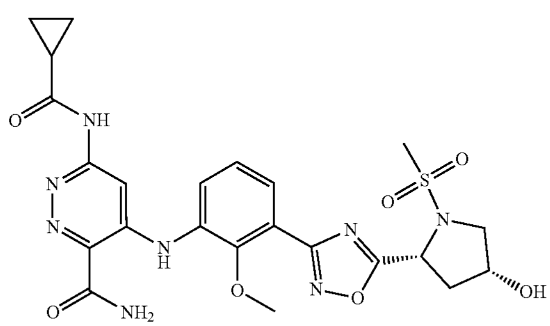 [SMILES: COc1c(Nc2cc(NC(=O)C3CC3)nnc2C(N)=O)cccc1-c1noc([C@H]2C[C@@H](O)CN2S(C)(=O)=O)n1] | 558.6 | 559.1 | 1.14 | QC-ACN-AA-XB |

TABLE 2-continued

| Ex. No. | Structure | MW | Obs. MS Ion | RT | QC Method |
|---|---|---|---|---|---|
| 63 | 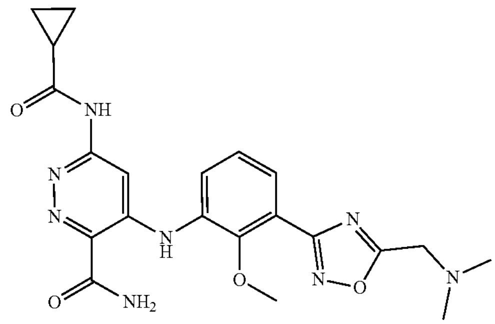 [SMILES: COc1c(Nc2cc(NC(=O)C3CC3)nnc2C(N)=O)cccc1-c1noc(CN(C)C)n1] | 452.5 | 453.1 | 1.34 | QC-ACN-AA-XB |
| 64 | 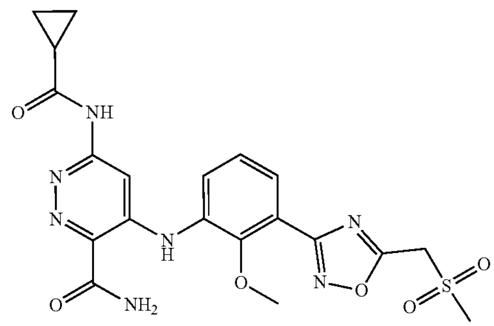 [SMILES: COc1c(Nc2cc(NC(=O)C3CC3)nnc2C(N)=O)cccc1-c1noc(CS(C)(=O)=O)n1] | 487.5 | 488 | 0.96 | QC-ACN-TFA-XB |
| 65 | 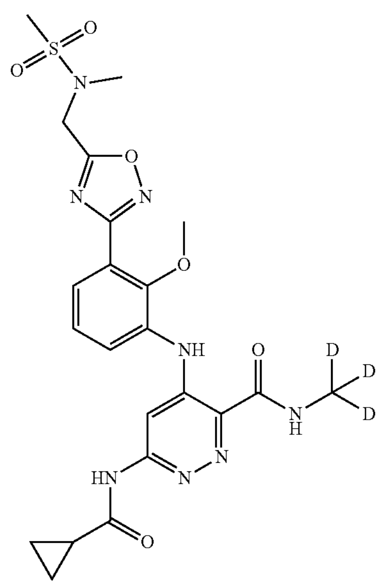 [SMILES: [2H]C([2H])([2H])NC(=O)c1nnc(NC(=O)C2CC2)cc1Nc1cccc(-c2noc(CN(C)S(C)(=O)=O)n2)c1OC] | 533.6 | 534.1 | 1.17 | QC-ACN-TFA-XB |
| 66 | 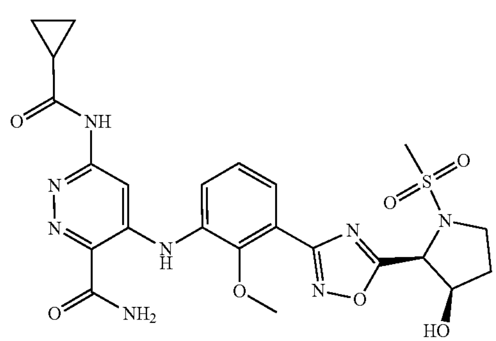 [SMILES: COc1c(Nc2cc(NC(=O)C3CC3)nnc2C(N)=O)cccc1-c1noc([C@@H]2[C@H](O)CCN2S(C)(=O)=O)n1] | 558.6 | 559.3 | 0.93 | QC-ACN-TFA-XB |

TABLE 2-continued

| Ex. No. | Structure | MW | Obs. MS Ion | RT | QC Method |
|---|---|---|---|---|---|
| 67 | 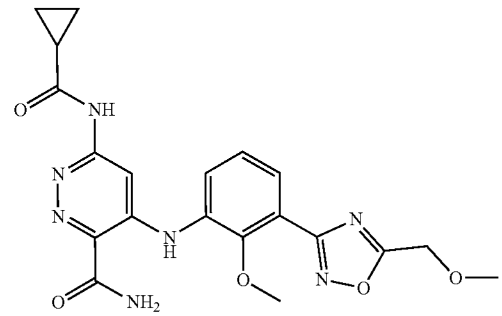 [SMILES: COCc1nc(-c2cccc(Nc3cc(NC(=O)C4CC4)nnc3C(N)=O)c2OC)no1] | 439.4 | 440.1 | 1.37 | QC-ACN-AA-XB |
| 68 | 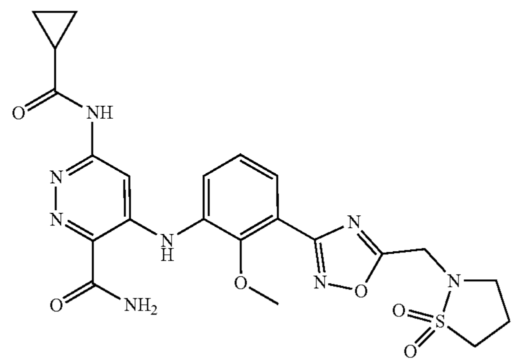 [SMILES: COc1c(Nc2cc(NC(=O)C3CC3)nnc2C(N)=O)cccc1-c1noc(CN2CCCS2(=O)=O)n1] | 528.5 | 529.1 | 1.26 | QC-ACN-AA-XB |
| 69 | 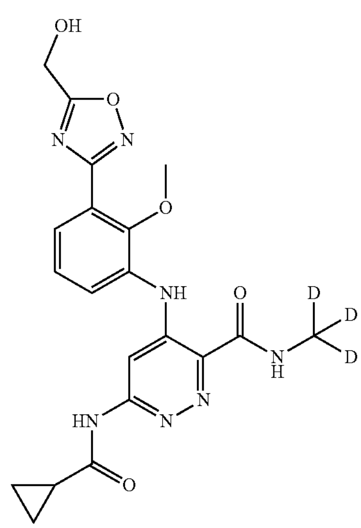 [SMILES: [2H]C([2H])([2H])NC(=O)c1nnc(NC(=O)C2CC2)cc1Nc1cccc(-c2noc(CO)n2)c1OC] | 442.5 | 443.3 | 0.95 | QC-ACN-TFA-XB |
| 70 | 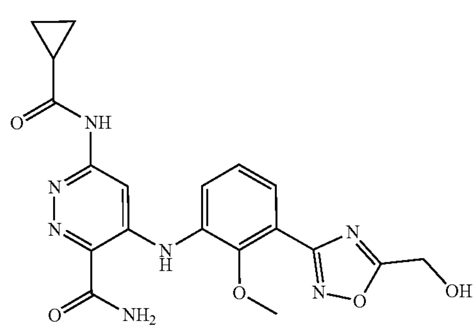 [SMILES: COc1c(Nc2cc(NC(=O)C3CC3)nnc2C(N)=O)cccc1-c1noc(CO)n1] | 425.4 | 426.2 | 0.85 | QC-ACN-TFA-XB |

TABLE 2-continued

| Ex. No. | Structure | MW | Obs. MS Ion | RT | QC Method |
|---|---|---|---|---|---|
| 71 | 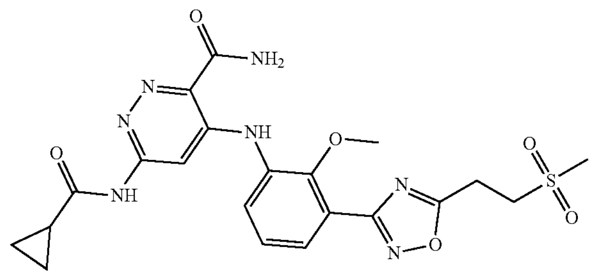 [SMILES: COc1c(Nc2cc(NC(=O)C3CC3)nnc2C(N)=O)cccc1-c1noc(CCS(C)(=O)=O)n1] | 501.5 | 502.1 | 0.97 | QC-ACN-TFA-XB |
| 72 | 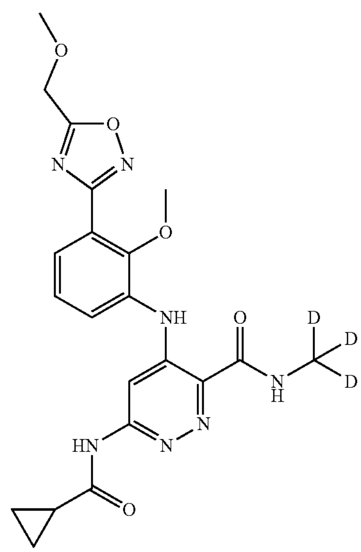 [SMILES: [2H]C([2H])([2H])NC(=O)c1nnc(NC(=O)C2CC2)cc1Nc1cccc(-c2noc(COC)n2)c1OC] | 456.5 | 457.2 | 1.65 | QC-ACN-AA-XB |
| 73 | 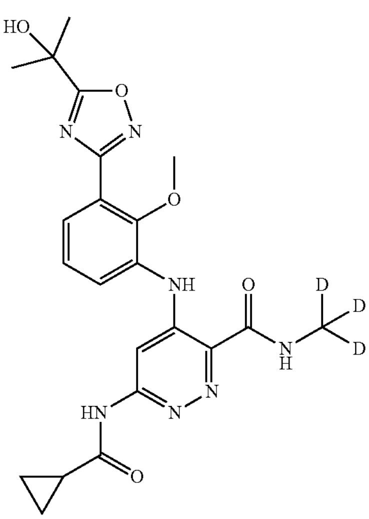 [SMILES: [2H]C([2H])([2H])NC(=O)c1nnc(NC(=O)C2CC2)cc1Nc1cccc(-c2noc(C(C)(C)O)n2)c1OC] | 470.5 | 471 | 1.18 | QC-ACN-TFA-XB |

TABLE 2-continued
| Ex. No. | Structure | MW | Obs. MS Ion | RT | QC Method |
|---|---|---|---|---|---|
| 74 | 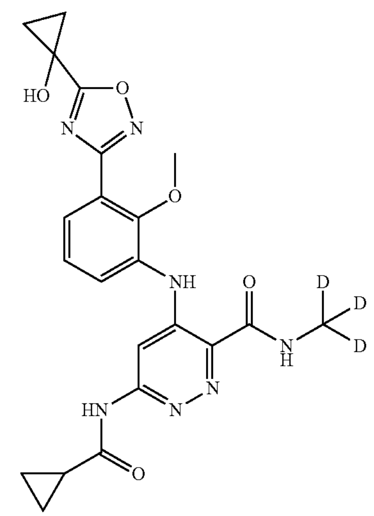 [SMILES: [2H]C([2H])([2H])NC(=O)c1nnc(NC(=O)C2CC2)cc1Nc1cccc(-c2noc(C3(O)CC3)n2)c1OC] | 468.5 | 469.3 | 1.39 | QC-ACN-AA-XB |
| 75 | 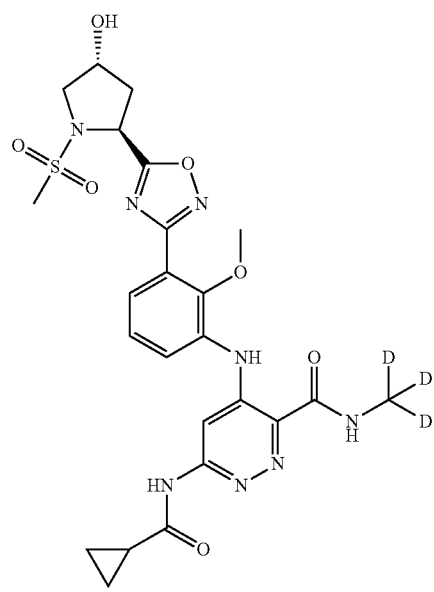 [SMILES: [2H]C([2H])([2H])NC(=O)c1nnc(NC(=O)C2CC2)cc1Nc1cccc(-c2noc([C@@H]3C[C@@H](O)CN3S(C)(=O)=O)n2)c1OC] | 575.6 | 576.2 | 1.06 | QC-ACN-TFA-XB |

TABLE 2-continued
| Ex. No. | Structure | MW | Obs. MS Ion | RT | QC Method |
|---|---|---|---|---|---|
| 76 | 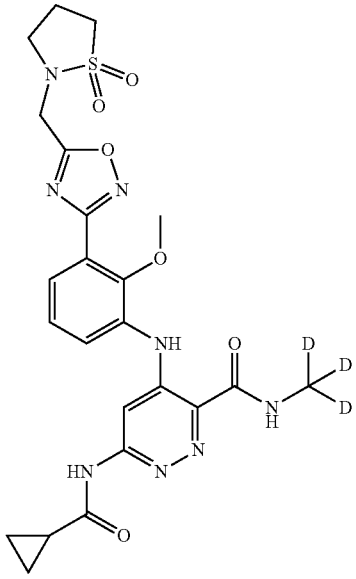 [SMILES: [2H]C([2H])([2H])NC(=O)c1nnc(NC(=O)C2CC2)cc1Nc1cccc(-c2noc(CN3CCCS3(=O)=O)n2)c1OC] | 545.6 | 546.2 | 1.11 | QC-ACN-TFA-XB |
| 77 | 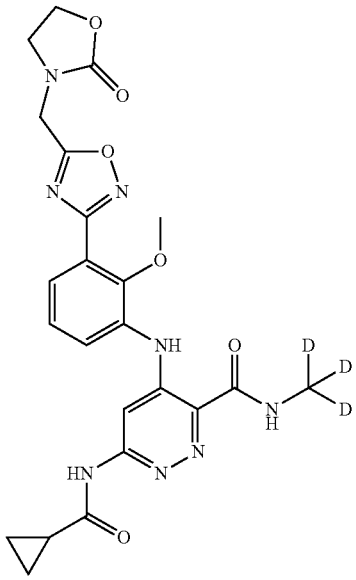 [SMILES: [2H]C([2H])([2H])NC(=O)c1nnc(NC(=O)C2CC2)cc1Nc1cccc(-c2noc(CN3CCOC3=O)n2)c1OC] | 511.5 | 512.2 | 1.24 | QC-ACN-AA-XB |

TABLE 2-continued
| Ex. No. | Structure | MW | Obs. MS Ion | RT | QC Method |
|---|---|---|---|---|---|
| 78 | 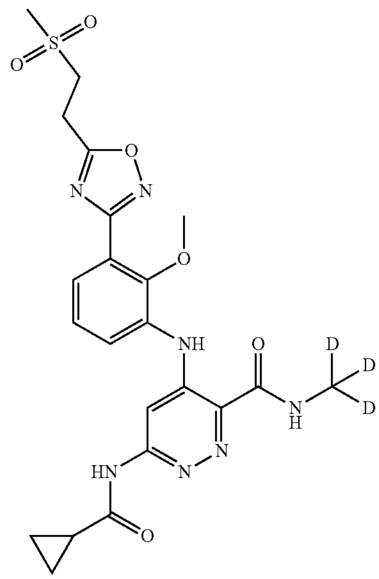 [SMILES: [2H]C([2H])([2H])NC(=O)c1nnc(NC(=O)C2CC2)cc1Nc1cccc(-c2noc(CCS(C)(=O)=O)n2)c1OC] | 518.6 | 519.3 | 1.08 | QC-ACN-AA-XB |
| 79 | 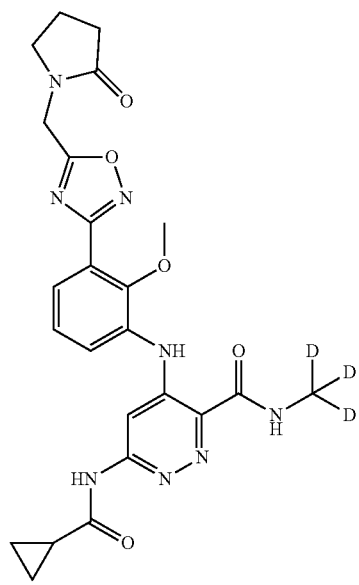 [SMILES: [2H]C([2H])([2H])NC(=O)c1nnc(NC(=O)C2CC2)cc1Nc1cccc(-c2noc(CN3CCCC3=O)n2)c1OC] | 509.5 | 510.3 | 1.37 | QC-ACN-TFA-XB |

TABLE 2-continued
| Ex. No. | Structure | MW | Obs. MS Ion | RT | QC Method |
|---|---|---|---|---|---|
| 80 | 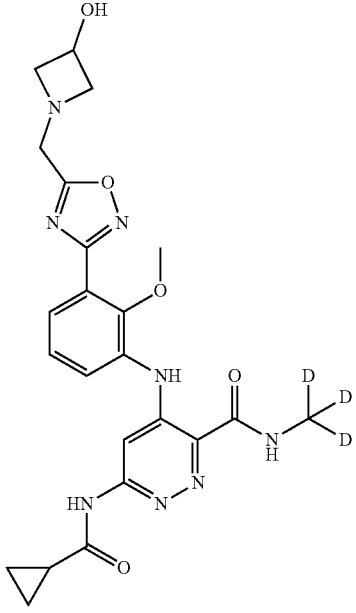 [SMILES: [2H]C([2H])([2H])NC(=O)c1nnc(NC(=O)C2CC2)cc1Nc1cccc(-c2noc(CN3CC(O)C3)n2)c1OC] | 497.5 | 498.2 | 1.11 | QC-ACN-TFA-XB |
| 81 | 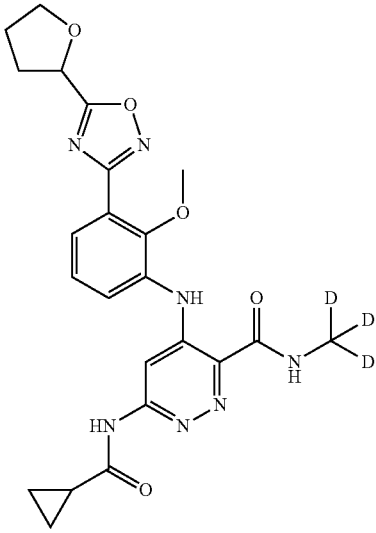 [SMILES: [2H]C([2H])([2H])NC(=O)c1nnc(NC(=O)C2CC2)cc1Nc1cccc(-c2noc(C3CCCO3)n2)c1OC] | 482.5 | 483.2 | 1.31 | QC-ACN-AA-XB |

TABLE 2-continued
| Ex. No. | Structure | MW | Obs. MS Ion | RT | QC Method |
|---|---|---|---|---|---|
| 82 | 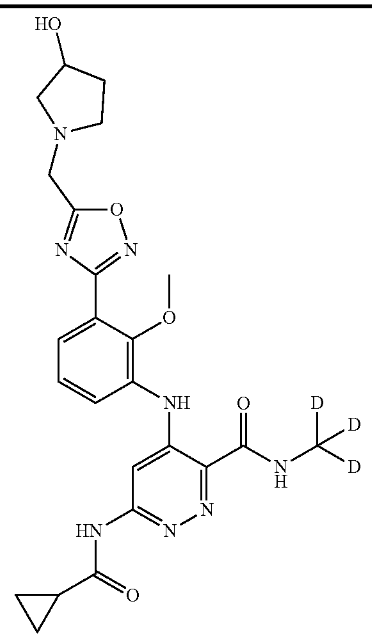 | 511.6 | 512.2 | 0.79 | QC-ACN-TFA-XB |
| 83 | 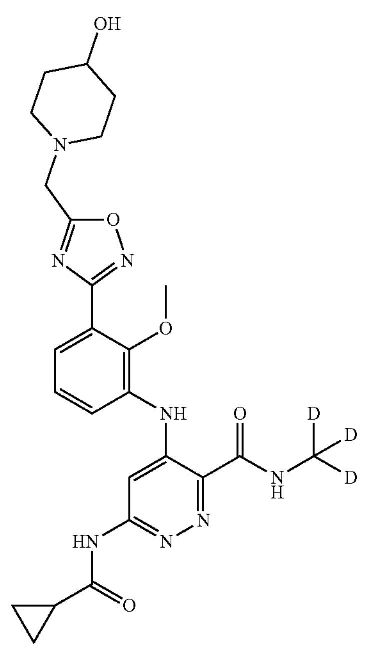 [SMILES: [2H]C([2H])([2H])NC(=O)c1nnc(NC(=O)C2CC2)cc1Nc1cccc(-c2noc(CN3CCC(O)CC3)n2)c1OC] | 525.6 | 526 | 1.22 | QC-ACN-AA-XB |

TABLE 2-continued
| Ex. No. | Structure | MW | Obs. MS Ion | RT | QC Method |
|---|---|---|---|---|---|
| 84 | 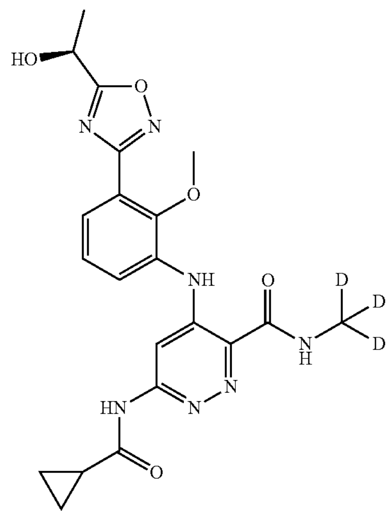 [SMILES: [2H]C([2H])([2H])NC(=O)c1nnc(NC(=O)C2CC2)cc1Nc1cccc(-c2noc([C@H](C)O)n2)c1OC] | 456.5 | 457 | 1.29 | QC-ACN-TFA-XB |
| 85 | 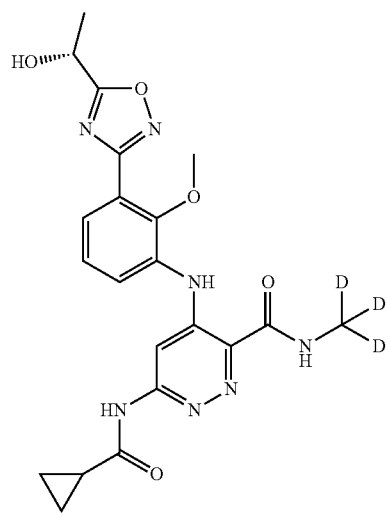 [SMILES: [2H]C([2H])([2H])NC(=O)c1nnc(NC(=O)C2CC2)cc1Nc1cccc(-c2noc([C@@H](C)O)n2)c1OC] | 456.5 | 457 | 1.46 | QC-ACN-AA-XB |

TABLE 2-continued
| Ex. No. | Structure | MW | Obs. MS Ion | RT | QC Method |
|---|---|---|---|---|---|
| 86 | 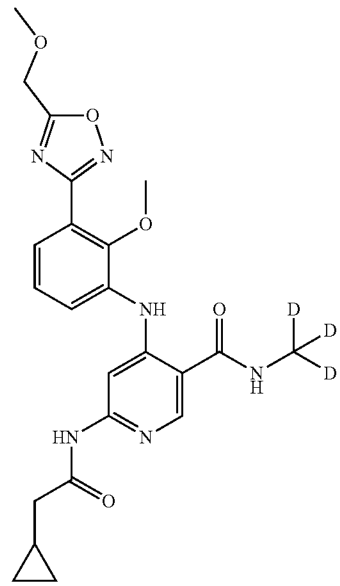 [SMILES: [2H]C([2H])([2H])NC(=O)c1cnc(NC(=O)CC2CC2)cc1Nc1cccc(-c2noc(COC)n2)c1OC] | 469.5 | 470.4 | 1.23 | QC-ACN-TFA-XB |
| 87 | 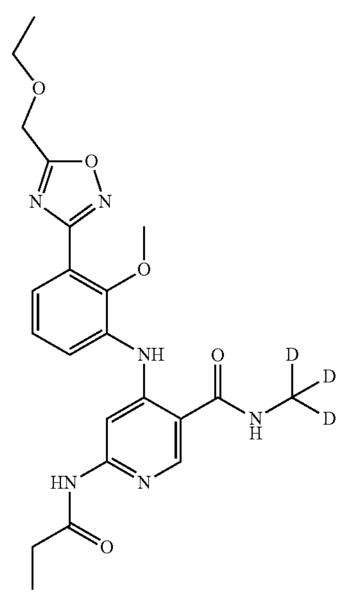 [SMILES: [2H]C([2H])([2H])NC(=O)c1cnc(NC(=O)CC)cc1Nc1cccc(-c2noc(COCC)n2)c1OC] | 457.5 | 458.3 | 1.53 | QC-ACN-AA-XB |

TABLE 2-continued
| Ex. No. | Structure | MW | Obs. MS Ion | RT | QC Method |
|---|---|---|---|---|---|
| 88 | 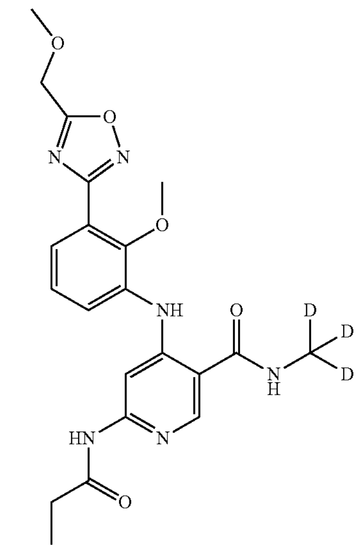 [SMILES: [2H]C([2H])([2H])NC(=O)c1cnc(NC(=O)CC)cc1Nc1cccc(-c2noc(COC)n2)c1OC] | 443.5 | 444 | 1.12 | QC-ACN-TFA-XB |
| 89 | 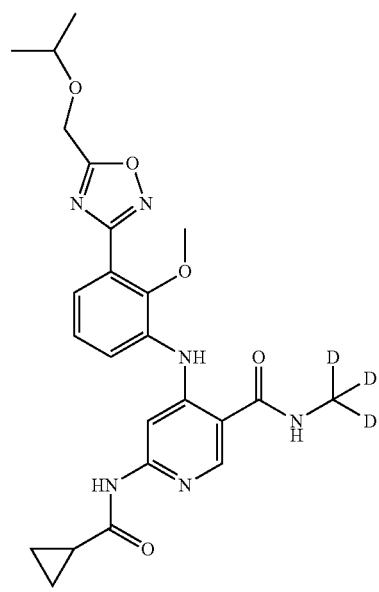 [SMILES: [2H]C([2H])([2H])NC(=O)c1cnc(NC(=O)C2CC2)cc1Nc1cccc(-c2noc(COC(C)C)n2)c1OC] | 483.5 | 484.2 | 1.73 | QC-ACN-AA-XB |

TABLE 2-continued
| Ex. No. | Structure | MW | Obs. MS Ion | RT | QC Method |
|---|---|---|---|---|---|
| 90 | 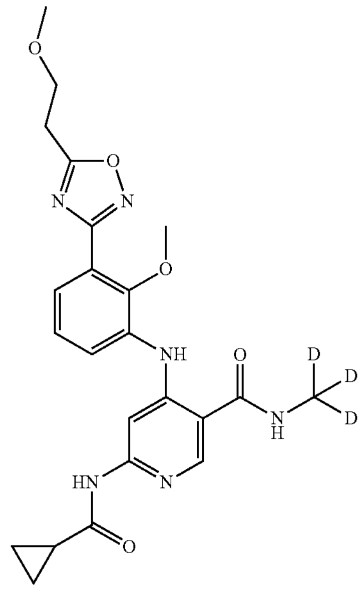 [SMILES: [2H]C([2H])([2H])NC(=O)c1cnc(NC(=O)C2CC2)cc1Nc1cccc(-c2noc(CCOC)n2)c1OC] | 469.5 | 470.2 | 1.43 | QC-ACN-AA-XB |
| 91 | 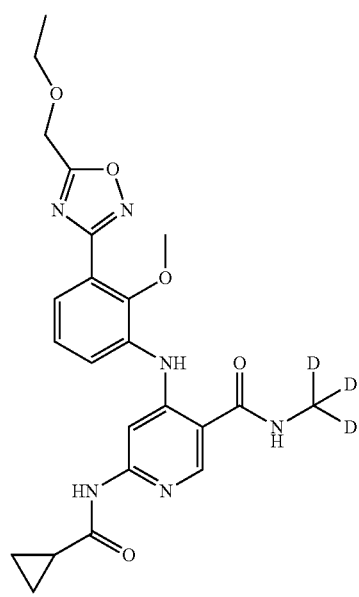 [SMILES: [2H]C([2H])([2H])NC(=O)c1cnc(NC(=O)C2CC2)cc1Nc1cccc(-c2noc(COCC)n2)c1OC] | 469.5 | 470.2 | 1.56 | QC-ACN-AA-XB |

TABLE 2-continued

| Ex. No. | Structure | MW | Obs. MS Ion | RT | QC Method |
|---|---|---|---|---|---|
| 92 | 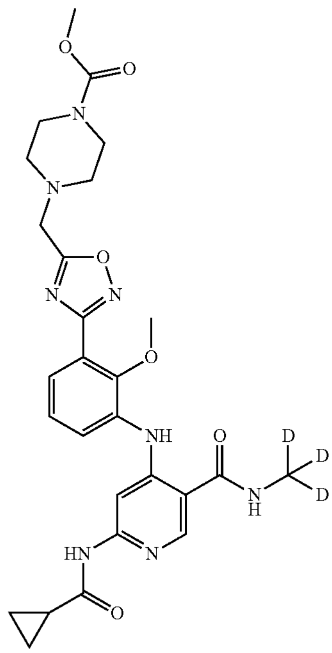 [SMILES: [2H]C([2H])([2H])NC(=O)c1cnc(NC(=O)C2CC2)cc1Nc1cccc(-c2noc(CN3CCN(C(=O)OC)CC3)n2)c1OC] | 567.6 | 568.2 | 1.42 | QC-ACN-AA-XB |
| 93 | 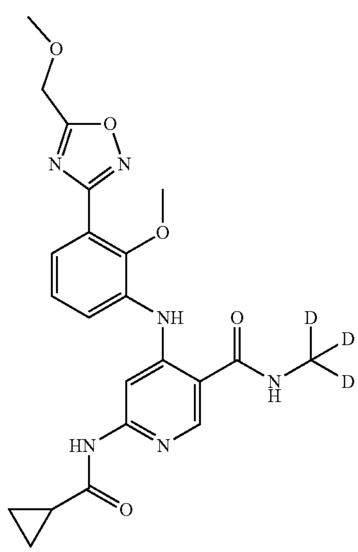 [SMILES: [2H]C([2H])([2H])NC(=O)c1cnc(NC(=O)C2CC2)cc1Nc1cccc(-c2noc(COC)n2)c1OC] | 455.5 | 456 | 1.08 | QC-ACN-TFA-XB |

TABLE 2-continued
| Ex. No. | Structure | MW | Obs. MS Ion | RT | QC Method |
|---|---|---|---|---|---|
| 94 | 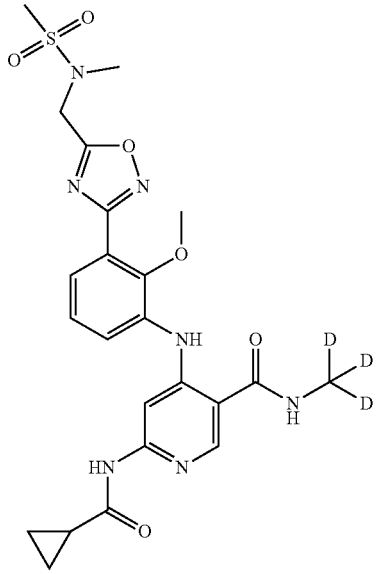 [SMILES: [2H]C([2H])([2H])NC(=O)c1cnc(NC(=O)C2CC2)cc1Nc1cccc(-c2noc(CN(C)S(C)(=O)=O)n2)c1OC] | 532.6 | 533.2 | 1.31 | QC-ACN-AA-XB |
| 95 | 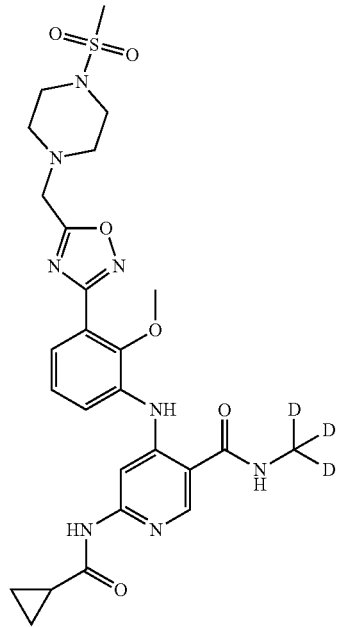 [SMILES: [2H]C([2H])([2H])NC(=O)c1cnc(NC(=O)C2CC2)cc1Nc1cccc(-c2noc(CN3CCN(S(C)(=O)=O)CC3)n2)c1OC] | 587.7 | 588 | 1.5 | QC-ACN-AA-XB |

TABLE 2-continued

| Ex. No. | Structure | MW | Obs. MS Ion | RT | QC Method |
|---|---|---|---|---|---|
| 96 | 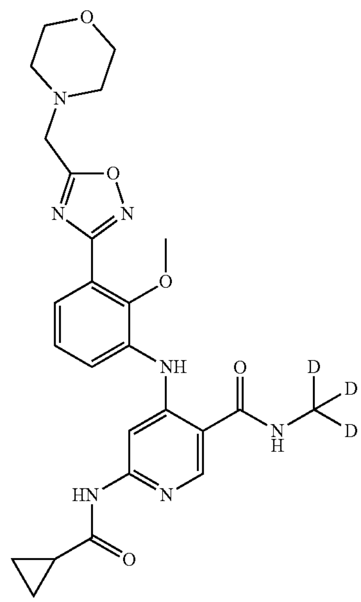 [SMILES: [2H]C([2H])([2H])NC(=O)c1cnc(NC(=O)C2CC2)cc1Nc1cccc(-c2noc(CN3CCOCC3)n2)c1OC] | 510.6 | 511.1 | 1.29 | QC-ACN-AA-XB |
| 97 | 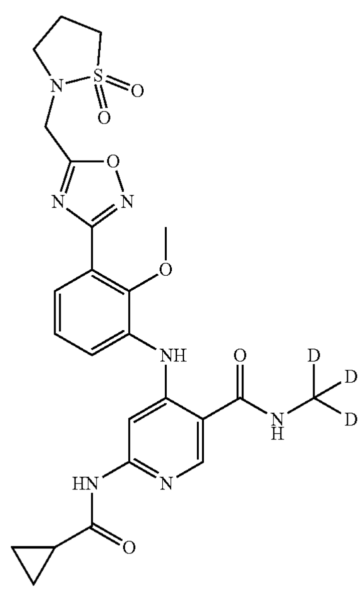 [SMILES: [2H]C([2H])([2H])NC(=O)c1cnc(NC(=O)C2CC2)cc1Nc1cccc(-c2noc(CN3CCCS3(=O)=O)n2)c1OC] | 544.6 | 545.1 | 1.3 | QC-ACN-AA-XB |

TABLE 2-continued
| Ex. No. | Structure | MW | Obs. MS Ion | RT | QC Method |
|---|---|---|---|---|---|
| 98 | 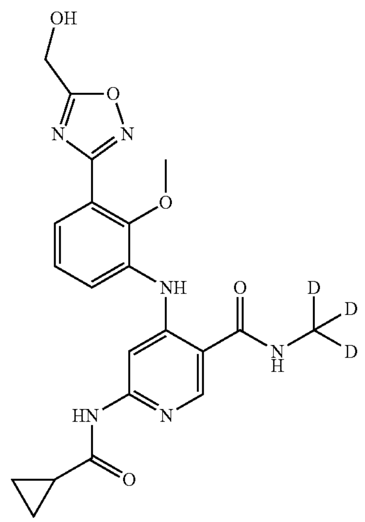 [SMILES: [2H]C([2H])([2H])NC(=O)c1cnc(NC(=O)C2CC2)cc1Nc1cccc(-c2noc(CO)n2)c1OC] | 441.5 | 442.2 | 1.19 | QC-ACN-TFA-XB |
| 99 | 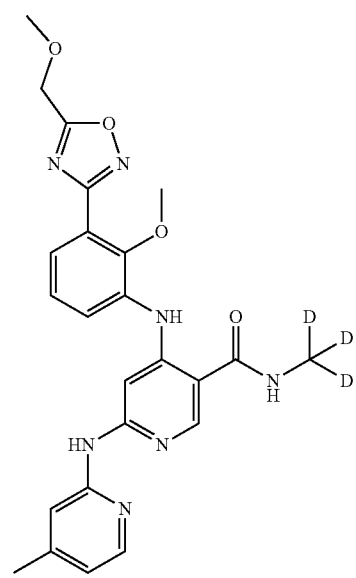 [SMILES: [2H]C([2H])([2H])NC(=O)c1cnc(Nc2cc(C)ccn2)cc1Nc1cccc(-c2noc(COC)n2)c1OC] | 478.5 | 479.1 | 1.5 | QC-ACN-AA-XB |

TABLE 2-continued

| Ex. No. | Structure | MW | Obs. MS Ion | RT | QC Method |
|---|---|---|---|---|---|
| 100 | 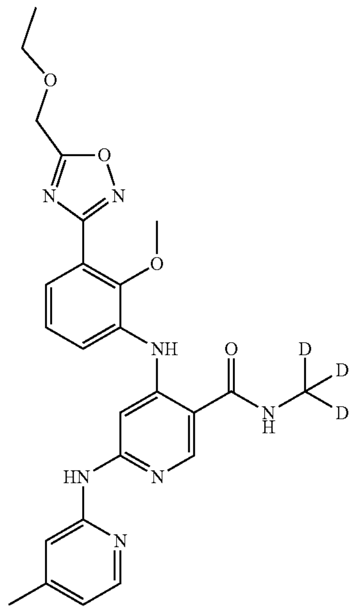 [SMILES: [2H]C([2H])([2H])NC(=O)c1cnc(Nc2cc(C)ccn2)cc1Nc1cccc(-c2noc(COCC)n2)c1OC] | 492.6 | 493.2 | 1.79 | QC-ACN-AA-XB |
| 101 | 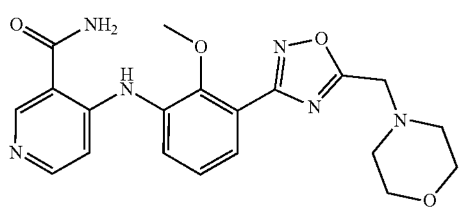 [SMILES: COc1c(Nc2ccncc2C(N)=O)cccc1-c1noc(CN2CCOCC2)n1] | 410.4 | 411.1 | 1.1 | QC-ACN-AA-XB |
| 102 | 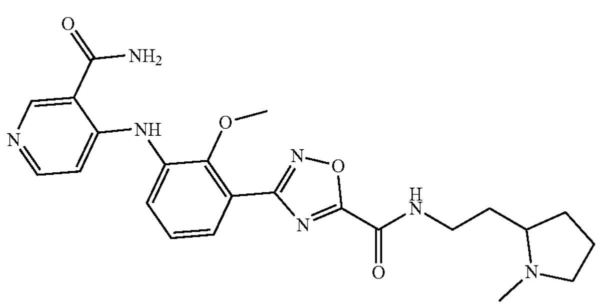 [SMILES: COc1c(Nc2ccncc2C(N)=O)cccc1-c1noc(C(=O)NCCC2CCCN2C)n1] | 465.5 | 466.4 | 0.76 | QC-ACN-AA-XB |
| 103 | 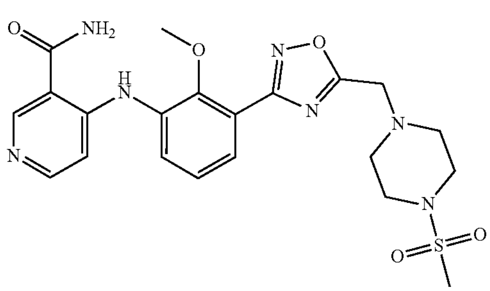 [SMILES: COc1c(Nc2ccncc2C(N)=O)cccc1-c1noc(CN2CCN(S(C)(=O)=O)CC2)n1] | 487.5 | 488.2 | 0.7 | QC-ACN-TFA-XB |

TABLE 2-continued

| Ex. No. | Structure | MW | Obs. MS Ion | RT | QC Method |
|---|---|---|---|---|---|
| 104 | 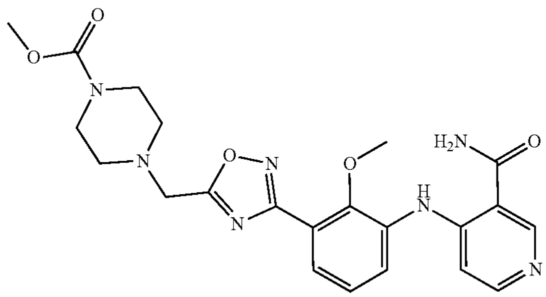 [SMILES: COC(=O)N1CCN(Cc2nc(-c3cccc(Nc4ccncc4C(N)=O)c3OC)no2)CC1] | 467.5 | 468.4 | 1.12 | QC-ACN-AA-XB |
| 105 | 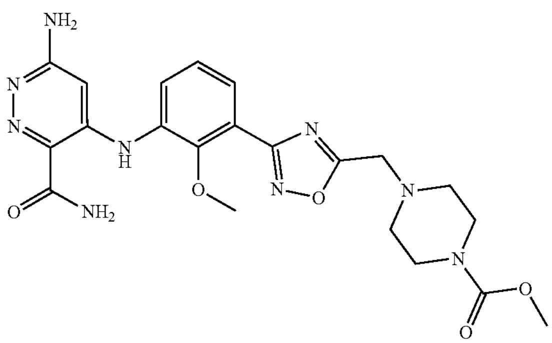 [SMILES: COC(=O)N1CCN(Cc2nc(-c3cccc(Nc4cc(N)nnc4C(N)=O)c3OC)no2)CC1] | 483.5 | 484.1 | 1.15 | QC-ACN-AA-XB |
| 106 | 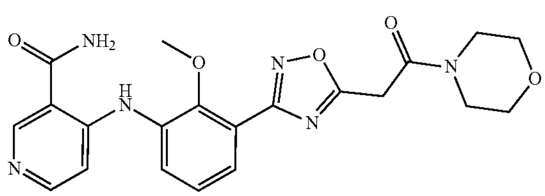 [SMILES: COc1c(Nc2ccncc2C(N)=O)cccc1-c1noc(CC(=O)N2CCOCC2)n1] | 438.4 | 439.2 | 0.88 | QC-ACN-AA-XB |
| 107 | 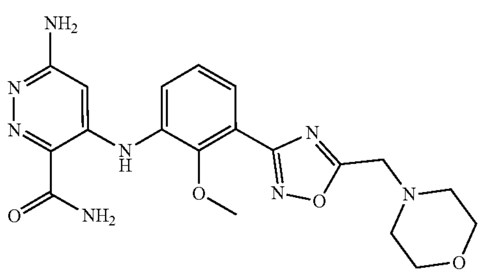 [SMILES: COc1c(Nc2cc(N)nnc2C(N)=O)cccc1-c1noc(CN2CCOCC2)n1] | 426.4 | 427.4 | 0.91 | QC-ACN-AA-XB |
| 108 | 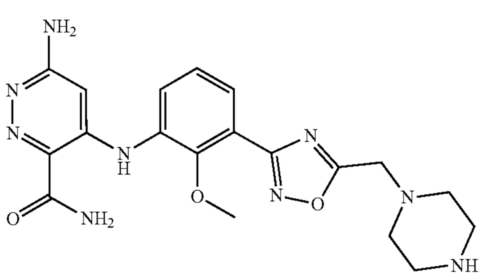 [SMILES: COc1c(Nc2cc(N)nnc2C(N)=O)cccc1-c1noc(CN2CCNCC2)n1] | 425.5 | 426.3 | 0.51 | QC-ACN-TFA-XB |

TABLE 2-continued

| Ex. No. | Structure | MW | Obs. MS Ion | RT | QC Method |
|---|---|---|---|---|---|
| 109 | 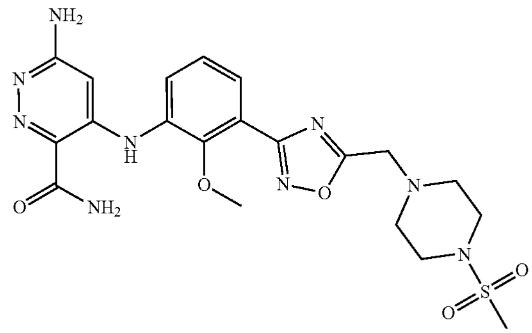 [SMILES: COc1c(Nc2cc(N)nnc2C(N)=O)cccc1-c1noc(CN2CCN(S(C)(=O)=O)CC2)n1] | 503.5 | 504.2 | 0.95 | QC-ACN-AA-XB |
| 110 | 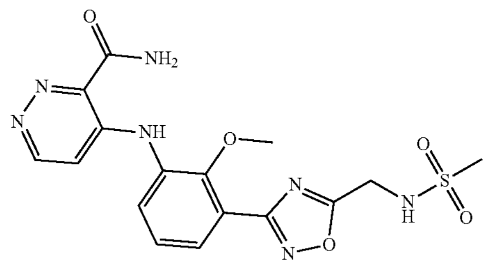 [SMILES: COc1c(Nc2ccnnc2C(N)=O)cccc1-c1noc(CNS(C)(=O)=O)n1] | 419.4 | 420.3 | 0.85 | QC-ACN-AA-XB |
| 111 | 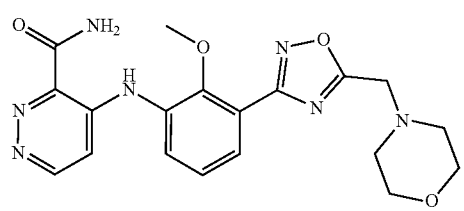 [SMILES: COc1c(Nc2ccnnc2C(N)=O)cccc1-c1noc(CN2CCOCC2)n1] | 411.4 | 412.2 | 0.99 | QC-ACN-AA-XB |
| 112 | 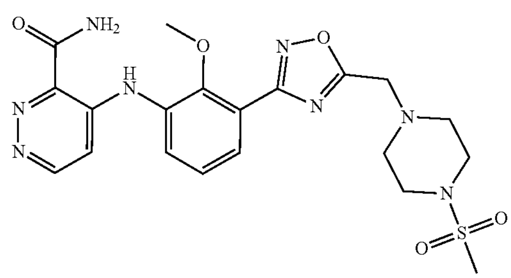 [SMILES: COc1c(Nc2ccnnc2C(N)=O)cccc1-c1noc(CN2CCN(S(C)(=O)=O)CC2)n1] | 488.5 | 489.2 | 1.05 | QC-ACN-AA-XB |
| 113 | 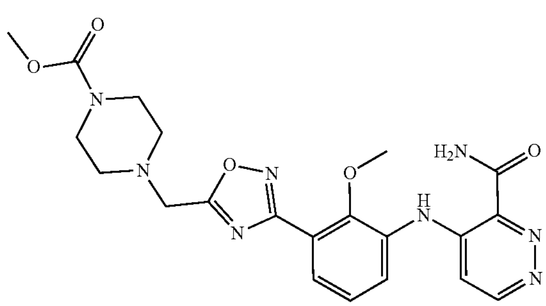 [SMILES: COC(=O)N1CCN(Cc2nc(-c3cccc(Nc4ccnnc4C(N)=O)c3OC)no2)CC1] | 468.5 | 469.4 | 1.14 | QC-ACN-AA-XB |

TABLE 2-continued

| Ex. No. | Structure | MW | Obs. MS Ion | RT | QC Method |
|---|---|---|---|---|---|
| 114 | 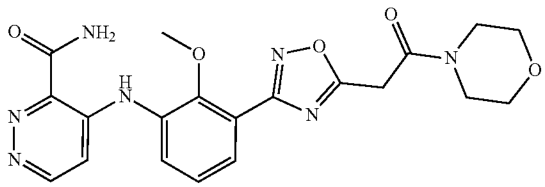 [SMILES: COc1c(Nc2ccnnc2C(N)=O)cccc1-c1noc(CC(=O)N2CCOCC2)n1] | 439.4 | 440.4 | 0.91 | QC-ACN-AA-XB |
| 115 | 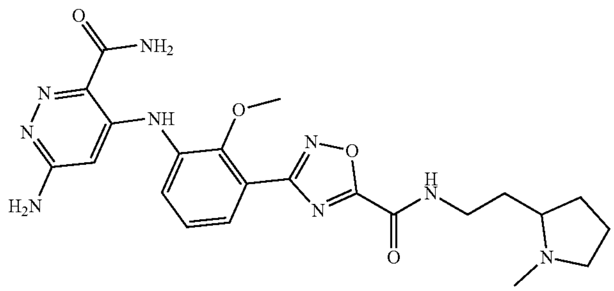 [SMILES: COc1c(Nc2cc(N)nnc2C(N)=O)cccc1-c1noc(C(=O)NCCC2CCCN2C)n1] | 481.5 | 482.2 | 0.73 | QC-ACN-AA-XB |
| 116 | 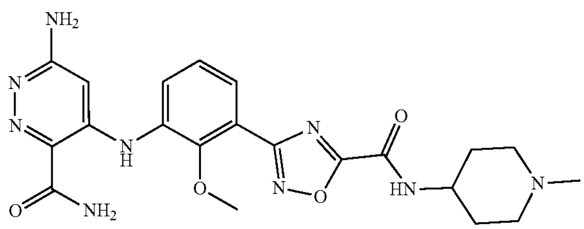 [SMILES: COc1c(Nc2cc(N)nnc2C(N)=O)cccc1-c1noc(C(=O)NC2CCN(C)CC2)n1] | 467.5 | 468.3 | 0.55 | QC-ACN-TFA-XB |
| 117 | 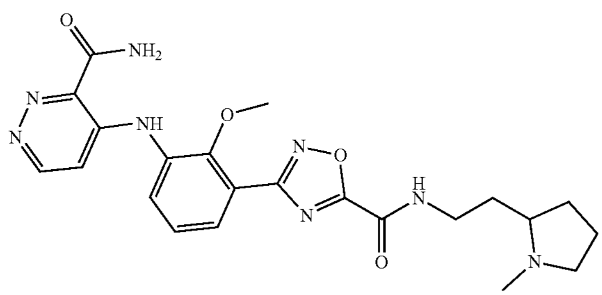 [SMILES: COc1c(Nc2ccnnc2C(N)=O)cccc1-c1noc(C(=O)NCCC2CCCN2C)n1] | 466.5 | 467.2 | 0.79 | QC-ACN-AA-XB |
| 118 | 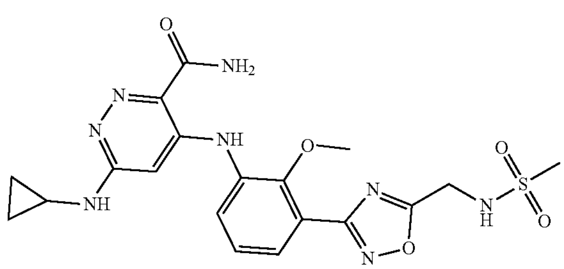 [SMILES: COc1c(Nc2cc(NC3CC3)nnc2C(N)=O)cccc1-c1noc(CNS(C)(=O)=O)n1] | 474.5 | 475.1 | 1.13 | QC-ACN-AA-XB |
| 119 | 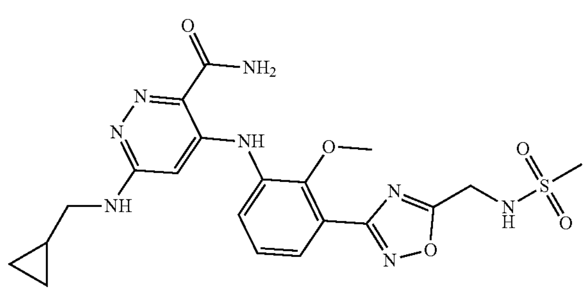 [SMILES: COc1c(Nc2cc(NCC3CC3)nnc2C(N)=O)cccc1-c1noc(CNS(C)(=O)=O)n1] | 488.5 | 489.3 | 1.22 | QC-ACN-AA-XB |

Example 120
4-((3-(3-((4-acetylpiperazin-1-yl)methyl)-1,2,4-oxadiazol-5-yl)-2-methoxyphenyl)amino)-6-(cyclopropanecarboxamido)-trideuteromethylpyridazine-3-carboxamide
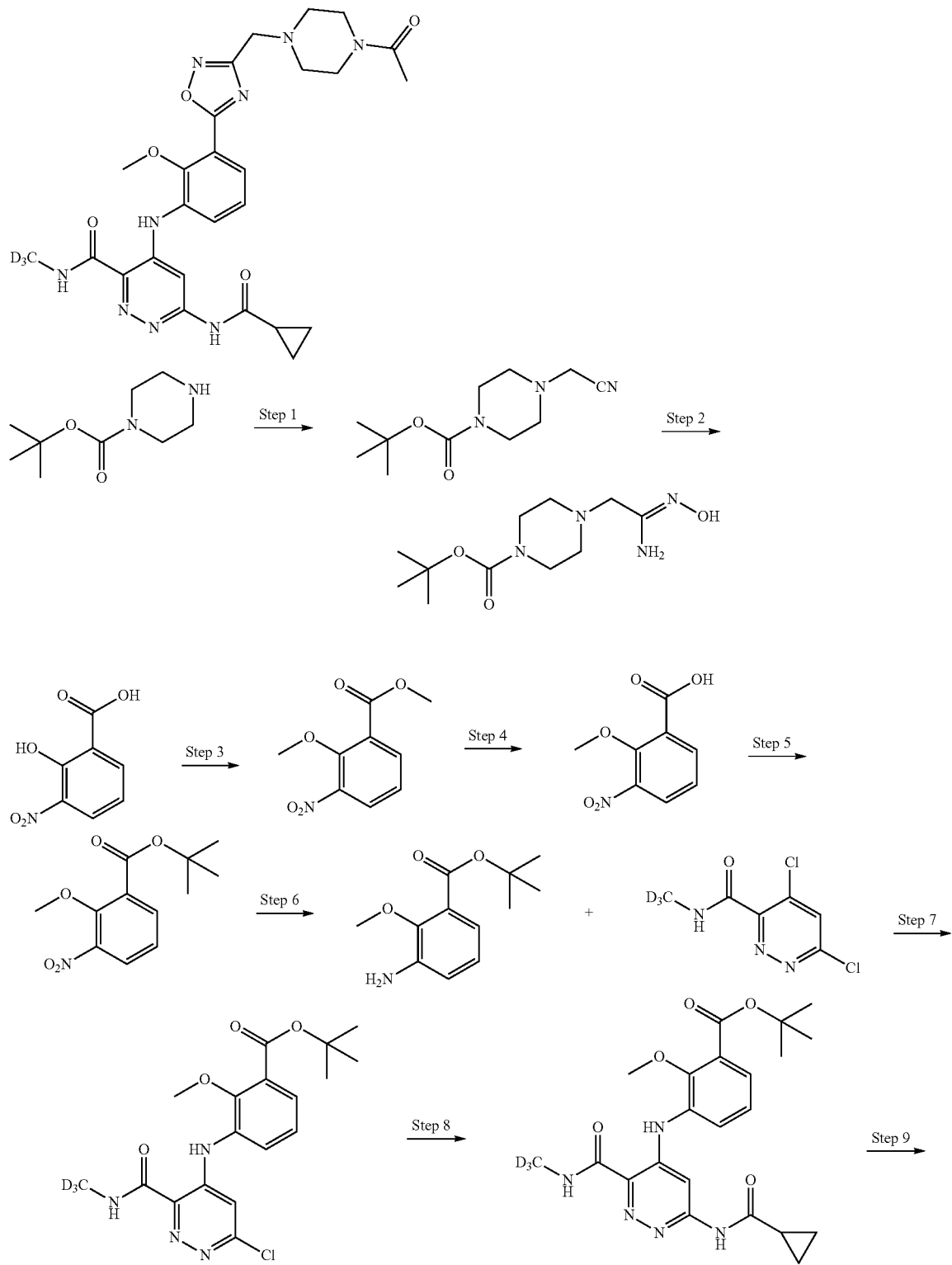

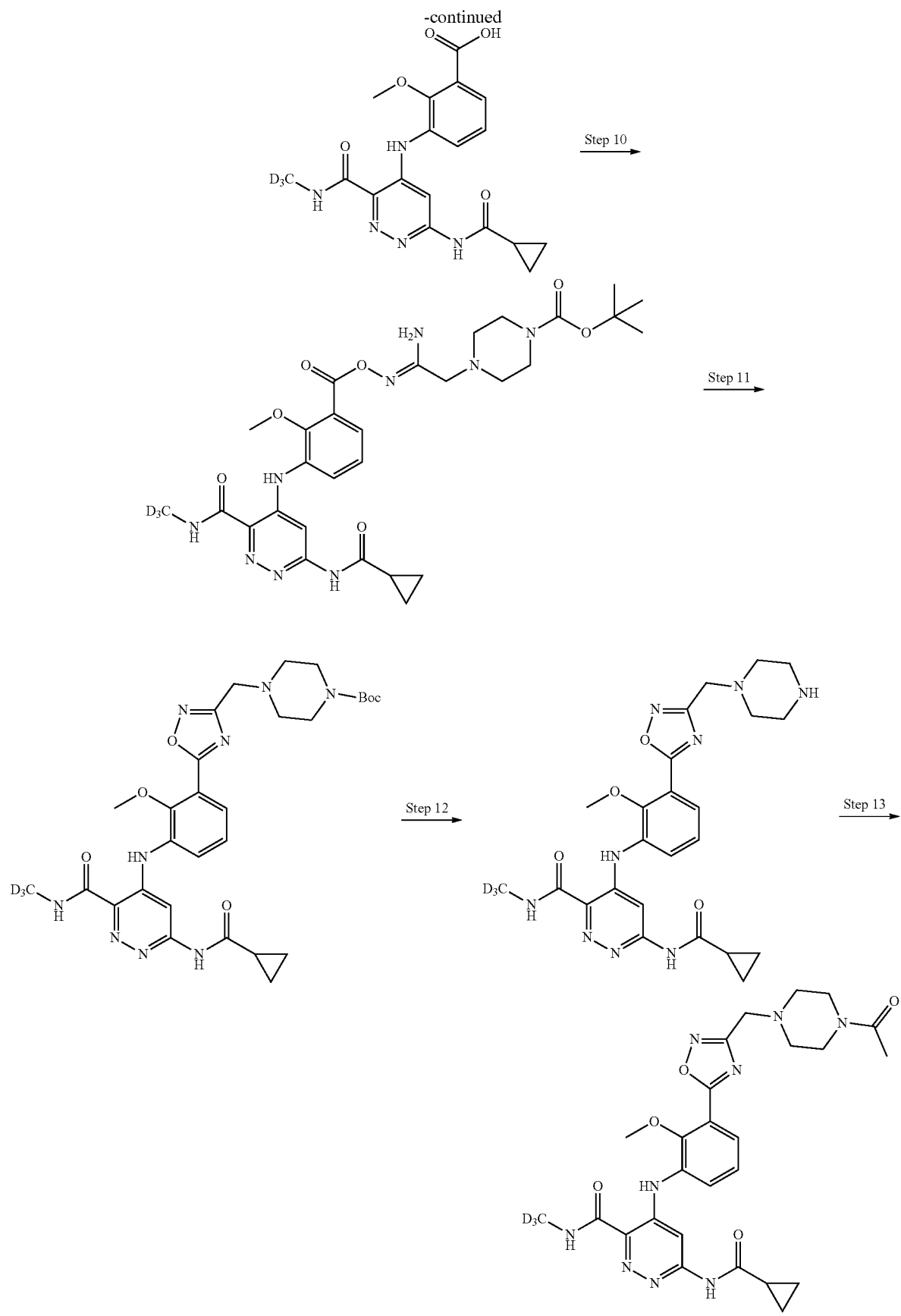

Step 1

A mixture of tert-butyl piperazine-1-carboxylate (0.931 g, 5 mmol), bromoacetonitrile (0.348 mL, 5.00 mmol) and potassium carbonate (1.037 g, 7.50 mmol) in DMF (20 mL) was stirred at rt for 18 hr. The reaction mixture was partitioned between EtOAc (75 ml) and water (75 ml). The organic layer was washed with 10% LiCl solution (2×75 ml) and brine (75 ml). After drying ($Na_2SO_4$) and filtration, the organic layer was concentrated to afford tert-butyl 4-(cyanomethyl)piperazine-1-carboxylate (1.08 g, 4.79 mmol, 96% yield) as a dark yellow solid. $^1$H NMR (400 MHz, chloroform-d) δ 3.53 (s, 2H), 3.51-3.45 (m, 4H), 2.60-2.47 (m, 4H), 1.47 (s, 9H).

Step 2

A mixture of tert-butyl 4-(cyanomethyl)piperazine-1-carboxylate (1.07 g, 4.75 mmol), hydroxylamine hydrochloride (0.495 g, 7.12 mmol) and sodium bicarbonate (0.798 g, 9.50 mmol) in tert-BuOH (20 mL) was stirred at 80° C. for 4 hr. After cooling to rt, the reaction mixture was partitioned between EtOAc (75 ml) and water (75 ml). The organic layer was washed with brine (50 ml), dried ($Na_2SO_4$) and concentrated to afford (Z)-tert-butyl 4-(2-amino-2-(hydroxyimino)ethyl)piperazine-1-carboxylate (987 mg, 3.82 mmol, 80% yield) as a white solid. $^1$H NMR (400 MHz, DMSO-$d_6$) δ 8.97 (s, 1H), 5.22 (s, 2H), 3.38-3.27 (m, 6H), 2.32-2.25 (m, 4H), 1.43-1.35 (m, 9H).

Step 3

A mixture of methyl 2-hydroxy-3-nitrobenzoate (6 g, 30.4 mmol), iodomethane (3.81 mL, 60.9 mmol) and potassium carbonate (10.52 g, 76 mmol) in DMF (100 mL) was stirred at rt for 3 days. Ice water (500 ml) was added and the resulting suspension was stirred for 30 minutes. Filtration and drying afforded methyl 2-methoxy-3-nitrobenzoate (5.17 g, 24.48 mmol, 80% yield) as a white solid. LCMS m/z 219.1 (M+H)$^+$; HPLC $t_R$ 1.46 min (analytical HPLC Method F); $^1$H NMR (400 MHz, chloroform-d) δ 8.03 (dd, J=7.9, 1.8 Hz, 1H), 7.91 (dd, J=8.1, 1.8 Hz, 1H), 7.31-7.24 (m, 1H), 4.01 (s, 3H), 3.96 (s, 3H).

Step 4

A mixture of methyl 2-methoxy-3-nitrobenzoate (5.16 g, 24.44 mmol) and NaOH, 1N (51.3 mL, 51.3 mmol) in MeOH (200 mL) was stirred at rt for 18 hr. The MeOH was removed on the rotovap and the remaining solution was diluted with 100 ml of water. The pH was adjusted to 1 with 1N HCl and the resulting suspension was filtered and dried to afford 2-methoxy-3-nitrobenzoic acid (4.65 g, 23.59 mmol, 97% yield) as a white solid. LCMS m/z 198.0 (M+H)$^+$; HPLC $t_R$ 1.01 min (analytical HPLC Method F); $^1$H NMR (400 MHz, chloroform-d) δ 8.30 (dd, J=7.9, 1.8 Hz, 1H), 8.04 (dd, J=8.1, 1.8 Hz, 1H), 7.38 (t, J=7.9 Hz, 1H), 4.09 (s, 3H) carboxylic acid proton not seen.

Step 5

To a mixture of 2-methoxy-3-nitrobenzoic acid (4.55 g, 23.08 mmol), 4-dimethylaminopyridine (0.282 g, 2.308 mmol) and tert-butanol (3.31 mL, 34.6 mmol) in DCM (200 mL) at 0° C. was added dicyclohexylcarbodiimide (4.76 g, 23.08 mmol) in 2 portions. The reaction mixture was allowed to warm and was stirred at rt for 16 hrs. After filtration through celite, the filtrate was washed with 1N HCl (2×200 ml) and brine (200 ml). After drying ($MgSO_4$) and filtration the organic layer was concentrated to a yellow semi-solid that was chromatographed on a 120 gm ISCO silica gel cartridge, eluting with a 0-30% EtOAc/Hex gradient. The pure fractions were concentrated to afford tert-butyl 2-methoxy-3-nitrobenzoate (5.11 g, 20.18 mmol, 87% yield) as a light yellow oil. $^1$H NMR (400 MHz, chloroform-d) δ 7.94 (dd, J=7.9, 1.8 Hz, 1H), 7.87 (dd, J=7.9, 1.8 Hz, 1H), 7.30-7.20 (m, 1H), 4.00 (s, 3H), 1.63 (s, 9H).

Step 6

A mixture of tert-butyl 2-methoxy-3-nitrobenzoate (5.1 g, 20.14 mmol) and 10% Pd/C (1.072 g, 1.007 mmol) in ethyl acetate (200 ml) was stirred under an atmosphere of hydrogen at rt for 16 hr. Filtration through a 0.45 micron nylon filter and concentration of the filtrate afforded tert-butyl 3-amino-2-methoxybenzoate (4.50 g, 20.16 mmol, 100% yield) as a yellow oil, The material became a crystalline solid upon standing. $^1$H NMR (400 MHz, chloroform-d) δ 7.11 (dd, J=7.7, 1.8 Hz, 1H), 6.96-6.89 (m, 1H), 6.88-6.83 (m, 1H), 3.90 (br s, 2H), 3.84 (s, 3H), 1.60 (s, 9H)

Step 7

To a solution of 4,6-dichloro-N-trideuteromethylpyridazine-3-carboxamide (see previous patents for preparation) (1 g, 4.78 mmol) and tert-butyl 3-amino-2-methoxybenzoate (1.067 g, 4.78 mmol) in THF (30 mL) at rt was added dropwise over 5 minutes LiHMDS, 1M in (11.96 mL, 11.96 mmol). The resulting solution was stirred at rt for 10 minutes. The reaction mixture was quenched with 10 ml of saturated ammonium chloride solution. The resulting mixture was partitioned between EtOAc (150 ml) and saturated ammonium chloride solution (150 ml). The organic layer was washed with brine (150 ml), dried ($Na_2SO_4$) and concentrated to an amber oil that was chromatographed on a 80 gm ISCO silica gel cartridge, eluting with a 0-60% EtOAc/Hex gradient. The pure fractions were concentrated to afford tert-butyl 3-((6-chloro-3-(trideuteromethylcarbamoyl)pyridazin-4-yl)amino)-2-methoxybenzoate (1.60 g, 4.04 mmol, 84% yield) as a light yellow solid. LCMS m/z 396.4/398.2 (M+H)$^+$; HPLC $t_R$ 2.93 min (analytical HPLC Method F)

Step 8

A mixture of tert-butyl 3-((6-chloro-3-(trideuteromethylcarbamoyl)pyridazin-4-yl)amino)-2-methoxybenzoate (1.2 g, 3.03 mmol), cyclopropanecarboxamide (0.516 g, 6.06 mmol), $Pd_2(dba)_3$, chloroform adduct (0.313 g, 0.303 mmol), Xantphos (0.351 g, 0.606 mmol) and $Cs_2CO_3$ (3.95 g, 12.13 mmol) in Dioxane (20 mL) was degassed by bubbling nitrogen through the mixture for 5 minutes. The reaction vessel was sealed and heated to 130° C. for 6 hr. After cooling to rt, the reaction mixture was partitioned between EtOAc (100 ml) and water (50 ml). The aqueous layer was extracted with EtOAc (50 ml) and the combined organics were dried (Na$_2$SO$_4$) and concentrated to afford a yellow oil that was chromatographed on a 80 gm ISCO silica gel cartridge, eluting with a 0-100% EtOAc/Hex gradient. The pure fractions were concentrated to afford tert-butyl 3-((6-(cyclopropanecarboxamido)-3-(trideuteromethylcarbamoyl)pyridazin-4-yl)amino)-2-methoxybenzoate (1.01 g, 2.272 mmol, 75.0% yield) as a yellow solid. LCMS m/z 445.5 (M+H)$^+$; HPLC t$_R$ 2.59 min (analytical HPLC Method F).

Step 9

A mixture of tert-butyl 3-((6-(cyclopropanecarboxamido)-3-(trideuteromethylcarbamoyl)pyridazin-4-yl) amino)-2-methoxybenzoate (1.01 g, 2.272 mmol) and HCl, 4N in dioxane (5.68 mL, 22.72 mmol) in DCM (10 mL) was stirred at rt for 8 hr. The reaction mixture was allowed to stand in the freezer for 3 days. The volatiles were removed in vacuo and the residue was dried to afford ((6-(cyclopropanecarboxamido)-3-(trideuteromethylcarbamoyl) pyridazin-4-yl)amino)-2-methoxybenzoic acid, HCl (0.96 g, 2.260 mmol, 99% yield) as a yellow solid. LCMS m/z 389.3 (M+H)$^+$; HPLC t$_R$ 1.48 min (analytical HPLC Method F).

Step 10

A mixture of 3-((6-(cyclopropanecarboxamido)-3-(trideuteromethylcarbamoyl)pyridazin-4-yl)amino)-2-methoxybenzoic acid (350 mg, 0.901 mmol), (Z)-tert-butyl 4-(2-amino-2-(hydroxyimino)ethyl)piperazine-1-carboxylate (233 mg, 0.901 mmol), 3-(Ethyliminomethyleneamino)-N, N-dimethylpropan-1-amine, HCl (190 mg, 0.991 mmol), 1-hydroxybenzotriazole (152 mg, 0.991 mmol) and triethylamine (377 µl, 2.70 mmol) in DMF was stirred 18 hr at rt. An additional amount equal to half of the initial aliquot of each reagent (except starting material) was added and stirring was continued at rt for 3 days. An additional amount of (Z)-tert-butyl 4-(2-amino-2-(hydroxyimino)ethyl)piperazine-1-carboxylate (100 mg) was added followed by BOP (199 mg, 0.451 mmol) and the mixture was stirred 1 hr at rt. The reaction mixture was partitioned between EtOAc (40 ml) and water (40 ml). The organic layer was washed with 10% LiCl solution (2×40 ml) and brine (40 ml). After drying (Na$_2$SO$_4$) and filtration the organic layer was concentrated to afford (Z)-tert-butyl 4-(2-amino-2-(((3-((6-(cyclopropanecarboxamido)-3-(trideuteromethylcarbamoyl)pyridazin-4-yl)amino)-2-methoxybenzoyl)oxy)imino)ethyl)piperazine-1-carboxylate (565 mg, 0.899 mmol, 100% yield) as a yellow solid. LCMS m/z 629.5 (M+H)$^+$; HPLC t$_R$ 2.28 min (analytical HPLC Method F).

Step 11

A mixture of (Z)-tert-butyl 4-(2-amino-2-(((3-((6-(cyclopropanecarboxamido)-3-(trideuteromethylcarbamoyl) pyridazin-4-yl)amino)-2-methoxybenzoyl)oxy) imino) ethyl)piperazine-1-carboxylate (565 mg, 0.899 mmol) and tetrabutylammonium fluoride, 1M in THF (1.348 mL, 1.348 mmol) in acetonitrile (9 mL) was stirred at rt for 16 hr. The reaction mixture was partitioned between EtOAc (30 ml) and waster (30 ml). An emulsion formed. ~1 gm of NaCl was added and the layers separated. The organic layer was washed with brine (30 ml). After drying (Na$_2$SO$_4$) and filtration, the organic layer was concentrated to afford a yellow oil that was chromatographed on a 24 gm ISCO silica gel cartridge, eluting with a 0-100% EtOAc/Hex gradient. The pure fractions were concentrated to afford tert-butyl 4-((5-(3-((6-(cyclopropanecarboxamido)-3-(trideuteromethylcarbamoyl)pyridazin-4-yl)amino)-2-methoxyphenyl)-1,2, 4-oxadiazol-3-yl)methyl)piperazine-1-carboxylate (213 mg, 0.349 mmol, 38.8% yield) as an off-white solid. LCMS m/z 611.5 (M+H)$^+$; HPLC t$_R$ 2.35 min (analytical HPLC Method F).

Step 12

A mixture of tert-butyl 4-((5-(3-((6-(cyclopropanecarboxamido)-3-(trideuteromethylcarbamoyl)pyridazin-4-yl) amino)-2-methoxyphenyl)-1,2,4-oxadiazol-3-yl)methyl) piperazine-1-carboxylate (201 mg, 0.329 mmol) and HCl, 4N in dioxane (0.823 mL, 3.29 mmol) in DCM (4 mL) was allowed to stand at rt overnight. Removal of the volatiles in vacuo and drying afforded 6-(cyclopropanecarboxamido)-4-((2-methoxy-3-(3-(piperazin-1-ylmethyl)-1,2,4-oxadiazol-5-yl)phenyl)amino)-N-trideuteromethylpyridazine-3-carboxamide, HCl (180 mg, 0.329 mmol, 100% yield) as a yellow solid. LCMS m/z 511.5 (M+H)$^+$; HPLC t$_R$ 1.91 min (analytical HPLC Method F).

Step 13

A mixture of 6-(cyclopropanecarboxamido)-4-((2-methoxy-3-(3-(piperazin-1-ylmethyl)-1,2,4-oxadiazol-5-yl) phenyl)amino)-N-trideuteromethylpyridazine-3-carboxamide, HCl (12 mg, 0.022 mmol), acetic anhydride (2.277 µl, 0.024 mmol) and triethylamine (0.012 ml, 0.088 mmol) in DCM (0.25 ml) was agitated at rt for 1 hr. MeOH (0.2 ml) was added and the volatiles were removed in vacuo. The residue was dissolved in DMSO and was purified via preparative LC/MS with the following conditions: Column: waters xbridge c-18, 19×100 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-80% B over 12 minutes, then a 5-minute hold at 100% B; Flow: 20 mL/min. Fractions containing the desired product were combined and dried via centrifugal evaporation to afford 4-((3-(3-((4-acetylpiperazin-1-yl)methyl)-1,2,4-oxadiazol-5-yl)-2-methoxyphenyl)amino)-6-(cyclopropanecarboxamido)-N-trideuteromethylpyridazine-3-carboxamide (10.3 mg, 0.0.018 mmol, 84% yield). LCMS m/z 553.2 (M+H)$^+$; HPLC t$_R$ 1.25 min (QC-ACN-AA-XB); $^1$H NMR (500 MHz, DMSO-d$_6$) δ 11.36 (s, 1H), 11.05 (s, 1H), 9.16 (s, 1H), 8.12 (s, 1H), 7.83 (d, J=7.4 Hz, 1H), 7.77 (d, J=8.1 Hz, 1H), 7.42 (t, J=7.9 Hz, 1H), 3.81 (s, 2H), 3.78 (s, 3H), 3.44 (d, J=4.7 Hz, 1H), 2.55 (d, J=4.7 Hz, 2H), 2.13-2.02 (m, 1H), 1.97 (s, 3H), 0.90-0.75 (m, 4H). Missing peaks co-resonate with solvent and water peaks.

The Examples in Table 3 were prepared using a similar procedure used to prepare Example 120.

TABLE 3
| Ex. No. | Structure | MW | Obs. MS Ion | RT | QC Method |
|---|---|---|---|---|---|
| 121 | 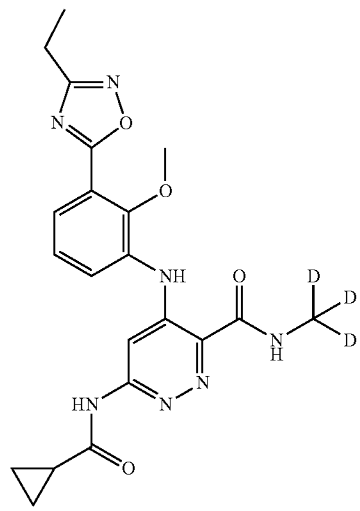 [SMILES: [2H]C([2H])([2H])NC(=O)c1nnc(NC(=O)C2CC2)cc1Nc1cccc(-c2nc(CC)no2)c1OC] | 440.5 | 441.3 | 1.44 | QC-ACN-TFA-XB |
| 122 | 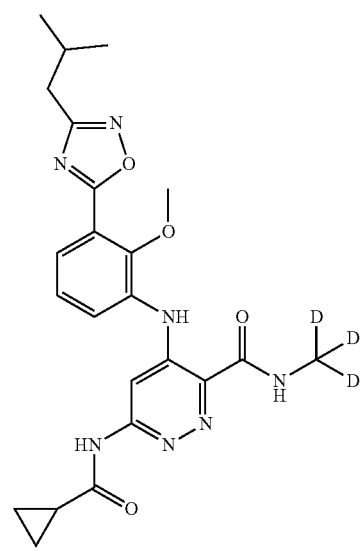 [SMILES: [2H]C([2H])([2H])NC(=O)c1nnc(NC(=O)C2CC2)cc1Nc1cccc(-c2nc(CC(C)C)no2)c1OC] | 468.5 | 469.3 | 2.02 | QC-ACN-AA-XB |

TABLE 3-continued
| Ex. No. | Structure | MW | Obs. MS Ion | RT | QC Method |
|---|---|---|---|---|---|
| 123 | 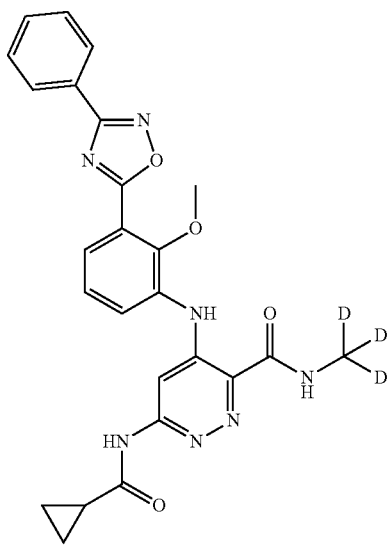 [SMILES: [2H]C([2H])([2H])NC(=O)c1nnc(NC(=O)C2CC2)cc1Nc1cccc(-c2nc(-c3ccccc3)no2)c1OC] | 488.5 | 489.3 | 1.74 | QC-ACN-TFA-XB |
| 124 | 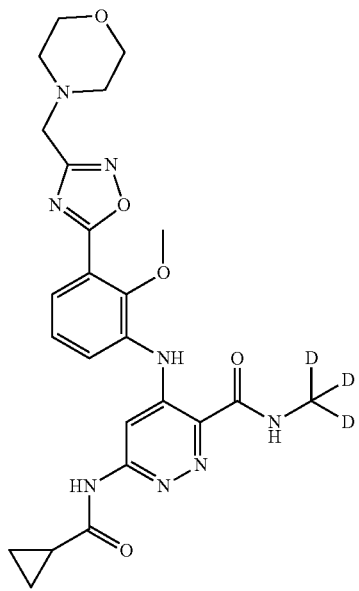 [SMILES: [2H]C([2H])([2H])NC(=O)c1nnc(NC(=O)C2CC2)cc1Nc1cccc(-c2nc(CN3CCOCC3)no2)c1OC] | 511.6 | 512.3 | 1.33 | QC-ACN-AA-XB |

TABLE 3-continued

| Ex. No. | Structure | MW | Obs. MS Ion | RT | QC Method |
|---|---|---|---|---|---|
| 125 | 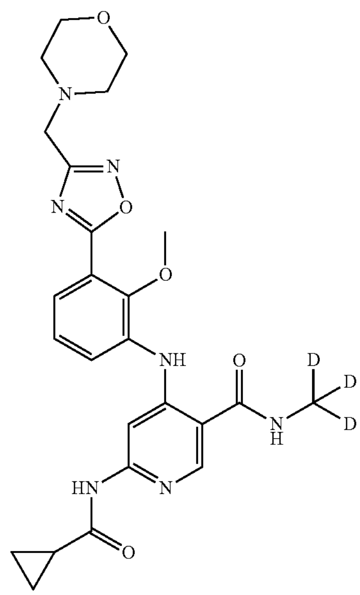 [SMILES: [2H]C([2H])([2H])NC(=O)c1cnc(NC(=O)C2CC2)cc1Nc1cccc(-c2nc(CN3CCOCC3)no2)c1OC] | 510.6 | 511.2 | 1.28 | QC-ACN-AA-XB |
| 126 | 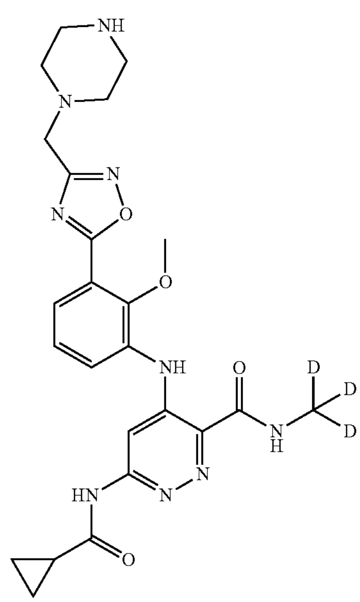 [SMILES: [2H]C([2H])([2H])NC(=O)c1nnc(NC(=O)C2CC2)cc1Nc1cccc(-c2nc(CN3CCNCC3)no2)c1OC] | 510.6 | 511.3 | 1.1 | QC-ACN-AA-XB |

TABLE 3-continued

| Ex. No. | Structure | MW | Obs. MS Ion | RT | QC Method |
|---|---|---|---|---|---|
| 127 | 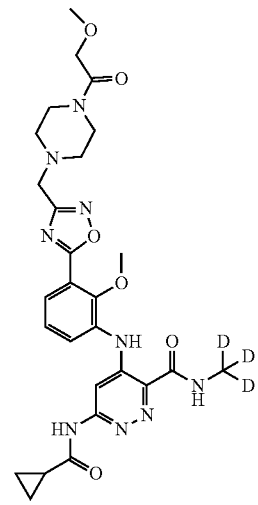 [SMILES: [2H]C([2H])([2H])NC(=O)c1nnc(NC(=O)C2CC2)cc1Nc1cccc(-c2nc(CN3CCN(C(=O)COC)CC3)no2)c1OC] | 582.6 | 583.2 | 1.26 | QC-ACN-AA-XB |
| 128 | 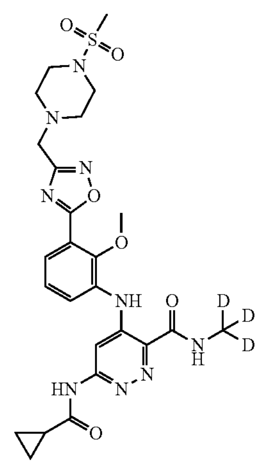 [SMILES: [2H]C([2H])([2H])NC(=O)c1nnc(NC(=O)C2CC2)cc1Nc1cccc(-c2nc(CN3CCN(S(C)(=O)=O)CC3)no2)c1OC] | 588.7 | 589.3 | 1.45 | QC-ACN-AA-XB |
| 129 | 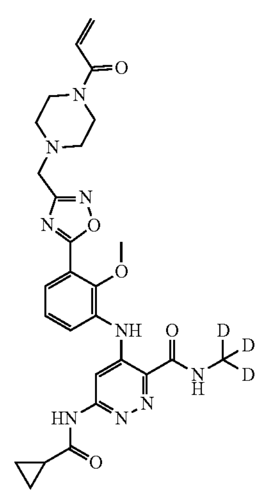 [SMILES: [2H]C([2H])([2H])NC(=O)c1nnc(NC(=O)C2CC2)cc1Nc1cccc(-c2nc(CN3CCN(C(=O)C=C)CC3)no2)c1OC] | 564.6 | 565.2 | 1.33 | QC-ACN-AA-XB |

TABLE 3-continued

| Ex. No. | Structure | MW | Obs. MS Ion | RT | QC Method |
|---|---|---|---|---|---|
| 130 | 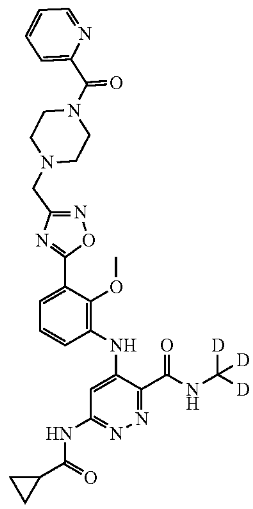 [SMILES: [2H]C([2H])([2H])NC(=O)c1nnc(NC(=O)C2CC2)cc1Nc1cccc(-c2nc(CN3CCN(C(=O)c4ccccn4)CC3)no2)c1OC] | 615.7 | 616.2 | 1.34 | QC-ACN-AA-XB |
| 131 | 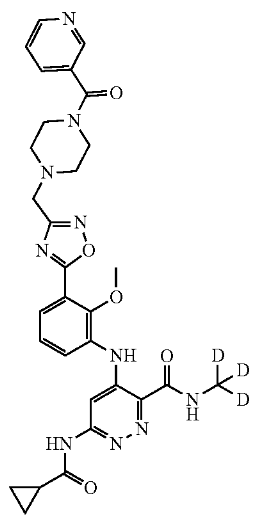 [SMILES: [2H]C([2H])([2H])NC(=O)c1nnc(NC(=O)C2CC2)cc1Nc1cccc(-c2nc(CN3CCN(C(=O)c4cccnc4)CC3)no2)c1OC] | 615.7 | 616.4 | 0.94 | QC-ACN-TFA-XB |
| 132 | 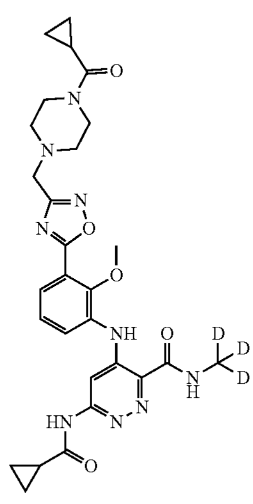 [SMILES: [2H]C([2H])([2H])NC(=O)c1nnc(NC(=O)C2CC2)cc1Nc1cccc(-c2nc(CN3CCN(C(=O)C4CC4)CC3)no2)c1OC] | 578.6 | 579.4 | 1.53 | QC-ACN-AA-XB |

TABLE 3-continued

| Ex. No. | Structure | MW | Obs. MS Ion | RT | QC Method |
|---|---|---|---|---|---|
| 133 | 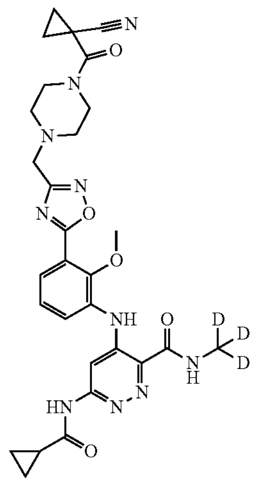 [SMILES: [2H]C([2H])([2H])NC(=O)c1nnc(NC(=O)C2CC2)cc1Nc1cccc(-c2nc(CN3CCN(C(=O)C4(C#N)CC4)CC3)no2)c1OC] | 603.7 | 604.2 | 1.44 | QC-ACN-AA-XB |
| 134 | 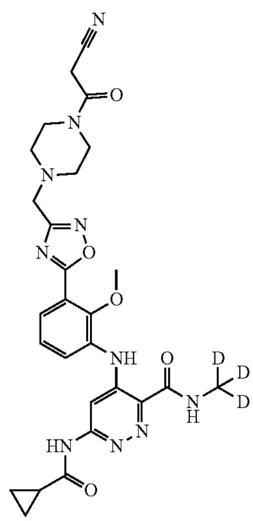 [SMILES: [2H]C([2H])([2H])NC(=O)c1nnc(NC(=O)C2CC2)cc1Nc1cccc(-c2nc(CN3CCN(C(=O)CC#N)CC3)no2)c1OC] | 577.6 | 578.4 | 1.41 | QC-ACN-AA-XB |
| 135 | 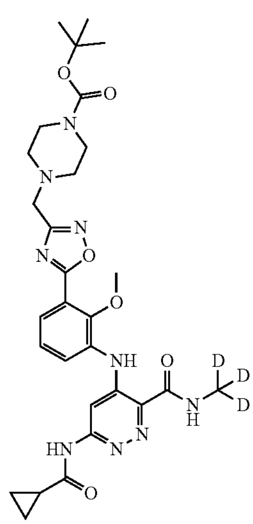 [SMILES: [2H]C([2H])([2H])NC(=O)c1nnc(NC(=O)C2CC2)cc1Nc1cccc(-c2nc(CN3CCN(C(=O)OC(C)(C)C)CC3)no2)c1OC] | 610.7 | 611.4 | 1.94 | QC-ACN-AA-XB |

TABLE 3-continued

| Ex. No. | Structure | MW | Obs. MS Ion | RT | QC Method |
|---|---|---|---|---|---|
| 136 | 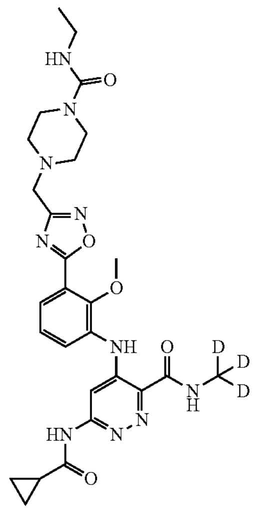 [SMILES: [2H]C([2H])([2H])NC(=O)c1nnc(NC(=O)C2CC2)cc1Nc1cccc(-c2nc(CN3CCN(C(=O)NCC)CC3)no2)c1OC] | 581.7 | 582.3 | 1.37 | QC-ACN-AA-XB |
| 137 | 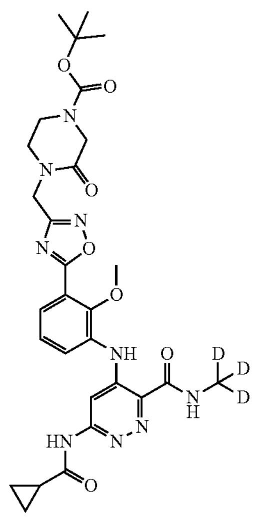 [SMILES: [2H]C([2H])([2H])NC(=O)c1nnc(NC(=O)C2CC2)cc1Nc1cccc(-c2nc(CN3CCN(C(=O)OC(C)(C)C)CC3=O)no2)c1OC] | 624.7 | 625.3 | 1.7 | QC-ACN-AA-XB |
| 138 | 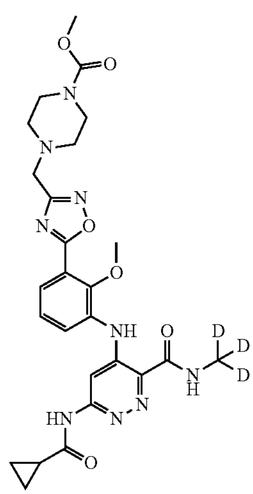 [SMILES: [2H]C([2H])([2H])NC(=O)c1nnc(NC(=O)C2CC2)cc1Nc1cccc(-c2nc(CN3CCN(C(=O)OC)CC3)no2)c1OC] | 568.6 | 569.3 | 1.46 | QC-ACN-AA-XB |

TABLE 3-continued

| Ex. No. | Structure | MW | Obs. MS Ion | RT | QC Method |
|---|---|---|---|---|---|
| 139 | 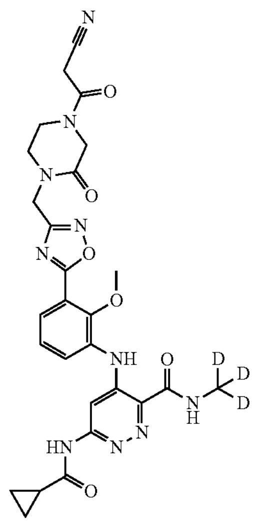 [SMILES: [2H]C([2H])([2H])NC(=O)c1nnc(NC(=O)C2CC2)cc1Nc1cccc(-c2nc(CN3CCN(C(=O)CC#N)CC3=O)no2)c1OC] | 591.6 | 592.4 | 1.17 | QC-ACN-AA-XB |
| 140 | 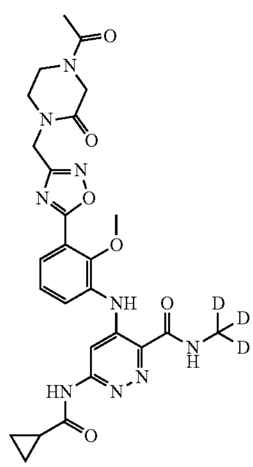 [SMILES: [2H]C([2H])([2H])NC(=O)c1nnc(NC(=O)C2CC2)cc1Nc1cccc(-c2nc(CN3CCN(C(C)=O)CC3=O)no2)c1OC] | 566.6 | 567.3 | 1.13 | QC-ACN-AA-XB |
| 141 | 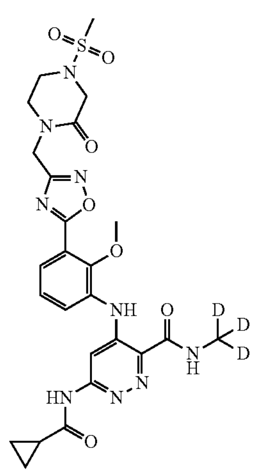 [SMILES: [2H]C([2H])([2H])NC(=O)c1nnc(NC(=O)C2CC2)cc1Nc1cccc(-c2nc(CN3CCN(S(C)(=O)=O)CC3=O)no2)c1OC] | 602.6 | 603.3 | 1.25 | QC-ACN-AA-XB |

TABLE 3-continued

| Ex. No. | Structure | MW | Obs. MS Ion | RT | QC Method |
|---|---|---|---|---|---|
| 142 | 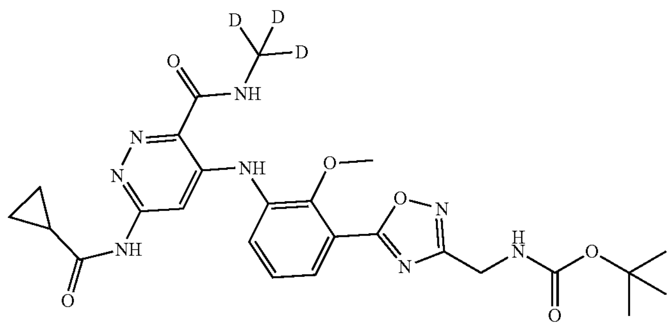 [SMILES: [2H]C([2H])([2H])NC(=O)c1nnc(NC(=O)C2CC2)cc1Nc1cccc(-c2nc(CNC(=O)OC(C)(C)C)no2)c1OC] | 541.6 | 542.3 | 1.74 | QC-ACN-AA-XB |
| 143 | 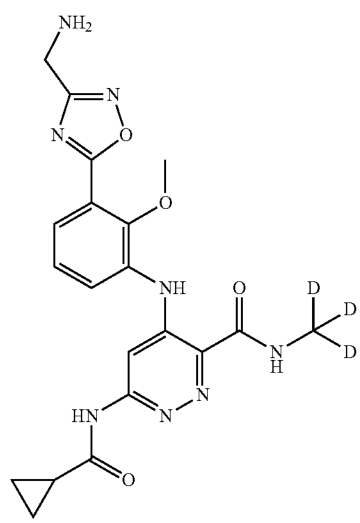 [SMILES: [2H]C([2H])([2H])NC(=O)c1nnc(NC(=O)C2CC2)cc1Nc1cccc(-c2nc(CN)no2)c1OC] | 441.5 | 442.2 | 1.13 | QC-ACN-AA-XB |
| 144 | 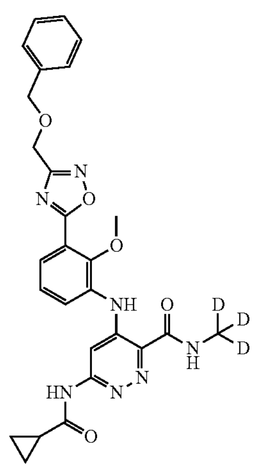 [SMILES: [2H]C([2H])([2H])NC(=O)c1nnc(NC(=O)C2CC2)cc1Nc1cccc(-c2nc(COCc3ccccc3)no2)c1OC] | 532.6 | 533.3 | 1.67 | QC-ACN-TFA-XB |

TABLE 3-continued
| Ex. No. | Structure | MW | Obs. MS Ion | RT | QC Method |
|---|---|---|---|---|---|
| 145 | 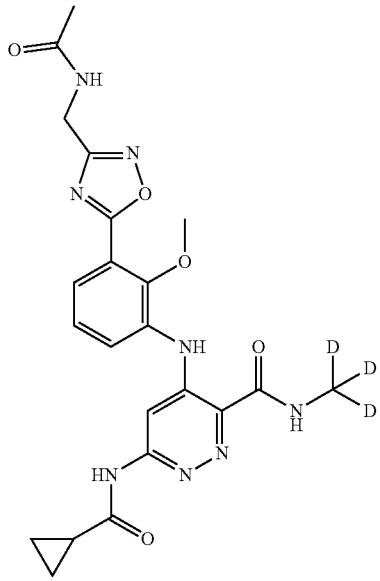 [SMILES: [2H]C([2H])([2H])NC(=O)c1nnc(NC(=O)C2CC2)cc1Nc1cccc(-c2nc(CNC(C)=O)no2)c1OC] | 483.5 | 484.2 | 1.16 | QC-ACN-AA-XB |
| 146 | 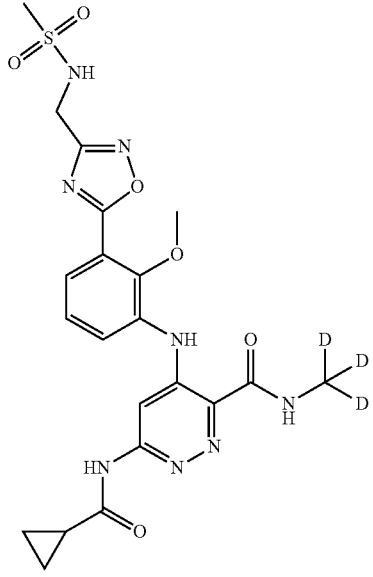 [SMILES: [2H]C([2H])([2H])NC(=O)c1nnc(NC(=O)C2CC2)cc1Nc1cccc(-c2nc(CNS(C)(=O)=O)no2)c1OC] | 519.6 | 520. | 1.08 | QC-ACN-TFA-XB |
| 147 | 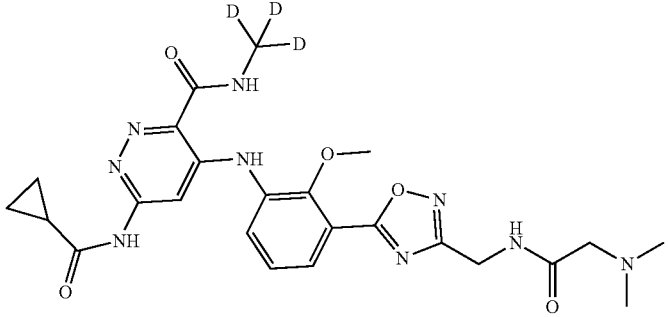 | 526.6 | 527.2 | 1.23 | QC-ACN-AA-XB |

TABLE 3-continued

| Ex. No. | Structure | MW | Obs. MS Ion | RT | QC Method |
|---|---|---|---|---|---|
| 148 | 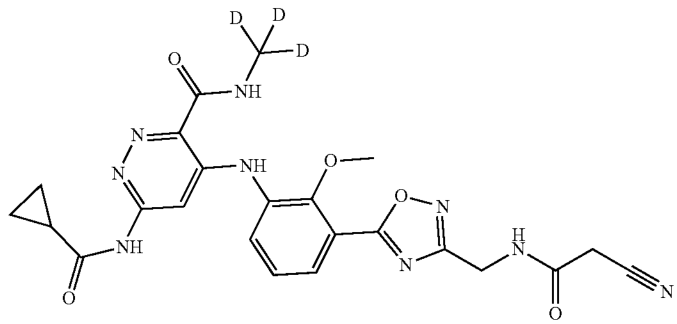 [SMILES: [2H]C([2H])([2H])NC(=O)c1nnc(NC(=O)C2CC2)cc1Nc1cccc(-c2nc(CNC(=O)CC#N)no2)c1OC] | 508.5 | 509.2 | 1.02 | QC-ACN-TFA-XB |
| 149 | 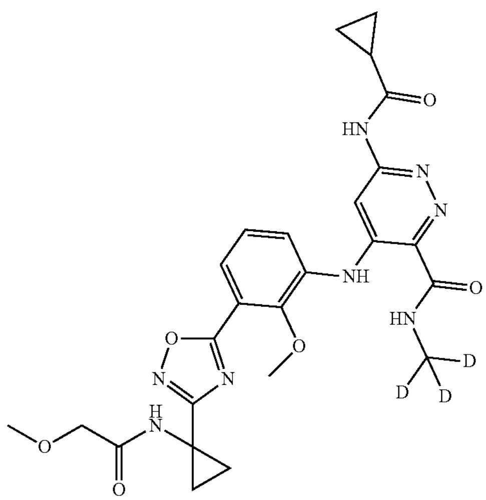 [SMILES: [2H]C([2H])([2H])NC(=O)c1nnc(NC(=O)C2CC2)cc1Nc1cccc(-c2nc(C3(NC(=O)COC)CC3)no2)c1OC] | 539.6 | 540.2 | 1.35 | QC-ACN-AA-XB |
| 150 | 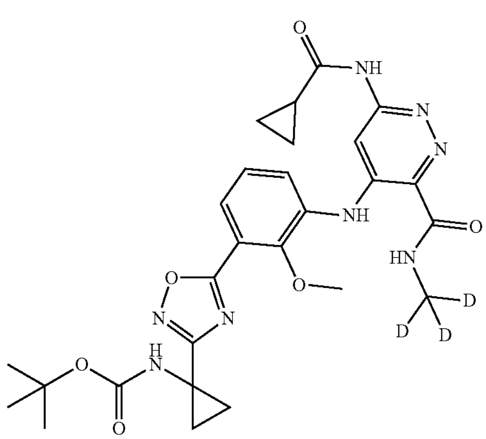 | 567.6 | 568.3 | 1.82 | QC-ACN-AA-XB |

TABLE 3-continued

| Ex. No. | Structure | MW | Obs. MS Ion | RT | QC Method |
|---|---|---|---|---|---|
| 151 | 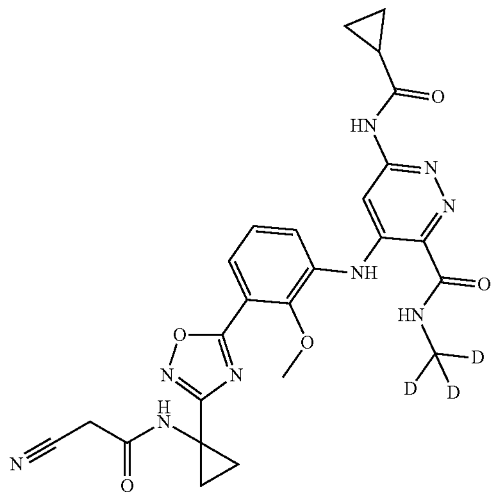 [SMILES: [2H]C([2H])([2H])NC(=O)c1nnc(NC(=O)C2CC2)cc1Nc1cccc(-c2nc(C3(NC(=O)CC#N)CC3)no2)c1OC] | 534.6 | 535.2 | 1.26 | QC-ACN-AA-XB |
| 152 | 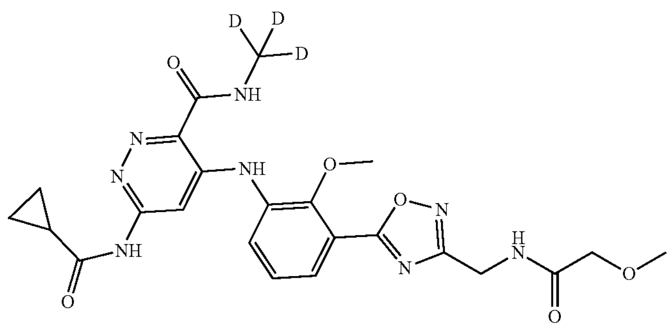 [SMILES: [2H]C([2H])([2H])NC(=O)c1nnc(NC(=O)C2CC2)cc1Nc1cccc(-c2nc(CNC(=O)COC)no2)c1OC] | 513.5 | 514.2 | 1.05 | QC-ACN-TFA-XB |
| 153 | 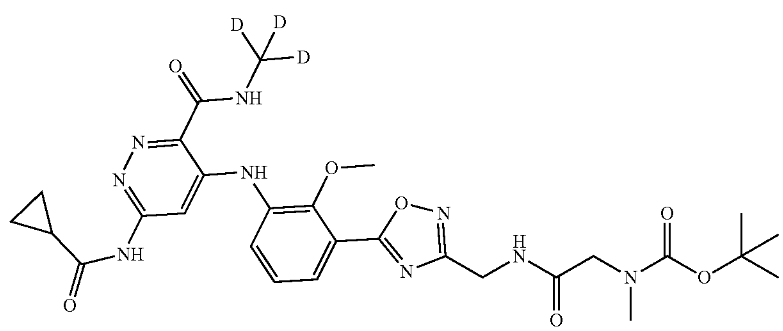 [SMILES: [2H]C([2H])([2H])NC(=O)c1nnc(NC(=O)C2CC2)cc1Nc1cccc(-c2nc(CNC(=O)CN(C)C(=O)OC(C)(C)C)no2)c1OC] | 612.7 | 613.3 | 1.5 | QC-ACN-AA-XB |
| 154 | 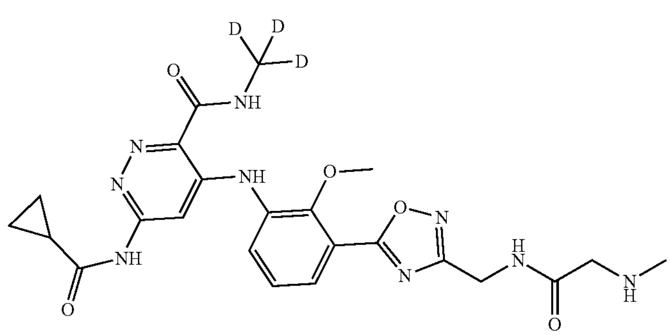 [SMILES: [2H]C([2H])([2H])NC(=O)c1nnc(NC(=O)C2CC2)cc1Nc1cccc(-c2nc(CNC(=O)CNC)no2)c1OC] | 512.5 | 513.1 | 0.81 | QC-ACN-TFA-XB |

TABLE 3-continued
| Ex. No. | Structure | MW | Obs. MS Ion | RT | QC Method |
|---|---|---|---|---|---|
| 155 | 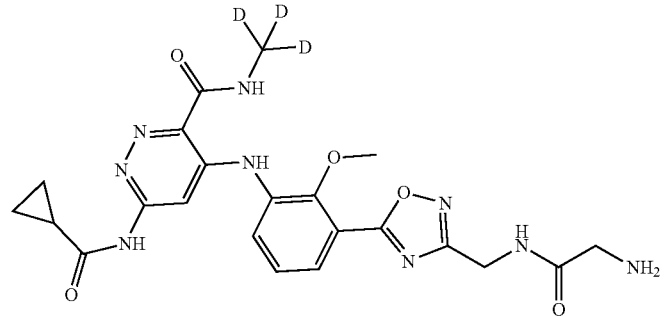 [SMILES: [2H]C([2H])([2H])NC(=O)c1nnc(NC(=O)C2CC2)cc1Nc1cccc(-c2nc(CNC(=O)CN)no2)c1OC] | 498.5 | 499.2 | 0.8 | QC-ACN-TFA-XB |
| 156 | 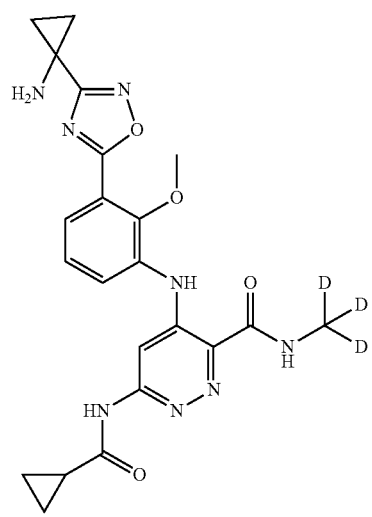 [SMILES: [2H]C([2H])([2H])NC(=O)c1nnc(NC(=O)C2CC2)cc1Nc1cccc(-c2nc(C3(N)CC3)no2)c1OC] | 467.5 | 468.2 | 0.86 | QC-ACN-TFA-XB |
| 157 | 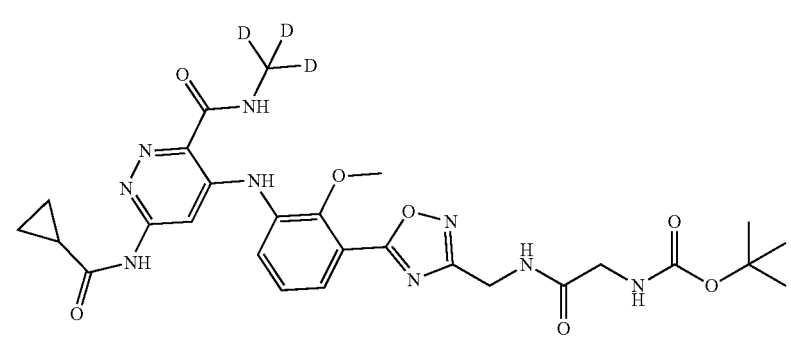 [SMILES: [2H]C([2H])([2H])NC(=O)c1nnc(NC(=O)C2CC2)cc1Nc1cccc(-c2nc(CNC(=O)CNC(=O)OC(C)(C)C)no2)c1OC] | 598.6 | 599.3 | 1.45 | QC-ACN-AA-XB |

TABLE 3-continued

| Ex. No. | Structure | MW | Obs. MS Ion | RT | QC Method |
|---|---|---|---|---|---|
| 158 | 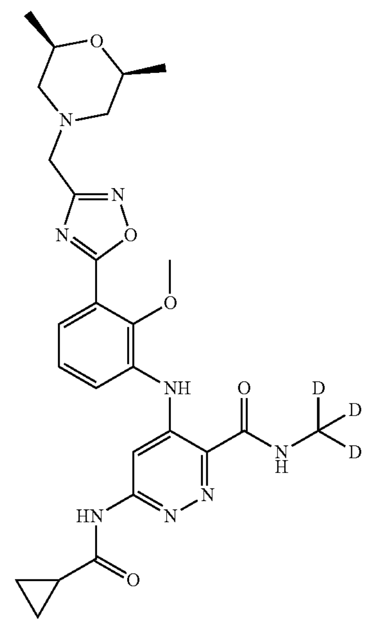 [SMILES: [2H]C([2H])([2H])NC(=O)c1nnc(NC(=O)C2CC2)cc1Nc1cccc(-c2nc(CN3C[C@@H](C)O[C@@H](C)C3)no2)c1OC] | 539.6 | 540.1 | 1.58 | QC-ACN-AA-XB |
| 159 | 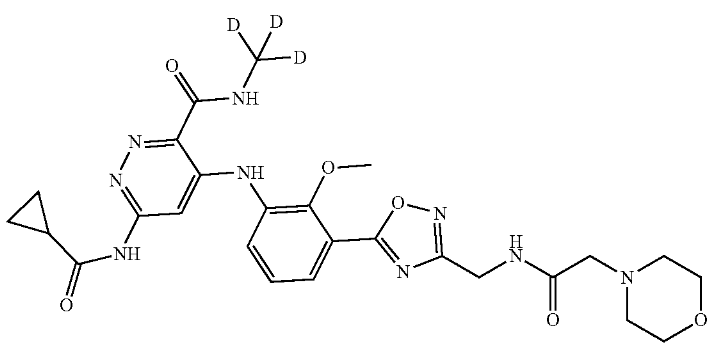 [SMILES: [2H]C([2H])([2H])NC(=O)c1nnc(NC(=O)C2CC2)cc1Nc1cccc(-c2nc(CNC(=O)CN3CCOCC3)no2)c1OC] | 568.6 | 569.1 | 1.21 | QC-ACN-AA-XB |
| 160 | 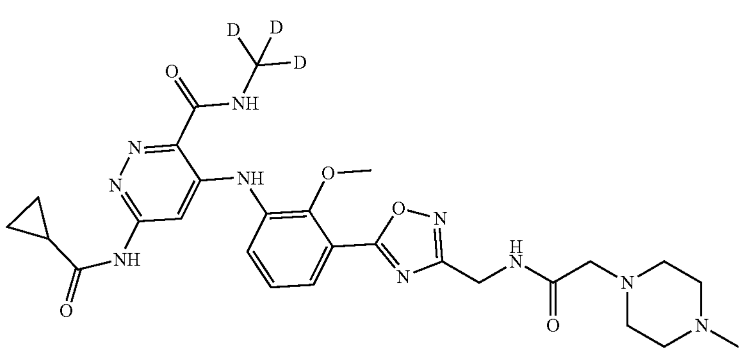 [SMILES: [2H]C([2H])([2H])NC(=O)c1nnc(NC(=O)C2CC2)cc1Nc1cccc(-c2nc(CNC(=O)CN3CCN(C)CC3)no2)c1OC] | 581.7 | 582.1 | 1.03 | QC-ACN-AA-XB |

TABLE 3-continued

| Ex. No. | Structure | MW | Obs. MS Ion | RT | QC Method |
|---|---|---|---|---|---|
| 161 | 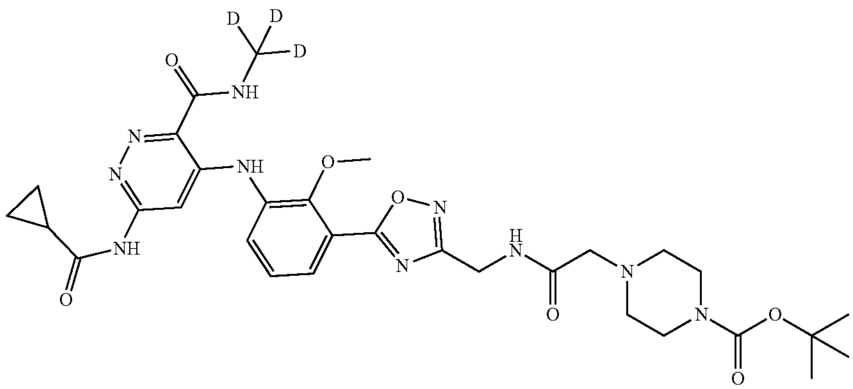 [SMILES: [2H]C([2H])([2H])NC(=O)c1nnc(NC(=O)C2CC2)cc1Nc1cccc(-c2nc(CNC(=O)CN3CCN(C(=O)OC(C)(C)C)CC3)no2)c1OC] | 667.7 | 668.2 | 1.13 | QC-ACN-TFA-XB |
| 162 | 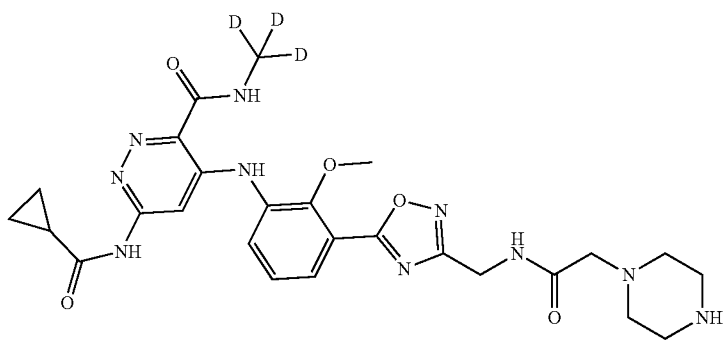 [SMILES: [2H]C([2H])([2H])NC(=O)c1nnc(NC(=O)C2CC2)cc1Nc1cccc(-c2nc(CNC(=O)CN3CCNCC3)no2)c1OC] | 567.6 | 568.3 | 0.94 | QC-ACN-AA-XB |
| 163 | 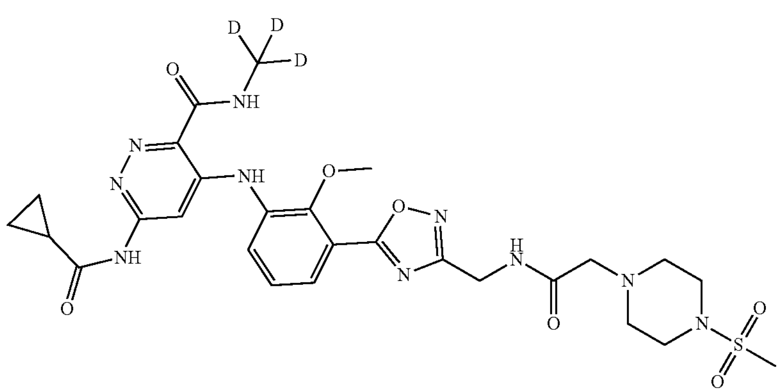 [SMILES: [2H]C([2H])([2H])NC(=O)c1nnc(NC(=O)C2CC2)cc1Nc1cccc(-c2nc(CNC(=O)CN3CCN(S(C)(=O)=O)CC3)no2)c1OC] | 645.7 | 646.4 | 0.94 | QC-ACN-TFA-XB |

TABLE 3-continued
| Ex. No. | Structure | MW | Obs. MS Ion | RT | QC Method |
|---|---|---|---|---|---|
| 164 | 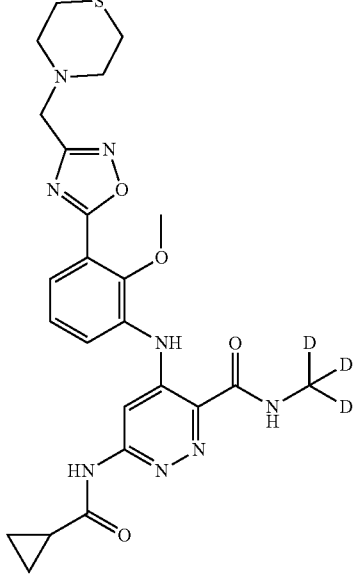 | 559.6 | 560.0 | 1.27 | QC-ACN-AA-XB |
| 165 | 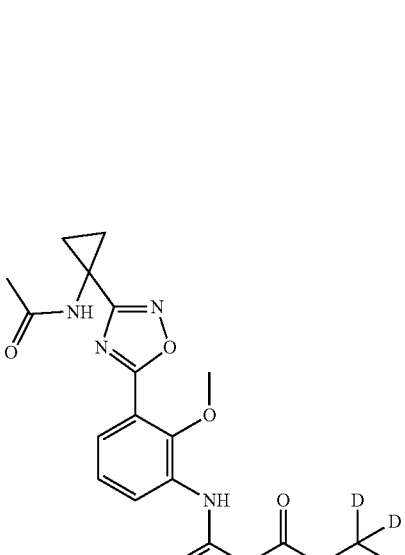 | 509.5 | 510.2 | 1.07 | QC-ACN-TFA-XB |

TABLE 3-continued

| Ex. No. | Structure | MW | Obs. MS Ion | RT | QC Method |
|---|---|---|---|---|---|
| 166 | 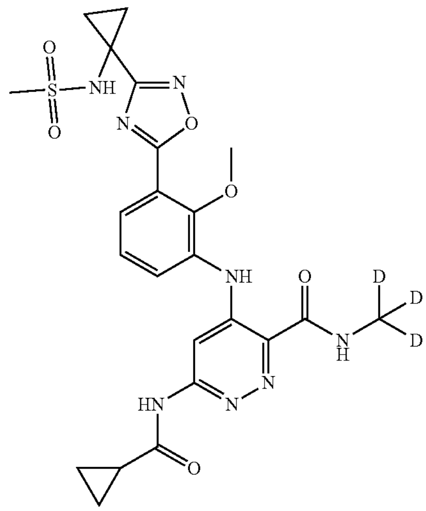 [SMILES: [2H]C([2H])([2H])NC(=O)c1nnc(NC(=O)C2CC2)cc1Nc1cccc(-c2nc(C3(NS(C)(=O)=O)CC3)no2)c1OC] | 545.6 | 546.3 | 1.37 | QC-ACN-AA-XB |
| 167 | 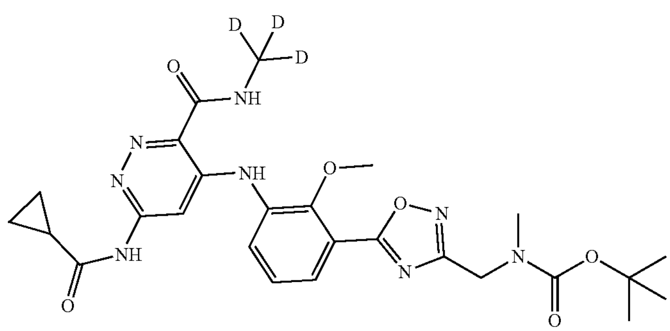 [SMILES: [2H]C([2H])([2H])NC(=O)c1nnc(NC(=O)C2CC2)cc1Nc1cccc(-c2nc(CN(C)C(=O)OC(C)(C)C)no2)c1OC] | 555.6 | 556.3 | 1.65 | QC-ACN-TFA-XB |
| 168 | 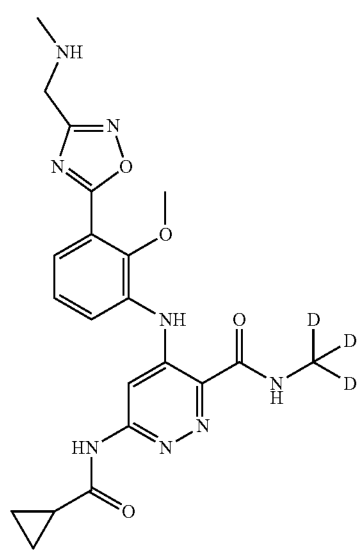 [SMILES: [2H]C([2H])([2H])NC(=O)c1nnc(NC(=O)C2CC2)cc1Nc1cccc(-c2nc(CNC)no2)c1OC] | 455.5 | 456.2 | 0.85 | QC-ACN-TFA-XB |

TABLE 3-continued

| Ex. No. | Structure | MW | Obs. MS Ion | RT | QC Method |
|---|---|---|---|---|---|
| 169 | 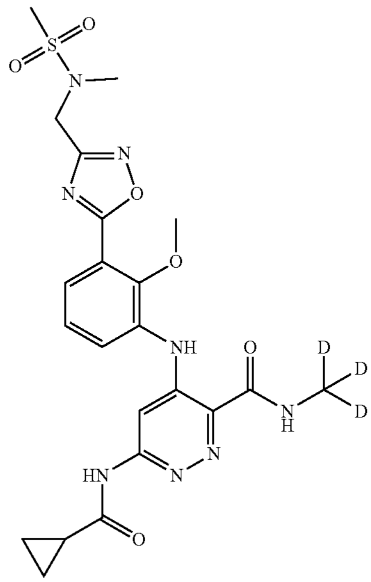 [SMILES: [2H]C([2H])([2H])NC(=O)c1nnc(NC(=O)C2CC2)cc1Nc1cccc(-c2nc(CN(C)S(C)(=O)=O)no2)c1OC] | 533.6 | 534.2 | 1.23 | QC-ACN-TFA-XB |
| 170 | 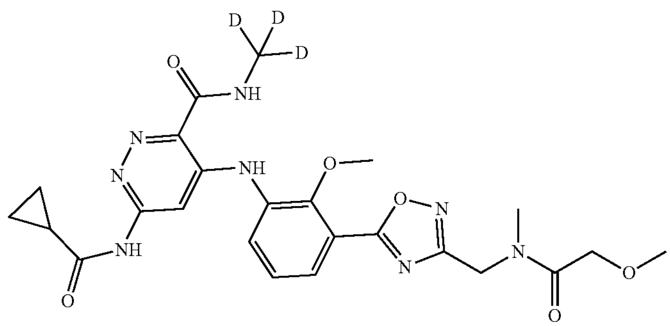 [SMILES: [2H]C([2H])([2H])NC(=O)c1nnc(NC(=O)C2CC2)cc1Nc1cccc(-c2nc(CN(C)C(=O)COC)no2)c1OC] | 527.6 | 528.2 | 1.29 | QC-ACN-AA-XB |
| 171 | 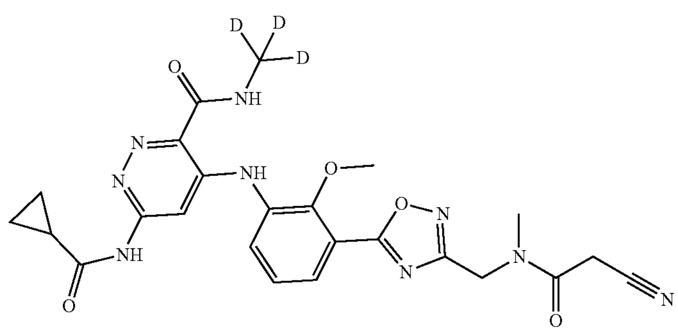 [SMILES: [2H]C([2H])([2H])NC(=O)c1nnc(NC(=O)C2CC2)cc1Nc1cccc(-c2nc(CN(C)C(=O)CC#N)no2)c1OC] | 522.5 | 523.2 | 1.3 | QC-ACN-AA-XB |
| 172 | 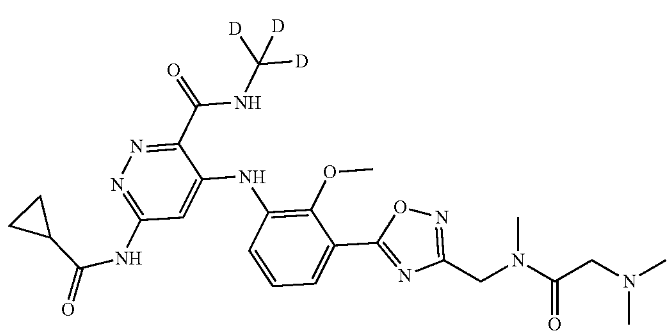 [SMILES: [2H]C([2H])([2H])NC(=O)c1nnc(NC(=O)C2CC2)cc1Nc1cccc(-c2nc(CN(C)C(=O)CN(C)C)no2)c1OC] | 540.6 | 541.3 | 1.26 | QC-ACN-AA-XB |

TABLE 3-continued

| Ex. No. | Structure | MW | Obs. MS Ion | RT | QC Method |
|---|---|---|---|---|---|
| 173 | 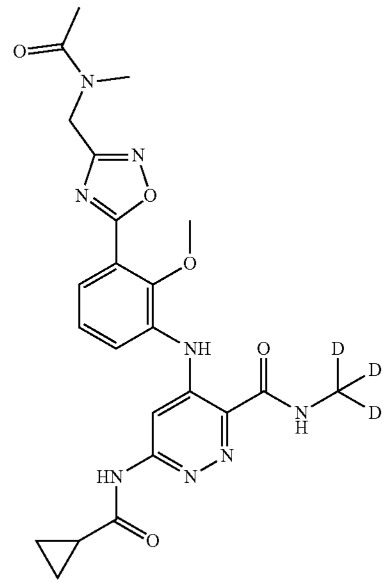 [SMILES: [2H]C([2H])([2H])NC(=O)c1nnc(NC(=O)C2CC2)cc1Nc1cccc(-c2nc(CN(C)C(C)=O)no2)c1OC] | 497.5 | 498.3 | 1.26 | QC-ACN-AA-XB |
| 174 | 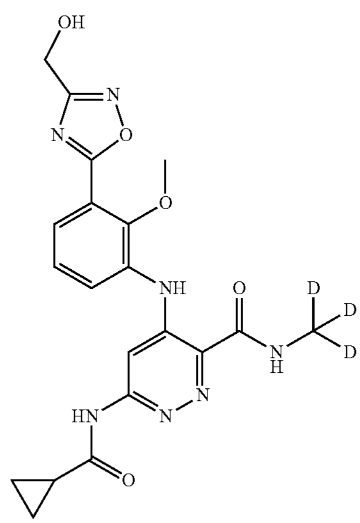 [SMILES: [2H]C([2H])([2H])NC(=O)c1nnc(NC(=O)C2CC2)cc1Nc1cccc(-c2nc(CO)no2)c1OC] | 442.5 | 443. | 1.18 | QC-ACN-AA-XB |
| 175 | 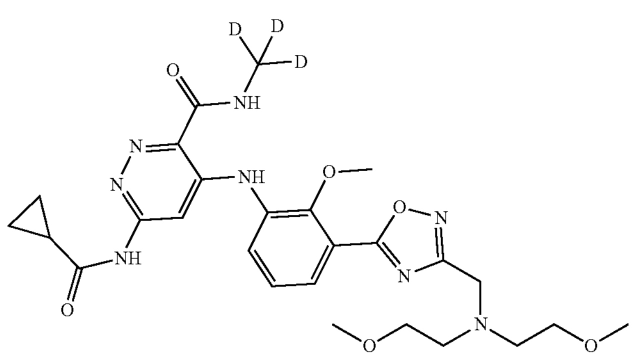 [SMILES: [2H]C([2H])([2H])NC(=O)c1nnc(NC(=O)C2CC2)cc1Nc1cccc(-c2nc(CN(CCOC)CCOC)no2)c1OC] | 557.6 | 558.1 | 1.58 | QC-ACN-AA-XB |

TABLE 3-continued

| Ex. No. | Structure | MW | Obs. MS Ion | RT | QC Method |
|---|---|---|---|---|---|
| 176 | 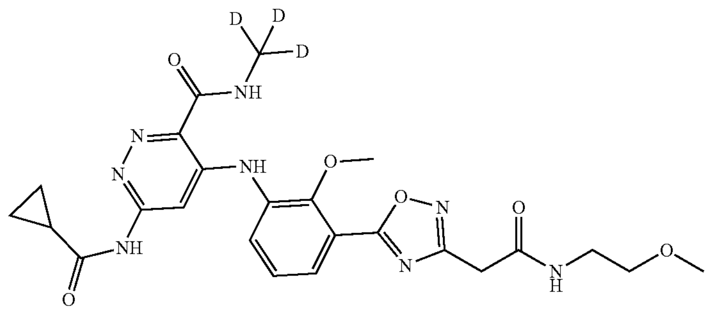 [SMILES: [2H]C([2H])([2H])NC(=O)c1nnc(NC(=O)C2CC2)cc1Nc1cccc(-c2nc(CC(=O)NCCOC)no2)c1OC] | 527.6 | 528.2 | 1.23 | QC-ACN-AA-XB |
| 177 | 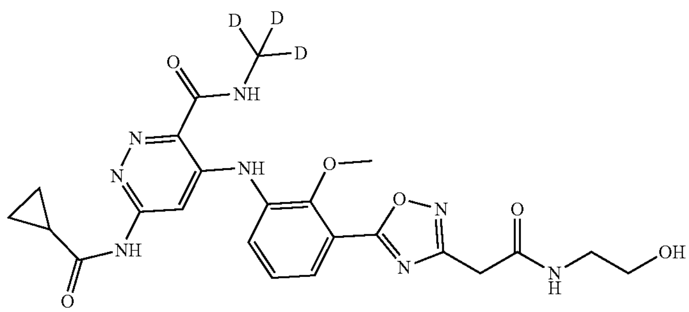 [SMILES: [2H]C([2H])([2H])NC(=O)c1nnc(NC(=O)C2CC2)cc1Nc1cccc(-c2nc(CC(=O)NCCO)no2)c1OC] | 513.5 | 514.2 | 1.09 | QC-ACN-AA-XB |
| 178 | 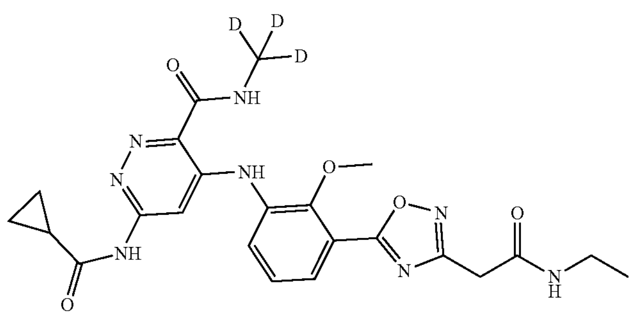 [SMILES: [2H]C([2H])([2H])NC(=O)c1nnc(NC(=O)C2CC2)cc1Nc1cccc(-c2nc(CC(=O)NCC)no2)c1OC] | 497.5 | 498.2 | 1.06 | QC-ACN-TFA-XB |
| 179 | 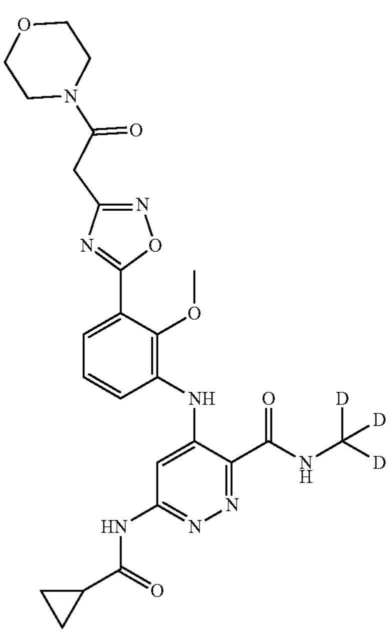 [SMILES: [2H]C([2H])([2H])NC(=O)c1nnc(NC(=O)C2CC2)cc1Nc1cccc(-c2nc(CC(=O)N3CCOCC3)no2)c1OC] | 539.6 | 540.0 | 1.23 | QC-ACN-AA-XB |

TABLE 3-continued

| Ex. No. | Structure | MW | Obs. MS Ion | RT | QC Method |
|---|---|---|---|---|---|
| 180 | 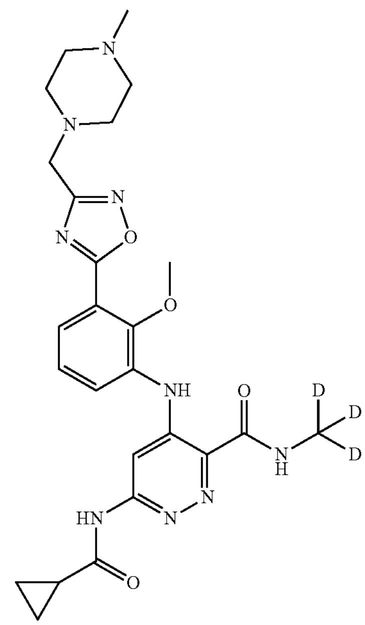 [SMILES: [2H]C([2H])([2H])NC(=O)c1nnc(NC(=O)C2CC2)cc1Nc1cccc(-c2nc(CN3CCN(C)CC3)no2)c1OC] | 524.6 | 525.3 | 1.05 | QC-ACN-AA-XB |
| 181 | 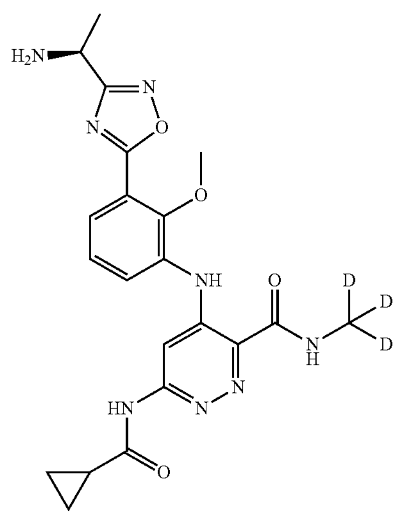 [SMILES: [2H]C([2H])([2H])NC(=O)c1nnc(NC(=O)C2CC2)cc1Nc1cccc(-c2nc([C@H](C)N)no2)c1OC] | 455.5 | 456.0 | 1.1 | QC-ACN-AA-XB |
| 182 | 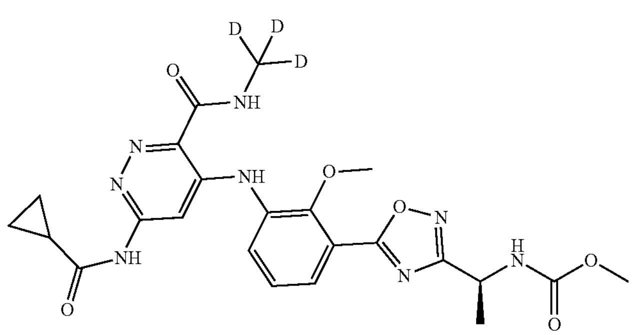 [SMILES: [2H]C([2H])([2H])NC(=O)c1nnc(NC(=O)C2CC2)cc1Nc1cccc(-c2nc([C@H](C)NC(=O)OC)no2)c1OC] | 5135 | 514.2 | 1.38 | QC-ACN-AA-XB |

TABLE 3-continued
| Ex. No. | Structure | MW | Obs. MS Ion | RT | QC Method |
|---|---|---|---|---|---|
| 183 | 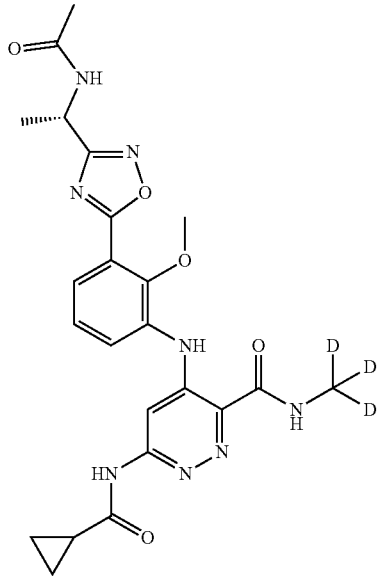 [SMILES: [2H]C([2H])([2H])NC(=O)c1nnc(NC(=O)C2CC2)cc1Nc1cccc(-c2nc([C@H](C)NC(C)=O)no2)c1OC] | 497.5 | 498.4 | 1.01 | QC-ACN-TFA-XB |
| 184 | 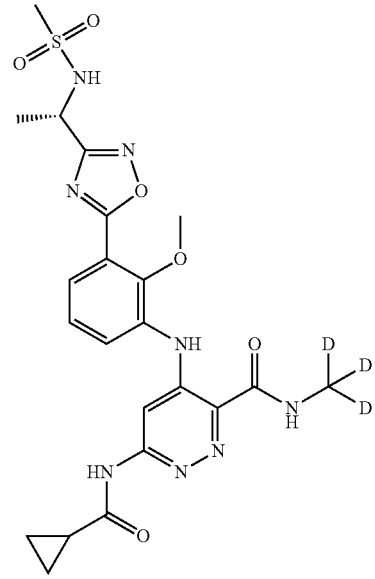 [SMILES: [2H]C([2H])([2H])NC(=O)c1nnc(NC(=O)C2CC2)cc1Nc1cccc(-c2nc([C@H](C)NS(C)(=O)=O)no2)c1OC] | 533.6 | 534.0 | 1.32 | QC-ACN-AA-XB |

TABLE 3-continued

| Ex. No. | Structure | MW | Obs. MS Ion | RT | QC Method |
|---|---|---|---|---|---|
| 185 | 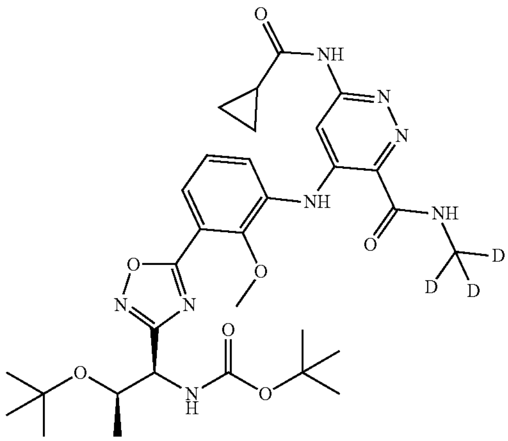 [SMILES: [2H]C([2H])([2H])NC(=O)c1nnc(NC(=O)C2CC2)cc1Nc1cccc(-c2nc([C@@H](NC(=O)OC(C)(C)C)[C@@H](C)OC(C)(C)C)no2)c1OC] | 641.7 | 642.4 | 2.21 | QC-ACN-AA-XB |
| 186 | 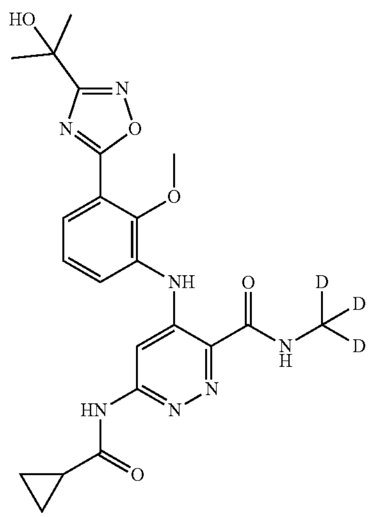 [SMILES: [2H]C([2H])([2H])NC(=O)c1nnc(NC(=O)C2CC2)cc1Nc1cccc(-c2nc(C(C)(C)O)no2)c1OC] | 470.5 | 471.2 | 1.38 | QC-ACN-AA-XB |
| 187 | 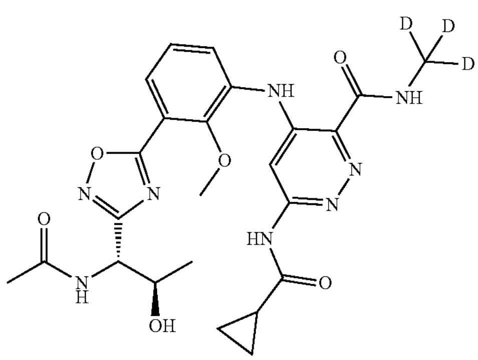 [SMILES: [2H]C([2H])([2H])NC(=O)c1nnc(NC(=O)C2CC2)cc1Nc1cccc(-c2nc([C@@H](NC(C)=O)[C@@H](C)O)no2)c1OC] | 527.6 | 528.2 | 1.16 | QC-ACN-AA-XB |

TABLE 3-continued

| Ex. No. | Structure | MW | Obs. MS Ion | RT | QC Method |
|---|---|---|---|---|---|
| 188 | 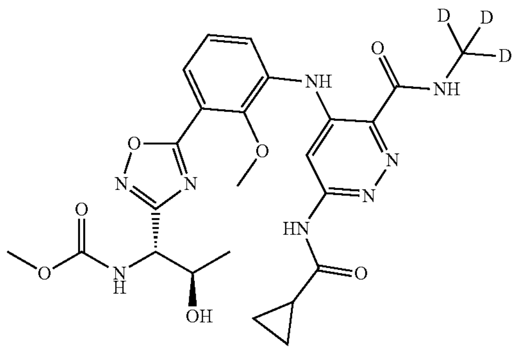 [SMILES: [2H]C([2H])([2H])NC(=O)c1nnc(NC(=O)C2CC2)cc1Nc1cccc(-c2nc([C@@H](NC(=O)OC)[C@@H](C)O)no2)c1OC] | 543.6 | 544.2 | 1.29 | QC-ACN-AA-XB |
| 189 | 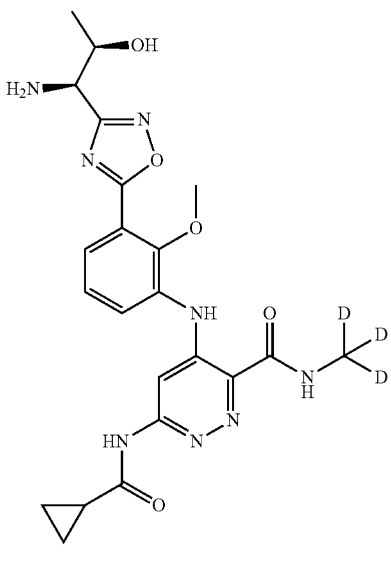 [SMILES: [2H]C([2H])([2H])NC(=O)c1nnc(NC(=O)C2CC2)cc1Nc1cccc(-c2nc([C@@H](N)[C@@H](C)O)no2)c1OC] | 485.5 | 486.4 | 1.07 | QC-ACN-AA-XB |
| 190 | 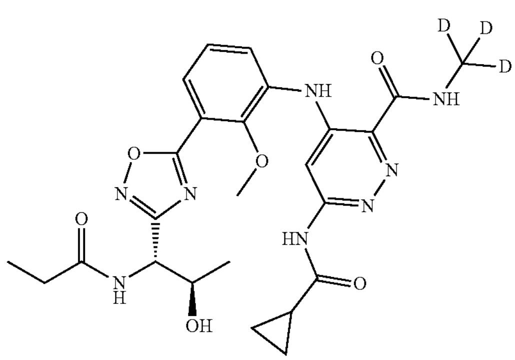 [SMILES: [2H]C([2H])([2H])NC(=O)c1nnc(NC(=O)C2CC2)cc1Nc1cccc(-c2nc([C@@H](NC(=O)CC)[C@@H](C)O)no2)c1OC] | 541.6 | 542.3 | 1.04 | QC-ACN-TFA-XB |

TABLE 3-continued

| Ex. No. | Structure | Obs. MW | MS Ion | RT | QC Method |
|---|---|---|---|---|---|
| 191 | 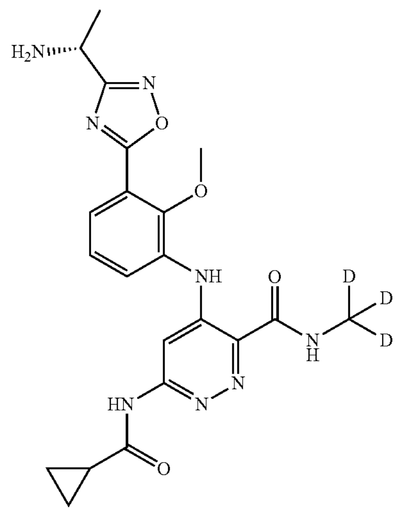 [SMILES: [2H]C([2H])([2H])NC(=O)c1nnc(NC(=O)C2CC2)cc1Nc1cccc(-c2nc([C@@H](C)N)no2)c1OC] | 455.5 | 456.4 | 1.14 | QC-ACN-AA-XB |
| 192 | 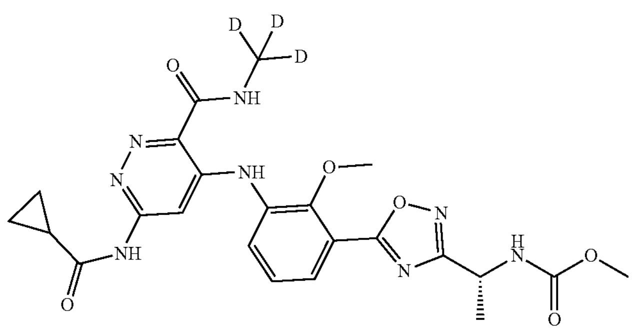 [SMILES: [2H]C([2H])([2H])NC(=O)c1nnc(NC(=O)C2CC2)cc1Nc1cccc(-c2nc([C@@H](C)NC(=O)OC)no2)c1OC] | 513.5 | 514.2 | 1.2 | QC-ACN-TFA-XB |
| 193 | 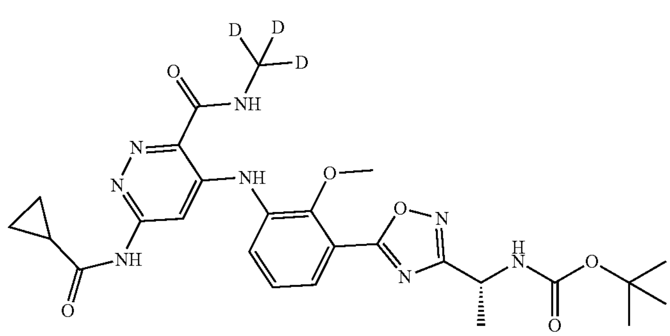 [SMILES: [2H]C([2H])([2H])NC(=O)c1nnc(NC(=O)C2CC2)cc1Nc1cccc(-c2nc([C@@H](C)NC(=O)OC(C)(C)C)no2)c1OC] | 555.6 | 556.3 | 1.76 | QC-ACN-AA-XB |

TABLE 3-continued

| Ex. No. | Structure | MW | Obs. MS Ion | RT | QC Method |
|---|---|---|---|---|---|
| 194 | 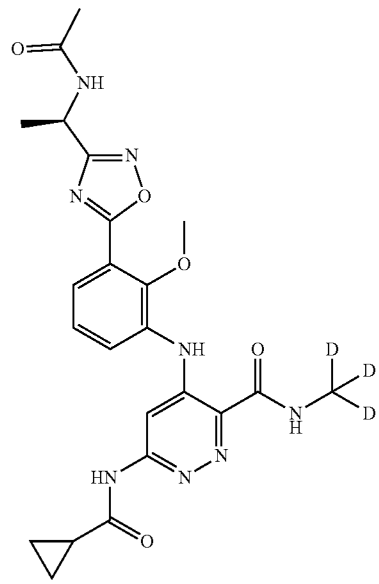 [SMILES: [2H]C([2H])([2H])NC(=O)c1nnc(NC(=O)C2CC2)cc1Nc1cccc(-c2nc([C@@H](C)NC(C)=O)no2)c1OC] | 497.5 | 498.2 | 1.21 | QC-ACN-AA-XB |
| 195 | 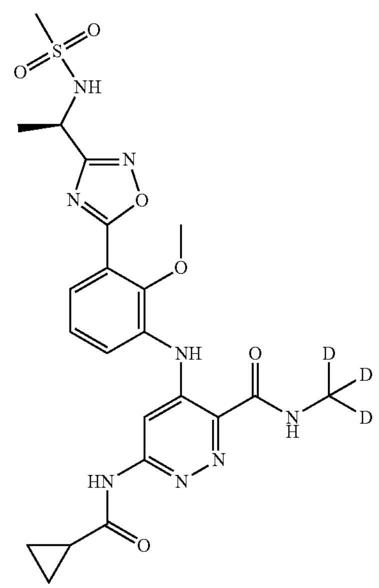 [SMILES: [2H]C([2H])([2H])NC(=O)c1nnc(NC(=O)C2CC2)cc1Nc1cccc(-c2nc([C@@H](C)NS(C)(=O)=O)no2)c1OC] | 533.6 | 534.2 | 1.33 | QC-ACN-AA-XB |
| 196 | 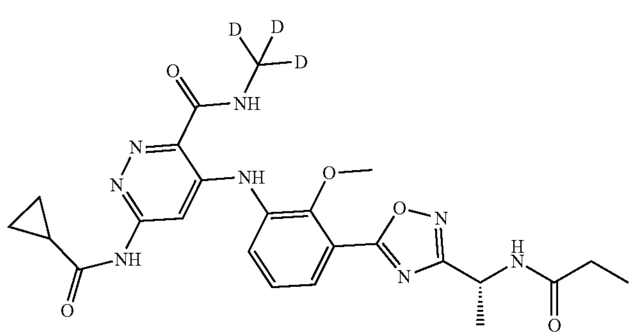 [SMILES: [2H]C([2H])([2H])NC(=O)c1nnc(NC(=O)C2CC2)cc1Nc1cccc(-c2nc([C@@H](C)NC(=O)CC)no2)c1OC] | 511.6 | 512.3 | 1.32 | QC-ACN-AA-XB |

TABLE 3-continued

| Ex. No. | Structure | MW | Obs. MS Ion | RT | QC Method |
|---|---|---|---|---|---|
| 197 | 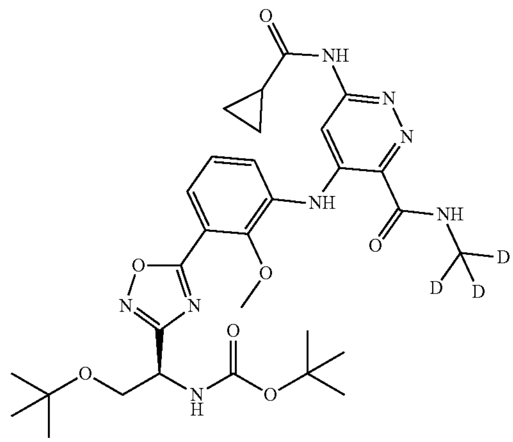 [SMILES: [2H]C([2H])([2H])NC(=O)c1nnc(NC(=O)C2CC2)cc1Nc1cccc(-c2nc([C@H](COC(C)(C)C)NC(=O)OC(C)(C)C)no2)c1OC] | 627.7 | 628.3 | 1.85 | QC-ACN-TFA-XB |
| 198 | 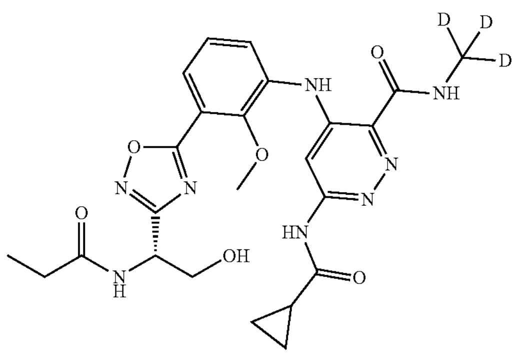 [SMILES: [2H]C([2H])([2H])NC(=O)c1nnc(NC(=O)C2CC2)cc1Nc1cccc(-c2nc([C@H](CO)NC(=O)CC)no2)c1OC] | 527.6 | 528.2 | 1.13 | QC-ACN-AA-XB |
| 199 | 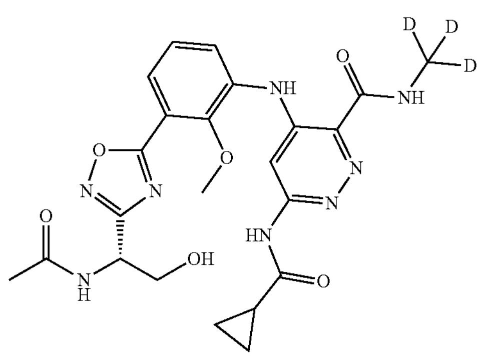 [SMILES: [2H]C([2H])([2H])NC(=O)c1nnc(NC(=O)C2CC2)cc1Nc1cccc(-c2nc([C@H](CO)NC(C)=O)no2)c1OC] | 513.5 | 514.1 | 1.1 | QC-ACN-AA-XB |

TABLE 3-continued

| Ex. No. | Structure | MW | Obs. MS Ion | RT | QC Method |
|---|---|---|---|---|---|
| 200 | 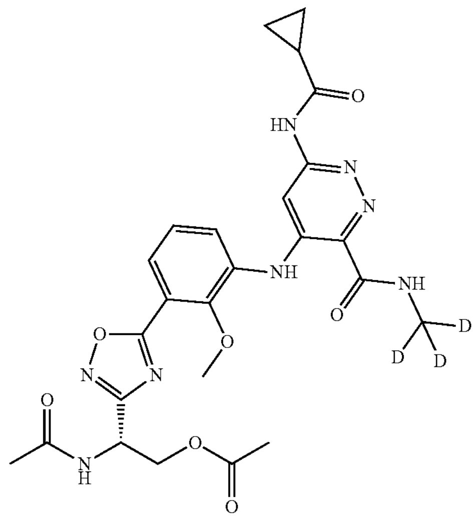 [SMILES: [2H]C([2H])([2H])NC(=O)c1nnc(NC(=O)C2CC2)cc1Nc1cccc(-c2nc([C@H](COC(C)=O)NC(C)=O)no2)c1OC] | 555.6 | 556.0 | 1.41 | QC-ACN-AA-XB |
| 201 | 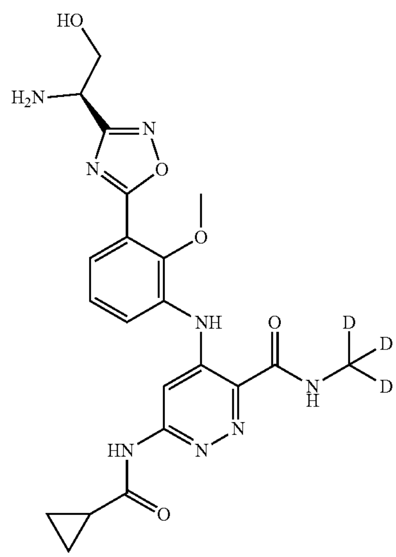 [SMILES: [2H]C([2H])([2H])NC(=O)c1nnc(NC(=O)C2CC2)cc1Nc1cccc(-c2nc([C@@H](N)CO)no2)c1OC] | 471.5 | 472.2 | 0.8 | QC-ACN-TFA-XB |
| 202 | 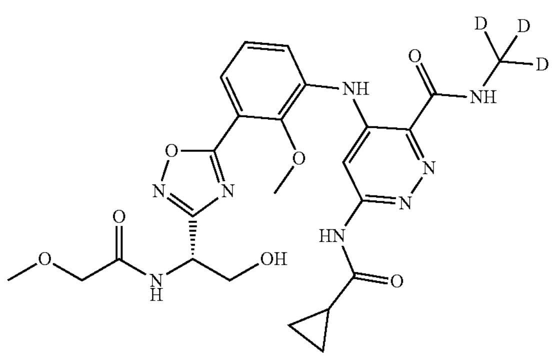 [SMILES: [2H]C([2H])([2H])NC(=O)c1nnc(NC(=O)C2CC2)cc1Nc1cccc(-c2nc([C@H](CO)NC(=O)COC)no2)c1OC] | 543.6 | 544.2 | 0.99 | QC-ACN-TFA-XB |

TABLE 3-continued

| Ex. No. | Structure | MW | Obs. MS Ion | RT | QC Method |
|---|---|---|---|---|---|
| 203 | 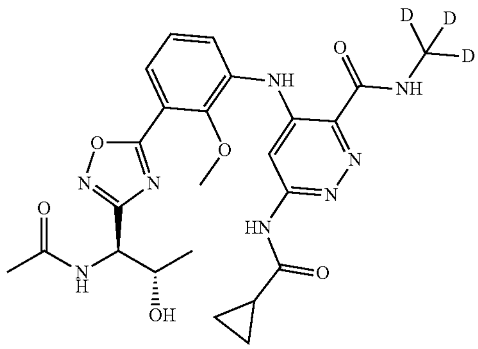 [SMILES: [2H]C([2H])([2H])NC(=O)c1nnc(NC(=O)C2CC2)cc1Nc1cccc(-c2nc([C@H](NC(C)=O)[C@H](C)O)no2)c1OC] | 527.6 | 528.1 | 1.16 | QC-ACN-AA-XB |
| 204 | 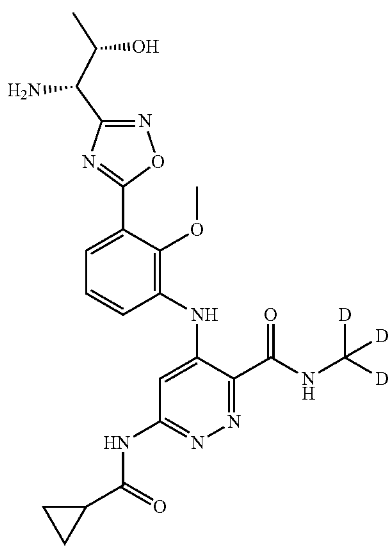 [SMILES: [2H]C([2H])([2H])NC(=O)c1nnc(NC(=O)C2CC2)cc1Nc1cccc(-c2nc([C@H](N)[C@H](C)O)no2)c1OC] | 485.5 | 486.2 | 1.07 | QC-ACN-AA-XB |
| 205 | 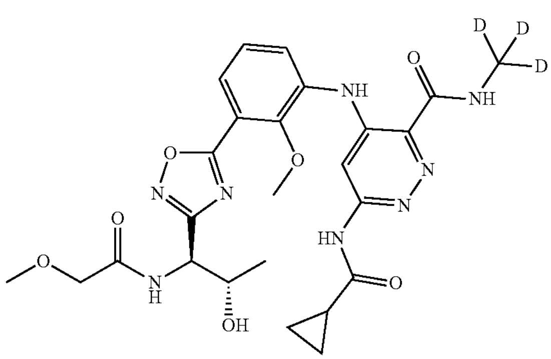 [SMILES: [2H]C([2H])([2H])NC(=O)c1nnc(NC(=O)C2CC2)cc1Nc1cccc(-c2nc([C@H](NC(=O)COC)[C@H](C)O)no2)c1OC] | 557.6 | 558.2 | 1.07 | QC-ACN-TFA-XB |

TABLE 3-continued

| Ex. No. | Structure | MW | Obs. MS Ion | RT | QC Method |
|---|---|---|---|---|---|
| 206 | 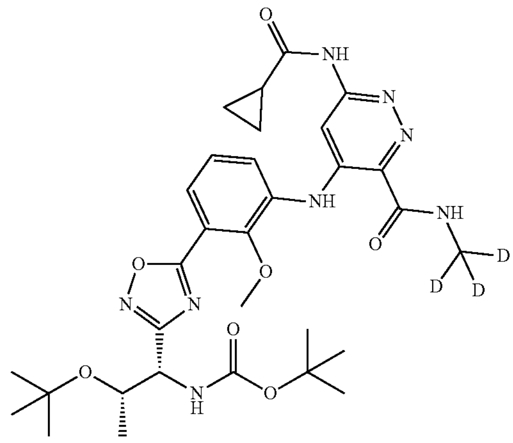 [SMILES: [2H]C([2H])([2H])NC(=O)c1nnc(NC(=O)C2CC2)cc1Nc1cccc(-c2nc([C@H](NC(=O)OC(C)(C)C)[C@H](C)OC(C)(C)C)no2)c1OC] | 641.7 | 642.2 | 1.99 | QC-ACN-TFA-XB |
| 207 | 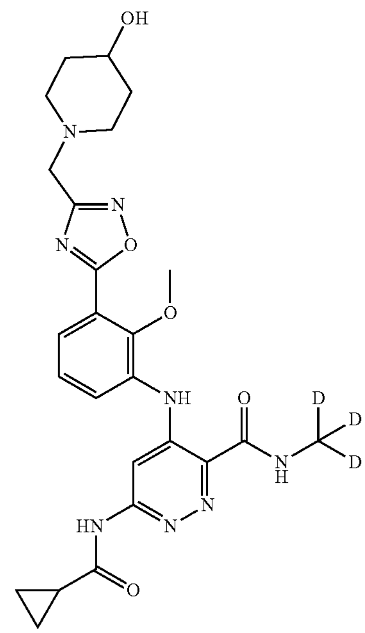 [SMILES: [2H]C([2H])([2H])NC(=O)c1nnc(NC(=O)C2CC2)cc1Nc1cccc(-c2nc(CN3CCC(O)CC3)no2)c1OC] | 525.6 | 526.2 | 0.83 | QC-ACN-TFA-XB |
| 208 | 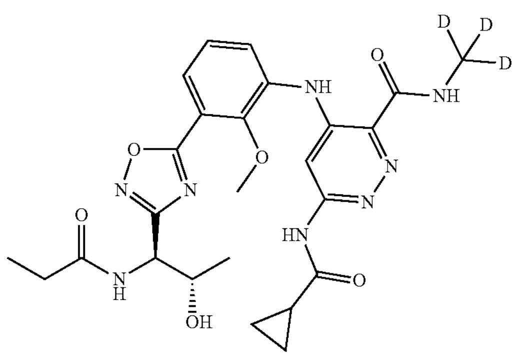 [SMILES: [2H]C([2H])([2H])NC(=O)c1nnc(NC(=O)C2CC2)cc1Nc1cccc(-c2nc([C@H](NC(=O)CC)[C@H](C)O)no2)c1OC] | 541.6 | 542.2 | 1.06 | QC-ACN-TFA-XB |

TABLE 3-continued
| Ex. No. | Structure | MW | Obs. MS Ion | RT | QC Method |
|---|---|---|---|---|---|
| 209 | 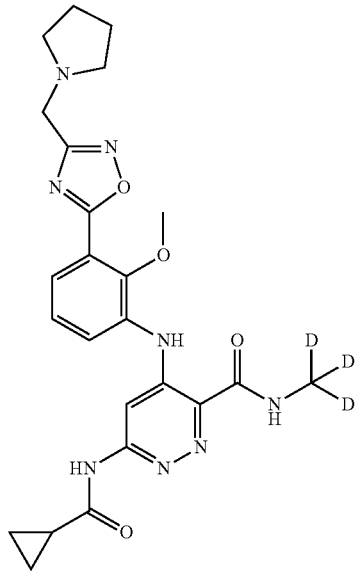 [SMILES: [2H]C([2H])([2H])NC(=O)c1nnc(NC(=O)C2CC2)cc1Nc1cccc(-c2nc(CN3CCCC3)no2)c1OC] | 495.6 | 496.2 | 1.45 | QC-ACN-AA-XB |
| 210 | 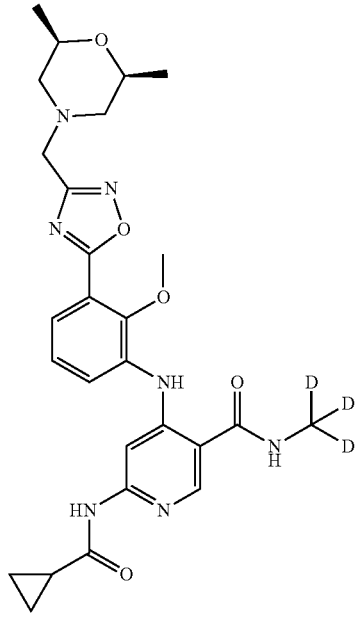 [SMILES: [2H]C([2H])([2H])NC(=O)c1cnc(NC(=O)C2CC2)cc1Nc1cccc(-c2nc(CN3C[C@@H](C)O[C@@H](C)C3)no2)c1OC] | 538.6 | 539.2 | 1.61 | QC-ACN-AA-XB |

TABLE 3-continued
| Ex. No. | Structure | MW | Obs. MS Ion | RT | QC Method |
|---|---|---|---|---|---|
| 211 | 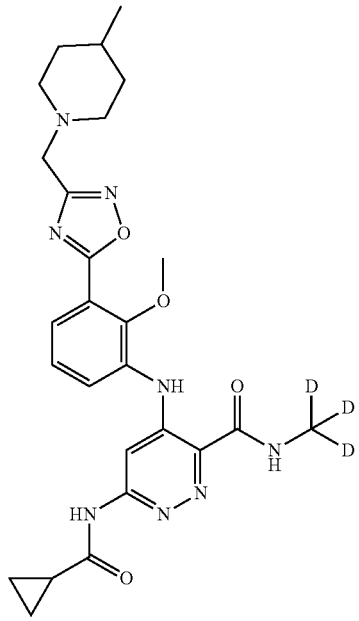 [SMILES: [2H]C([2H])([2H])NC(=O)c1nnc(NC(=O)C2CC2)cc1Nc1cccc(-c2nc(CN3CCC(C)CC3)no2)c1OC] | 523.6 | 524.2 | 1.12 | QC-ACN-TFA-XB |
| 212 | 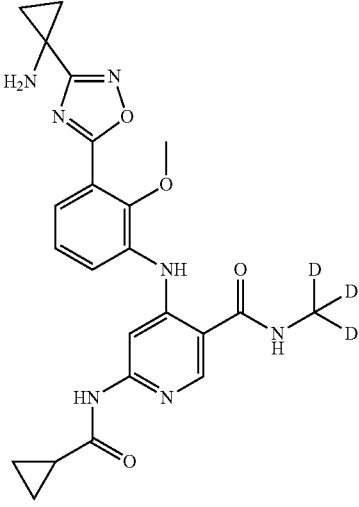 | 466.5 | 467.2 | 1.34 | QC-ACN-AA-XB |
| 213 | 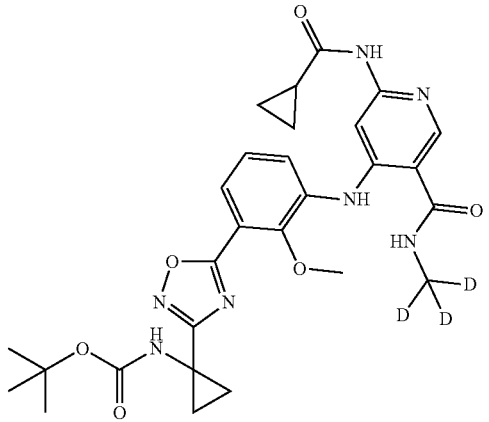 [SMILES: [2H]C([2H])([2H])NC(=O)c1cnc(NC(=O)C2CC2)cc1Nc1cccc(-c2nc(C3(NC(=O)OC(C)(C)C)CC3)no2)c1OC] | 566.6 | 567.1 | 1.71 | QC-ACN-AA-XB |

TABLE 3-continued
| Ex. No. | Structure | MW | Obs. MS Ion | RT | QC Method |
|---|---|---|---|---|---|
| 214 | 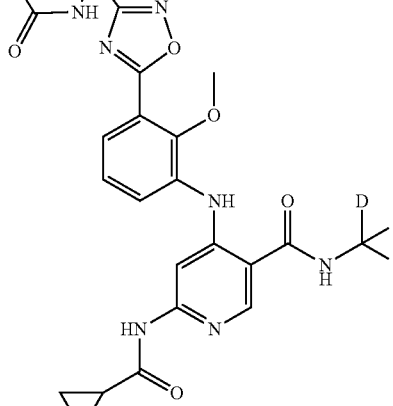 | 508.6 | 509.1 | 0.91 | QC-ACN-TFA-XB |
| 215 | 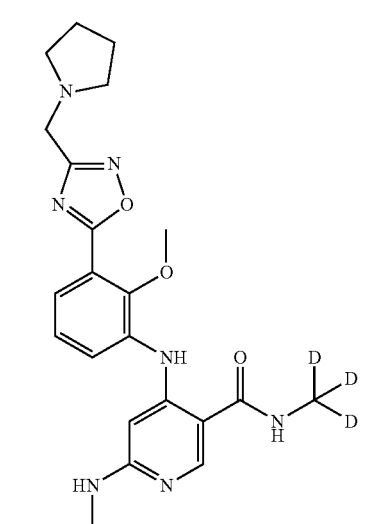 | 494.6 | 495.2 | 1.51 | QC-ACN-AA-XB |
| 216 | 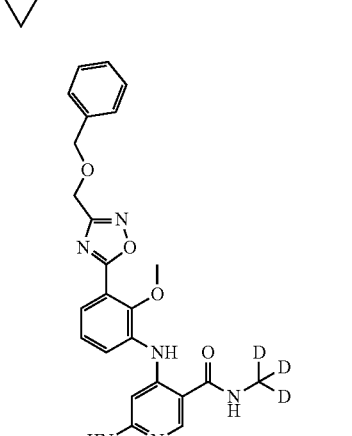 | 531.6 | 532.2 | 1.83 | QC-ACN-AA-XB |

TABLE 3-continued

| Ex. No. | Structure | MW | Obs. MS Ion | RT | QC Method |
|---|---|---|---|---|---|
| 217 | 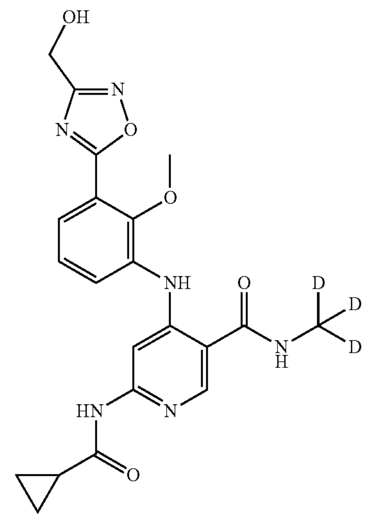 [SMILES: [2H]C([2H])([2H])NC(=O)c1cnc(NC(=O)C2CC2)cc1Nc1cccc(-c2nc(CO)no2)c1OC] | 441.5 | 442.1 | 0.83 | QC-ACN-TFA-XB |
| 218 | 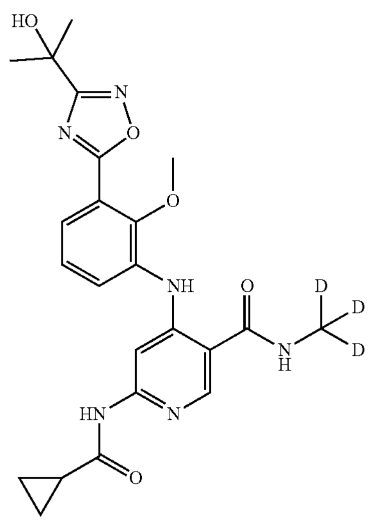 [SMILES: [2H]C([2H])([2H])NC(=O)c1cnc(NC(=O)C2CC2)cc1Nc1cccc(-c2nc(C(C)(C)O)no2)c1OC] | 469.5 | 470.2 | 1.39 | QC-ACN-AA-XB |
| 219 | 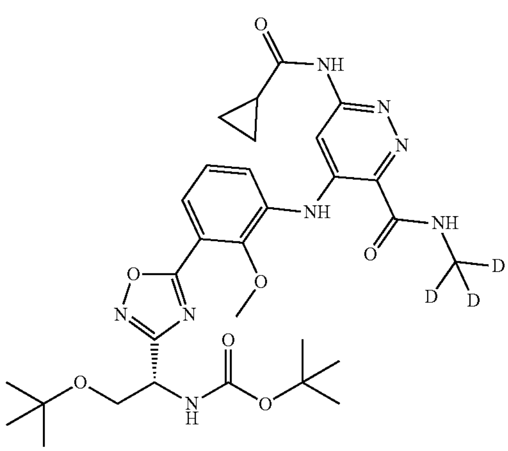 [SMILES: [2H]C([2H])([2H])NC(=O)c1nnc(NC(=O)C2CC2)cc1Nc1cccc(-c2nc([C@@H](COC(C)(C)C)NC(=O)OC(C)(C)C)no2)c1OC] | 627.7 | 628.4 | 2.09 | QC-ACN-AA-XB |

TABLE 3-continued

| Ex. No. | Structure | MW | Obs. MS Ion | RT | QC Method |
|---|---|---|---|---|---|
| 220 | 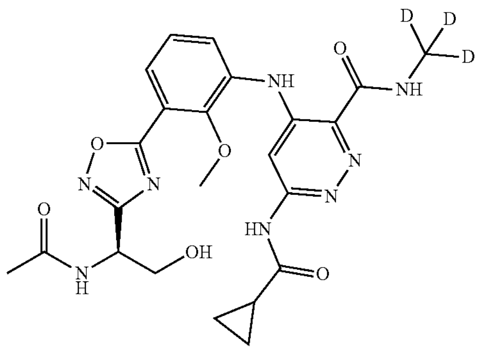 [SMILES: [2H]C([2H])([2H])NC(=O)c1nnc(NC(=O)C2CC2)cc1Nc1cccc(-c2nc([C@@H](CO)NC(C)=O)no2)c1OC] | 513.5 | 514.3 | 1.03 | QC-ACN-AA-XB |
| 221 | 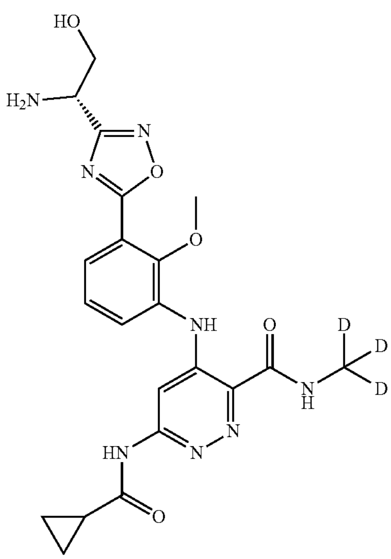 [SMILES: [2H]C([2H])([2H])NC(=O)c1nnc(NC(=O)C2CC2)cc1Nc1cccc(-c2nc([C@H](N)CO)no2)c1OC] | 471.5 | 472.2 | 1 | QC-ACN-AA-XB |
| 222 | 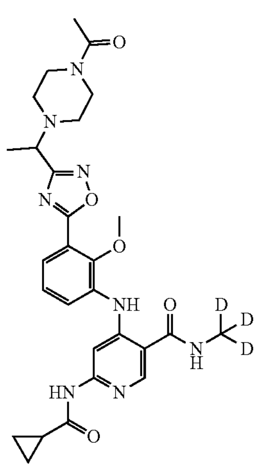 [SMILES: [2H]C([2H])([2H])NC(=O)c1cnc(NC(=O)C2CC2)cc1Nc1cccc(-c2nc(C(C)N3CCN(C(C)=O)CC3)no2)c1OC] | 565.6 | 566.2 | 1.28 | QC-ACN-AA-XB |

TABLE 3-continued
| Ex. No. | Structure | MW | Obs. MS Ion | RT | QC Method |
|---|---|---|---|---|---|
| 223 | 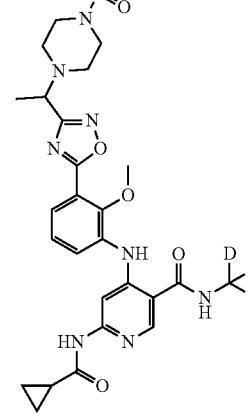 | 601.7 | 602.3 | 1.4 | QC-ACN-AA-XB |
| 224 | 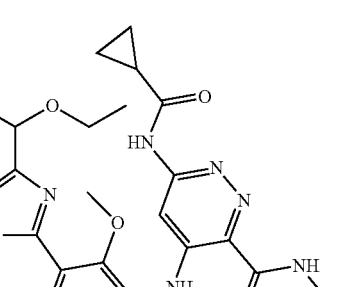 | 514.6 | 515.5 | 1.06 | E |
| 225 | 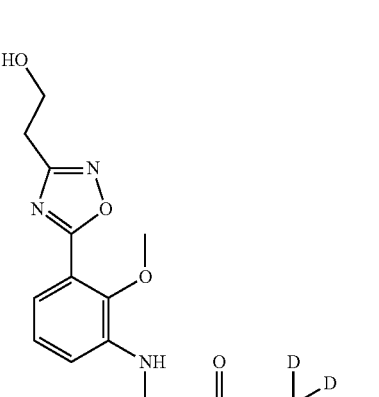 | 456.5 | 457.2 | 1.31 | QC-ACN-AA-XB |

TABLE 3-continued

| Ex. No. | Structure | MW | Obs. MS Ion | RT | QC Method |
|---|---|---|---|---|---|
| 226 | 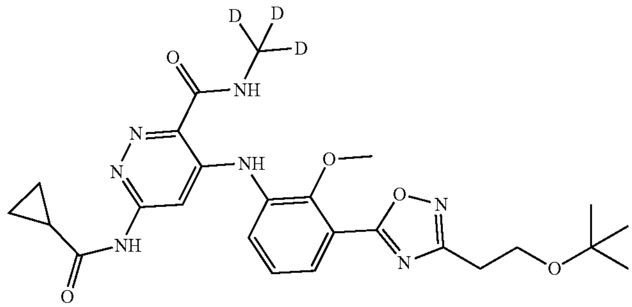 [SMILES: [2H]C([2H])([2H])NC(=O)c1nnc(NC(=O)C2CC2)cc1Nc1cccc(-c2nc(CCOC(C)(C)C)no2)c1OC] | 512.6 | 513.2 | 1.6 | QC-ACN-TFA-XB |
| 227 | 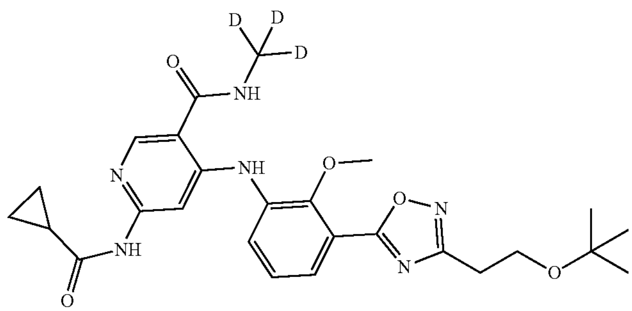 [SMILES: [2H]C([2H])([2H])NC(=O)c1cnc(NC(=O)C2CC2)cc1Nc1cccc(-c2nc(CCOC(C)(C)C)no2)c1OC] | 511.6 | 512.2 | 1.76 | QC-ACN-AA-XB |
| 228 | 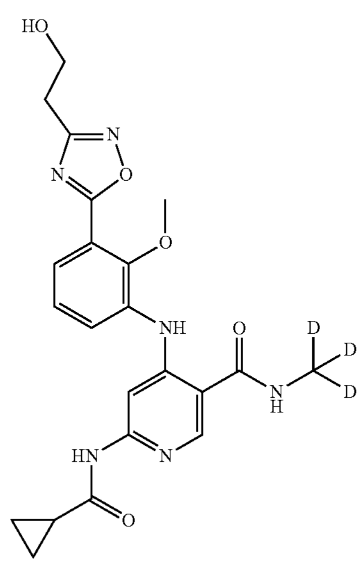 [SMILES: [2H]C([2H])([2H])NC(=O)c1cnc(NC(=O)C2CC2)cc1Nc1cccc(-c2nc(CCO)no2)c1OC] | 455.5 | 456.2 | 1.11 | QC-ACN-AA-XB |

TABLE 3-continued
| Ex. No. | Structure | MW | Obs. MS Ion | RT | QC Method |
|---|---|---|---|---|---|
| 229 | 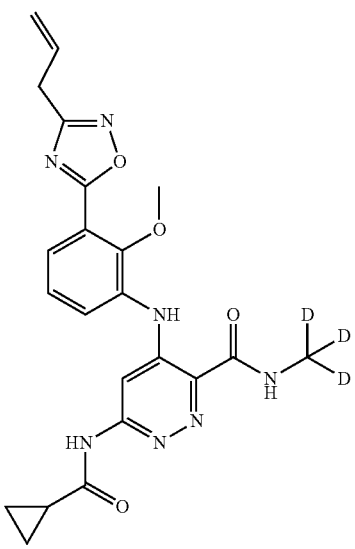 [SMILES: [2H]C([2H])([2H])NC(=O)c1nnc(NC(=O)C2CC2)cc1Nc1cccc(-c2nc(CC=C)no2)c1OC] | 452.5 | 453.1 | 1.86 | QC-ACN-AA-XB |
| 230 | 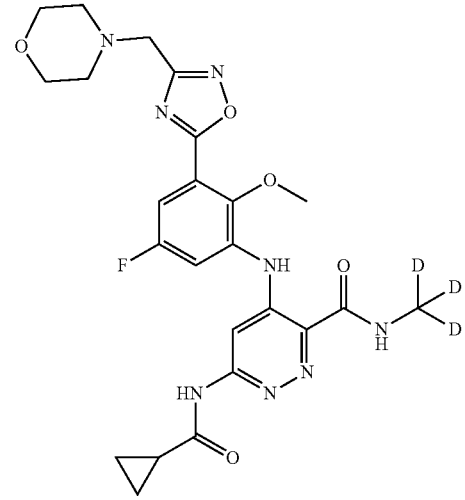 [SMILES: [2H]C([2H])([2H])NC(=O)c1nnc(NC(=O)C2CC2)cc1Nc1cc(F)cc(-c2nc(CN3CCOCC3)no2)c1OC] | 529.5 | 530.2 | 1.53 | QC-ACN-AA-XB |
| 231 | 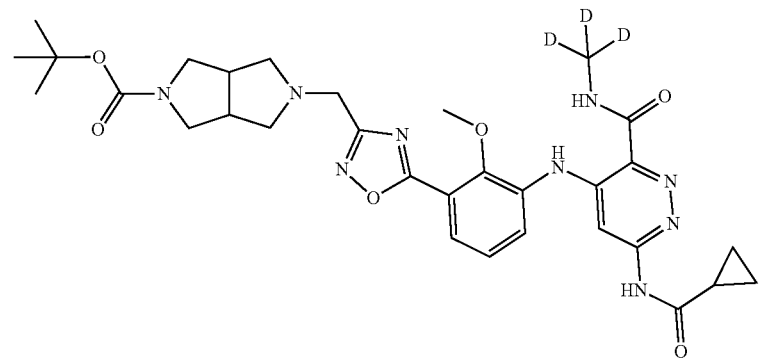 [SMILES: [2H]C([2H])([2H])NC(=O)c1nnc(NC(=O)C2CC2)cc1Nc1cccc(-c2nc(CN3CC4CN(C(=O)OC(C)(C)C)CC4C3)no2)c1OC] | 636.7 | 637.5 | 1.92 | QC-ACN-AA-XB |

TABLE 3-continued

| Ex. No. | Structure | MW | Obs. MS Ion | RT | QC Method |
|---|---|---|---|---|---|
| 232 | 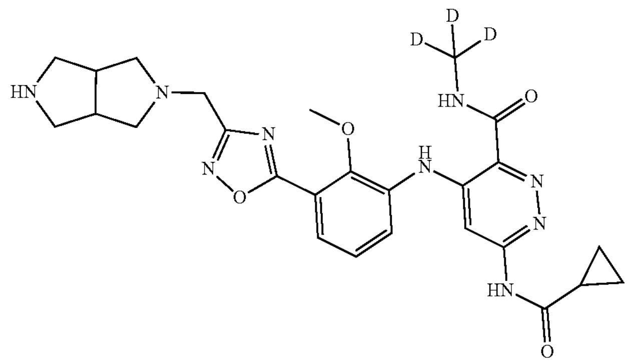 [SMILES: [2H]C([2H])([2H])NC(=O)c1nnc(NC(=O)C2CC2)cc1Nc1cccc(-c2nc(CN3CC4CNCC4C3)no2)c1OC] | 536.6 | 537.2 | 0.72 | QC-ACN-TFA-XB |
| 233 | 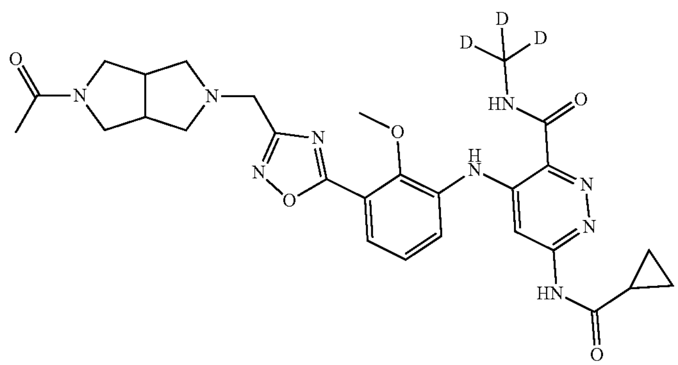 [SMILES: [2H]C([2H])([2H])NC(=O)c1nnc(NC(=O)C2CC2)cc1Nc1cccc(-c2nc(CN3CC4CN(C(C)=O)CC4C3)no2)c1OC] | 578.6 | 579.2 | 1.34 | QC-ACN-AA-XB |
| 234 | 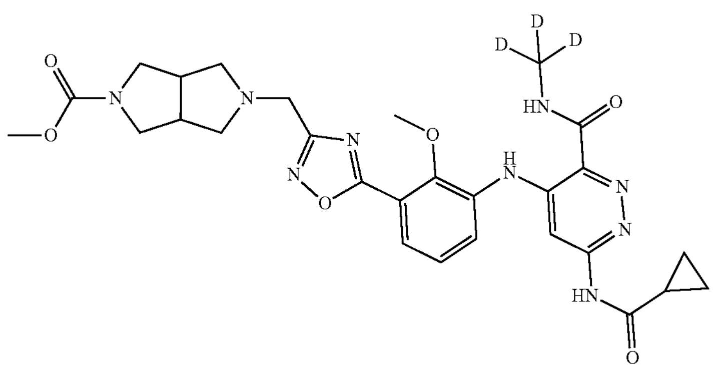 [SMILES: [2H]C([2H])([2H])NC(=O)c1nnc(NC(=O)C2CC2)cc1Nc1cccc(-c2nc(CN3CC4CN(C(=O)OC)CC4C3)no2)c1OC] | 594.6 | 595.4 | 1.56 | QC-ACN-AA-XB |
| 235 | 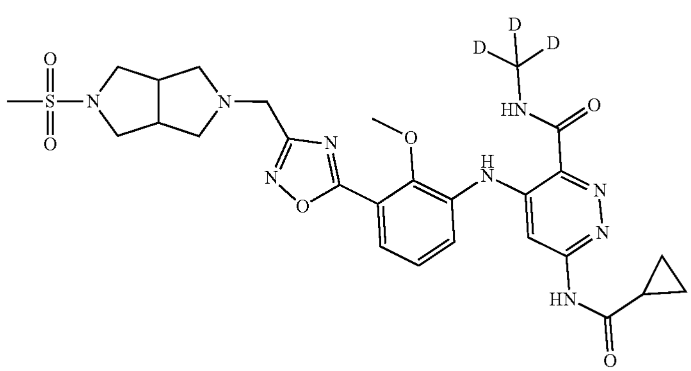 [SMILES: [2H]C([2H])([2H])NC(=O)c1nnc(NC(=O)C2CC2)cc1Nc1cccc(-c2nc(CN3CC4CN(S(C)(=O)=O)CC4C3)no2)c1OC] | 614.7 | 615.1 | 1.23 | QC-ACN-AA-XB |

TABLE 3-continued
| Ex. No. | Structure | MW | Obs. MS Ion | RT | QC Method |
|---|---|---|---|---|---|
| 236 | 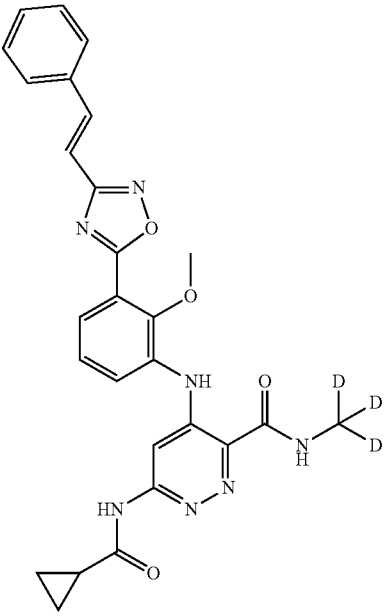 [SMILES: [2H]C([2H])([2H])NC(=O)c1nnc(NC(=O)C2CC2)cc1Nc1cccc(-c2nc(/C=C/c3ccccc3)no2)c1OC] | 514.6 | 515.0 | 2.14 | QC-ACN-AA-XB |
| 237 | 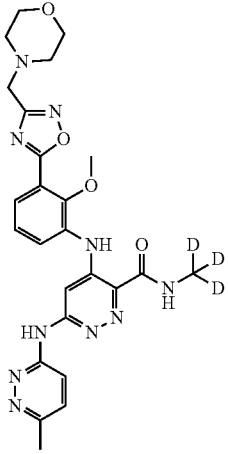 [SMILES: [2H]C([2H])([2H])NC(=O)c1nnc(Nc2ccc(C)nn2)cc1Nc1cccc(-c2nc(CN3CCOCC3)no2)c1OC] | 535.6 | 536.3 | 0.81 | QC-ACN-TFA-XB |
| 238 | 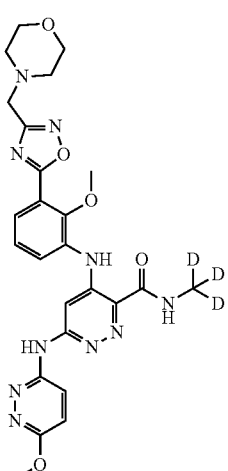 | 551.6 | 552.3 | 0.88 | QC-ACN-TFA-XB |

Example 239
5-(3-((6-(cyclopropanecarboxamido)-3-((methyl-d3)
carbamoyl)pyridazin-4-yl)amino)-2-methoxyphe-
nyl)-N,N-dimethylthiazole-2-carboxamide
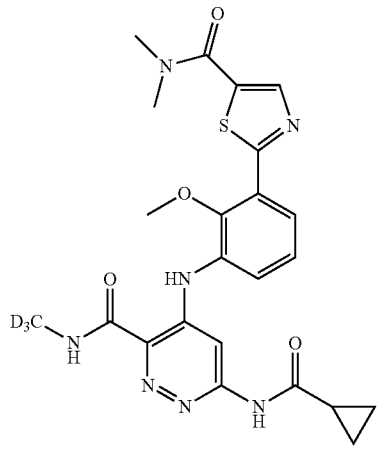
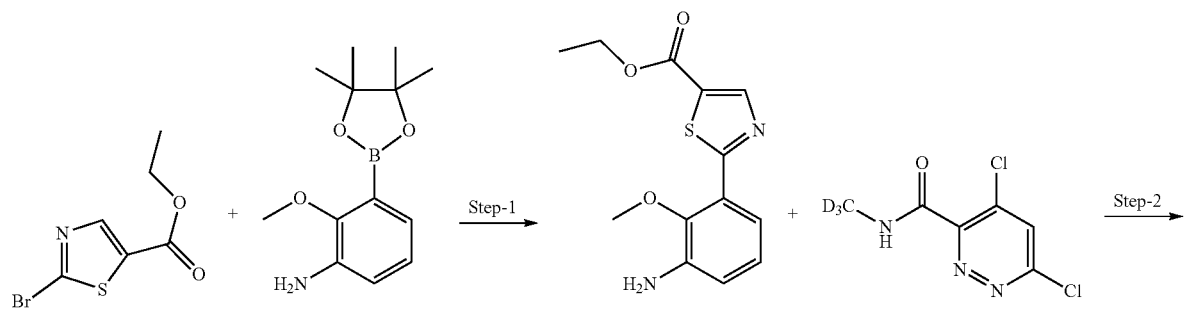
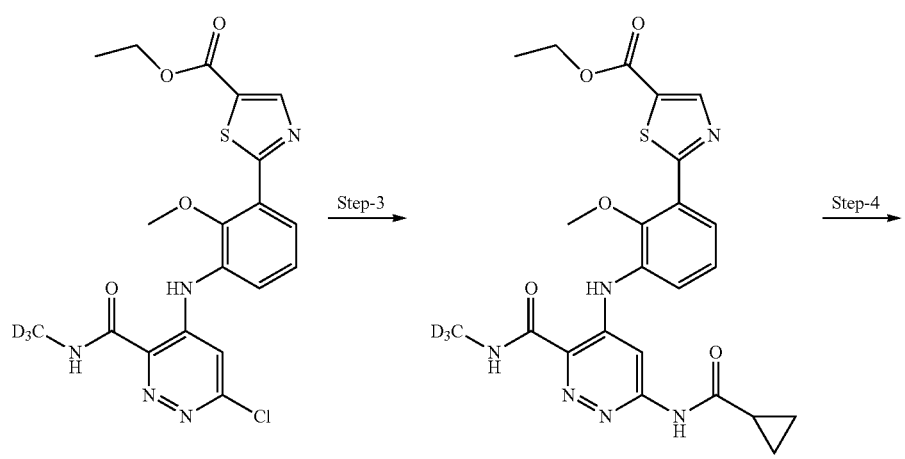

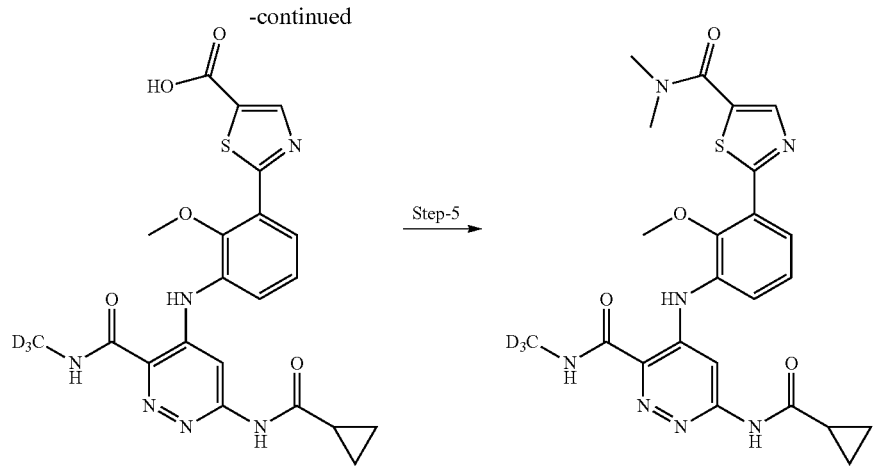

Step 1

A stirred mixture of ethyl 2-bromothiazole-5-carboxylate (116 mg, 0.491 mmol), 2-methoxy-3-(4,4,5,5-tetramethyl-1,3,2-dioxaborolan-2-yl)aniline (135 mg, 0.540 mmol) and 1,1'-bis(di-tert-butylphosphino)ferrocene palladium dichloride (16.01 mg, 0.025 mmol) in Dioxane (4 mL) was degassed by bubbling nitrogen through the mixture for 5 minutes. 2M $K_3PO_4$ (aq) (0.737 mL, 1.474 mmol) was quickly added and the reaction mixture heated at 100° C. for one hour. LC-MS showed complete conversion to the desired product mass. The reaction mixture was cooled to room temperature. The reaction mixture was diluted with EtOAc (75 mL) and then dried over sodium sulfate, filtered, concentrated and purified by flash chromatography, eluting with 0-100% EtOAc in hexanes. This afforded ethyl 2-(3-amino-2-methoxyphenyl)thiazole-5-carboxylate (84 mg, 0.299 mmol, 60.8% yield) as a yellow oil. LCMS m/z 279.2 (M+H)$^+$; HPLC $t_R$ 0.86 min (HPLC Method A).

Step 2

To a solution of 4,6-dichloro-N-trideuteromethylpyridazine-3-carboxamide (62 mg, 0.297 mmol) and ethyl 2-(3-amino-2-methoxyphenyl)thiazole-5-carboxylate (83 mg, 0.297 mmol) in Tetrahydrofuran (2.5 mL) at rt was added dropwise over 5 minutes LiHMDS, 1M (0.741 mL, 0.741 mmol). The resulting solution was stirred at rt for 30 minutes. The reaction mixture was quenched with 1 ml of saturated $NH_4Cl$ solution. The resulting mixture was partitioned between EtOAc (30 ml) and saturated $NH_4Cl$ solution (30 ml). The organic layer was washed with brine (30 ml), dried ($Na_2SO_4$) and concentrated to an amber oil that was chromatographed on a 12 gm ISCO silica gel cartridge, eluting with a 0-60% EtOAc/Hex gradient. The pure fractions were concentrated to afford ethyl 2-(3-((6-chloro-3-(trideuteromethylcarbamoyl)pyridazin-4-yl)amino)-2-methoxyphenyl)thiazole-5-carboxylate (80 mg, 0.176 mmol, 59.2% yield) as a white solid. LCMS m/z 451.2 (M+H)$^+$; HPLC $t_R$ 1.02 min (analytical HPLC Method A).

Step 3

A mixture of 4-(3-((2-chloro-5-(trideuteromethylcarbamoyl)pyridin-4-yl)amino)-5-fluoro-2-methoxyphenyl)-N-(2-methoxyethyl)thiazole-2-carboxamide (80 mg, 0.177 mmol), Xantphos (20.53 mg, 0.035 mmol), and cyclopropanecarboxamide (75 mg, 0.887 mmol) in dioxane (3 mL) was degassed by bubbling $N_2$ through it for 5 minutes. Then $Cs_2CO_3$ (231 mg, 0.710 mmol) and $Pd_2(dba)_3$ (16.25 mg, 0.018 mmol) were added, the vessel was sealed, and the reaction was stirred at 130° C. for 45 minutes. The reaction was complete by LC-MS. The reaction was cooled to room temperature, then concentrated and loaded directly onto a 12 g ISCO column for purification by flash chromatography, eluting with 0-15% MeOH in DCM. This afforded ethyl 2-(3-((6-(cyclopropanecarboxamido)-3-(trideuteromethylcarbamoyl)pyridazin-4-yl)amino)-2-methoxyphenyl)thiazole-5-carboxylate (66 mg, 0.129 mmol, 73.0% yield) as a pale yellow solid. LCMS m/z 500.2 (M+H)$^+$; HPLC $t_R$ 0.89 min (analytical HPLC Method A)

Step 4

To a solution of ethyl 2-(3-((6-(cyclopropanecarboxamido)-3-(trideuteromethylcarbamoyl)pyridazin-4-yl)amino)-2-methoxyphenyl)thiazole-5-carboxylate (41 mg, 0.082 mmol) in THF (2 ml) was added a solution of lithium hydroxide, $H_2O$ (4.13 mg, 0.098 mmol) in water (0.5 mL). The resulting solution was stirred at room temperature over the weekend. The volatiles were removed in vacuo to afford 2-(3-((6-(cyclopropanecarboxamido)-3-((methyl-$d_3$)carbamoyl)pyridazin-4-yl)amino)-2-methoxyphenyl)thiazole-5-carboxylic acid, lithium salt (38 mg, 0.081 mmol, 98% yield) as a yellow solid. Used as is. LCMS m/z 472.4 (M+H)$^+$; HPLC $t_R$ 0.72 min (analytical HPLC Method A).

Step 5

A mixture of 2-(3-((6-(cyclopropanecarboxamido)-3-((methyl-$d_3$)carbamoyl)pyridazin-4-yl)amino)-2-methoxyphenyl)thiazole-5-carboxylic acid, lithium salt (13 mg, 0.028 mmol), dimethylamine, 2M in THF (0.069 mL, 0.138 mmol), BOP (18.29 mg, 0.041 mmol) and $Et_3N$ (0.019 mL, 0.138 mmol) in DMF (0.5 mL) was agitated at rt overnight. The reaction was complete by LC-MS, so the reaction was diluted to 1.5 mL with methanol, then filtered and submitted for purification. This afforded 2-(3-((6-(cyclopropanecarboxamido)-3-(trideuteromethylcarbamoyl)pyridazin-4-yl)amino)-2-methoxyphenyl)-N,N-dimethylthiazole-5-carboxamide (1.9 mg, 3.70 µmol, 13.41% yield) LCMS m/z 499.5 (M+H)$^+$; HPLC $t_R$ 0.72 min (analytical HPLC Method A); $^1$H NMR (500 MHz, DMSO-$d_6$) δ 11.35 (s, 1H), 10.96 (s, 1H), 9.18 (s, 1H), 8.30 (s, 1H), 8.12 (br d, J=8.1 Hz, 1H), 8.06 (s, 1H), 7.59 (br d, J=7.7 Hz, 1H), 7.38 (t, J=7.9 Hz, 1H), 3.80 (s, 3H), 3.53-3.40 (m, 3H), 3.25 (br s, 2H), 3.17 (br s, 1H), 3.04 (br s, 2H), 2.56-2.53 (m, 1H), 2.06 (br s, 1H), 0.86-0.77 (m, 4H)

The Examples in Table 4 were prepared using a similar procedure used to prepare Example 239.

TABLE 4

| Ex. No. | Structure | MW | Obs. MS Ion | RT | QC Method |
|---|---|---|---|---|---|
| 240 | 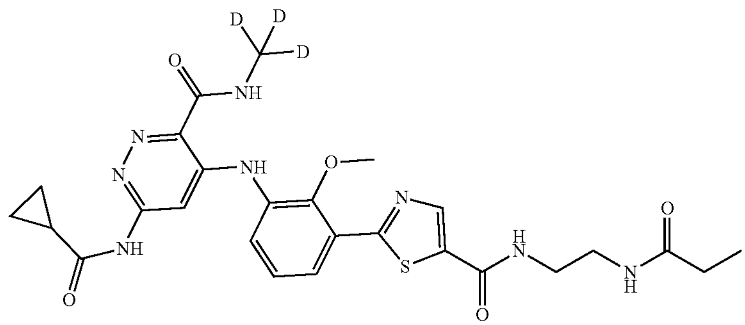 [SMILES: [2H]C([2H])([2H])NC(=O)c1nnc(NC(=O)C2CC2)cc1Nc1cccc(-c2ncc(C(=O)NCCNC(=O)CC)s2)c1OC] | 569.7 | 570.2 | 1.29 | QC-ACN-AA-XB |
| 241 | 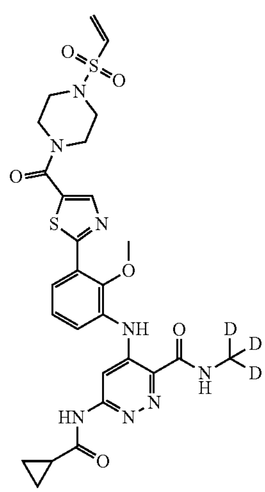 [SMILES: [2H]C([2H])([2H])NC(=O)c1nnc(NC(=O)C2CC2)cc1Nc1cccc(-c2ncc(C(=O)N3CCN(S(=O)(=O)C=C)CC3)s2)c1OC] | 629.7 | 630.3 | 1.36 | QC-ACN-TFA-XB |
| 242 | 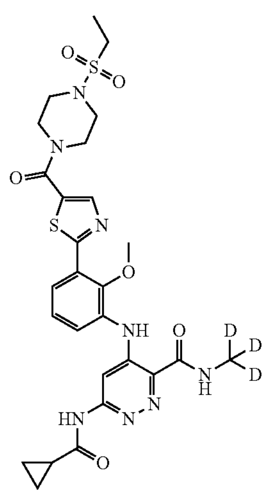 [SMILES: [2H]C([2H])([2H])NC(=O)c1nnc(NC(=O)C2CC2)cc1Nc1cccc(-c2ncc(C(=O)N3CCN(S(=O)(=O)CC)CC3)s2)c1OC] | 631.7 | 632.5 | 1.44 | QC-ACN-AA-XB |

TABLE 4-continued

| Ex. No. | Structure | MW | Obs. MS Ion | RT | QC Method |
|---|---|---|---|---|---|
| 243 | 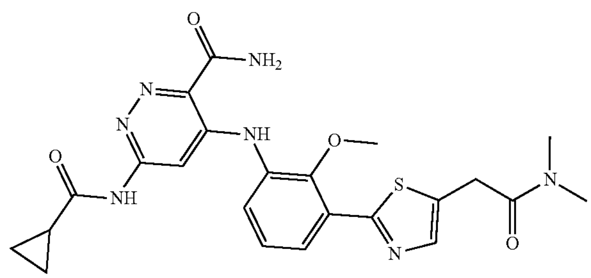 [SMILES: COc1c(Nc2cc(NC(=O)C3CC3)nnc2C(N)=O)cccc1-c1ncc(CC(=O)N(C)C)s1] | 495.6 | 496.2 | 0.99 | QC-ACN-TFA-XB |
| 244 | 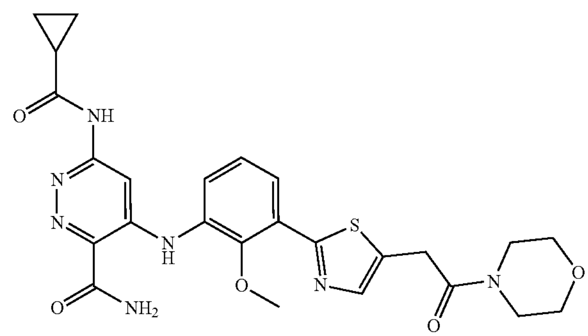 [SMILES: COc1c(Nc2cc(NC(=O)C3CC3)nnc2C(N)=O)cccc1-c1ncc(CC(=O)N2CCOCC2)s1] | 537.6 | 538.2 | 1.08 | QC-ACN-TFA-XB |
| 245 | 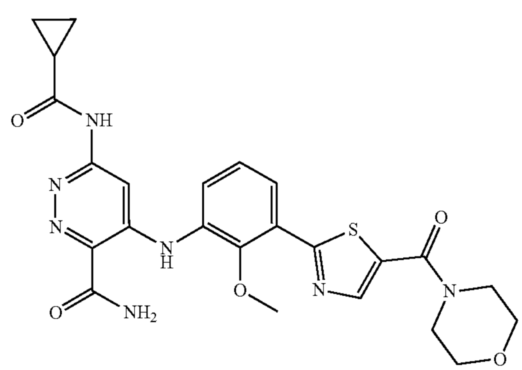 [SMILES: COc1c(Nc2cc(NC(=O)C3CC3)nnc2C(N)=O)cccc1-c1ncc(C(=O)N2CCOCC2)s1] | 523.6 | 524.2 | 5.8 | I |
| 246 | 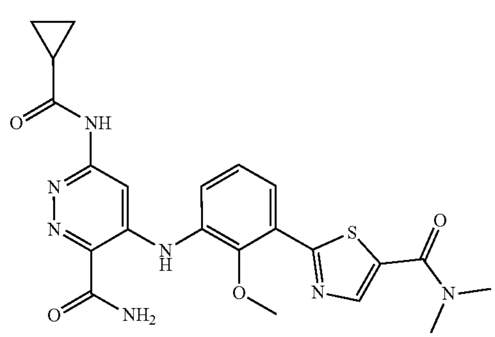 [SMILES: COc1c(Nc2cc(NC(=O)C3CC3)nnc2C(N)=O)cccc1-c1ncc(C(=O)N(C)C)s1] | 481.5 | 482.1 | 5.8 | I |

TABLE 4-continued
| Ex. No. | Structure | MW | Obs. MS Ion | RT | QC Method |
|---|---|---|---|---|---|
| 247 | 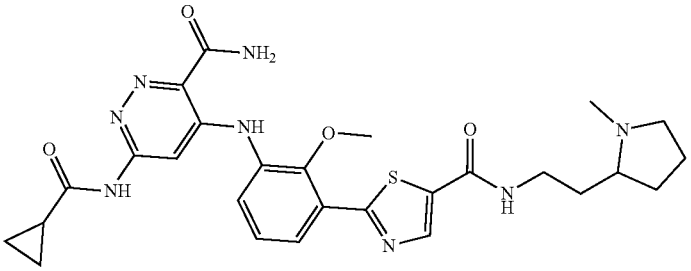 [SMILES: COc1c(Nc2cc(NC(=O)C3CC3)nnc2C(N)=O)cccc1-c1ncc(C(=O)NCCC2CCCN2C)s1] | 564.7 | 565.2 | 4.4 | I |
| 248 | 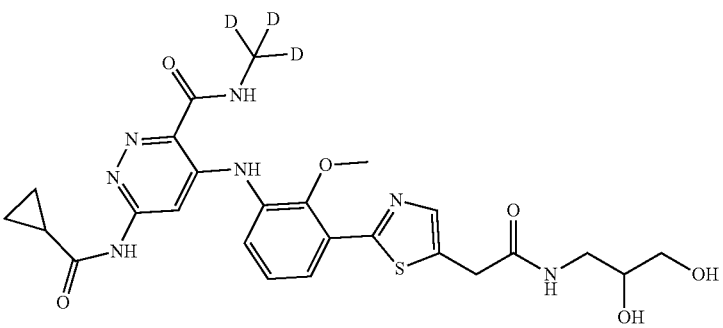 [SMILES: [2H]C([2H])([2H])NC(=O)c1nnc(NC(=O)C2CC2)cc1Nc1cccc(-c2ncc(CC(=O)NCC(O)CO)s2)c1OC] | 558.6 | 559.2 | 1.11 | QC-ACN-AA-XB |
| 249 | 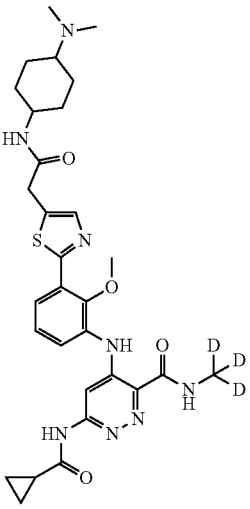 [SMILES: [2H]C([2H])([2H])NC(=O)c1nnc(NC(=O)C2CC2)cc1Nc1cccc(-c2ncc(CC(=O)NC3CCC(N(C)C)CC3)s2)c1OC] | 609.8 | 610.3 | 5.63 | I |

TABLE 4-continued

| Ex. No. | Structure | MW | Obs. MS Ion | RT | QC Method |
|---|---|---|---|---|---|
| 250 | 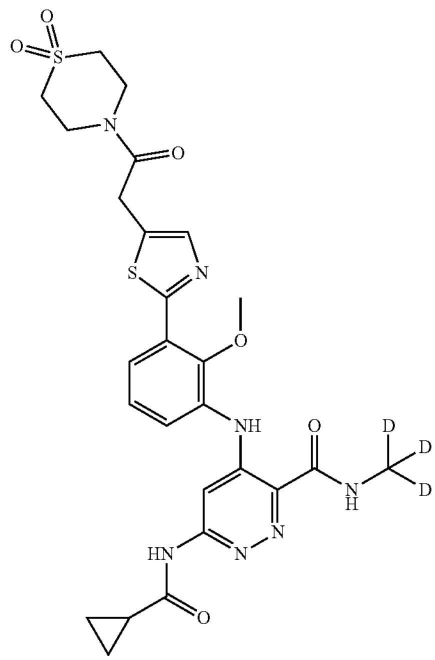 [SMILES: [2H]C([2H])([2H])NC(=O)c1nnc(NC(=O)C2CC2)cc1Nc1cccc(-c2ncc(CC(=O)N3CCS(=O)(=O)CC3)s2)c1OC] | 602.7 | 603.1 | 1.03 | QC-ACN-TFA-XB |
| 251 | 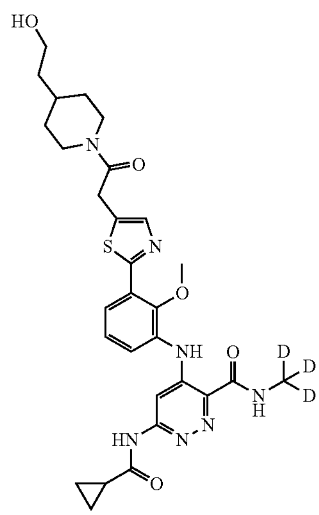 [SMILES: [2H]C([2H])([2H])NC(=O)c1nnc(NC(=O)C2CC2)cc1Nc1cccc(-c2ncc(CC(=O)N3CCC(CCO)CC3)s2)c1OC] | 596.7 | 597.3 | 1.37 | QC-ACN-AA-XB |
| 252 | 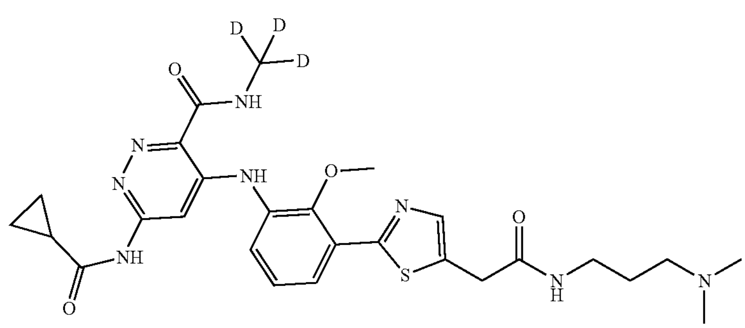 [SMILES: [2H]C([2H])([2H])NC(=O)c1nnc(NC(=O)C2CC2)cc1Nc1cccc(-c2ncc(CC(=O)NCCCN(C)C)s2)c1OC] | 569.7 | 570.1 | 1.12 | QC-ACN-AA-XB |

… TABLE 4-continued
| Ex. No. | Structure | MW | Obs. MS Ion | RT | QC Method |
|---|---|---|---|---|---|
| 253 | 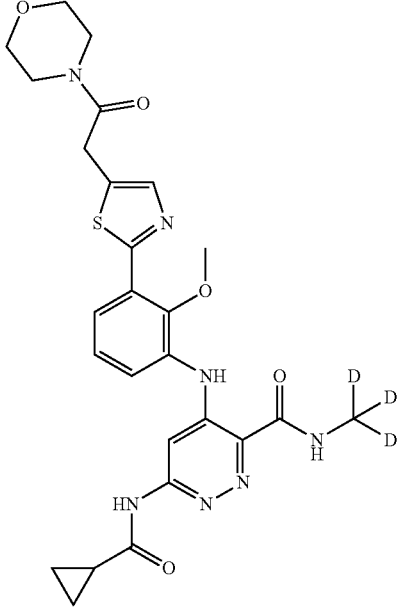 [SMILES: [2H]C([2H])([2H])NC(=O)c1nnc(NC(=O)C2CC2)cc1Nc1cccc(-c2ncc(CC(=O)N3CCOCC3)s2)c1OC] | 554.6 | 555.3 | 1.35 | QC-ACN-AA-XB |
| 254 | 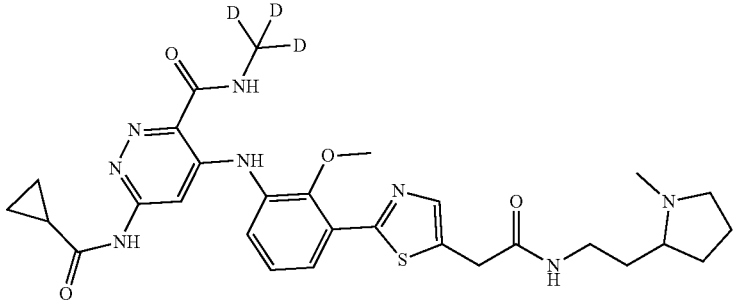 [SMILES: [2H]C([2H])([2H])NC(=O)c1nnc(NC(=O)C2CC2)cc1Nc1cccc(-c2ncc(CC(=O)NCCC3CCCN3C)s2)c1OC] | 595.7 | 596.3 | 1.14 | QC-ACN-AA-XB |
| 255 | 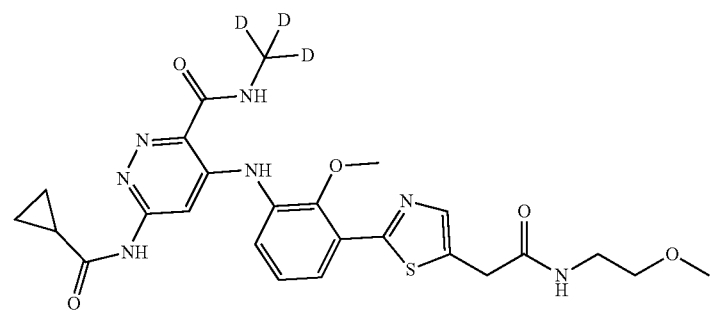 [SMILES: [2H]C([2H])([2H])NC(=O)c1nnc(NC(=O)C2CC2)cc1Nc1cccc(-c2ncc(CC(=O)NCCOC)s2)c1OC] | 542.6 | 543.4 | 1.29 | QC-ACN-AA-XB |

TABLE 4-continued
| Ex. No. | Structure | MW | Obs. MS Ion | RT | QC Method |
|---|---|---|---|---|---|
| 256 | 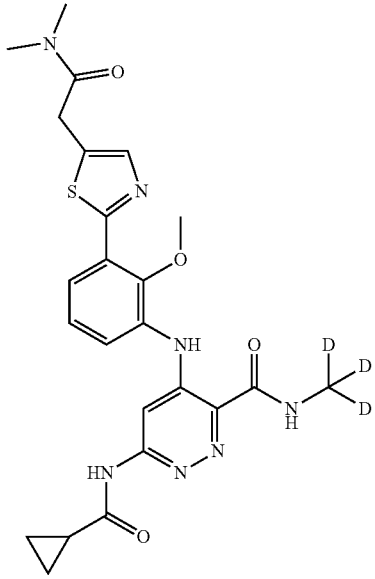 [SMILES: [2H]C([2H])([2H])NC(=O)c1nnc(NC(=O)C2CC2)cc1Nc1cccc(-c2ncc(CC(=O)N(C)C)s2)c1OC] | 512.6 | 513.4 | 1.06 | QC-ACN-TFA-XB |
| 257 | 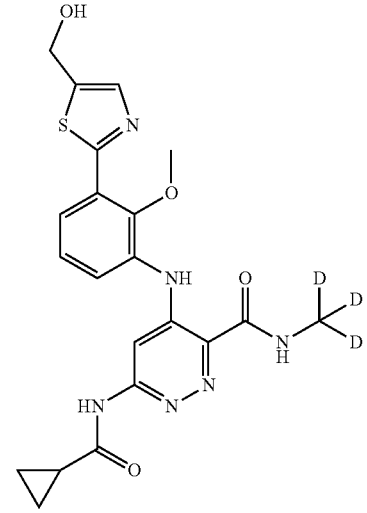 [SMILES: [2H]C([2H])([2H])NC(=O)c1nnc(NC(=O)C2CC2)cc1Nc1cccc(-c2ncc(CO)s2)c1OC] | 457.5 | 458.2 | 1.31 | QC-ACN-AA-XB |

TABLE 4-continued
| Ex. No. | Structure | MW | Obs. MS Ion | RT | QC Method |
|---|---|---|---|---|---|
| 258 | 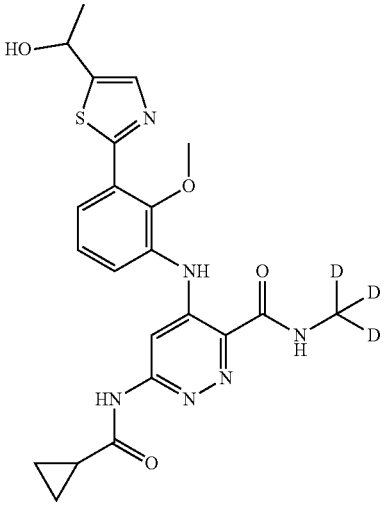 [SMILES: [2H]C([2H])([2H])NC(=O)c1nnc(NC(=O)C2CC2)cc1Nc1cccc(-c2ncc(C(C)O)s2)c1OC] | 471.6 | 472.2 | 1.41 | QC-ACN-AA-XB |
| 259 | 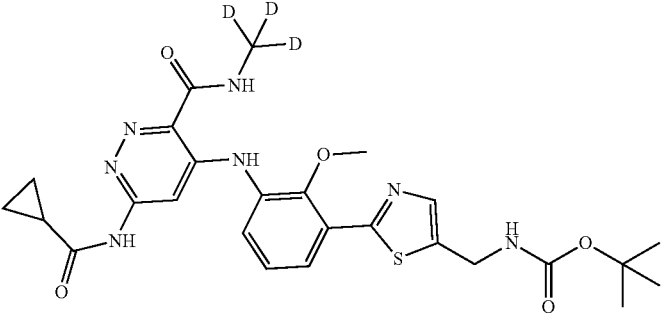 [SMILES: [2H]C([2H])([2H])NC(=O)c1nnc(NC(=O)C2CC2)cc1Nc1cccc(-c2ncc(CNC(=O)OC(C)(C)C)s2)c1OC] | 556.7 | 557.1 | 1.77 | QC-ACN-AA-XB |
| 260 | 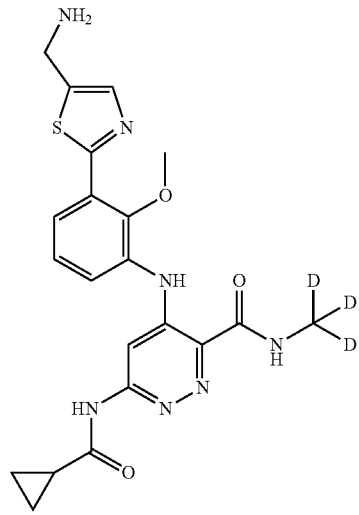 [SMILES: [2H]C([2H])([2H])NC(=O)c1nnc(NC(=O)C2CC2)cc1Nc1cccc(-c2ncc(CN)s2)c1OC] | 456.5 | 457.3 | 1.07 | QC-ACN-AA-XB |

TABLE 4-continued

| Ex. No. | Structure | MW | Obs. MS Ion | RT | QC Method |
|---|---|---|---|---|---|
| 261 | 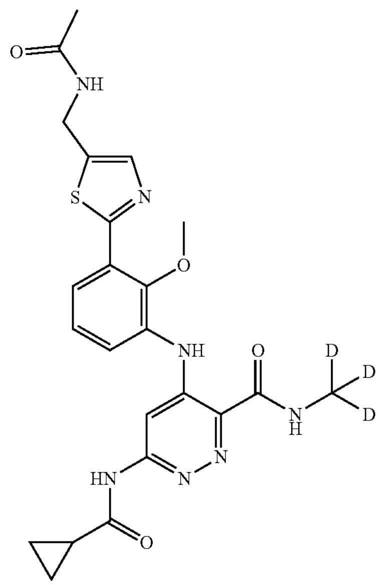 [SMILES: [2H]C([2H])([2H])NC(=O)c1nnc(NC(=O)C2CC2)cc1Nc1cccc(-c2ncc(CNC(C)=O)s2)c1OC] | 498.6 | 499.1 | 1.24 | QC-ACN-AA-XB |
| 262 | 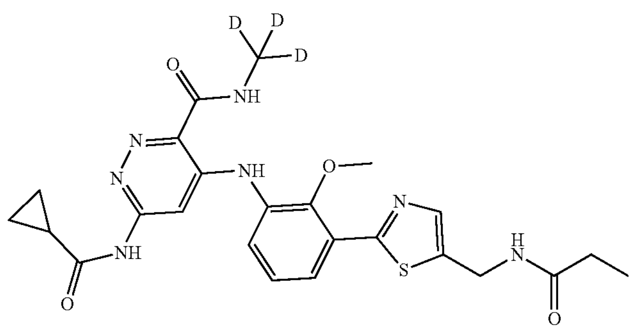 [SMILES: [2H]C([2H])([2H])NC(=O)c1nnc(NC(=O)C2CC2)cc1Nc1cccc(-c2ncc(CNC(=O)CC)s2)c1OC] | 512.6 | 513.3 | 1.06 | QC-ACN-TFA-XB |
| 263 | 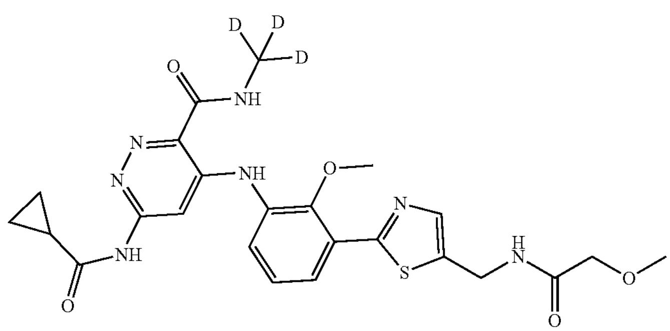 [SMILES: [2H]C([2H])([2H])NC(=O)c1nnc(NC(=O)C2CC2)cc1Nc1cccc(-c2ncc(CNC(=O)COC)s2)c1OC] | 528.6 | 529.3 | 1.32 | QC-ACN-AA-XB |
| 264 | 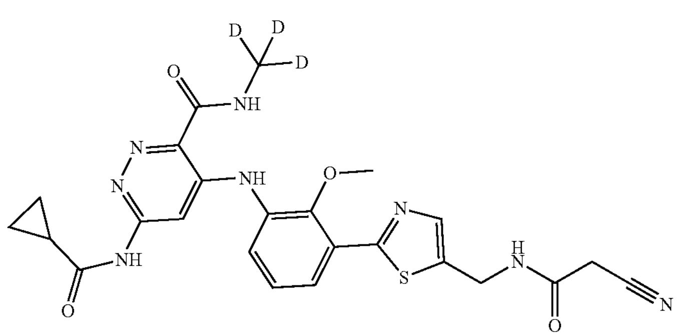 [SMILES: [2H]C([2H])([2H])NC(=O)c1nnc(NC(=O)C2CC2)cc1Nc1cccc(-c2ncc(CNC(=O)CC#N)s2)c1OC] | 523.6 | 524.2 | 1.3 | QC-ACN-AA-XB |

TABLE 4-continued
| Ex. No. | Structure | MW | Obs. MS Ion | RT | QC Method |
|---|---|---|---|---|---|
| 265 | 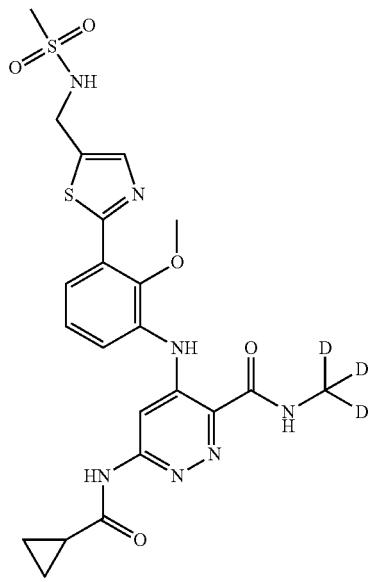 [SMILES: [2H]C([2H])([2H])NC(=O)c1nnc(NC(=O)C2CC2)cc1Nc1cccc(-c2ncc(CNS(C)(=O)=O)s2)c1OC] | 534.6 | 535.4 | 1.07 | QC-ACN-TFA-XB |
| 266 | 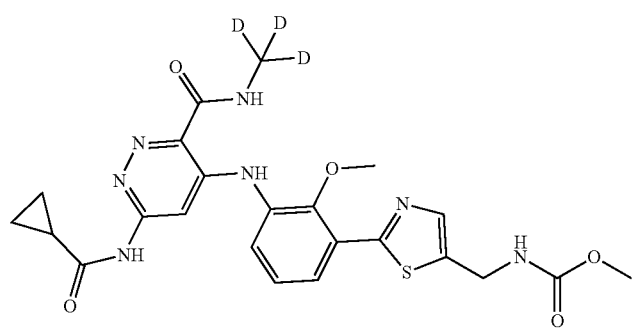 [SMILES: [2H]C([2H])([2H])NC(=O)c1nnc(NC(=O)C2CC2)cc1Nc1cccc(-c2ncc(CNC(=O)OC)s2)c1OC] | 514.6 | 515.4 | 1.42 | QC-ACN-AA-XB |
| 267 | 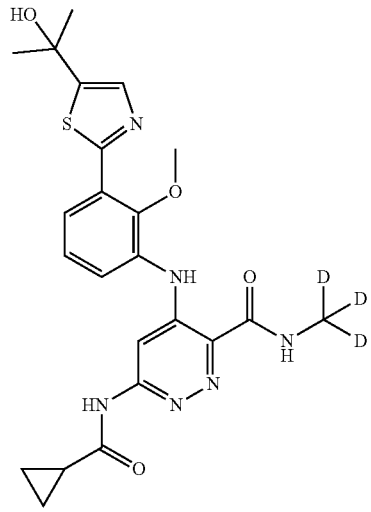 [SMILES: [2H]C([2H])([2H])NC(=O)c1nnc(NC(=O)C2CC2)cc1Nc1cccc(-c2ncc(C(C)(C)O)s2)c1OC] | 485.6 | 486.5 | 0.73 | A |

TABLE 4-continued
| Ex. No. | Structure | MW | Obs. MS Ion | RT | QC Method |
|---|---|---|---|---|---|
| 268 | 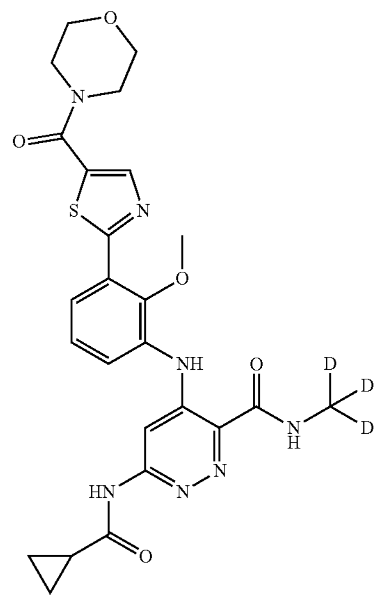 [SMILES: [2H]C([2H])([2H])NC(=O)c1nnc(NC(=O)C2CC2)cc1Nc1cccc(-c2ncc(C(=O)N3CCOCC3)s2)c1OC] | 540.6 | 541.2 | 1.36 | QC-ACN-AA-XB |
| 269 | 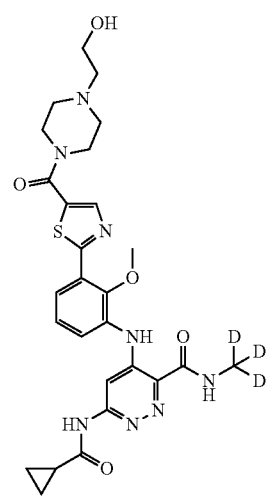 [SMILES: [2H]C([2H])([2H])NC(=O)c1nnc(NC(=O)C2CC2)cc1Nc1cccc(-c2ncc(C(=O)N3CCN(CCO)CC3)s2)c1OC] | 583.7 | 584.2 | 1.26 | QC-ACN-AA-XB |

TABLE 4-continued

| Ex. No. | Structure | MW | Obs. MS Ion | RT | QC Method |
|---|---|---|---|---|---|
| 270 | 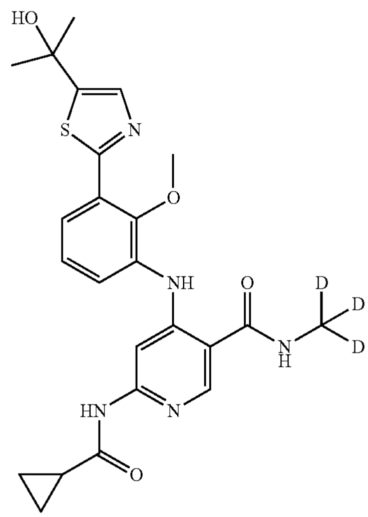 [SMILES: [2H]C([2H])([2H])NC(=O)c1cnc(NC(=O)C2CC2)cc1Nc1cccc(-c2ncc(C(C)(C)O)s2)c1OC] | 484.6 | 485.1 | 1.38 | QC-ACN-AA-XB |
| 271 | 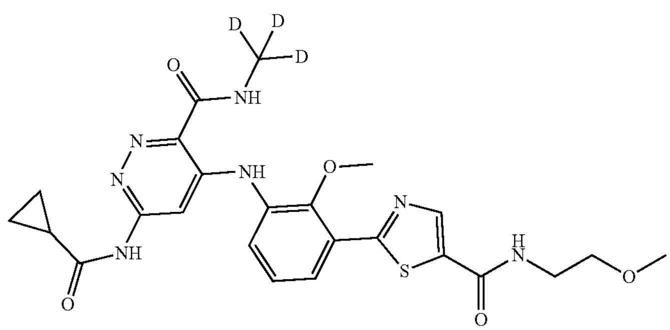 [SMILES: [2H]C([2H])([2H])NC(=O)c1nnc(NC(=O)C2CC2)cc1Nc1cccc(-c2ncc(C(=O)NCCOC)s2)c1OC] | 528.6 | 529.4 | 1.38 | QC-ACN-AA-XB |
| 272 | 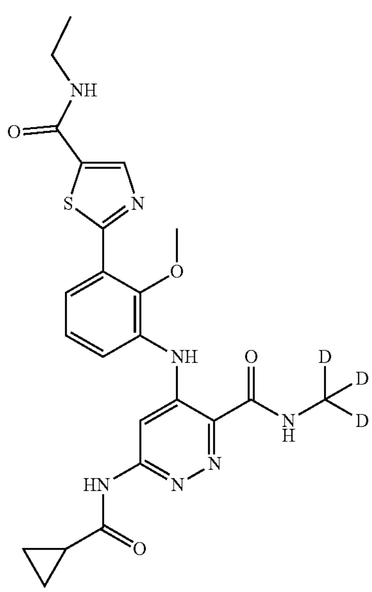 [SMILES: [2H]C([2H])([2H])NC(=O)c1nnc(NC(=O)C2CC2)cc1Nc1cccc(-c2ncc(C(=O)NCC)s2)c1OC] | 498.6 | 499.4 | 1.44 | QC-ACN-AA-XB |

TABLE 4-continued
| Ex. No. | Structure | MW | Obs. MS Ion | RT | QC Method |
|---|---|---|---|---|---|
| 273 | 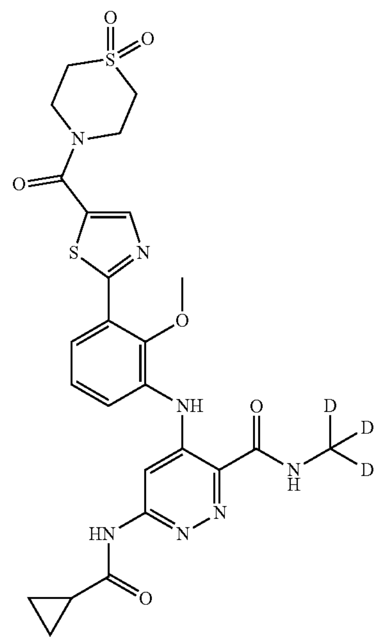 [SMILES: [2H]C([2H])([2H])NC(=O)c1nnc(NC(=O)C2CC2)cc1Nc1cccc(-c2ncc(C(=O)N3CCS(=O)(=O)CC3)s2)c1OC] | 588.7 | 589.1 | 1.33 | QC-ACN-AA-XB |
| 274 | 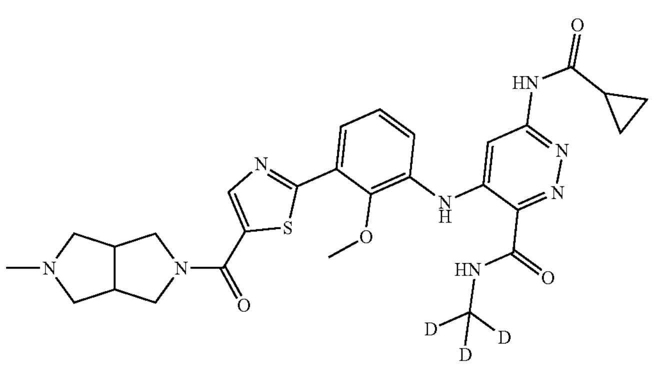 [SMILES: [2H]C([2H])([2H])NC(=O)c1nnc(NC(=O)C2CC2)cc1Nc1cccc(-c2ncc(C(=O)N3CC4CN(C)CC4C3)s2)c1OC] | 579.7 | 580.2 | 0.86 | QC-ACN-TFA-XB |
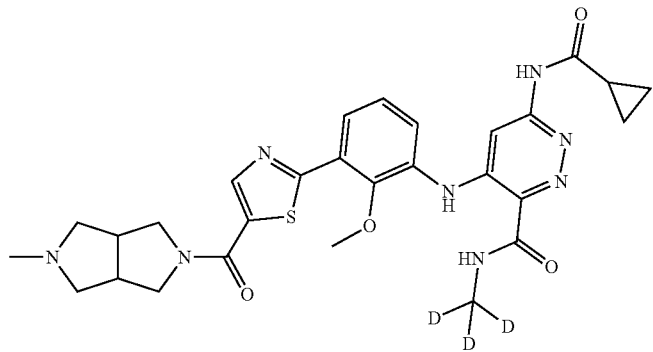

TABLE 4-continued

| Ex. No. | Structure | MW | Obs. MS Ion | RT | QC Method |
|---|---|---|---|---|---|
| 275 | 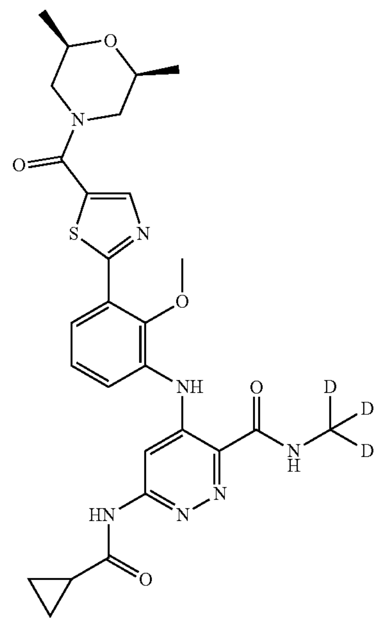 [SMILES: [2H]C([2H])([2H])NC(=O)c1nnc(NC(=O)C2CC2)cc1Nc1cccc(-c2ncc(C(=O)N3C[C@@H](C)O[C@@H](C)C3)s2)c1OC] | 568.7 | 569.3 | 1.64 | QC-ACN-AA-XB |
| 276 | 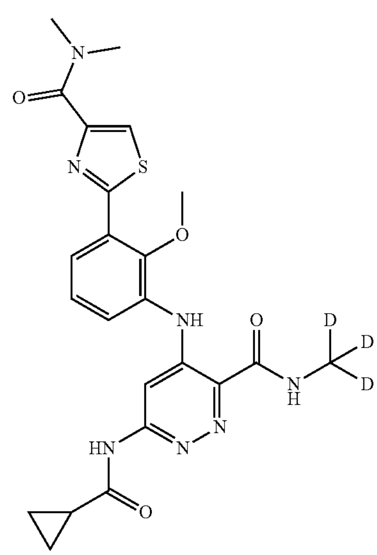 [SMILES: [2H]C([2H])([2H])NC(=O)c1nnc(NC(=O)C2CC2)cc1Nc1cccc(-c2nc(C(=O)N(C)C)cs2)c1OC] | 498.6 | 499.3 | 1.45 | QC-ACN-AA-XB |

TABLE 4-continued

| Ex. No. | Structure | MW | Obs. MS Ion | RT | QC Method |
|---|---|---|---|---|---|
| 277 | 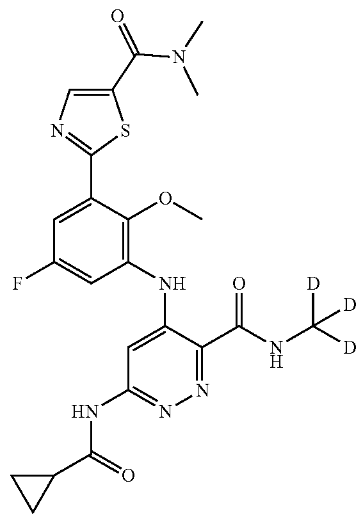 [SMILES: [2H]C([2H])([2H])NC(=O)c1nnc(NC(=O)C2CC2)cc1Nc1cc(F)cc(-c2ncc(C(=O)N(C)C)s2)c1OC] | 516.6 | 517.2 | 1.6 | QC-ACN-AA-XB |
| 278 | 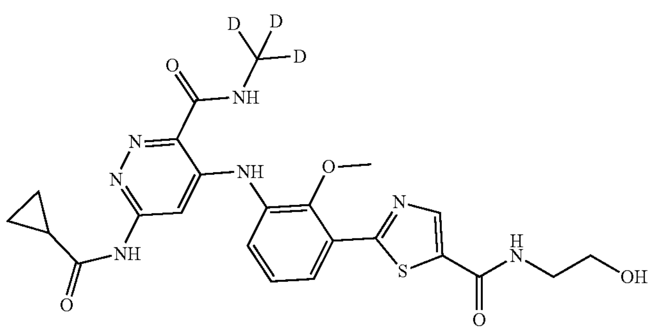 [SMILES: [2H]C([2H])([2H])NC(=O)c1nnc(NC(=O)C2CC2)cc1Nc1cccc(-c2ncc(C(=O)NCCO)s2)c1OC] | 514.6 | 515.2 | 1.23 | QC-ACN-AA-XB |
| 279 | 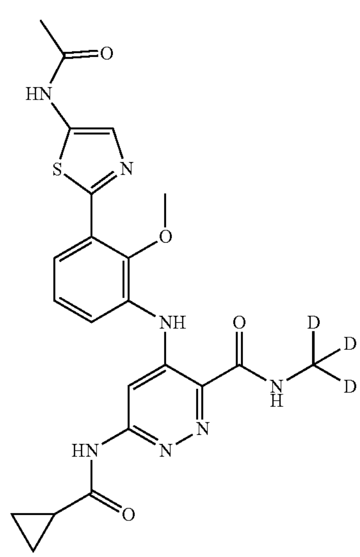 [SMILES: [2H]C([2H])([2H])NC(=O)c1nnc(NC(=O)C2CC2)cc1Nc1cccc(-c2ncc(NC(C)=O)s2)c1OC] | 484.6 | 485.2 | 1.3 | QC-ACN-AA-XB |

TABLE 4-continued
| Ex. No. | Structure | MW | Obs. MS Ion | RT | QC Method |
|---|---|---|---|---|---|
| 280 | 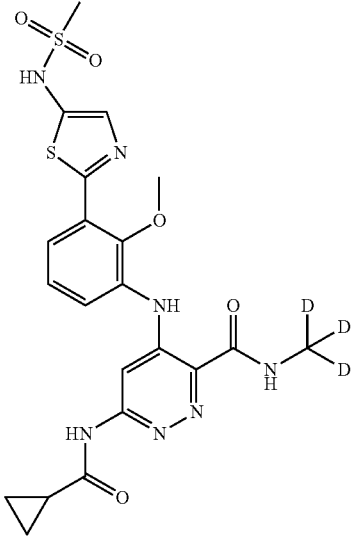 [SMILES: [2H]C([2H])([2H])NC(=O)c1nnc(NC(=O)C2CC2)cc1Nc1cccc(-c2ncc(NS(C)(=O)=O)s2)c1OC] | 520.6 | 521.2 | 1.18 | QC-ACN-TFA-XB |
| 281 | 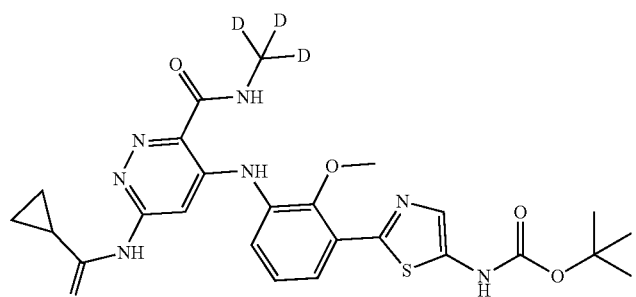 | 542.6 | 543.3 | 1.81 | QC-ACN-AA-XB |
| 282 | 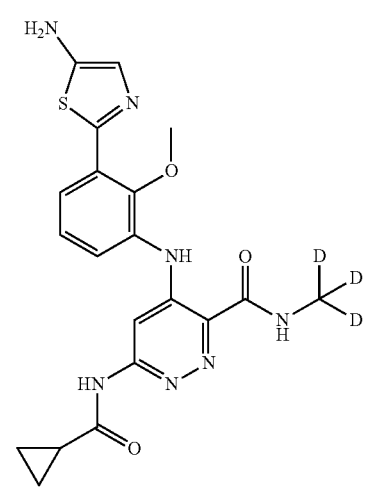 [SMILES: [2H]C([2H])([2H])NC(=O)c1nnc(NC(=O)C2CC2)cc1Nc1cccc(-c2ncc(N)s2)c1OC] | 442.5 | 443.2 | 0.98 | QC-ACN-TFA-XB |

TABLE 4-continued

| Ex. No. | Structure | MW | Obs. MS Ion | RT | QC Method |
|---|---|---|---|---|---|
| 283 | 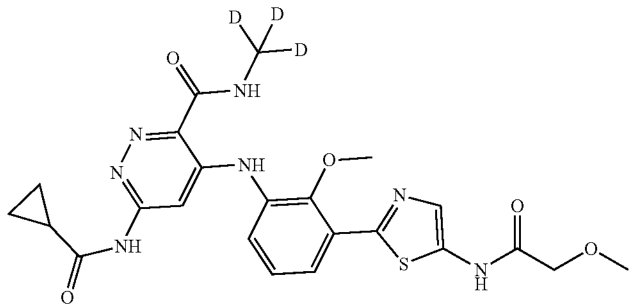 [SMILES: [2H]C([2H])([2H])NC(=O)c1nnc(NC(=O)C2CC2)cc1Nc1cccc(-c2ncc(NC(=O)COC)s2)c1OC] | 514.6 | 515.3 | 1.39 | QC-ACN-AA-XB |
| 284 | 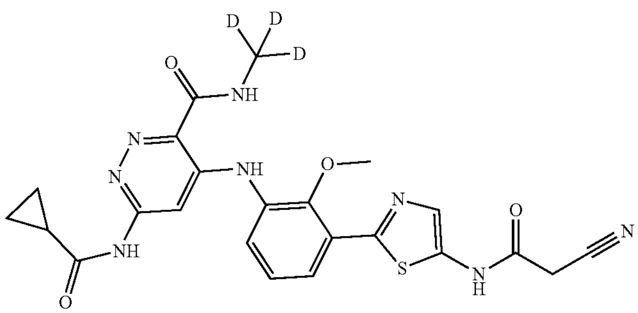 [SMILES: [2H]C([2H])([2H])NC(=O)c1nnc(NC(=O)C2CC2)cc1Nc1cccc(-c2ncc(NC(=O)CC#N)s2)c1OC] | 509.6 | 510.2 | 1.33 | QC-ACN-AA-XB |
| 285 | 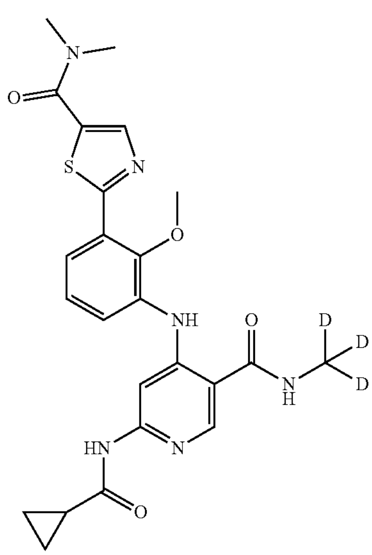 [SMILES: [2H]C([2H])([2H])NC(=O)c1cnc(NC(=O)C2CC2)cc1Nc1cccc(-c2ncc(C(=O)N(C)C)s2)c1OC] | 497.6 | 498.3 | 1.36 | QC-ACN-AA-XB |

TABLE 4-continued

| Ex. No. | Structure | MW | Obs. MS Ion | RT | QC Method |
|---|---|---|---|---|---|
| 286 | 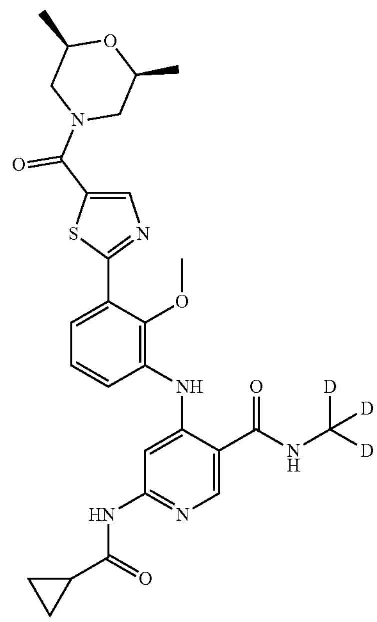 [SMILES: [2H]C([2H])([2H])NC(=O)c1cnc(NC(=O)C2CC2)cc1Nc1cccc(-c2ncc(C(=O)N3C[C@@H](C)O[C@@H](C)C3)s2)c1OC] | 567.7 | 568.5 | 1.58 | QC-ACN-AA-XB |
| 287 | 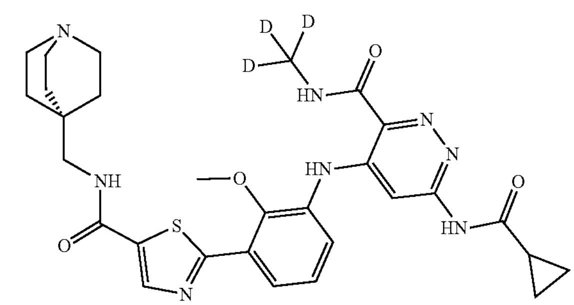 | 593.7 | 594.3 | 0.91 | QC-ACN-TFA-XB |
| 288 | 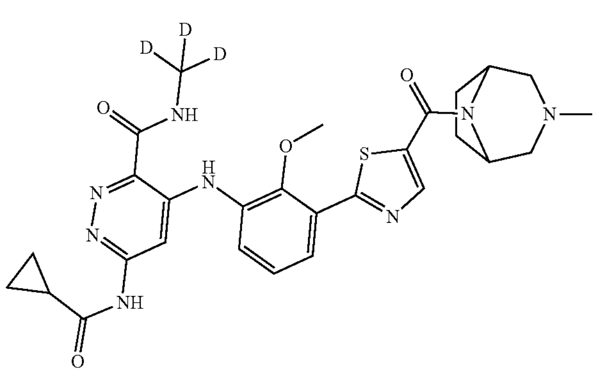 [SMILES: [2H]C([2H])([2H])NC(=O)c1nnc(NC(=O)C2CC2)cc1Nc1cccc(-c2ncc(C(=O)N3C4CCC3CN(C)C4)s2)c1OC] | 579.7 | 580.3 | 0.9 | QC-ACN-TFA-XB |

TABLE 4-continued
| Ex. No. | Structure | MW | Obs. MS Ion | RT | QC Method |
|---|---|---|---|---|---|
| 289 | 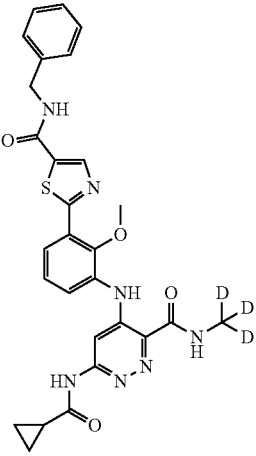 [SMILES: [2H]C([2H])([2H])NC(=O)c1nnc(NC(=O)C2CC2)cc1Nc1cccc(-c2ncc(C(=O)NCc3ccccc3)s2)c1OC] | 560.7 | 561.2 | 1.56 | QC-ACN-TFA-XB |
| 290 | 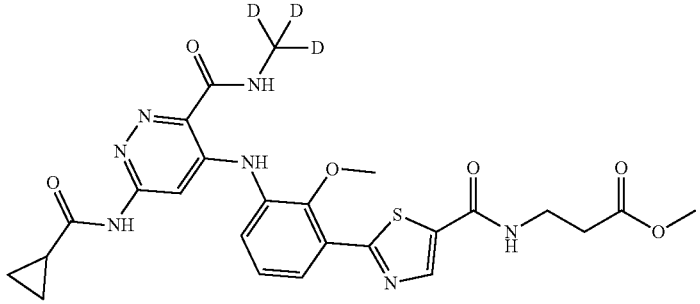 [SMILES: [2H]C([2H])([2H])NC(=O)c1nnc(NC(=O)C2CC2)cc1Nc1cccc(-c2ncc(C(=O)NCCC(=O)OC)s2)c1OC] | 556.6 | 557.2 | 1.25 | QC-ACN-TFA-XB |
| 291 | 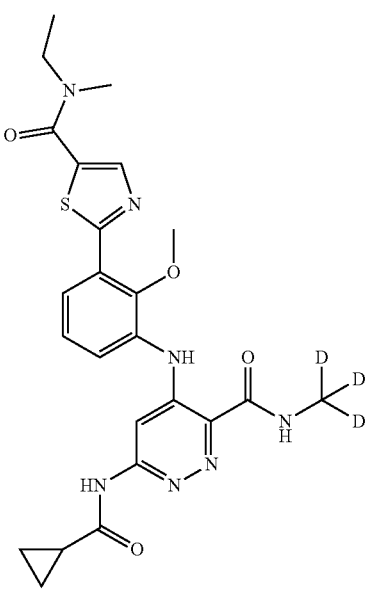 [SMILES: [2H]C([2H])([2H])NC(=O)c1nnc(NC(=O)C2CC2)cc1Nc1cccc(-c2ncc(C(=O)N(C)CC)s2)c1OC] | 512.6 | 513.3 | 1.56 | QC-ACN-AA-XB |

TABLE 4-continued
| Ex. No. | Structure | MW | Obs. MS Ion | RT | QC Method |
|---|---|---|---|---|---|
| 292 | 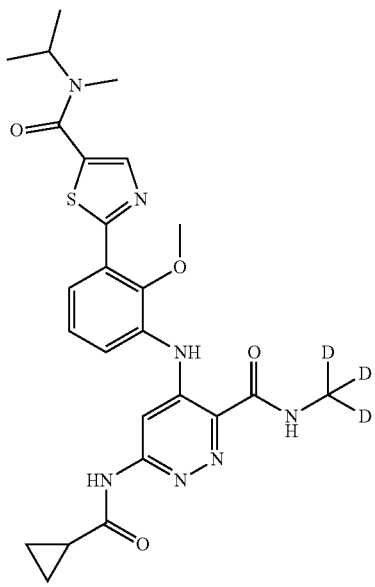 [SMILES: [2H]C([2H])([2H])NC(=O)c1nnc(NC(=O)C2CC2)cc1Nc1cccc(-c2ncc(C(=O)N(C)C(C)C)s2)c1OC] | 526.6 | 527.2 | 1.67 | QC-ACN-AA-XB |
| 293 | 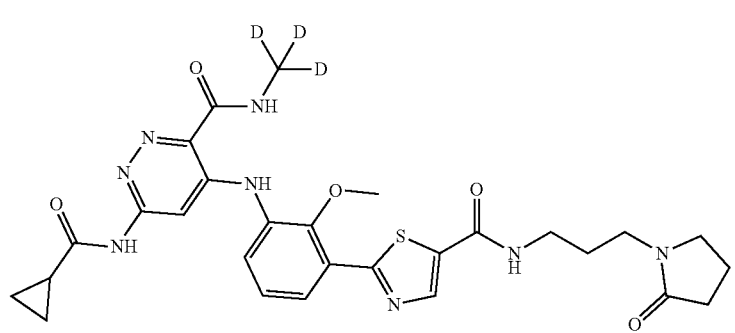 [SMILES: [2H]C([2H])([2H])NC(=O)c1nnc(NC(=O)C2CC2)cc1Nc1cccc(-c2ncc(C(=O)NCCCN3CCCC3=O)s2)c1OC] | 595.7 | 596.3 | 1.36 | QC-ACN-AA-XB |
| 294 | 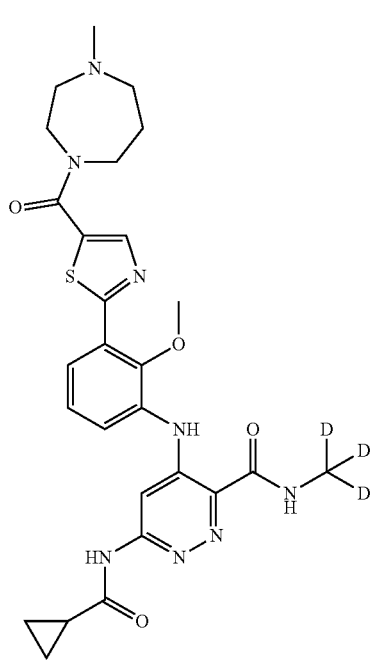 [SMILES: [2H]C([2H])([2H])NC(=O)c1nnc(NC(=O)C2CC2)cc1Nc1cccc(-c2ncc(C(=O)N3CCCN(C)CC3)s2)c1OC] | 567.7 | 568.4 | 1.18 | QC-ACN-AA-XB |

TABLE 4-continued
| Ex. No. | Structure | MW | Obs. MS Ion | RT | QC Method |
|---|---|---|---|---|---|
| 295 | 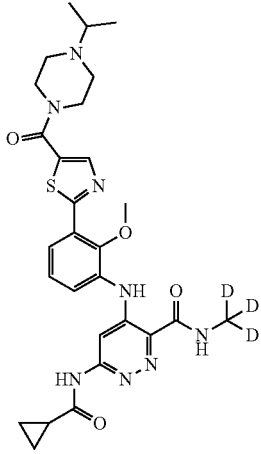 [SMILES: [2H]C([2H])([2H])NC(=O)c1nnc(NC(=O)C2CC2)cc1Nc1cccc(-c2ncc(C(=O)N3CCN(C(C)C)CC3)s2)c1OC] | 581.7 | 582.4 | 1.45 | QC-ACN-AA-XB |
| 296 | 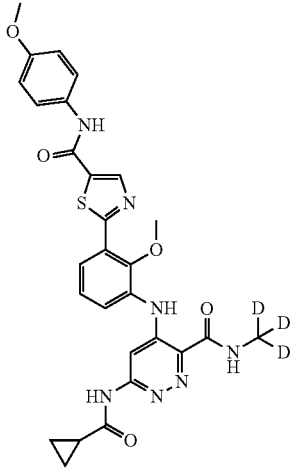 [SMILES: [2H]C([2H])([2H])NC(=O)c1nnc(NC(=O)C2CC2)cc1Nc1cccc(-c2ncc(C(=O)Nc3ccc(OC)cc3)s2)c1OC] | 576.7 | 577.4 | 1.77 | QC-ACN-AA-XB |
| 297 | 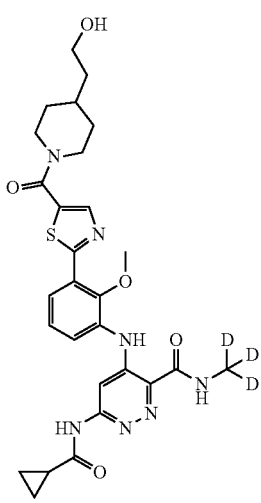 [SMILES: [2H]C([2H])([2H])NC(=O)c1nnc(NC(=O)C2CC2)cc1Nc1cccc(-c2ncc(C(=O)N3CCC(CCO)CC3)s2)c1OC] | 582.7 | 583.2 | 1.42 | QC-ACN-AA-XB |

TABLE 4-continued

| Ex. No. | Structure | MW | Obs. MS Ion | RT | QC Method |
|---|---|---|---|---|---|
| 298 | 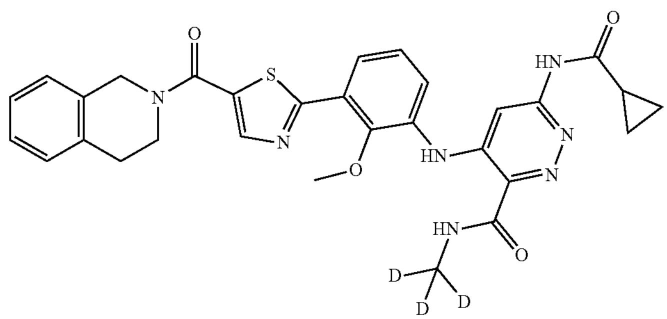 [SMILES: [2H]C([2H])([2H])NC(=O)c1nnc(NC(=O)C2CC2)cc1Nc1cccc(-c2ncc(C(=O)N3CCc4ccccc4C3)s2)c1OC] | 586.7 | 587.2 | 1.92 | QC-ACN-AA-XB |
| 299 | 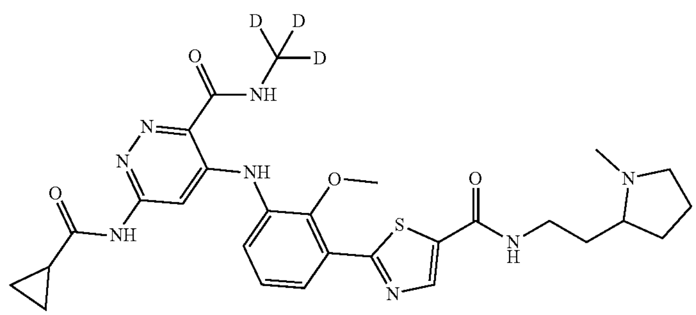 [SMILES: [2H]C([2H])([2H])NC(=O)c1nnc(NC(=O)C2CC2)cc1Nc1cccc(-c2ncc(C(=O)NCCC3CCCN3C)s2)c1OC] | 581.7 | 582.4 | 1.17 | QC-ACN-AA-XB |
| 300 | 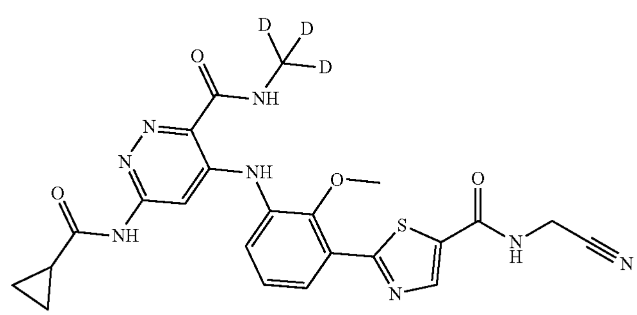 [SMILES: [2H]C([2H])([2H])NC(=O)c1nnc(NC(=O)C2CC2)cc1Nc1cccc(-c2ncc(C(=O)NCC#N)s2)c1OC] | 509.6 | 510.4 | 1.37 | QC-ACN-AA-XB |
| 301 | 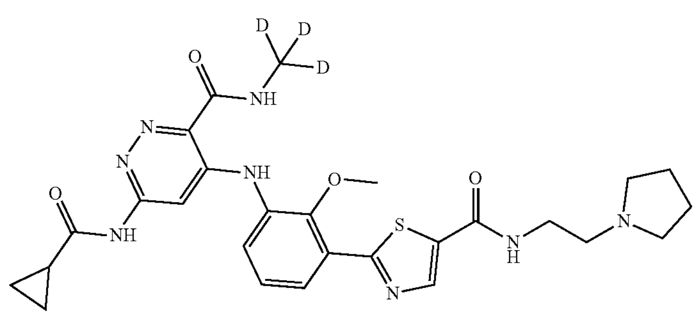 [SMILES: [2H]C([2H])([2H])NC(=O)c1nnc(NC(=O)C2CC2)cc1Nc1cccc(-c2ncc(C(=O)NCCN3CCCC3)s2)c1OC] | 567.7 | 568.4 | 1.14 | QC-ACN-AA-XB |

TABLE 4-continued
| Ex. No. | Structure | MW | Obs. MS Ion | RT | QC Method |
|---|---|---|---|---|---|
| 302 | 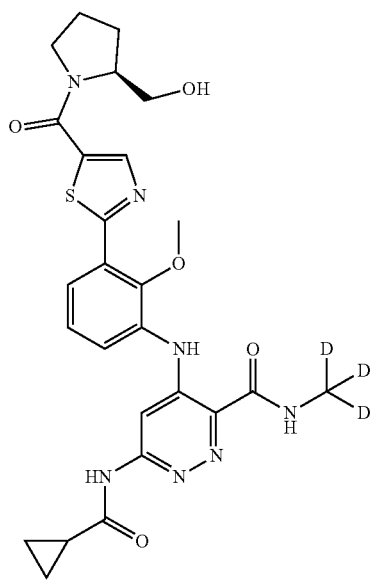 [SMILES: [2H]C([2H])([2H])NC(=O)c1nnc(NC(=O)C2CC2)cc1Nc1cccc(-c2ncc(C(=O)N3CCC[C@H]3CO)s2)c1OC] | 554.6 | 555.4 | 1.41 | QC-ACN-AA-XB |
| 303 | 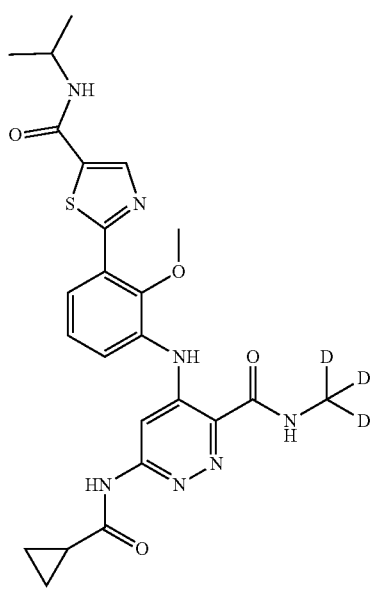 [SMILES: [2H]C([2H])([2H])NC(=O)c1nnc(NC(=O)C2CC2)cc1Nc1cccc(-c2ncc(C(=O)NC(C)C)s2)c1OC] | 512.6 | 513.3 | 1.57 | QC-ACN-AA-XB |
| 304 | 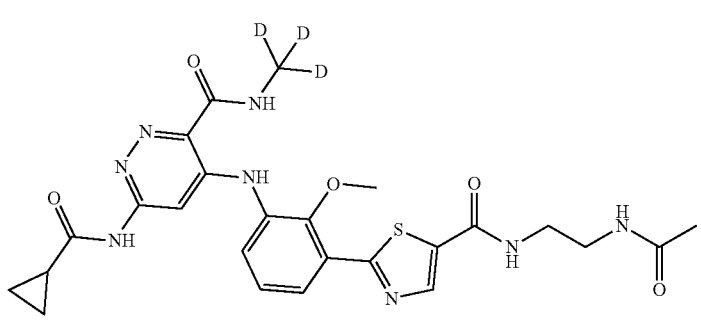 [SMILES: [2H]C([2H])([2H])NC(=O)c1nnc(NC(=O)C2CC2)cc1Nc1cccc(-c2ncc(C(=O)NCCNC(C)=O)s2)c1OC] | 555.6 | 556.3 | 1.21 | QC-ACN-AA-XB |

TABLE 4-continued
| Ex. No. | Structure | MW | Obs. MS Ion | RT | QC Method |
|---|---|---|---|---|---|
| 305 | 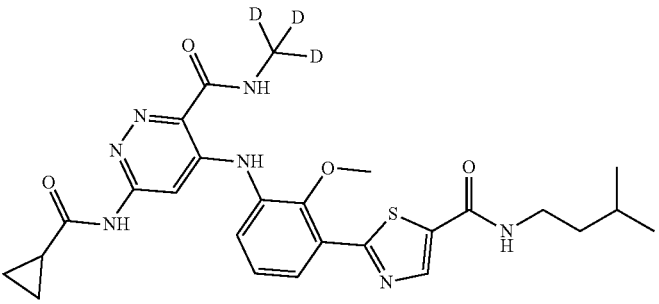 [SMILES: [2H]C([2H])([2H])NC(=O)c1nnc(NC(=O)C2CC2)cc1Nc1cccc(-c2ncc(C(=O)NCCC(C)C)s2)c1OC] | 540.7 | 541.4 | 1.84 | QC-ACN-AA-XB |
| 306 | 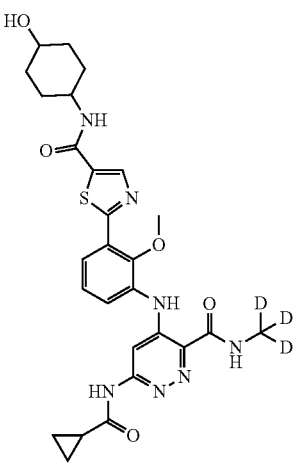 [SMILES: [2H]C([2H])([2H])NC(=O)c1nnc(NC(=O)C2CC2)cc1Nc1cccc(-c2ncc(C(=O)NC3CCC(O)CC3)s2)c1OC] | 568.7 | 569.4 | 1.35 | QC-ACN-AA-XB |
| 307 | 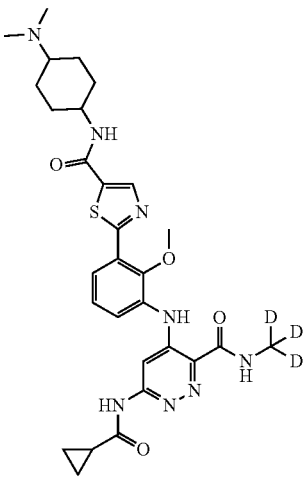 [SMILES: [2H]C([2H])([2H])NC(=O)c1nnc(NC(=O)C2CC2)cc1Nc1cccc(-c2ncc(C(=O)NC3CCC(N(C)C)CC3)s2)c1OC] | 595.7 | 596.4 | 1.06 | QC-ACN-TFA-XB |

TABLE 4-continued
| Ex. No. | Structure | MW | Obs. MS Ion | RT | QC Method |
|---|---|---|---|---|---|
| 308 | 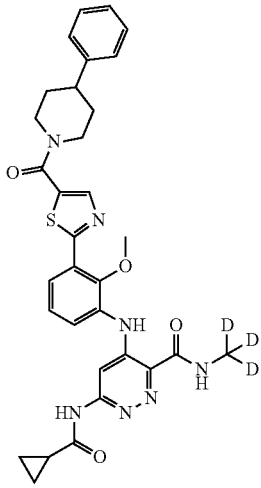 [SMILES: [2H]C([2H])([2H])NC(=O)c1nnc(NC(=O)C2CC2)cc1Nc1cccc(-c2ncc(C(=O)N3CCC(c4ccccc4)CC3)s2)c1OC] | 614.7 | 615.4 | 2.06 | QC-ACN-AA-XB |
| 309 | 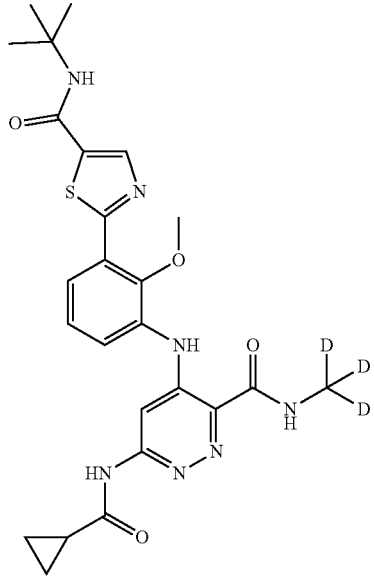 [SMILES: [2H]C([2H])([2H])NC(=O)c1nnc(NC(=O)C2CC2)cc1Nc1cccc(-c2ncc(C(=O)NC(C)(C)C)s2)c1OC] | 526.6 | 527.2 | 1.55 | QC-ACN-TFA-XB |
| 310 | 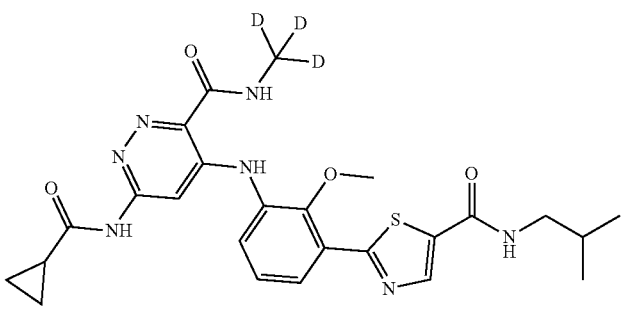 [SMILES: [2H]C([2H])([2H])NC(=O)c1nnc(NC(=O)C2CC2)cc1Nc1cccc(-c2ncc(C(=O)NCC(C)C)s2)c1OC] | 526.6 | 527.2 | 1.7 | QC-ACN-AA-XB |

TABLE 4-continued
| Ex. No. | Structure | MW | Obs. MS Ion | RT | QC Method |
|---|---|---|---|---|---|
| 311 | 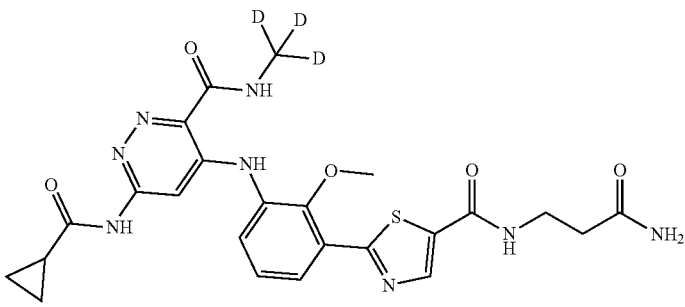 [SMILES: [2H]C([2H])([2H])NC(=O)c1nnc(NC(=O)C2CC2)cc1Nc1cccc(-c2ncc(C(=O)NCCC(N)=O)s2)c1OC] | 541.6 | 542.1 | 1.16 | QC-ACN-AA-XB |
| 312 | 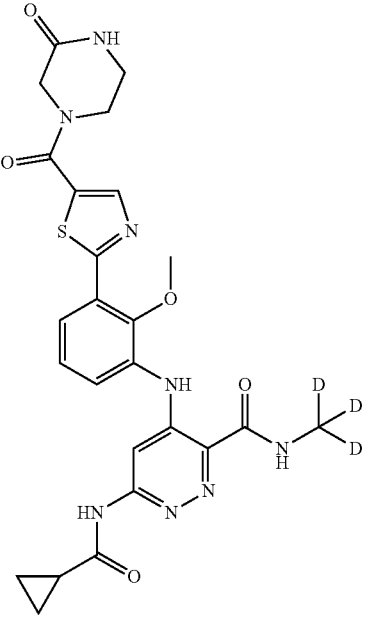 [SMILES: [2H]C([2H])([2H])NC(=O)c1nnc(NC(=O)C2CC2)cc1Nc1cccc(-c2ncc(C(=O)N3CCNC(=O)C3)s2)c1OC] | 553.6 | 554.4 | 1.18 | QC-ACN-AA-XB |
| 313 | 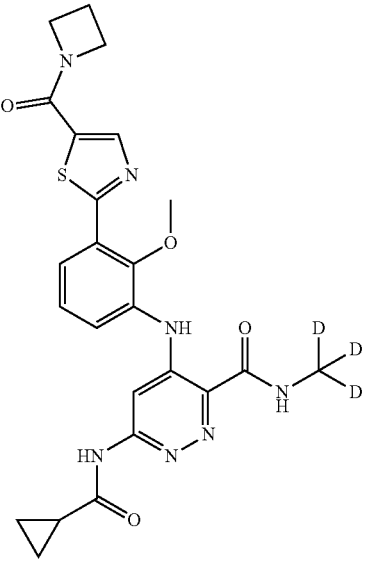 [SMILES: [2H]C([2H])([2H])NC(=O)c1nnc(NC(=O)C2CC2)cc1Nc1cccc(-c2ncc(C(=O)N3CCC3)s2)c1OC] | 510.6 | 511.3 | 1.46 | QC-ACN-AA-XB |

TABLE 4-continued

| Ex. No. | Structure | MW | Obs. MS Ion | RT | QC Method |
|---|---|---|---|---|---|
| 314 | 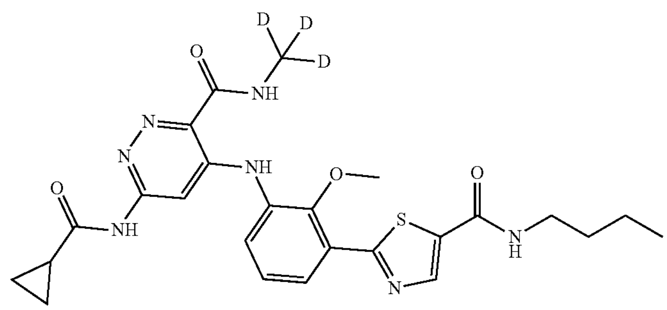 [SMILES: [2H]C([2H])([2H])NC(=O)c1nnc(NC(=O)C2CC2)cc1Nc1cccc(-c2ncc(C(=O)NCCCC)s2)c1OC] | 526.6 | 527.2 | 1.72 | QC-ACN-AA-XB |
| 315 | 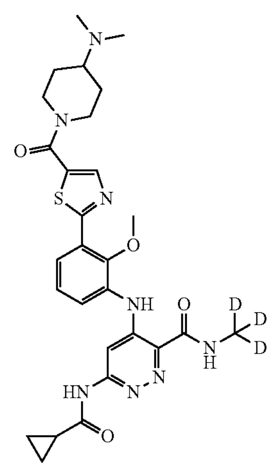 [SMILES: [2H]C([2H])([2H])NC(=O)c1nnc(NC(=O)C2CC2)cc1Nc1cccc(-c2ncc(C(=O)N3CCC(N(C)C)CC3)s2)c1OC] | 581.7 | 582.2 | 1.1 | QC-ACN-AA-XB |
| 316 | 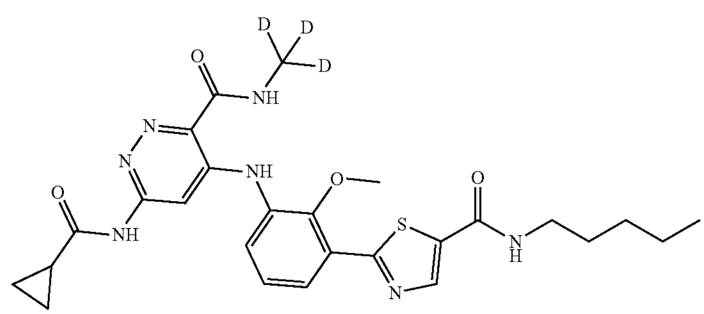 [SMILES: [2H]C([2H])([2H])NC(=O)c1nnc(NC(=O)C2CC2)cc1Nc1cccc(-c2ncc(C(=O)NCCCCC)s2)c1OC] | 540.7 | 541.4 | 1.57 | QC-ACN-TFA-XB |
| 317 | 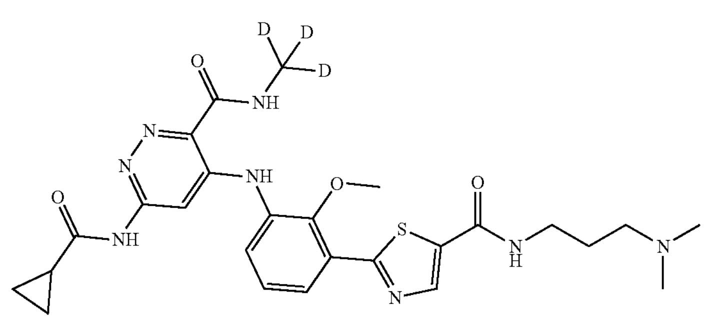 [SMILES: [2H]C([2H])([2H])NC(=O)c1nnc(NC(=O)C2CC2)cc1Nc1cccc(-c2ncc(C(=O)NCCCN(C)C)s2)c1OC] | 555.7 | 556.2 | 1.11 | QC-ACN-AA-XB |

TABLE 4-continued
| Ex. No. | Structure | MW | Obs. MS Ion | RT | QC Method |
|---|---|---|---|---|---|
| 318 | 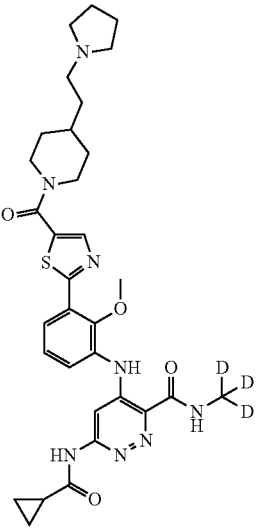 [SMILES: [2H]C([2H])([2H])NC(=O)c1nnc(NC(=O)C2CC2)cc1Nc1cccc(-c2ncc(C(=O)N3CCC(CCN4CCCC4)CC3)s2)c1OC] | 635.8 | 318.8 | 1.14 | QC-ACN-TFA-XB |
| 319 | 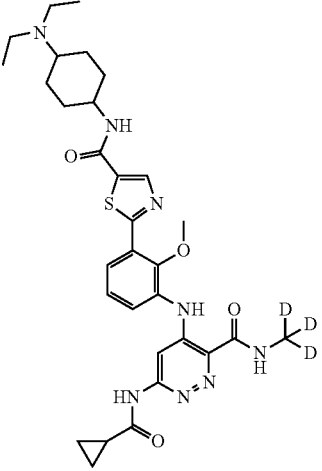 [SMILES: [2H]C([2H])([2H])NC(=O)c1nnc(NC(=O)C2CC2)cc1Nc1cccc(-c2ncc(C(=O)NC3CCC(N(CC)CC)CC3)s2)c1OC] | 623.8 | 312.8 | 1.13 | QC-ACN-TFA-XB |

TABLE 4-continued

| Ex. No. | Structure | MW | Obs. MS Ion | RT | QC Method |
|---|---|---|---|---|---|
| 320 | 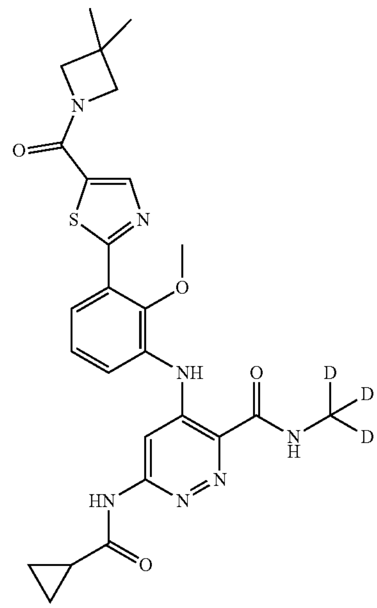 [SMILES: [2H]C([2H])([2H])NC(=O)c1nnc(NC(=O)C2CC2)cc1Nc1cccc(-c2ncc(C(=O)N3CC(C)(C)C3)s2)c1OC] | 538.6 | 539.3 | 1.76 | QC-ACN-AA-XB |
| 321 | 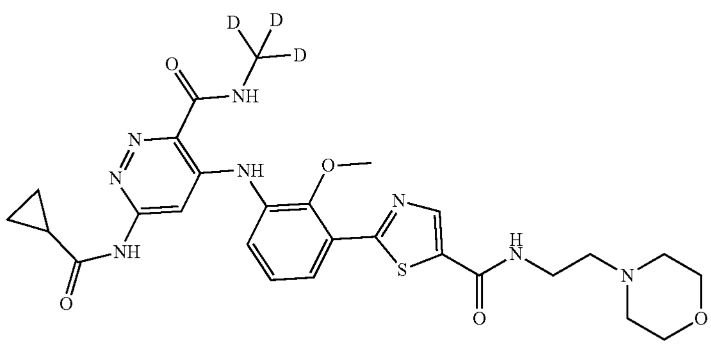 [SMILES: [2H]C([2H])([2H])NC(=O)c1nnc(NC(=O)C2CC2)cc1Nc1cccc(-c2ncc(C(=O)NCCN3CCOCC3)s2)c1OC] | 583.7 | 584.3 | 1.33 | QC-ACN-AA-XB |
| 322 | 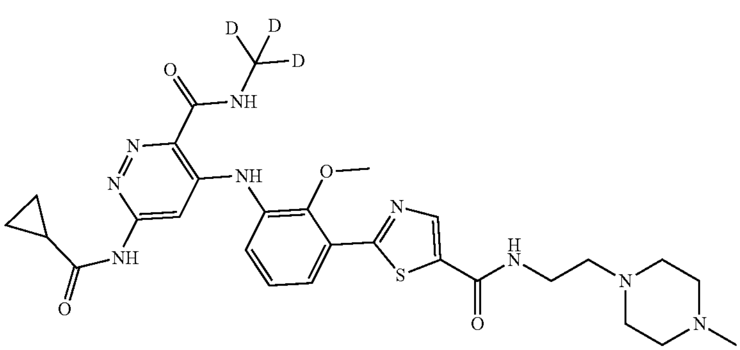 [SMILES: [2H]C([2H])([2H])NC(=O)c1nnc(NC(=O)C2CC2)cc1Nc1cccc(-c2ncc(C(=O)NCCN3CCN(C)CC3)s2)c1OC] | 596.7 | 597.2 | 0.96 | QC-ACN-TFA-XB |

TABLE 4-continued

| Ex. No. | Structure | MW | Obs. MS Ion | RT | QC Method |
|---|---|---|---|---|---|
| 323 | 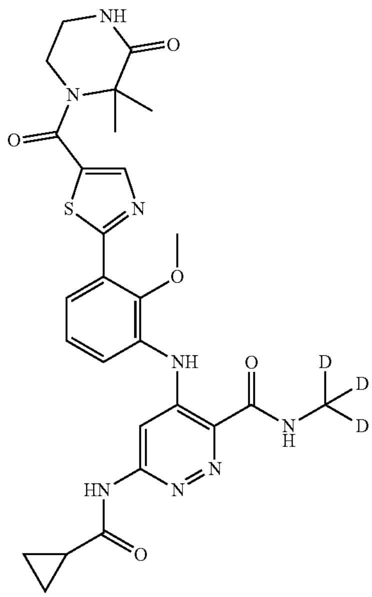 [SMILES: [2H]C([2H])([2H])NC(=O)c1nnc(NC(=O)C2CC2)cc1Nc1cccc(-c2ncc(C(=O)N3CCNC(=O)C3(C)C)s2)c1OC] | 581.7 | 582.4 | 1.37 | QC-ACN-AA-XB |
| 324 | 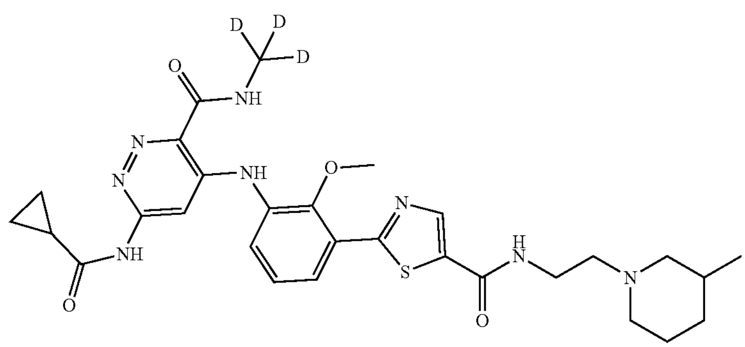 [SMILES: [2H]C([2H])([2H])NC(=O)c1nnc(NC(=O)C2CC2)cc1Nc1cccc(-c2ncc(C(=O)NCCN3CCCC(C)C3)s2)c1OC] | 595.7 | 596.2 | 1.16 | QC-ACN-TFA-XB |
| 325 | 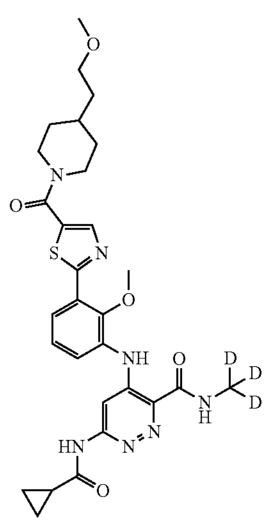 [SMILES: [2H]C([2H])([2H])NC(=O)c1nnc(NC(=O)C2CC2)cc1Nc1cccc(-c2ncc(C(=O)N3CCC(CCOC)CC3)s2)c1OC] | 596.7 | 597.1 | 1.75 | QC-ACN-AA-XB |

TABLE 4-continued
| Ex. No. | Structure | MW | Obs. MS Ion | RT | QC Method |
|---|---|---|---|---|---|
| 326 | 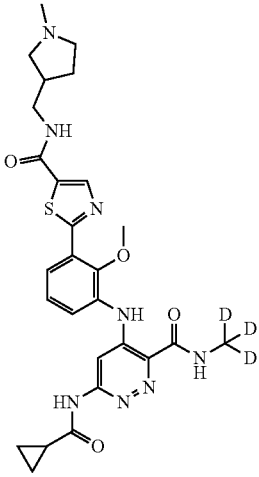 [SMILES: [2H]C([2H])([2H])NC(=O)c1nnc(NC(=O)C2CC2)cc1Nc1cccc(-c2ncc(C(=O)NCC3CCN(C)C3)s2)c1OC] | 567.7 | 568.4 | 1.02 | QC-ACN-TFA-XB |
| 327 | 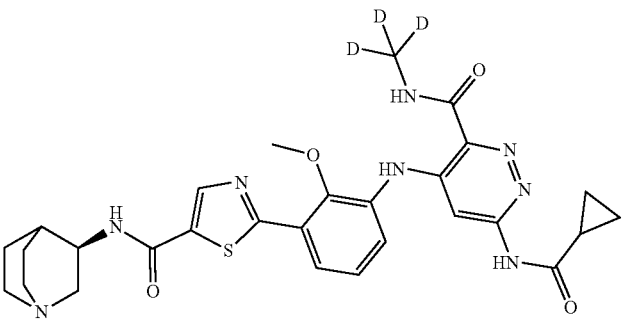 [SMILES: [2H]C([2H])([2H])NC(=O)c1nnc(NC(=O)C2CC2)cc1Nc1cccc(-c2ncc(C(=O)N[C@H]3CN4CCC3CC4)s2)c1OC] | 579.7 | 580.4 | 1.05 | QC-ACN-TFA-XB |
| 328 | 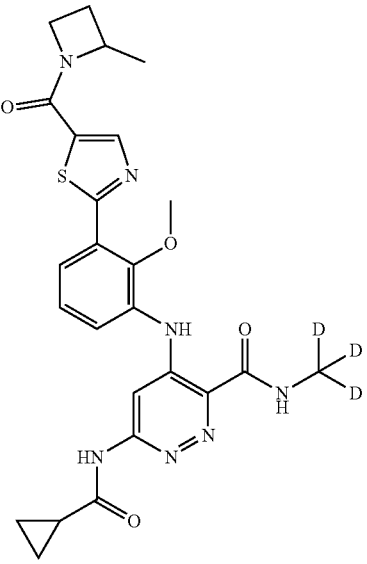 [SMILES: [2H]C([2H])([2H])NC(=O)c1nnc(NC(=O)C2CC2)cc1Nc1cccc(-c2ncc(C(=O)N3CCC3C)s2)c1OC] | 524.6 | 525.3 | 1.59 | QC-ACN-AA-XB |

TABLE 4-continued

| Ex. No. | Structure | MW | Obs. MS Ion | RT | QC Method |
|---|---|---|---|---|---|
| 329 | 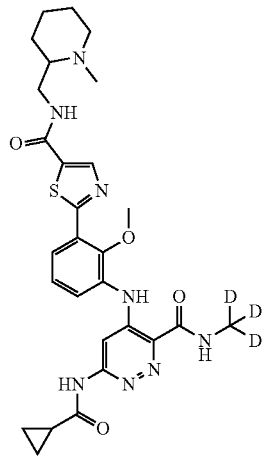 [SMILES: [2H]C([2H])([2H])NC(=O)c1nnc(NC(=O)C2CC2)cc1Nc1cccc(-c2ncc(C(=O)NCC3CCCCN3C)s2)c1OC] | 581.7 | 582.4 | 1.07 | QC-ACN-TFA-XB |
| 330 | 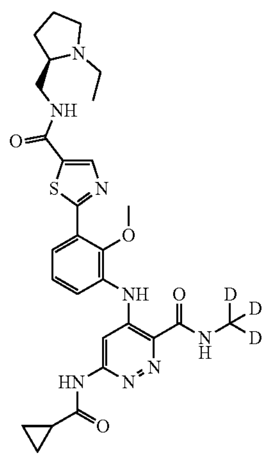 [SMILES: [2H]C([2H])([2H])NC(=O)c1nnc(NC(=O)C2CC2)cc1Nc1cccc(-c2ncc(C(=O)NC[C@H]3CCCN3CC)s2)c1OC] | 581.7 | 582.2 | 1.09 | QC-ACN-TFA-XB |
| 331 | 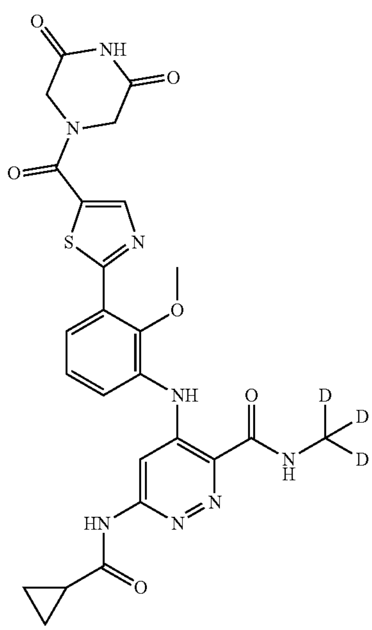 [SMILES: [2H]C([2H])([2H])NC(=O)c1nnc(NC(=O)C2CC2)cc1Nc1cccc(-c2ncc(C(=O)N3CC(=O)NC(=O)C3)s2)c1OC] | 567.6 | 568.2 | 1.32 | QC-ACN-AA-XB |

TABLE 4-continued

| Ex. No. | Structure | MW | Obs. MS Ion | RT | QC Method |
|---|---|---|---|---|---|
| 332 | 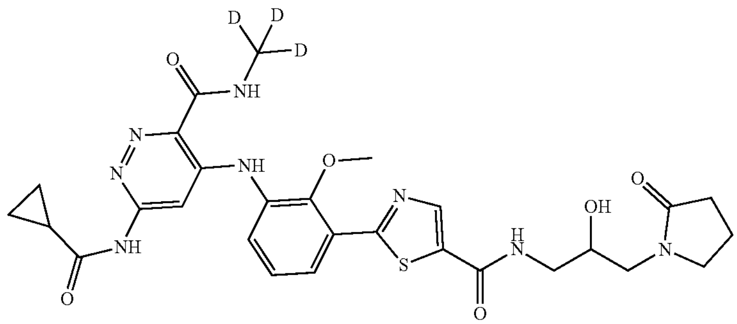 [SMILES: [2H]C([2H])([2H])NC(=O)c1nnc(NC(=O)C2CC2)cc1Nc1cccc(-c2ncc(C(=O)NCC(O)CN3CCCC3=O)s2)c1OC] | 611.7 | 612.4 | 1.24 | QC-ACN-AA-XB |
| 333 | 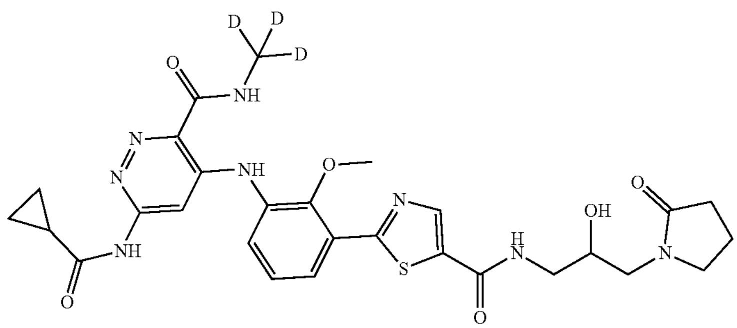 [SMILES: [2H]C([2H])([2H])NC(=O)c1nnc(NC(=O)C2CC2)cc1Nc1cccc(-c2ncc(C(=O)NCC(O)CN3CCCC3=O)s2)c1OC] | 611.7 | 612.4 | 2.18 | QC-ACN-AA-XB |
| 334 | 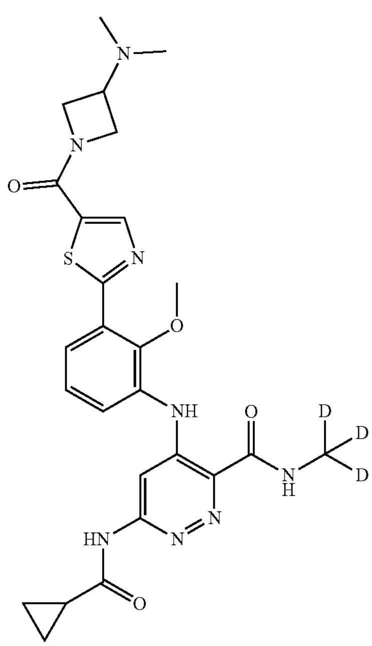 [SMILES: [2H]C([2H])([2H])NC(=O)c1nnc(NC(=O)C2CC2)cc1Nc1cccc(-c2ncc(C(=O)N3CC(N(C)C)C3)s2)c1OC] | 553.7 | 554.3 | 1.39 | QC-ACN-AA-XB |

TABLE 4-continued

| Ex. No. | Structure | MW | Obs. MS Ion | RT | QC Method |
|---|---|---|---|---|---|
| 335 | 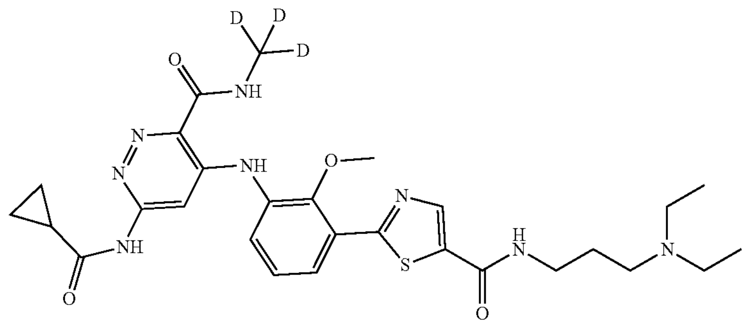 [SMILES: [2H]C([2H])([2H])NC(=O)c1nnc(NC(=O)C2CC2)cc1Nc1cccc(-c2ncc(C(=O)NCCCN(CC)CC)s2)c1OC] | 583.7 | 584.4 | 1.08 | QC-ACN-TFA-XB |
| 336 | 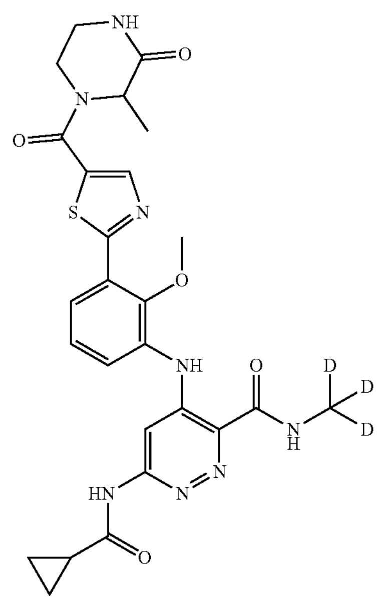 [SMILES: [2H]C([2H])([2H])NC(=O)c1nnc(NC(=O)C2CC2)cc1Nc1cccc(-c2ncc(C(=O)N3CCNC(=O)C3C)s2)c1OC] | 567.6 | 568.3 | 1.11 | QC-ACN-TFA-XB |
| 337 | 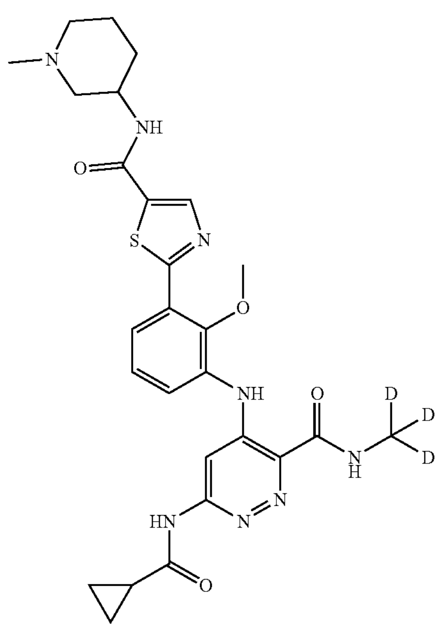 [SMILES: [2H]C([2H])([2H])NC(=O)c1nnc(NC(=O)C2CC2)cc1Nc1cccc(-c2ncc(C(=O)NC3CCCN(C)C3)s2)c1OC] | 567.7 | 568.3 | 1.04 | QC-ACN-TFA-XB |

TABLE 4-continued

| Ex. No. | Structure | MW | Obs. MS Ion | RT | QC Method |
|---|---|---|---|---|---|
| 338 | 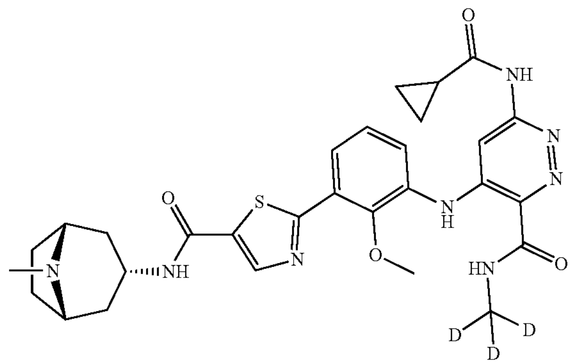 [SMILES: [2H]C([2H])([2H])NC(=O)c1nnc(NC(=O)C2CC2)cc1Nc1cccc(-c2ncc(C(=O)N[C@H]3C[C@H]4CC[C@@H](C3)N4C)s2)c1OC] | 593.7 | 594.4 | 1.16 | QC-ACN-AA-XB |
| 339 | 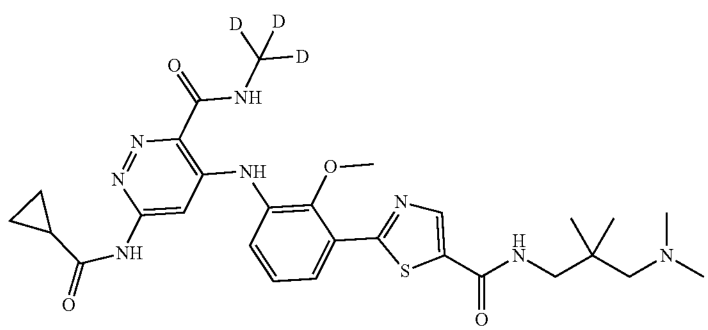 [SMILES: [2H]C([2H])([2H])NC(=O)c1nnc(NC(=O)C2CC2)cc1Nc1cccc(-c2ncc(C(=O)NCC(C)(C)CN(C)C)s2)c1OC] | 583.7 | 584.4 | 1.09 | QC-ACN-TFA-XB |
| 340 | 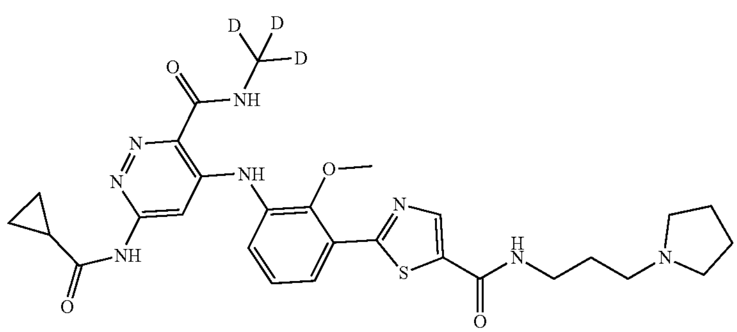 [SMILES: [2H]C([2H])([2H])NC(=O)c1nnc(NC(=O)C2CC2)cc1Nc1cccc(-c2ncc(C(=O)NCCCN3CCCC3)s2)c1OC] | 581.7 | 582.4 | 1.18 | QC-ACN-AA-XB |
| 341 | 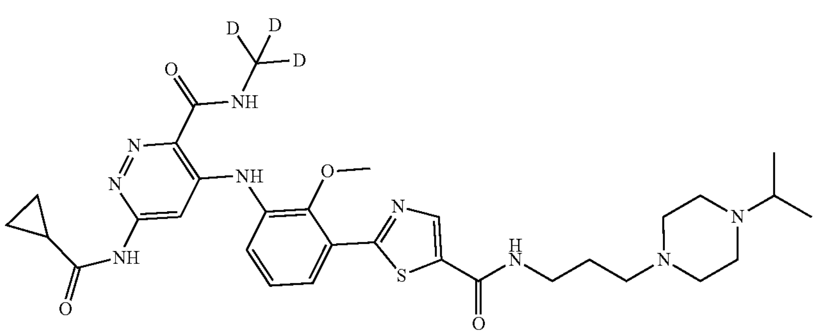 [SMILES: [2H]C([2H])([2H])NC(=O)c1nnc(NC(=O)C2CC2)cc1Nc1cccc(-c2ncc(C(=O)NCCCN3CCN(C(C)C)CC3)s2)c1OC] | 638.8 | 639.5 | 0.97 | QC-ACN-TFA-XB |

TABLE 4-continued
| Ex. No. | Structure | MW | Obs. MS Ion | RT | QC Method |
|---|---|---|---|---|---|
| 342 | 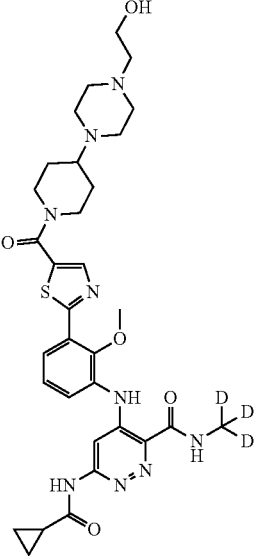 [SMILES: [2H]C([2H])([2H])NC(=O)c1nnc(NC(=O)C2CC2)cc1Nc1cccc(-c2ncc(C(=O)N3CCC(N4CCN(CCO)CC4)CC3)s2)c1OC] | 666.8 | 667.3 | 1.16 | QC-ACN-AA-XB |
| 343 | 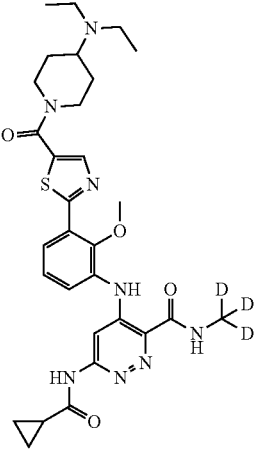 [SMILES: [2H]C([2H])([2H])NC(=O)c1nnc(NC(=O)C2CC2)cc1Nc1cccc(-c2ncc(C(=O)N3CCC(N(CC)CC)CC3)s2)c1OC] | 609.8 | 610.1 | 1.07 | QC-ACN-TFA-XB |
| 344 | 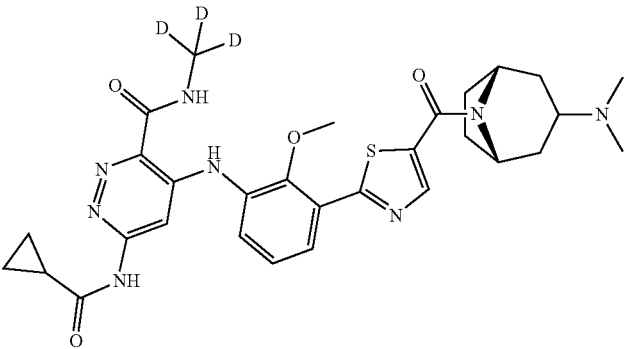 [SMILES: [2H]C([2H])([2H])NC(=O)c1nnc(NC(=O)C2CC2)cc1Nc1cccc(-c2ncc(C(=O)N3[C@@H]4CC[C@H]3CC(N(C)C)C4)s2)c1OC] | 607.8 | 608.4 | 1.32 | QC-ACN-AA-XB |

TABLE 4-continued

| Ex. No. | Structure | MW | Obs. MS Ion | RT | QC Method |
|---|---|---|---|---|---|
| 345 | 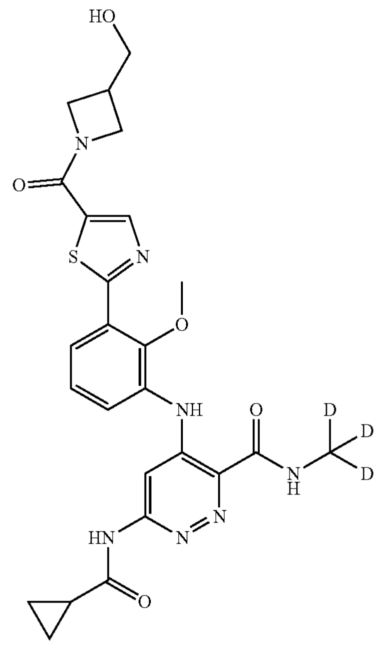 [SMILES: [2H]C([2H])([2H])NC(=O)c1nnc(NC(=O)C2CC2)cc1Nc1cccc(-c2ncc(C(=O)N3CC(CO)C3)s2)c1OC] | 540.6 | 541.3 | 1.29 | QC-ACN-AA-XB |
| 346 | 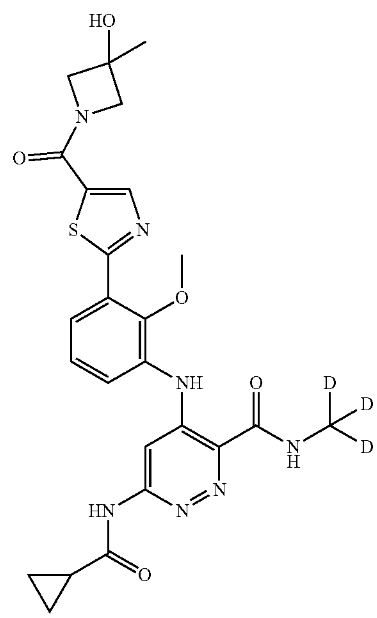 [SMILES: [2H]C([2H])([2H])NC(=O)c1nnc(NC(=O)C2CC2)cc1Nc1cccc(-c2ncc(C(=O)N3CC(C)(O)C3)s2)c1OC] | 540.6 | 541.4 | 1.35 | QC-ACN-AA-XB |
| 347 | 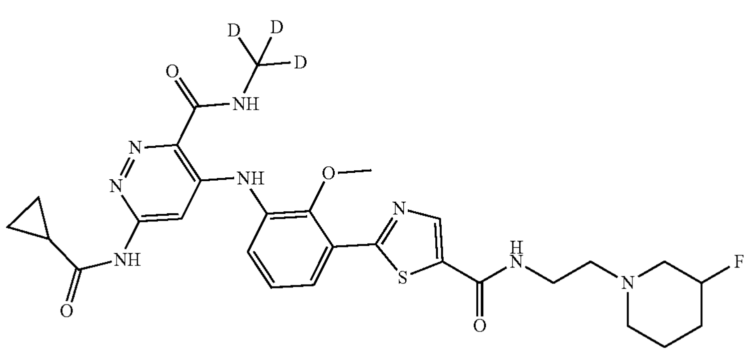 [SMILES: [2H]C([2H])([2H])NC(=O)c1nnc(NC(=O)C2CC2)cc1Nc1cccc(-c2ncc(C(=O)NCCN3CCCC(F)C3)s2)c1OC] | 599.7 | 600.4 | 1.06 | QC-ACN-TFA-XB |

TABLE 4-continued

| Ex. No. | Structure | MW | Obs. MS Ion | RT | QC Method |
|---|---|---|---|---|---|
| 348 | 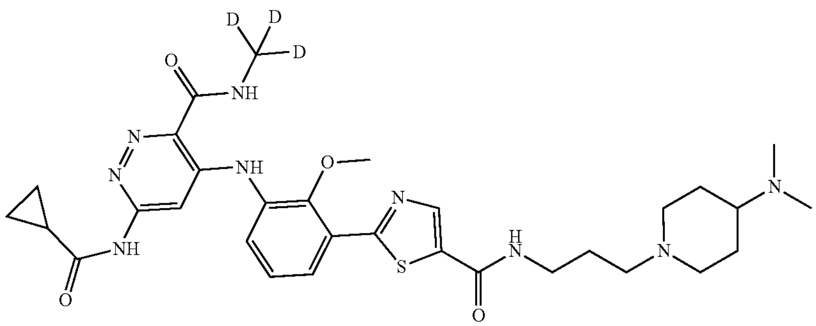 [SMILES: [2H]C([2H])([2H])NC(=O)c1nnc(NC(=O)C2CC2)cc1Nc1cccc(-c2ncc(C(=O)NCCCN3CCC(N(C)C)CC3)s2)c1OC] | 638.8 | 639.3 | 1.17 | QC-ACN-AA-XB |
| 349 | 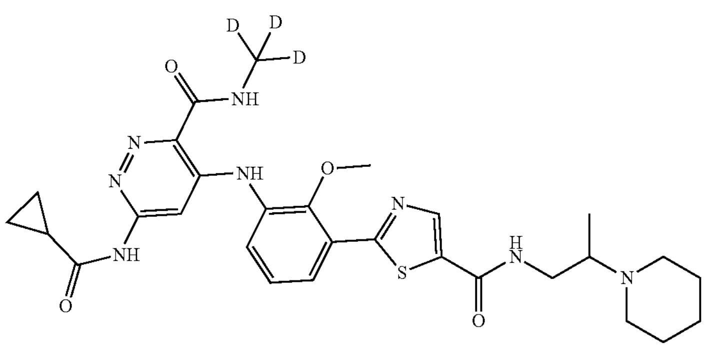 [SMILES: [2H]C([2H])([2H])NC(=O)c1nnc(NC(=O)C2CC2)cc1Nc1cccc(-c2ncc(C(=O)NCC(C)N3CCCCC3)s2)c1OC] | 595.7 | 596.4 | 1.29 | QC-ACN-AA-XB |
| 350 | 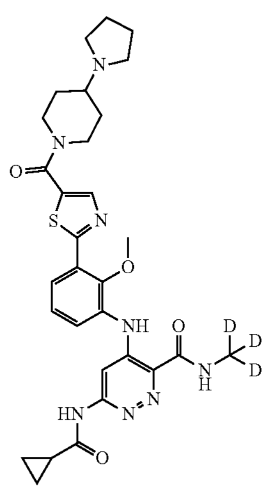 [SMILES: [2H]C([2H])([2H])NC(=O)c1nnc(NC(=O)C2CC2)cc1Nc1cccc(-c2ncc(C(=O)N3CCC(N4CCCC4)CC3)s2)c1OC] | 607.8 | 608.2 | 1.19 | QC-ACN-AA-XB |

TABLE 4-continued
| Ex. No. | Structure | MW | Obs. MS Ion | RT | QC Method |
|---|---|---|---|---|---|
| 351 | 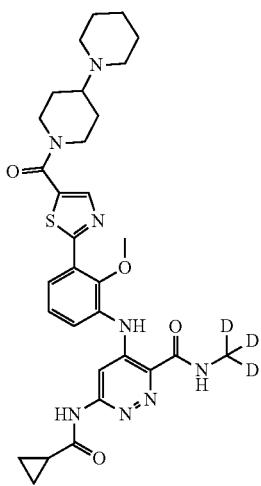 [SMILES: [2H]C([2H])([2H])NC(=O)c1nnc(NC(=O)C2CC2)cc1Nc1cccc(-c2ncc(C(=O)N3CCC(N4CCCCC4)CC3)s2)c1OC] | 621.8 | 622.4 | 1.08 | QC-ACN-TFA-XB |
| 352 | 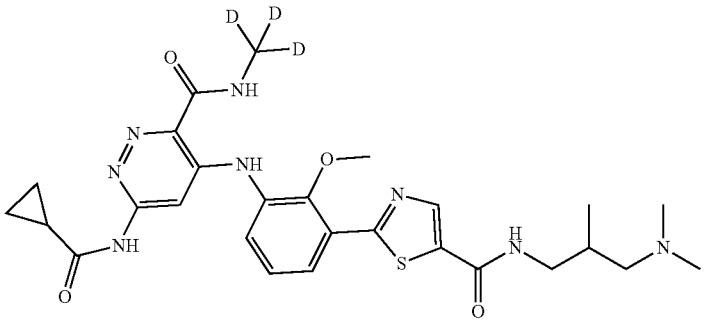 [SMILES: [2H]C([2H])([2H])NC(=O)c1nnc(NC(=O)C2CC2)cc1Nc1cccc(-c2ncc(C(=O)NCC(C)CN(C)C)s2)c1OC] | 569.7 | 570.1 | 1.06 | QC-ACN-TFA-XB |
| 353 | 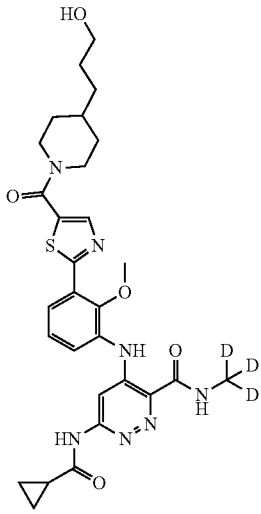 [SMILES: [2H]C([2H])([2H])NC(=O)c1nnc(NC(=O)C2CC2)cc1Nc1cccc(-c2ncc(C(=O)N3CCC(CCCO)CC3)s2)c1OC] | 596.7 | 597.2 | 1.34 | QC-ACN-TFA-XB |

TABLE 4-continued
| Ex. No. | Structure | MW | Obs. MS Ion | RT | QC Method |
|---|---|---|---|---|---|
| 354 | 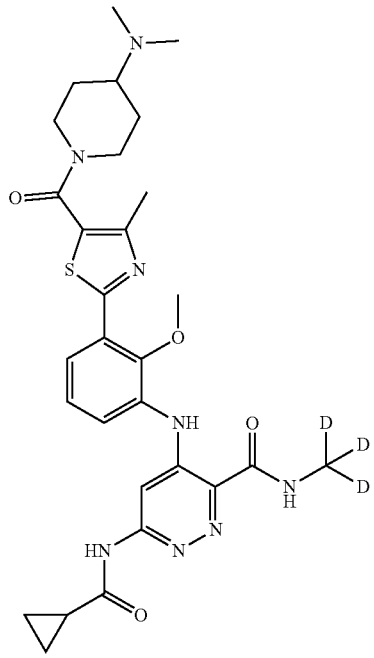 [SMILES: [2H]C([2H])([2H])NC(=O)c1nnc(NC(=O)C2CC2)cc1Nc1cccc(-c2nc(C)c(C(=O)N3CCC(N(C)C)CC3)s2)c1OC] | 595.7 | 596.2 | 1.25 | QC-ACN-AA-XB |
| 355 | 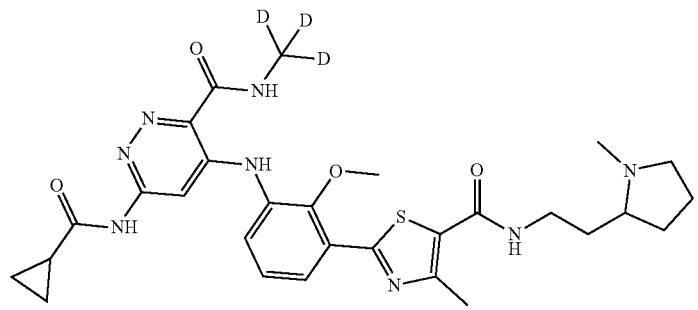 [SMILES: [2H]C([2H])([2H])NC(=O)c1nnc(NC(=O)C2CC2)cc1Nc1cccc(-c2nc(C)c(C(=O)NCCC3CCCN3C)s2)c1OC] | 595.7 | 596.3 | 1.14 | QC-ACN-TFA-XB |
| 356 | 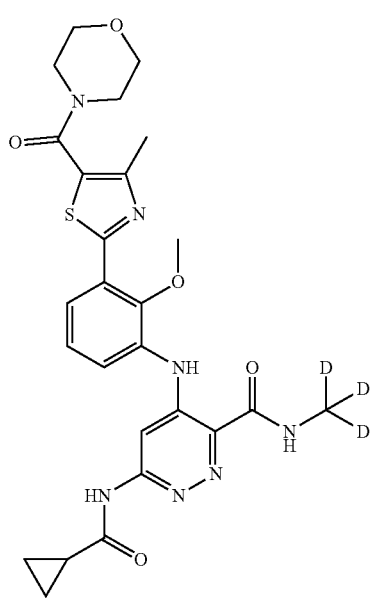 [SMILES: [2H]C([2H])([2H])NC(=O)c1nnc(NC(=O)C2CC2)cc1Nc1cccc(-c2nc(C)c(C(=O)N3CCOCC3)s2)c1OC] | 554.6 | 555.2 | 1.51 | QC-ACN-AA-XB |

TABLE 4-continued

| Ex. No. | Structure | MW | Obs. MS Ion | RT | QC Method |
|---|---|---|---|---|---|
| 357 | 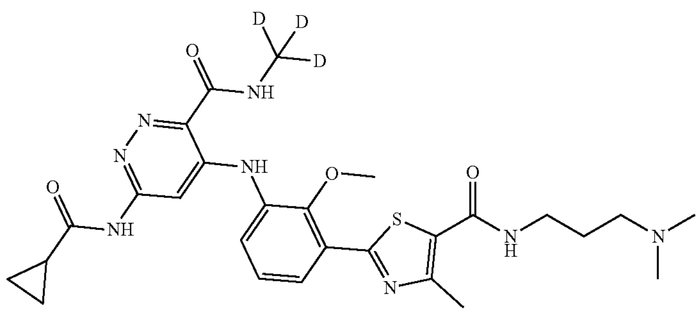 [SMILES: [2H]C([2H])([2H])NC(=O)c1nnc(NC(=O)C2CC2)cc1Nc1cccc(-c2nc(C)c(C(=O)NCCCN(C)C)s2)c1OC] | 569.7 | 570.3 | 1.25 | QC-ACN-AA-XB |
| 358 | 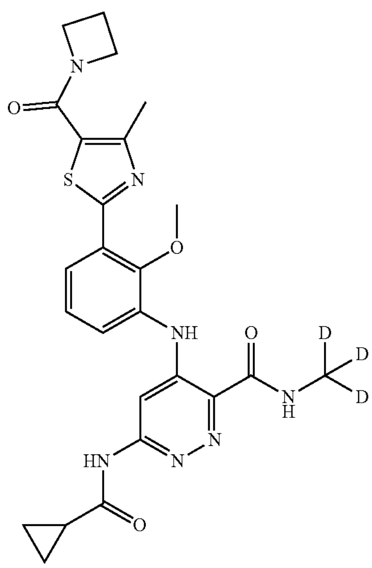 [SMILES: [2H]C([2H])([2H])NC(=O)c1nnc(NC(=O)C2CC2)cc1Nc1cccc(-c2nc(C)c(C(=O)N3CCC3)s2)c1OC] | 524.6 | 525.4 | 1.28 | QC-ACN-TFA-XB |
| 359 | 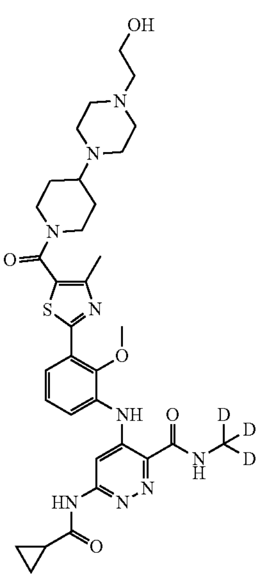 [SMILES: [2H]C([2H])([2H])NC(=O)c1nnc(NC(=O)C2CC2)cc1Nc1cccc(-c2nc(C)c(C(=O)N3CCC(N4CCN(CCO)CC4)CC3)s2)c1OC] | 680.8 | 681.4 | 1.22 | QC-ACN-AA-XB |

TABLE 4-continued

| Ex. No. | Structure | MW | Obs. MS Ion | RT | QC Method |
|---|---|---|---|---|---|
| 360 | 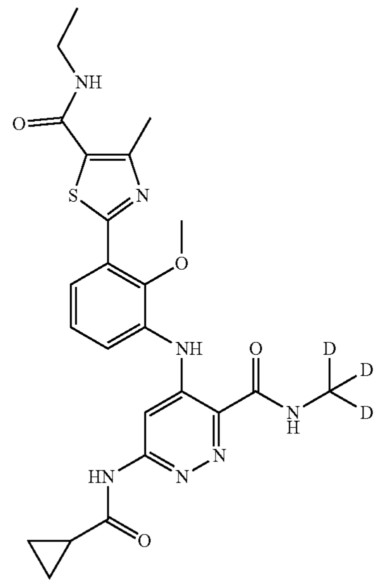 [SMILES: [2H]C([2H])([2H])NC(=O)c1nnc(NC(=O)C2CC2)cc1Nc1cccc(-c2nc(C)c(C(=O)NCC)s2)c1OC] | 512.6 | 513.2 | 1.59 | QC-ACN-AA-XB |
| 361 | 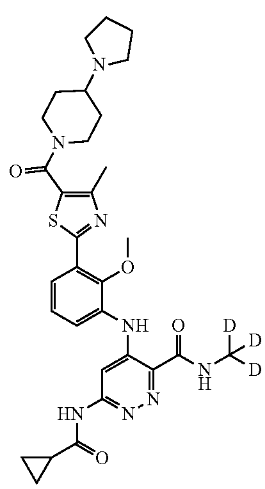 [SMILES: [2H]C([2H])([2H])NC(=O)c1nnc(NC(=O)C2CC2)cc1Nc1cccc(-c2nc(C)c(C(=O)N3CCC(N4CCCC4)CC3)s2)c1OC] | 621.8 | 622.3 | 1.32 | QC-ACN-AA-XB |

TABLE 4-continued
| Ex. No. | Structure | MW | Obs. MS Ion | RT | QC Method |
|---|---|---|---|---|---|
| 362 | 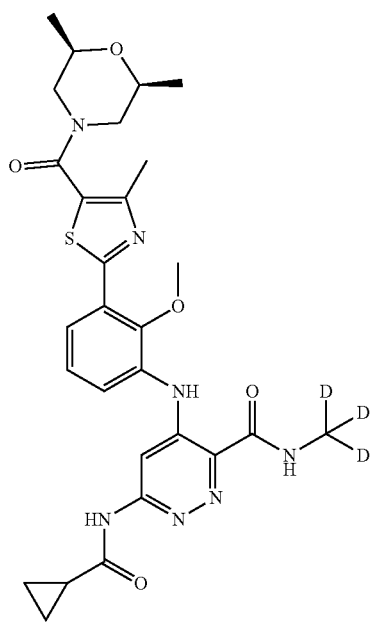 [SMILES: [2H]C([2H])([2H])NC(=O)c1nnc(NC(=O)C2CC2)cc1Nc1cccc(-c2nc(C)c(C(=O)N3C[C@@H](C)O[C@@H](C)C3)s2)c1OC] | 582.7 | 583.3 | 1.44 | QC-ACN-TFA-XB |
| 363 | 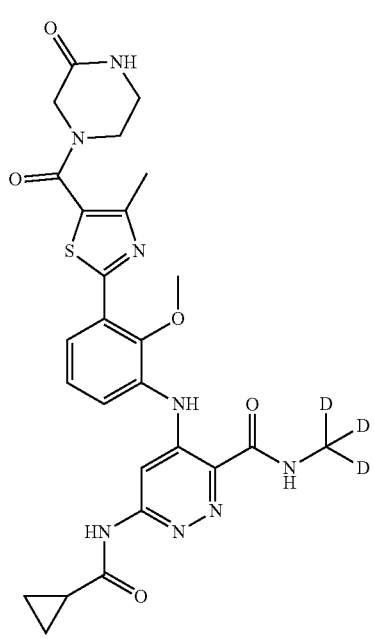 [SMILES: [2H]C([2H])([2H])NC(=O)c1nnc(NC(=O)C2CC2)cc1Nc1cccc(-c2nc(C)c(C(=O)N3CCNC(=O)C3)s2)c1OC] | 567.6 | 568.2 | 1.28 | QC-ACN-AA-XB |

TABLE 4-continued

| Ex. No. | Structure | MW | Obs. MS Ion | RT | QC Method |
|---|---|---|---|---|---|
| 364 | 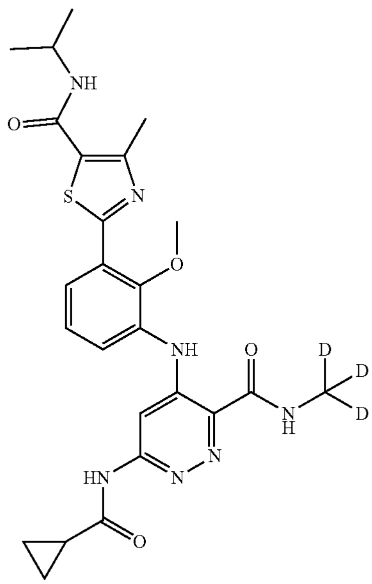 [SMILES: [2H]C([2H])([2H])NC(=O)c1nnc(NC(=O)C2CC2)cc1Nc1cccc(-c2nc(C)c(C(=O)NC(C)C)s2)c1OC] | 526.6 | 527.3 | 1.73 | QC-ACN-AA-XB |
| 365 | 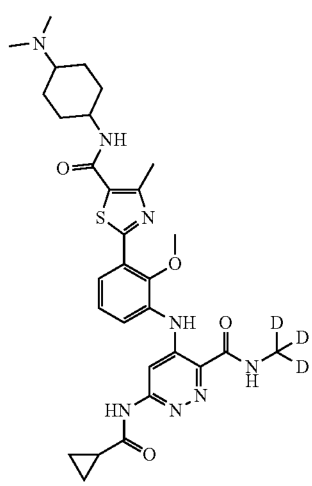 [SMILES: [2H]C([2H])([2H])NC(=O)c1nnc(NC(=O)C2CC2)cc1Nc1cccc(-c2nc(C)c(C(=O)NC3CCC(N(C)C)CC3)s2)c1OC] | 609.8 | 610.4 | 1.02 | QC-ACN-TFA-XB |
| 366 | 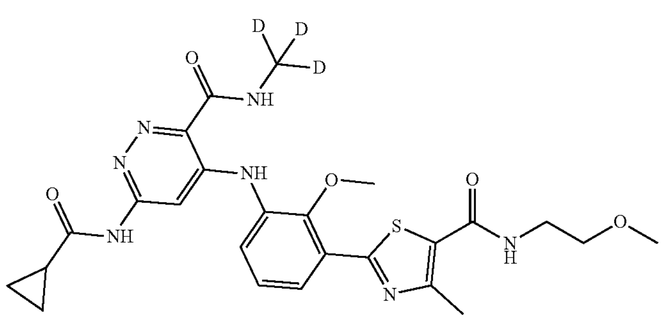 [SMILES: [2H]C([2H])([2H])NC(=O)c1nnc(NC(=O)C2CC2)cc1Nc1cccc(-c2nc(C)c(C(=O)NCCOC)s2)c1OC] | 542.6 | 543.4 | 1.58 | QC-ACN-AA-XB |

TABLE 4-continued
| Ex. No. | Structure | MW | Obs. MS Ion | RT | QC Method |
|---|---|---|---|---|---|
| 367 | 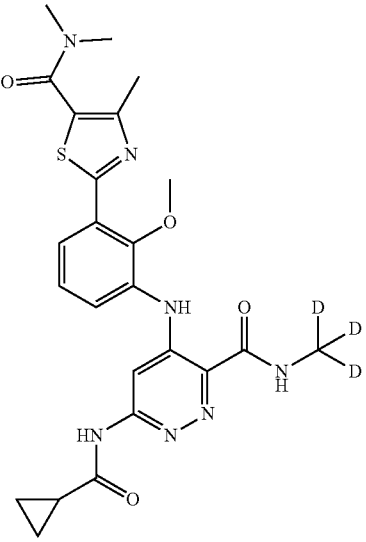 [SMILES: [2H]C([2H])([2H])NC(=O)c1nnc(NC(=O)C2CC2)cc1Nc1cccc(-c2nc(C)c(C(=O)N(C)C)s2)c1OC] | 512.6 | 513.2 | 1.28 | QC-ACN-TFA-XB |
| 368 | 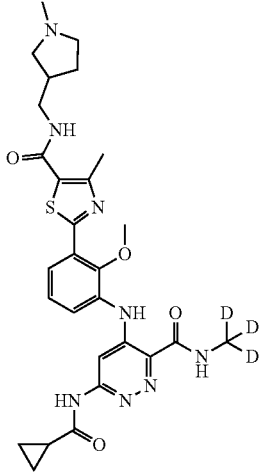 [SMILES: [2H]C([2H])([2H])NC(=O)c1nnc(NC(=O)C2CC2)cc1Nc1cccc(-c2nc(C)c(C(=O)NCC3CCN(C)C3)s2)c1OC] | 581.7 | 582.3 | 1.17 | QC-ACN-AA-XB |
| 369 | 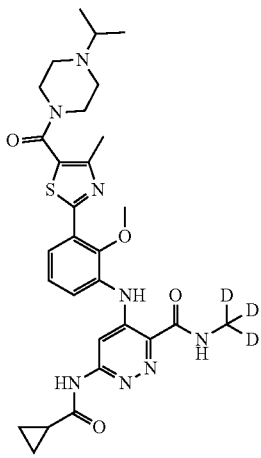 [SMILES: [2H]C([2H])([2H])NC(=O)c1nnc(NC(=O)C2CC2)cc1Nc1cccc(-c2nc(C)c(C(=O)N3CCN(C(C)C)CC3)s2)c1OC] | 595.7 | 596.2 | 1.08 | QC-ACN-TFA-XB |

TABLE 4-continued
| Ex. No. | Structure | MW | Obs. MS Ion | RT | QC Method |
|---|---|---|---|---|---|
| 370 | 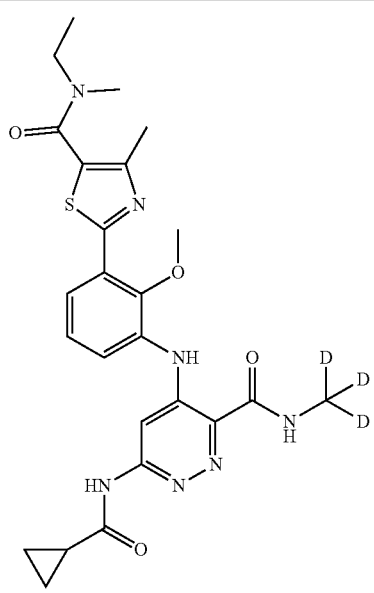 [SMILES: [2H]C([2H])([2H])NC(=O)c1nnc(NC(=O)C2CC2)cc1Nc1cccc(-c2nc(C)c(C(=O)N(C)CC)s2)c1OC] | 526.6 | 527.2 | 1.4 | QC-ACN-TFA-XB |
| 371 | 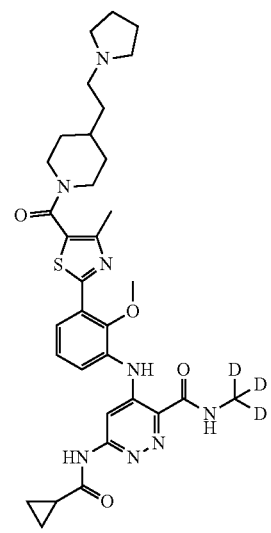 [SMILES: [2H]C([2H])([2H])NC(=O)c1nnc(NC(=O)C2CC2)cc1Nc1cccc(-c2nc(C)c(C(=O)N3CCC(CCN4CCCC4)CC3)s2)c1OC] | 649.8 | 650.4 | 1.26 | QC-ACN-AA-XB |

TABLE 4-continued

| Ex. No. | Structure | MW | Obs. MS Ion | RT | QC Method |
|---|---|---|---|---|---|
| 372 | 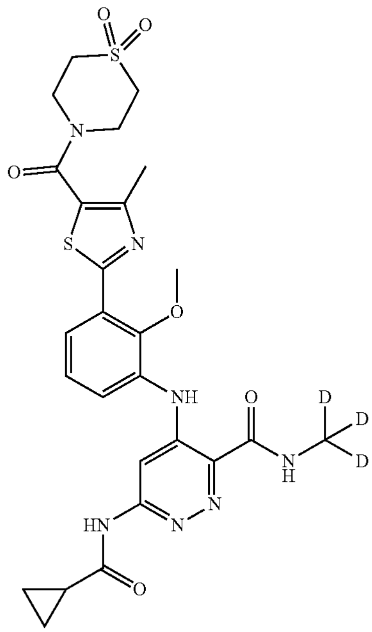 [SMILES: [2H]C([2H])([2H])NC(=O)c1nnc(NC(=O)C2CC2)cc1Nc1cccc(-c2nc(C)c(C(=O)N3CCS(=O)(=O)CC3)s2)c1OC] | 602.7 | 603.2 | 1.23 | QC-ACN-TFA-XB |
| 373 | 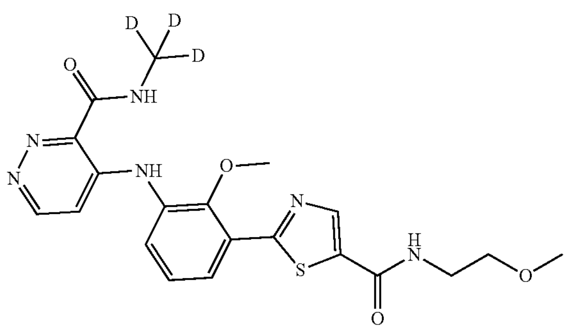 [SMILES: [2H]C([2H])([2H])NC(=O)c1nnccc1Nc1cccc(-c2ncc(C(=O)NCCOC)s2)c1OC] | 445.5 | 446.4 | 1.19 | QC-ACN-AA-XB |
| 374 | 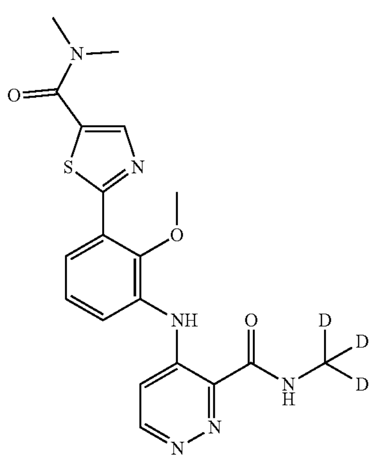 [SMILES: [2H]C([2H])([2H])NC(=O)c1nnccc1Nc1cccc(-c2ncc(C(=O)N(C)C)s2)c1OC] | 415.5 | 416.4 | 0.82 | QC-ACN-TFA-XB |

TABLE 4-continued

| Ex. No. | Structure | MW | Obs. MS Ion | RT | QC Method |
|---|---|---|---|---|---|
| 375 | 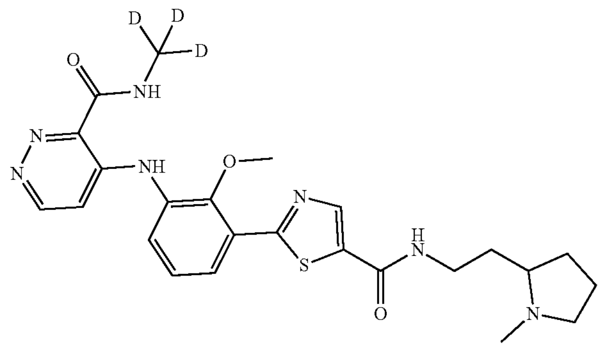 [SMILES: [2H]C([2H])([2H])NC(=O)c1nnccc1Nc1cccc(-c2ncc(C(=O)NCCC3CCCN3C)s2)c1OC] | 498.6 | 499.4 | 0.65 | QC-ACN-TFA-XB |
| 376 | 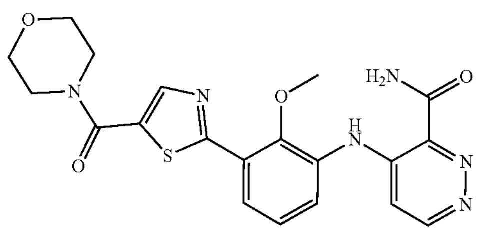 [SMILES: COc1c(Nc2ccnnc2C(N)=O)cccc1-c1ncc(C(=O)N2CCOCC2)s1] | 440.5 | 441.2 | 1.01 | QC-ACN-AA-XB |
| 377 | 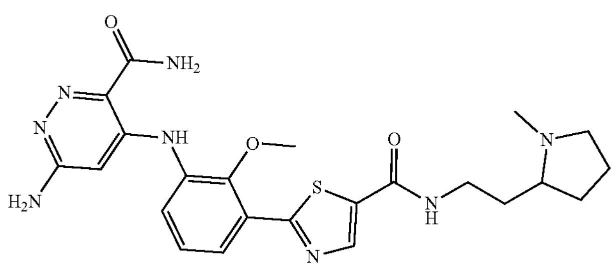 [SMILES: COc1c(Nc2cc(N)nnc2C(N)=O)cccc1-c1ncc(C(=O)NCCC2CCCN2C)s1] | 496.6 | 497.3 | 0.74 | QC-ACN-AA-XB |
| 378 | 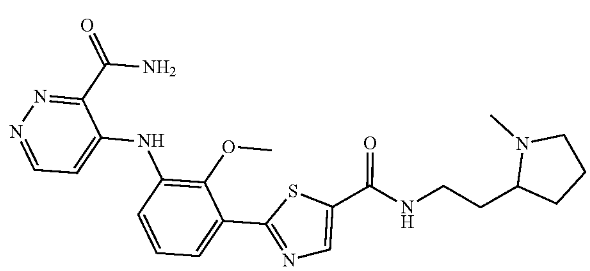 [SMILES: COc1c(Nc2ccnnc2C(N)=O)cccc1-c1ncc(C(=O)NCCC2CCCN2C)s1] | 481.6 | 482.2 | 0.79 | QC-ACN-AA-XB |

| Ex. No. | Structure | MW | Obs. MS Ion | RT | QC Method |
|---|---|---|---|---|---|
| 379 | 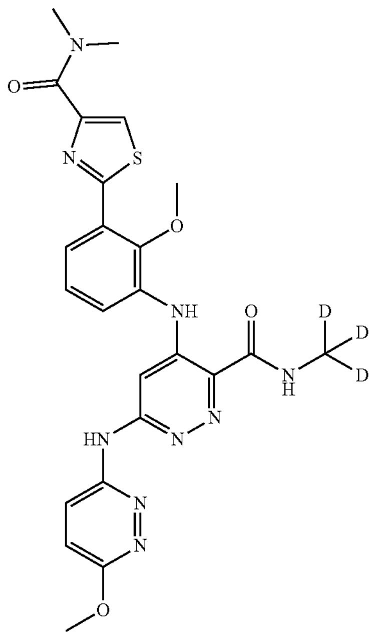 [SMILES: [2H]C([2H])([2H])NC(=O)c1nnc(Nc2ccc(OC)nn2)cc1Nc1cccc(-c2nc(C(=O)N(C)C)cs2)c1OC] | 538.6 | 539.1 | 1.07 | QC-ACN-TFA-XB |
| 380 | 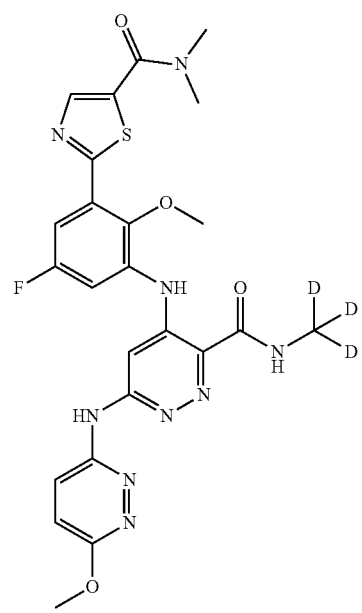 [SMILES: [2H]C([2H])([2H])NC(=O)c1nnc(Nc2ccc(OC)nn2)cc1Nc1cc(F)cc(-c2ncc(C(=O)N(C)C)s2)c1OC] | 556.6 | 557.1 | 1.57 | QC-ACN-AA-XB |

TABLE 4-continued

| Ex. No. | Structure | MW | Obs. MS Ion | RT | QC Method |
|---|---|---|---|---|---|
| 381 | 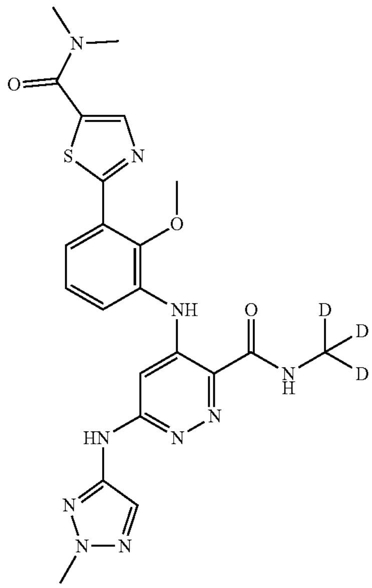 [SMILES: [2H]C([2H])([2H])NC(=O)c1nnc(Nc2cnn(C)n2)cc1Nc1cccc(-c2ncc(C(=O)N(C)C)s2)c1OC] | 511.6 | 512.2 | 1.36 | QC-ACN-AA-XB |
| 382 | 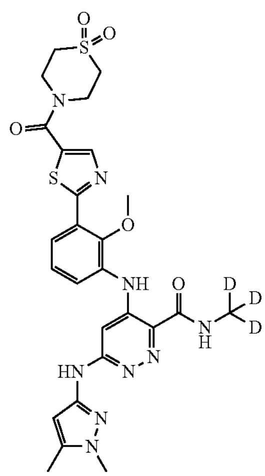 [SMILES: [2H]C([2H])([2H])NC(=O)c1nnc(Nc2cc(C)n(C)n2)cc1Nc1cccc(-c2ncc(C(=O)N3CCS(=O)(=O)CC3)s2)c1OC] | 614.7 | 615.1 | 1.34 | QC-ACN-AA-XB |
| 383 | 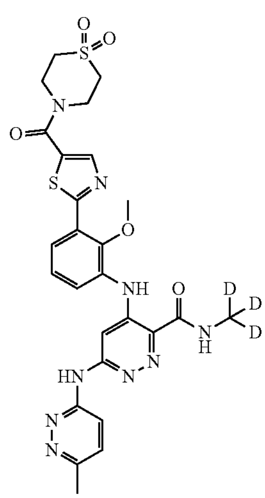 [SMILES: [2H]C([2H])([2H])NC(=O)c1nnc(Nc2ccc(C)nn2)cc1Nc1cccc(-c2ncc(C(=O)N3CCS(=O)(=O)CC3)s2)c1OC] | 612.7 | 613.2 | 1.25 | QC-ACN-AA-XB |

TABLE 4-continued
| Ex. No. | Structure | MW | Obs. MS Ion | RT | QC Method |
|---|---|---|---|---|---|
| 384 | 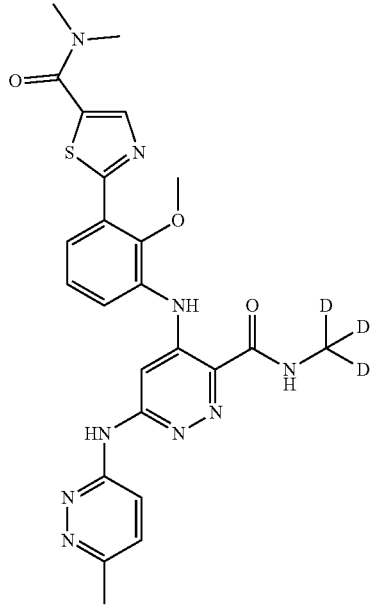 [SMILES: [2H]C([2H])([2H])NC(=O)c1nnc(Nc2ccc(C)nn2)cc1Nc1cccc(-c2ncc(C(=O)N(C)C)s2)c1OC] | 522.6 | 523.3 | 1.3 | QC-ACN-AA-XB |
| 385 | 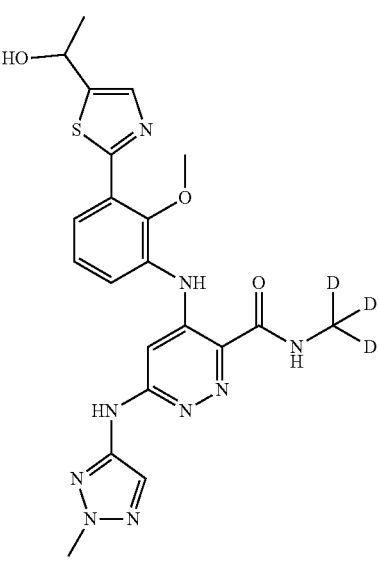 [SMILES: [2H]C([2H])([2H])NC(=O)c1nnc(Nc2cnn(C)n2)cc1Nc1cccc(-c2ncc(C(C)O)s2)c1OC] | 484.6 | 485.2 | 1.34 | QC-ACN-AA-XB |

TABLE 4-continued

| Ex. No. | Structure | MW | Obs. MS Ion | RT | QC Method |
|---|---|---|---|---|---|
| 386 | 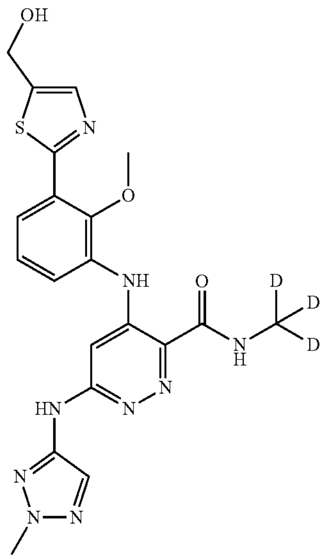 [SMILES: [2H]C([2H])([2H])NC(=O)c1nnc(Nc2cnn(C)n2)cc1Nc1cccc(-c2ncc(CO)s2)c1OC] | 470.5 | 471.1 | 0.91 | QC-ACN-TFA-XB |
| 387 | 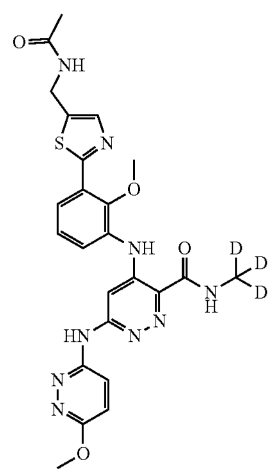 [SMILES: [2H]C([2H])([2H])NC(=O)c1nnc(Nc2ccc(OC)nn2)cc1Nc1cccc(-c2ncc(CNC(C)=O)s2)c1OC] | 538.6 | 539.3 | 1.25 | QC-ACN-AA-XB |
| 388 | 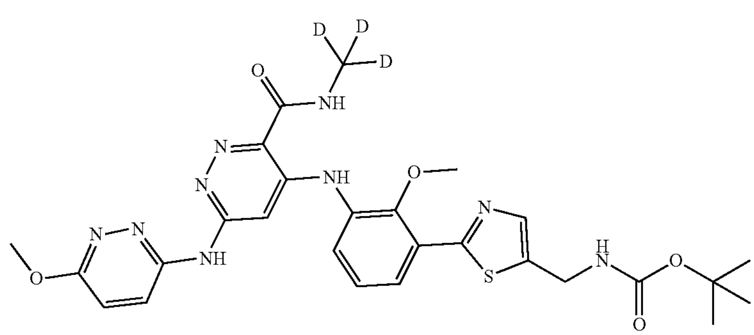 [SMILES: [2H]C([2H])([2H])NC(=O)c1nnc(Nc2ccc(OC)nn2)cc1Nc1cccc(-c2ncc(CNC(=O)OC(C)(C)C)s2)c1OC] | 596.7 | 597.2 | 1.33 | QC-ACN-TFA-XB |

TABLE 4-continued
| Ex. No. | Structure | MW | Obs. MS Ion | RT | QC Method |
|---|---|---|---|---|---|
| 389 | 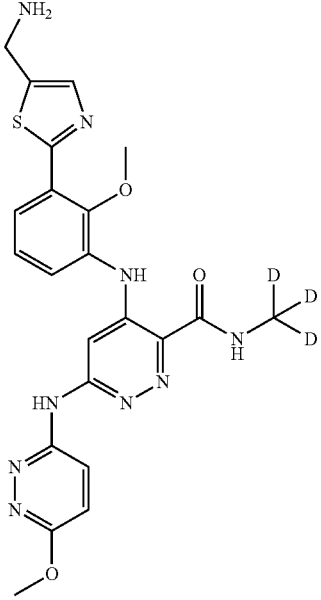 [SMILES: [2H]C([2H])([2H])NC(=O)c1nnc(Nc2ccc(OC)nn2)cc1Nc1cccc(-c2ncc(CN)s2)c1OC] | 496.6 | 497.2 | 1.08 | QC-ACN-AA-XB |
| 390 | 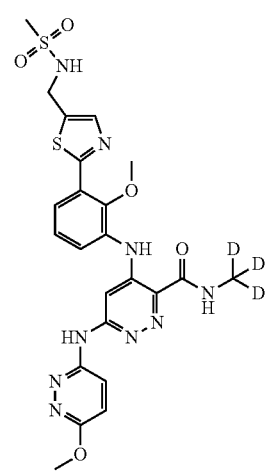 [SMILES: [2H]C([2H])([2H])NC(=O)c1nnc(Nc2ccc(OC)nn2)cc1Nc1cccc(-c2ncc(CNS(C)(=O)=O)s2)c1OC] | 574.7 | 575.1 | 1.35 | QC-ACN-AA-XB |
| 391 | 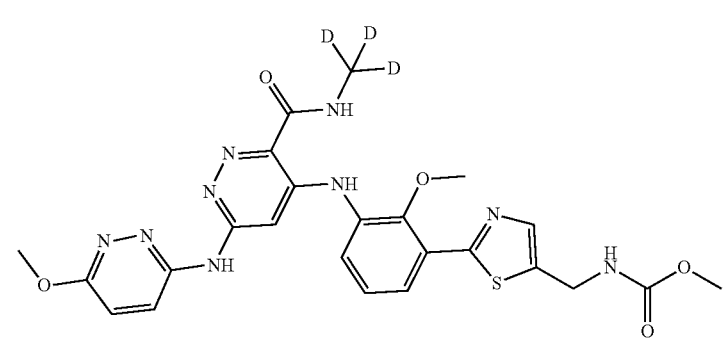 | 554.6 | 555.0 | 1.17 | QC-ACN-TFA-XB |

TABLE 4-continued
| Ex. No. | Structure | MW | Obs. MS Ion | RT | QC Method |
|---|---|---|---|---|---|
| 392 | 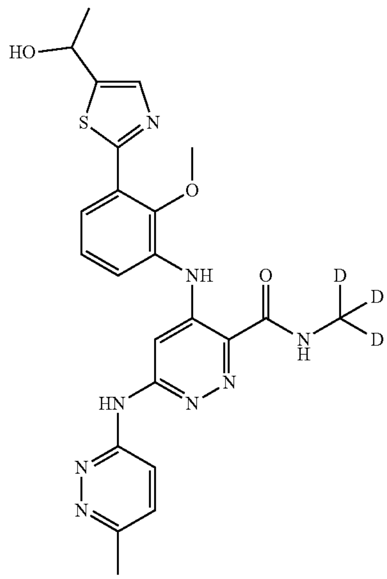 [SMILES: [2H]C([2H])([2H])NC(=O)c1nnc(Nc2ccc(C)nn2)cc1Nc1cccc(-c2ncc(C(C)O)s2)c1OC] | 495.6 | 496.2 | 1.26 | QC-ACN-AA-XB |
| 393 | 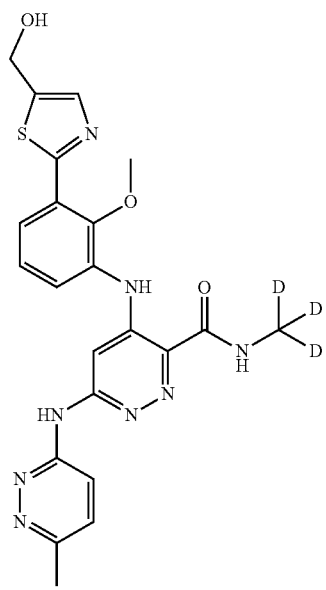 [SMILES: [2H]C([2H])([2H])NC(=O)c1nnc(Nc2ccc(C)nn2)cc1Nc1cccc(-c2ncc(CO)s2)c1OC] | 481.6 | 482.0 | 1.18 | QC-ACN-AA-XB |

TABLE 4-continued

| Ex. No. | Structure | MW | Obs. MS Ion | RT | QC Method |
|---|---|---|---|---|---|
| 394 | 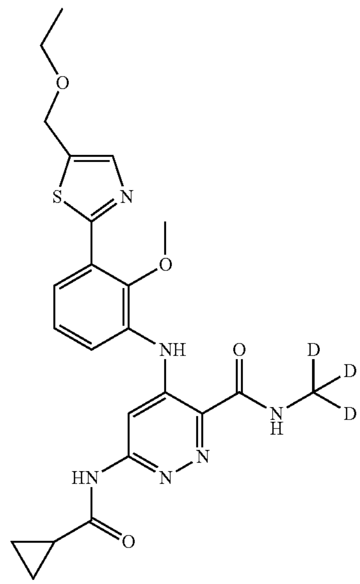 [SMILES: [2H]C([2H])([2H])NC(=O)c1nnc(NC(=O)C2CC2)cc1Nc1cccc(-c2ncc(COCC)s2)c1OC] | 485.6 | 486.1 | 1.75 | QC-ACN-AA-XB |
| 395 | 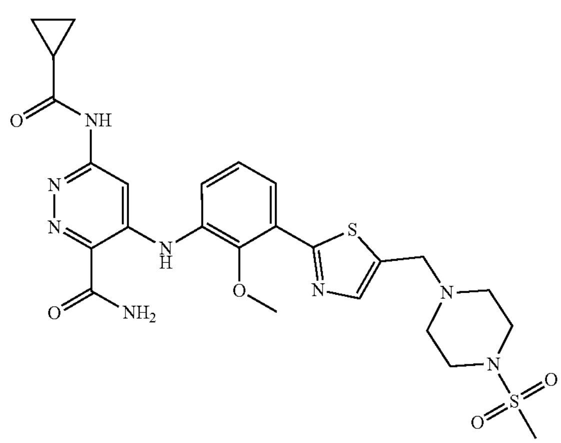 [SMILES: COc1c(Nc2cc(NC(=O)C3CC3)nnc2C(N)=O)cccc1-c1ncc(CN2CCN(S(C)(=O)=O)CC2)s1] | 586.7 | 587.0 | 1.48 | QC-ACN-AA-XB |
| 396 | 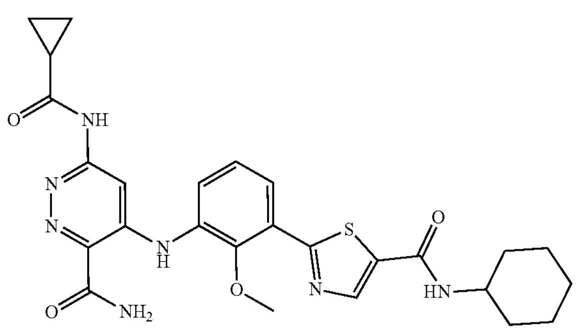 [SMILES: COc1c(Nc2cc(NC(=O)C3CC3)nnc2C(N)=O)cccc1-c1ncc(C(=O)NC2CCCCC2)s1] | 535.6 | 536.1 | 1.73 | QC-ACN-AA-XB |

TABLE 4-continued
| Ex. No. | Structure | MW | Obs. MS Ion | RT | QC Method |
|---|---|---|---|---|---|
| 397 | 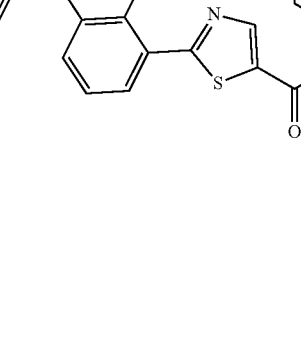 | 606.8 | 607.3 | 1.12 | QC-ACN-AA-XB |
| 398 | 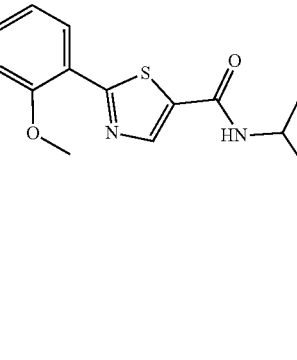 | 551.6 | 552.1 | 1.28 | QC-ACN-AA-XB |
| 399 | 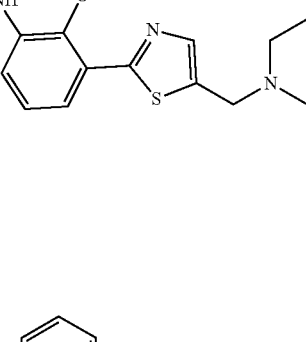 | 566.7 | 567.4 | 0.64 | QC-ACN-TFA-XB |
| 400 | 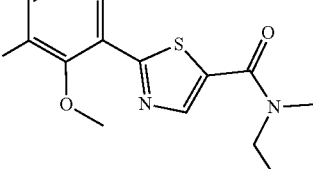 | 565.7 | 566.2 | 1.31 | QC-ACN-AA-XB |

TABLE 4-continued

| Ex. No. | Structure | MW | Obs. MS Ion | RT | QC Method |
|---|---|---|---|---|---|
| 401 | 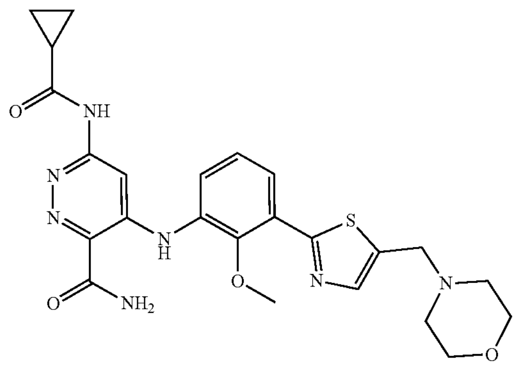 [SMILES: COc1c(Nc2cc(NC(=O)C3CC3)nnc2C(N)=O)cccc1-c1ncc(CN2CCOCC2)s1] | 509.6 | 510.3 | 1.35 | QC-ACN-AA-XB |
| 402 | 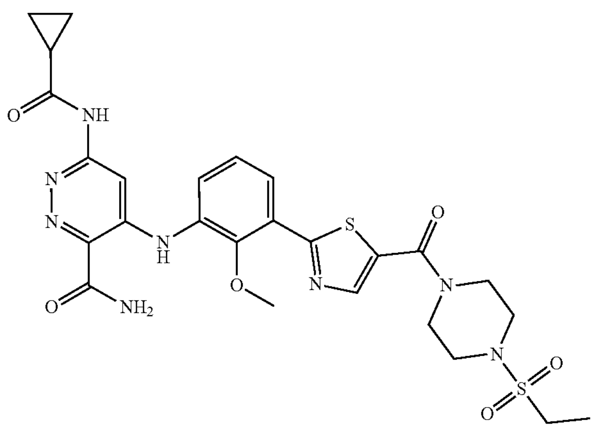 [SMILES: CCS(=O)(=O)N1CCN(C(=O)c2cnc(-c3cccc(Nc4cc(NC(=O)C5CC5)nnc4C(N)=O)c3OC)s2)CC1] | 614.7 | 615.1 | 1.2 | QC-ACN-TFA-XB |
| 403 | 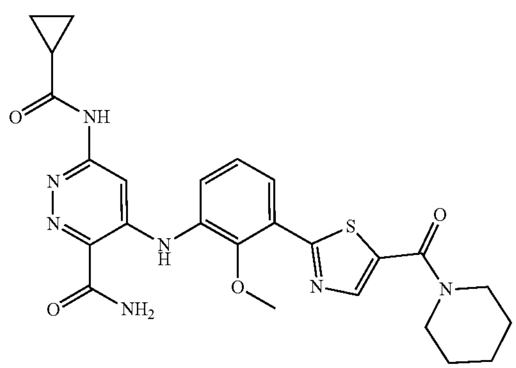 [SMILES: COc1c(Nc2cc(NC(=O)C3CC3)nnc2C(N)=O)cccc1-c1ncc(C(=O)N2CCCCC2)s1] | 521.6 | 522.3 | 1.55 | QC-ACN-AA-XB |
| 404 | 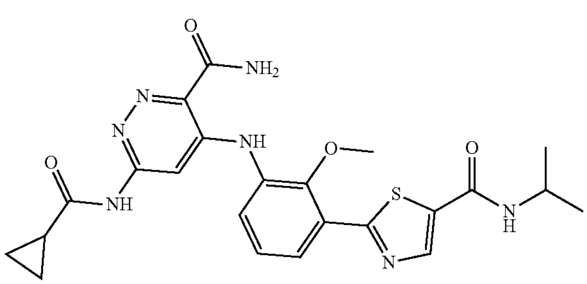 [SMILES: COc1c(Nc2cc(NC(=O)C3CC3)nnc2C(N)=O)cccc1-c1ncc(C(=O)NC(C)C)s1] | 495.6 | 496.1 | 1.39 | QC-ACN-AA-XB |

TABLE 4-continued

| Ex. No. | Structure | MW | Obs. MS Ion | RT | QC Method |
|---|---|---|---|---|---|
| 405 | 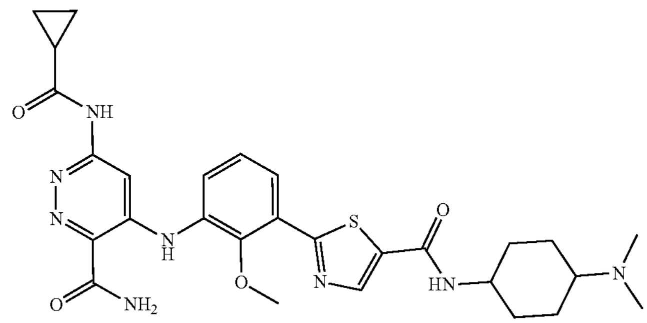 [SMILES: COc1c(Nc2cc(NC(=O)C3CC3)nnc2C(N)=O)cccc1-c1ncc(C(=O)NC2CCC(N(C)C)CC2)s1] | 578.7 | 579.2 | 1.27 | QC-ACN-AA-XB |
| 406 | 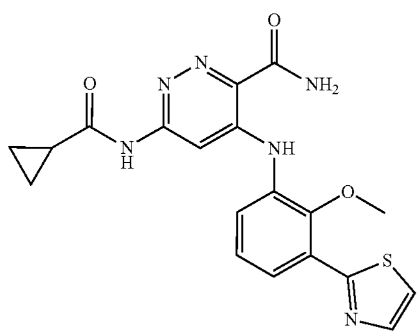 [SMILES: COc1c(Nc2cc(NC(=O)C3CC3)nnc2C(N)=O)cccc1-c1nccs1] | 410.5 | 411.3 | 1.39 | QC-ACN-AA-XB |
| 407 | 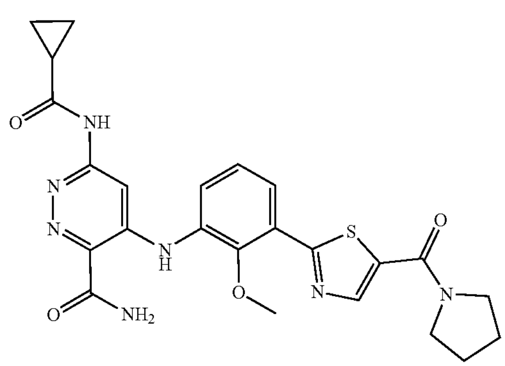 [SMILES: COc1c(Nc2cc(NC(=O)C3CC3)nnc2C(N)=O)cccc1-c1ncc(C(=O)N2CCCC2)s1] | 507.6 | 508.2 | 1.29 | QC-ACN-TFA-XB |
| 408 | 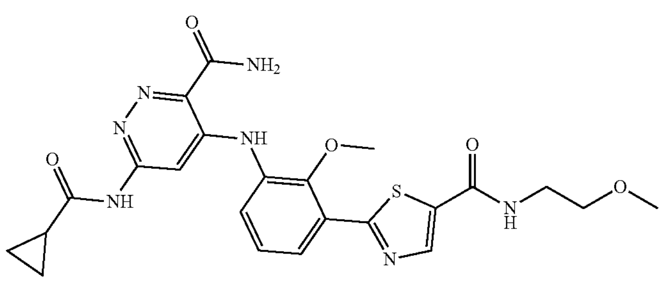 [SMILES: COCCNC(=O)c1cnc(-c2cccc(Nc3cc(NC(=O)C4CC4)nnc3C(N)=O)c2OC)s1] | 511.6 | 512.1 | 1.27 | QC-ACN-AA-XB |

Example 409

N-(5-((2-methoxy-3-(1-methyl-1H-1,2,4-triazol-3-yl)phenyl)amino)-6-methylpyridazin-3-yl)cyclopropanecarboxamide

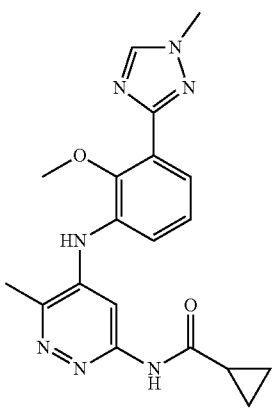

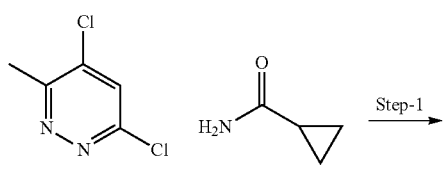 Step-1 →

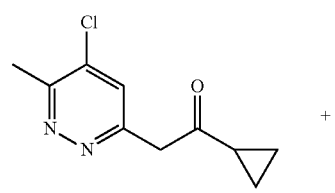

+

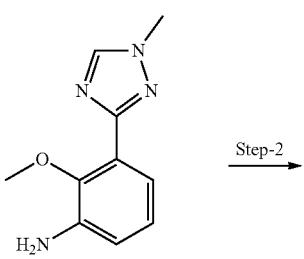 Step-2 →

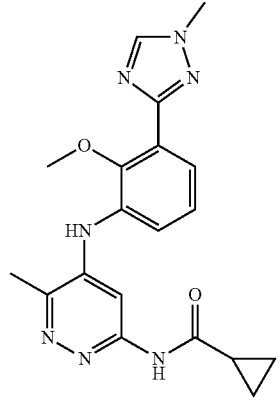

Step 1

A mixture of 4,6-dichloro-3-methylpyridazine (112 mg, 0.687 mmol), cyclopropanecarboxamide (64.3 mg, 0.756 mmol), $Cs_2CO_3$ (448 mg, 1.374 mmol), xantphos (59.6 mg, 0.103 mmol) and $Pd_2(dba)_3$ (62.9 mg, 0.069 mmol) in 1,4-Dioxane (1 mL) was placed in a microwave vessel, sparged with $N_2$ for 5 minutes, sealed, and heated at 130° C. for 20 minutes. Cooled and filtered then purified by HPLC. HPLC conditions: Phenomenex Luna 5 micron C18 column (30×100 mm); MeCN (0.1% TFA)/water (0.1% TFA); 10%-100% gradient over 15 minutes; 30 mL/min. Isolated product fractions and diluted with AcOEt (50 mL), which was washed with sat $NaHCO_3$ (30 mL), dried over $MgSO_4$ and concentrated under vacuo to give N-(5-chloro-6-methylpyridazin-3-yl)cyclopropanecarboxamide (35 mg, 0.165 mmol, 24.07% yield). LCMS m/z 211.9/213.9 $(M+H)^+$; HPLC $t_R$ 0.72 min (analytical HPLC Method A); $^1$H NMR (400 MHz, CHLOROFORM-d) δ 9.74-9.46 (m, 1H), 8.60 (s, 1H), 2.72 (s, 3H), 1.95 (tt, J=7.9, 4.6 Hz, 1H), 1.22-1.10 (m, 2H), 1.03-0.92 (m, 2H).

Step 2

A mixture of N-(5-chloro-6-methylpyridazin-3-yl)cyclopropanecarboxamide (10 mg, 0.047 mmol), 2-methoxy-3-(1-methyl-1H-1,2,4-triazol-3-yl)aniline (19.30 mg, 0.094 mmol), $Pd_2(dba)_3$ (4.33 mg, 4.72 µmol), xantphos (5.47 mg, 9.45 µmol) and $Cs_2CO_3$ (46.2 mg, 0.142 mmol) in 1,4-Dioxane (1 mL) was sparged with $N_2$ for 5 minutes. The reaction vessel was sealed and heated to 130° C. in a microwave for 30 min. Cooled and filtered then purified by HPLC to give N-(5-((2-methoxy-3-(1-methyl-1H-1,2,4-triazol-3-yl)phenyl)amino)-6-methylpyridazin-3-yl)cyclopropanecarboxamide (2.5 mg, 6.52 µmol, 13.81% yield). LCMS m/z 380.2 $(M+H)^+$; HPLC $t_R$ 1.00 min (analytical HPLC Method QC-ACN-AA-XB); $^1$H NMR (500 MHz, DMSO-$d_6$) δ 10.85 (s, 1H), 8.54 (s, 1H), 7.90 (s, 1H), 7.73 (d, J=6.7 Hz, 1H), 7.37-7.31 (m, 2H), 7.29-7.23 (m, 1H), 3.93 (s, 3H), 2.56 (d, J=3.1 Hz, 6H), 1.93 (br. s., 1H), 0.80-0.61 (m, 4H)

Example 410
6-(cyclopropanecarboxamido)-4-((3-(5-(2-(dimethyl-amino)-2-oxoethyl)oxazol-2-yl)-2-methoxyphenyl)amino)-N-(methyl-d3)pyridazine-3-carboxamide
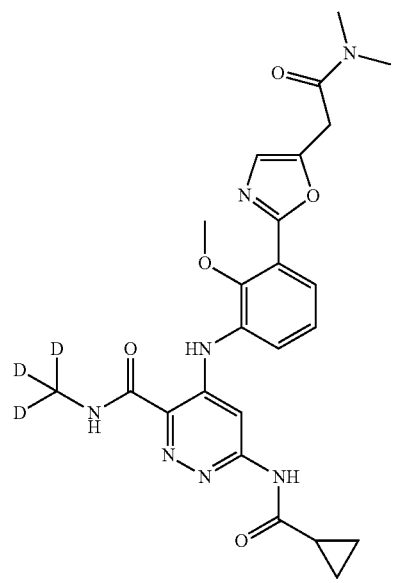
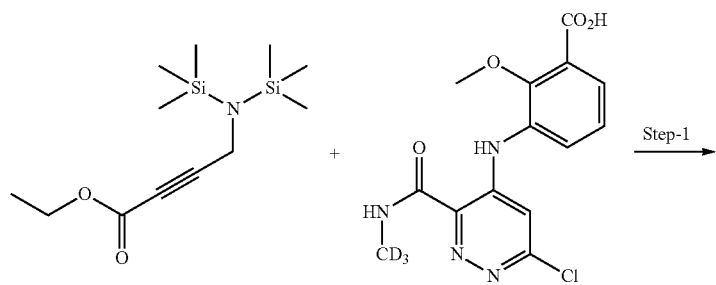
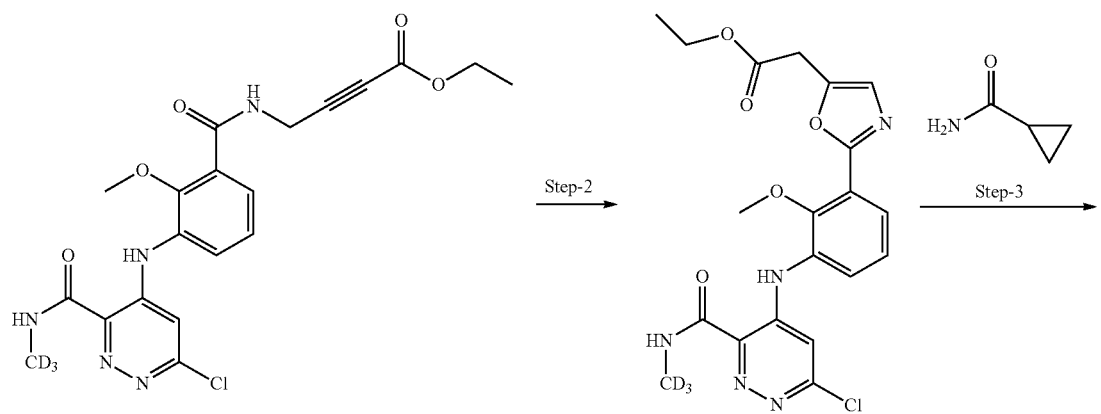

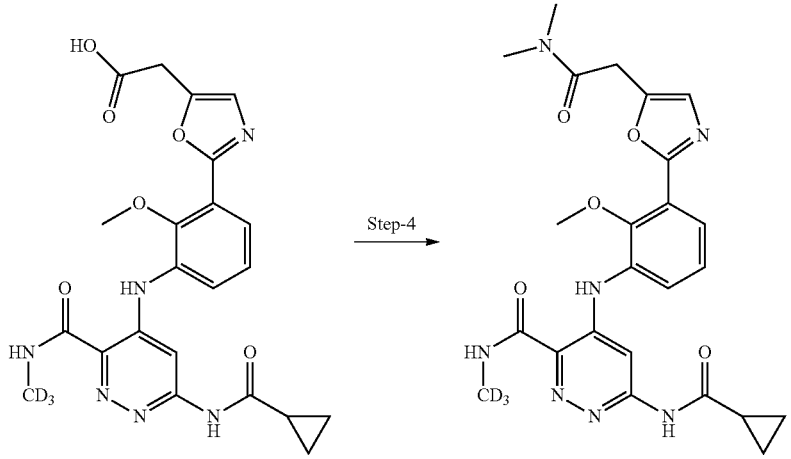 [SMILES: [2H]C([2H])([2H])NC(=O)c1nnc(NC(=O)C2CC2)cc1Nc1cccc(-c2ncc(CC(=O)O)o2)c1OC ; [2H]C([2H])([2H])NC(=O)c1nnc(NC(=O)C2CC2)cc1Nc1cccc(-c2ncc(CC(=O)N(C)C)o2)c1OC]

Step-4

Step 1

To a mixture of 3-((6-chloro-3-((methyl-d3)carbamoyl)pyridazin-4-yl)amino)-2-methoxybenzoic acid (ref: Wipf, P. et al.; Org. Lett., 2004, vol. 6, #20, p. 3593-3595 (98 mg, 0.288 mmol) in dichloromethane (5 mL) and THF (5 mL) was added oxalyl chloride (0.050 mL, 0.577 mmol) and 1 drop of DMF. Stirred for one hour. Reaction mixture was concentrated in vacuo then dissolved in THF (5 mL). Ethyl 4-(bis(trimethylsilyl)amino)but-2-ynoate (102 mg, 0.375 mmol) and TBAF (0.288 mL, 0.288 mmol) were added. Stirred at rt overnight then quenched with water. The reaction mixture was diluted with ethyl acetate and washed with sat NaCl. The organic layer was dried with MgSO$_4$, filtered and concentrated. The crude material was purified on a silica gel cartridge (24 g) using an EtOAc/Hex gradient (0-100% EtOAc over 13 CV) to give ethyl 4-(3-((6-chloro-3-((methyl-d3)carbamoyl)pyridazin-4-yl)amino)-2-methoxybenzamido)but-2-ynoate (55 mg, 0.123 mmol, 42.5% yield). $^1$H NMR (400 MHz, CHLOROFORM-d) δ 11.10 (s, 1H), 8.28 (br s, 1H), 8.08-7.84 (m, 2H), 7.52 (dd, J=7.9, 1.5 Hz, 1H), 7.35 (t, J=7.9 Hz, 1H), 7.02 (s, 1H), 4.46 (d, J=5.3 Hz, 2H), 4.26 (d, J=7.3 Hz, 2H), 3.86 (s, 3H), 1.69 (br s, 3H), 1.33 (t, J=7.0 Hz, 3H)

Step 2

To a mixture of ethyl 4-(3-((6-chloro-3-((methyl-d3)carbamoyl)pyridazin-4-yl)amino)-2-methoxybenzamido)but-2-ynoate (55 mg, 0.123 mmol) in CH$_2$Cl$_2$ (5 mL) was added silica. The reaction was stirred at rt for 5 days. Reaction mixture was filtered washing well with 5% MeOH/DCM. Filtrate was concentrated. The crude material was purified on a silica gel cartridge (12 g) using an EtOAc/Hex gradient (0-100% EtOAc over 20 CV) to give ethyl 2-(2-(3-((6-chloro-3-((methyl-d3)carbamoyl)pyridazin-4-yl)amino)-2-methoxyphenyl)oxazol-5-yl)acetate (40 mg, 0.089 mmol, 72.7% yield). LCMS m/z 449.1 (M+H)$^+$; HPLC $t_R$ 0.84 min (analytical HPLC Method B).

Step 3

A mixture of ethyl 2-(2-(3-((6-chloro-3-((methyl-d3)carbamoyl)pyridazin-4-yl)amino)-2-methoxyphenyl)oxazol-5-yl)acetate (40 mg, 0.089 mmol), cyclopropanecarboxamide (7.58 mg, 0.089 mmol), cesium carbonate (58.1 mg, 0.178 mmol), xantphos (7.73 mg, 0.013 mmol) and Pd$_2$(dba)$_3$ (8.16 mg, 8.91 µmol) in 1,4-Dioxane (2 mL) was placed in a microwave vessel, sparged with N$_2$ for 5 minutes, sealed, and heated at 130° C. for 20 minutes. After cooling the reaction mixture was diluted with ethyl acetate and washed with sat NaCl. The organic layer was dried with MgSO$_4$, filtered and concentrated. The crude material was purified on a silica gel cartridge (12 g) using an EtOAc/Hex gradient (0-100% EtOAc over 21 CV then held at 100% for 9CV) to give ethyl 2-(2-(3-((6-(cyclopropanecarboxamido)-3-((methyl-d3)carbamoyl)pyridazin-4-yl)amino)-2-methoxyphenyl)oxazol-5-yl)acetate (31 mg, 0.062 mmol, 69.9% yield). To a mixture of ethyl 2-(2-(3-((6-(cyclopropanecarboxamido)-3-((methyl-d3)carbamoyl)pyridazin-4-yl)amino)-2-methoxyphenyl)oxazol-5-yl)acetate (31 mg, 0.062 mmol) in THF was added 1N NaOH (1 mL). Stirred at rt for 2 hours. The reaction mixture was diluted with ethyl acetate and washed with sat KH$_2$PO$_4$. The organic layer was dried with MgSO$_4$, filtered and concentrated to afford 2-(2-(3-((6-(cyclopropanecarboxamido)-3-((methyl-d3)carbamoyl)pyridazin-4-yl)amino)-2-methoxyphenyl)oxazol-5-yl)acetic acid (24 mg, 0.051 mmol, 84% yield). LCMS m/z 470.21 (M+H)$^+$; HPLC $t_R$ 0.69 min (analytical HPLC Method B).

Step 4

To a mixture of 2-(2-(3-((6-(cyclopropanecarboxamido)-3-((methyl-d3)carbamoyl)pyridazin-4-yl)amino)-2-methoxyphenyl)oxazol-5-yl)acetic acid (24 mg, 0.051 mmol, 84%), dimethylamine hydrochloride (6.95 mg, 0.085 mmol), and BOP (11.31 mg, 0.026 mmol) in DMF (1 mL) was added Et$_3$N (0.012 mL, 0.085 mmol). Stirred at rt for 1 hour. Filtered and purified by HPLC to give 6-(cyclopropanecarboxamido)-4-((3-(5-(2-(dimethylamino)-2-oxoethyl)oxazol-2-yl)-2-methoxyphenyl)amino)-N-(methyl-d3)pyridazine-3-carboxamide (3.7 mg, 7.30 µmol, 42.9% yield). LCMS m/z 497.2 (M+H)$^+$; HPLC $t_R$ 1.25 min (analytical HPLC Method QC-ACN-AA-XB); 1H NMR in DMSO-d6 is consistent with desired product (500 MHz, DMSO-d6) δ 11.34 (s, 1H), 11.02 (s, 1H), 9.14 (s, 1H), 8.15 (s, 1H), 7.68 (d, J=7.8 Hz, 1H), 7.60 (d, J=7.8 Hz, 1H), 7.33 (t, J=7.9 Hz, 1H), 7.18 (s, 1H), 3.97 (s, 2H), 3.73 (s, 3H), 3.08 (s, 3H), 2.86 (s, 3H), 2.07 (t, J=5.2 Hz, 1H), 0.92-0.72 (m, 4H).

The Examples in Table 5 were prepared using a similar procedure used to prepare Example 410.

TABLE 5
| Ex. No. | Structure | MW | Obs. MS Ion | RT | QC Method |
|---|---|---|---|---|---|
| 411 | 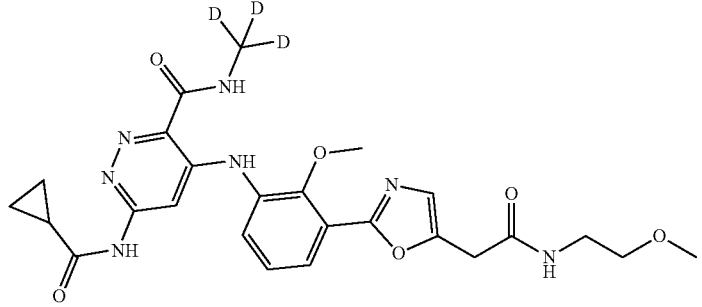 [SMILES: [2H]C([2H])([2H])NC(=O)c1nnc(NC(=O)C2CC2)cc1Nc1cccc(-c2ncc(CC(=O)NCCOC)o2)c1OC] | 526.6 | 527.4 | 0.95 | QC-ACN-TFA-XB |
| 412 | 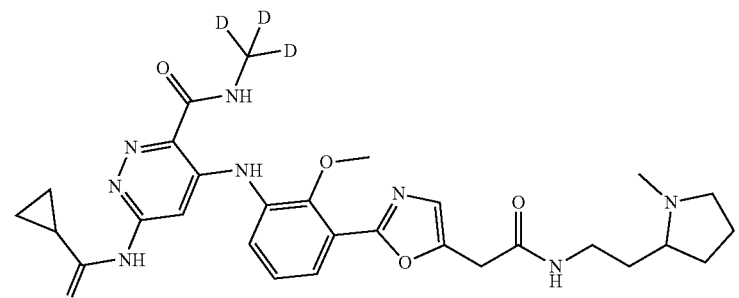 | 579.7 | 580.2 | 1.04 | QC-ACN-AA-XB |
| 413 | 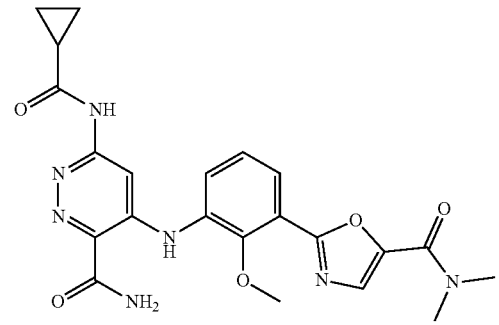 [SMILES: COc1c(Nc2cc(NC(=O)C3CC3)nnc2C(N)=O)cccc1-c1ncc(C(=O)N(C)C)o1] | 465.5 | 466.4 | 1.14 | QC-ACN-AA-XB |
| 414 | 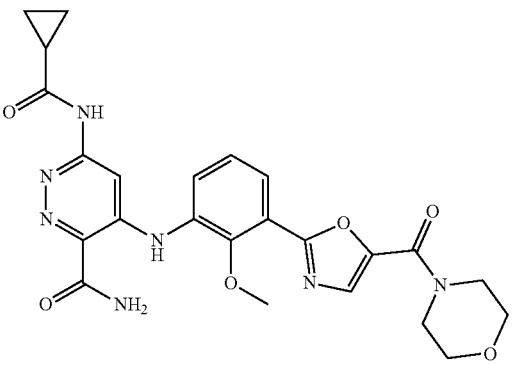 [SMILES: COc1c(Nc2cc(NC(=O)C3CC3)nnc2C(N)=O)cccc1-c1ncc(C(=O)N2CCOCC2)o1] | 507.5 | 508.4 | 1.15 | QC-ACN-AA-XB |

TABLE 5-continued

| Ex. No. | Structure | MW | Obs. MS Ion | RT | QC Method |
|---|---|---|---|---|---|
| 415 | 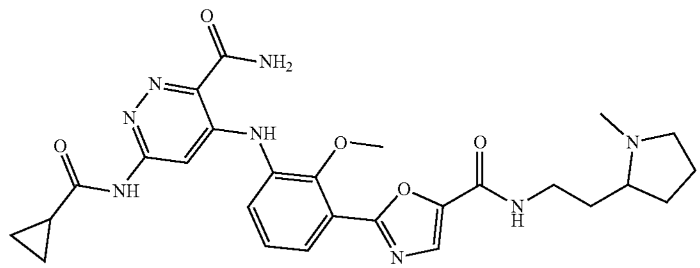 [SMILES: COc1c(Nc2cc(NC(=O)C3CC3)nnc2C(N)=O)cccc1-c1ncc(C(=O)NCCC2CCCN2C)o1] | 548.6 | 549.2 | 1.13 | QC-ACN-AA-XB |
| 416 | 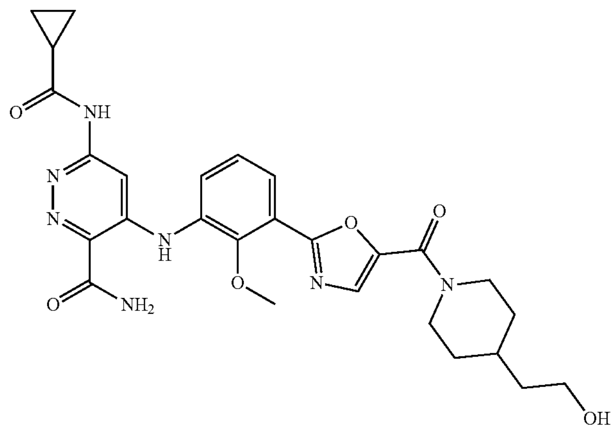 [SMILES: COc1c(Nc2cc(NC(=O)C3CC3)nnc2C(N)=O)cccc1-c1ncc(C(=O)N2CCC(CCO)CC2)o1] | 549.6 | 550.1 | 1.05 | QC-ACN-TFA-XB |
| 417 | 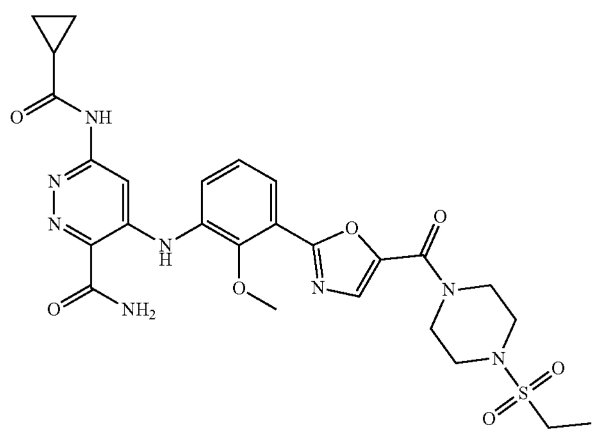 [SMILES: CCS(=O)(=O)N1CCN(C(=O)c2cnc(-c3cccc(Nc4cc(NC(=O)C5CC5)nnc4C(N)=O)c3OC)o2)CC1] | 598.6 | 599.4 | 1.25 | QC-ACN-AA-XB |
| 418 | 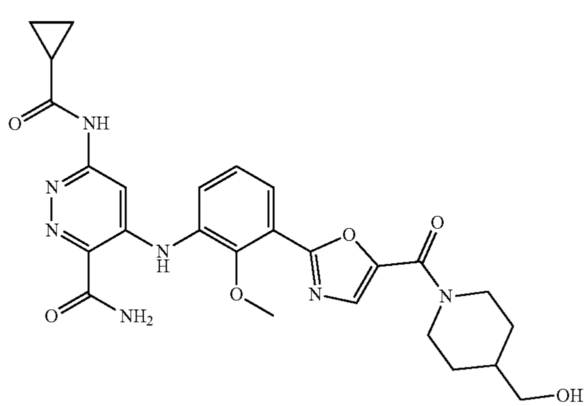 [SMILES: COc1c(Nc2cc(NC(=O)C3CC3)nnc2C(N)=O)cccc1-c1ncc(C(=O)N2CCC(CO)CC2)o1] | 535.6 | 536.1 | 0.99 | QC-ACN-TFA-XB |

TABLE 5-continued

| Ex. No. | Structure | MW | Obs. MS Ion | RT | QC Method |
|---|---|---|---|---|---|
| 419 | 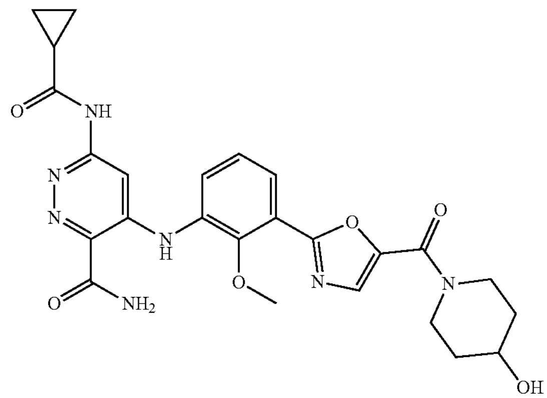 [SMILES: COc1c(Nc2cc(NC(=O)C3CC3)nnc2C(N)=O)cccc1-c1ncc(C(=O)N2CCC(O)CC2)o1] | 521.5 | 522.2 | 1.11 | QC-ACN-AA-XB |
| 420 | 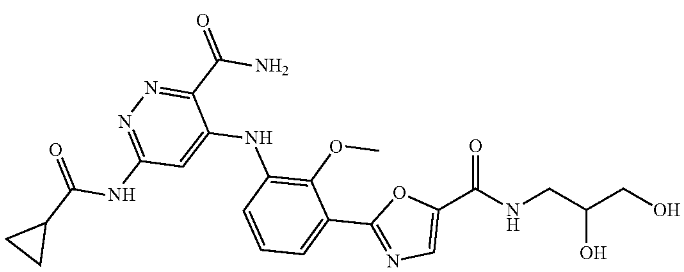 [SMILES: COc1c(Nc2cc(NC(=O)C3CC3)nnc2C(N)=O)cccc1-c1ncc(C(=O)NCC(O)CO)o1] | 511.5 | 512.1 | 0.98 | QC-ACN-AA-XB |
| 421 | 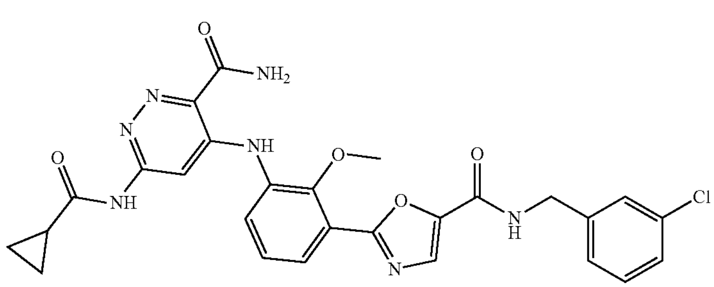 [SMILES: COc1c(Nc2cc(NC(=O)C3CC3)nnc2C(N)=O)cccc1-c1ncc(C(=O)NCc2cccc(Cl)c2)o1] | 562.0 | 562.3 | 1.45 | QC-ACN-TFA-XB |

Example 422

6-(cyclopropanecarboxamido)-4-((2-methoxy-3-(1-(2-morpholinoethyl)-1H-1,2,3-triazol-4-yl)phenyl)amino)-N-(methyl-d3)pyridazine-3-carboxamide

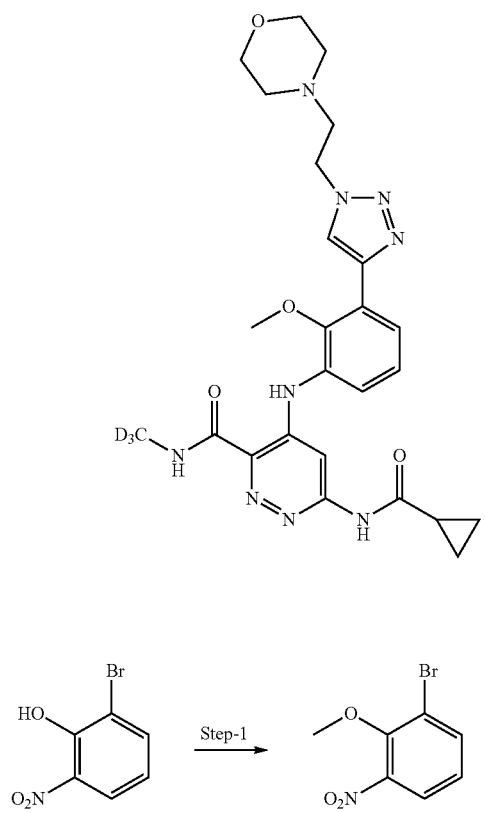

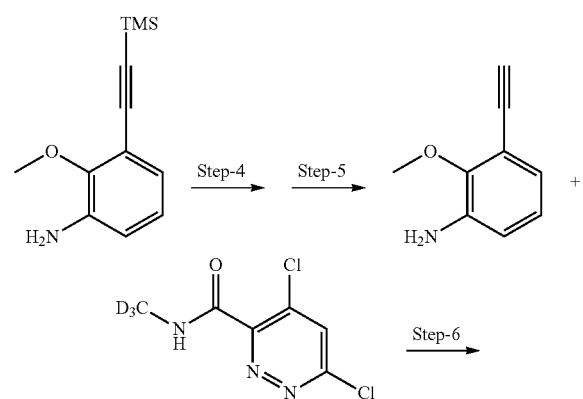

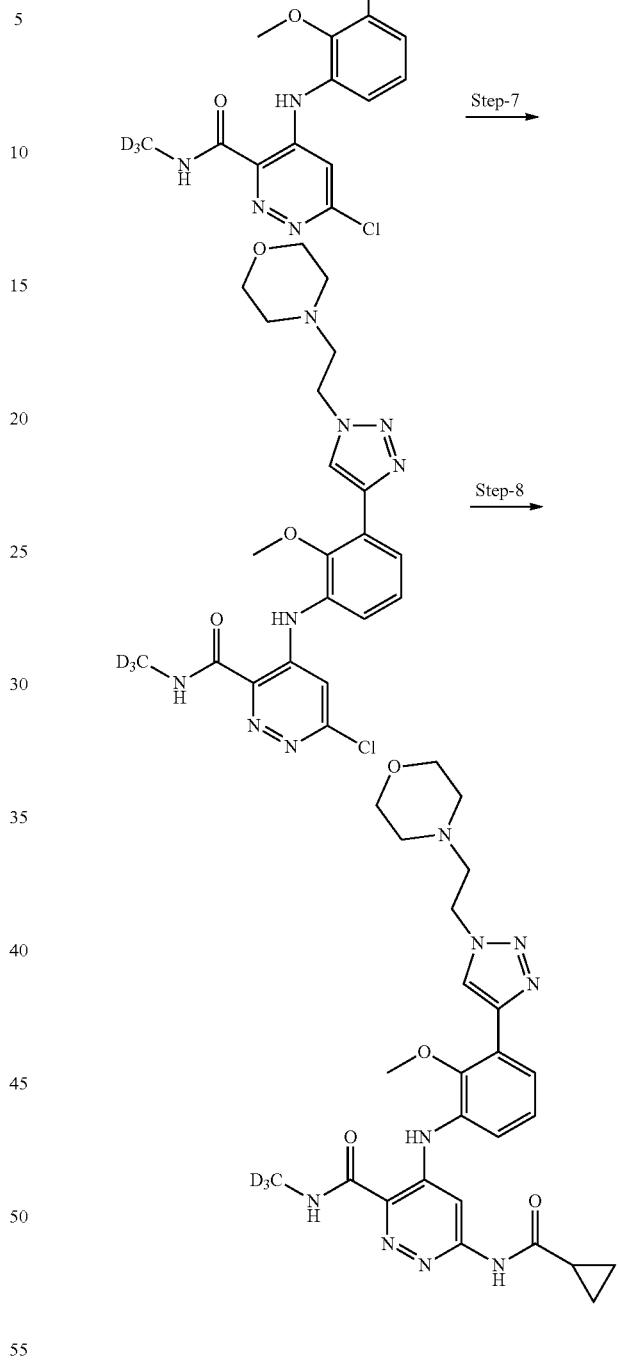

Step 1

To a solution of 2-bromo-6-nitrophenol (5 g, 22.94 mmol) in DMF (18 ml) was added potassium carbonate (9.51 g, 68.8 mmol). The resulting mixture was stirred for 15 minutes, then iodomethane (2.87 ml, 45.9 mmol) was added. The resulting mixture was stirred at room temperature overnight.

HPLC and LC-MS indicated complete conversion to product. Cold water was added (75 mL), and the resulting mixture was stirred and sonicated. Next, the solid was collected with filtration. This material was then dissolved in EtOAc (150 mL). This solution was washed 1× with 10% LiCl and 1× with brine. The reaction mixture was dried over sodium sulfate, then filtered and concentrated. This was loaded onto a 120 g ISCO column, then purified by flash chromatography eluting with 0-50% EtOAc in hexanes. The reaction afforded a pale yellow solid, 1-bromo-2-methoxy-3-nitrobenzene (4.997 g, 20.46 mmol, 89% yield) HPLC $t_R$ 0.92 min (analytical HPLC Method A).

Step 2

A mixture of 1-bromo-2-methoxy-3-nitrobenzene (2.48 g, 9.62 mmol), zinc (6.29 g, 96 mmol) and ammonium chloride (5.15 g, 96 mmol) in ethanol (40 mL) and water (5.71 mL) was stirred at room temperature overnight. The reaction was then diluted with dichloromethane (200 ml), and filtered. The filtrate was washed with water (50 ml), dried ($Na_2SO_4$), and concentrated. Redissolved this material in DCM, and loaded onto a 80 g column for purification by flash chromatography, eluting with 0-100% EtOAc in hexanes. The reaction afforded 3-bromo-2-methoxyaniline (1.95 g, 9.17 mmol, 95% yield) as a colorless oil.
HPLC $t_R$ 0.77 min (analytical HPLC Method A).

Step 3

A mixture of 3-bromo-2-methoxyaniline (1.0 g, 4.95 mmol), Bis(triphenylphosphine)palladium(II) chloride (0.347 g, 0.495 mmol), and Copper(I) iodide (0.377 g, 1.980 mmol) in DMA (20 mL) was stirred at room temperature and degassed by bubbling dry nitrogen through it for 10 minutes. Then ethynyltrimethylsilane (3.50 mL, 24.75 mmol) and diisopropylamine (15.41 mL, 109 mmol) were added and the reaction mixture immediately became a yellow solution. The pressure vessel was then sealed and placed into a warm 105° C. bath. Stirred at 105° C. overnight.

The diisopropylamine was evaporated and the excess TMS-acetylene, then diluted with 100 mL ethyl acetate. The organic solution was washed with 1×1:1 ammonium hydroxide:sat. ammonium chloride, 1× sat. ammonium chloride, 1×10% aq. LiCl, 1× brine and dried over sodium sulfate. This was then filtered and concentrated, and loaded onto a 80 g ISCO column for purification by flash chromatography eluting with 0-100% EtOAc in hexanes to afforded 2-methoxy-3-((trimethylsilyl)ethynyl)aniline (995 mg, 2.95 mmol, 59.6% yield) as an impure brown solid. Carried on as-is to deprotection. LCMS m/z 220.2 $(M+H)^+$; HPLC $t_R$ 0.94 min (analytical HPLC Method A).

Step 4

A mixture of 2-methoxy-3-((trimethylsilyl)ethynyl)aniline (995 mg, 4.54 mmol) and potassium carbonate (1881 mg, 13.61 mmol) in methanol (15 mL) was stirred at room temperature for 30 minutes. After 30 minutes, the reaction was complete. Partitioned between EtOAc (50 mL) and water (25 mL). The aqueous layer was washed with 1× EtOAc, then washed combined EtOAc layer 1× saturated ammonium chloride, 1× brine. The reaction mixture was dried over sodium sulfate, then filtered and concentrated. The oil was loaded onto a 12 g ISCO column, then purified by flash chromatography, eluting with 0-10% MeOH in DCM to afford 3-ethynyl-2-methoxyaniline (301 mg, 2.004 mmol, 44.2% yield) as an orange oil. HPLC $t_R$ 0.52 min (analytical HPLC Method A).

Step 5

4,6-dichloro-N-(methyl-d3)pyridazine-3-carboxamide (220 mg, 1.052 mmol) was dissolved in Tetrahydrofuran (6 mL) and 3-ethynyl-2-methoxyaniline (163 mg, 1.105 mmol) was added. To this solution was added lithium bis(trimethylsilyl)amide (2.63 mL, 2.63 mmol) in a dropwise manner (<2 min) using a needle and syringe and the reaction stirred until complete by LCMS (~15 min). HCl (1M aq) (1.579 mL, 1.579 mmol) was added to quench the residual base. Then the reaction was partitioned between EtOAc and water. The water layer was washed 1× ethyl acetate, and then the combined organic layer was washed 1× ammonium chloride (sat.), 1× brine. It was then dried over sodium sulfate, then filtered and concentrated to afford the crude acetylene as a tan solid. The reaction mixture was redissolved in DCM, then loaded onto a 24 g ISCO column for purification by flash chromatography eluting with 0-100% EtOAc in hexanes. The reaction afforded 6-chloro-4-((3-ethynyl-2-methoxyphenyl)amino)-N-(methyl-d3)pyridazine-3-carboxamide (228 mg, 0.677 mmol, 64.4% yield) as a white solid. LCMS m/z 320.2 $(M+H)^+$; HPLC $t_R$ 0.90 min (analytical HPLC Method A).

Step 6

Benzoic acid (2 mg, 0.016 mmol), L-Ascorbic acid sodium salt (2 mg, 10.10 µmol), and Copper(II) sulfate (2 mg, 0.013 mmol) were all weighed into the small flask containing 6-chloro-4-((3-ethynyl-2-methoxyphenyl)amino)-N-(methyl-d3)pyridazine-3-carboxamide (77 mg, 0.241 mmol). A solution of 4-(2-azidoethyl)morpholine (75 mg, 0.482 mmol) in t-BuOH (1.5 mL) and Water (1.5 mL) was added and the mixture was stirred at room temperature. After stirring overnight, the reaction was complete. Diluted with EtOAc (50 mL) and 10 mL water. Washed organic layer 1× brine, then dried over sodium sulfate, filtered and concentrated. Loaded onto a 12 g column, purified by flash chromatography eluting with 0-100% EtOAc in hexanes. The reaction afforded 6-chloro-4-((2-methoxy-3-(1-(2-morpholinoethyl)-1H-1,2,3-triazol-4-yl)phenyl)amino)-N-trideuteromethylpyridazine-3-carboxamide (108 mg, 0.216 mmol, 90% yield), a colorless oil. LCMS m/z 476.4 $(M+H)^+$; HPLC $t_R$ 0.62 min (analytical HPLC Method A).

Step 7

A mixture of 6-chloro-4-((2-methoxy-3-(1-(2-morpholinoethyl)-1H-1,2,3-triazol-4-yl)phenyl)amino)-N-trideuteromethylpyridazine-3-carboxamide (26 mg, 0.055 mmol), Xantphos (6.32 mg, 10.93 µmol), and cyclopropanecarboxamide (9.30 mg, 0.109 mmol) in dioxane (1 mL) was degassed by bubbling $N_2$ through it for 5 minutes. Then $Cs_2CO_3$ (71.2 mg, 0.219 mmol) and $Pd_2(dba)_3$ (5.00 mg, 5.46 µmol) were added. Then the vessel was sealed, and the reaction was stirred at 120° C. for 2 h. The reaction was complete by LC-MS. Diluted with DMF, filtered and submitted for purification. The reaction afforded 6-(cyclopropanecarboxamido)-4-((2-methoxy-3-(1-(2-morpholinoethyl)-1H-1,2,3-triazol-4-yl)phenyl)amino)-N-trideuteromethylpyridazine-3-carboxamide (15.3 mg, 0.029 mmol, 52.3% yield). LCMS m/z 525.5 $(M+H)^+$; HPLC $t_R$ 0.58 min (analytical HPLC Method A); $^1$H NMR (500 MHz, DMSO-$d_6$) δ 11.33 (s, 1H), 10.98 (s, 1H), 9.16 (s, 1H), 8.50 (s, 1H), 8.13 (s, 1H), 7.95 (d, J=8.1 Hz, 1H), 7.43 (d, J=7.4 Hz, 1H), 7.34-7.28 (m, 1H), 4.59 (t, J=5.7 Hz, 2H), 3.66 (s, 3H), 3.54 (br. s., 2H), 2.90 (s, 1H), 2.82 (br. s., 1H), 2.74 (s, 1H), 2.46 (br. s., 3H), 2.11-2.04 (m, 1H), 0.85-0.79 (m, 4H)

The Examples in Table 6 were prepared using a similar procedure used to prepare Example 422.

TABLE 6

| Ex. No. | Structure | MW | Obs. MS Ion | RT | QC Method |
|---|---|---|---|---|---|
| 423 | 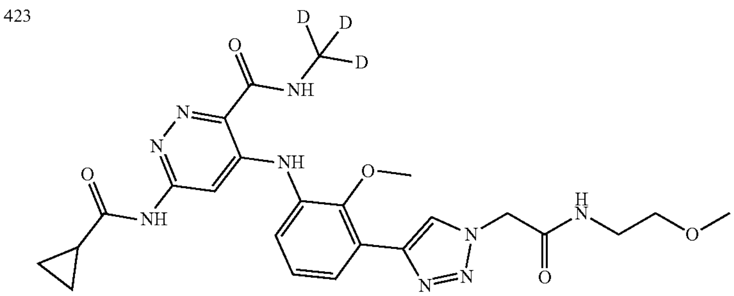 | 526.6 | 527.2 | 1.21 | QC-ACN-AA-XB |
| 424 | 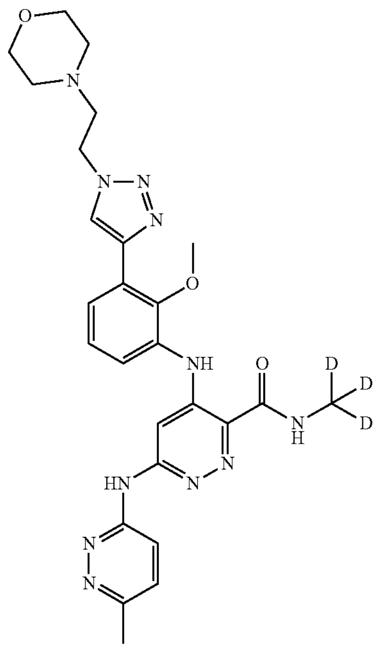 [SMILES: [2H]C([2H])([2H])NC(=O)c1nnc(Nc2ccc(C)nn2)cc1Nc1cccc(-c2cn(CCN3CCOCC3)nn2)c1OC] | 548.6 | 549.4 | 1.32 | QC-ACN-AA-XB |
| 425 | 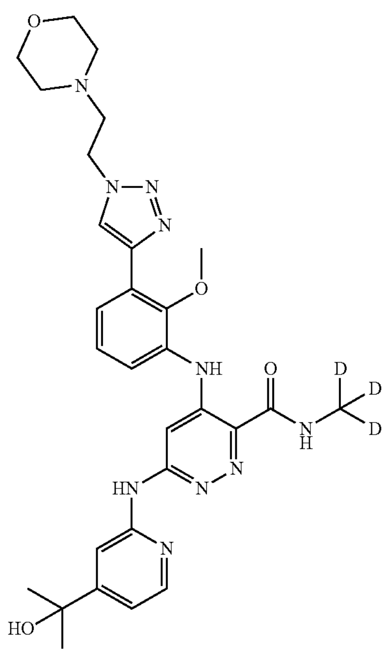 [SMILES: [2H]C([2H])([2H])NC(=O)c1nnc(Nc2cc(C(C)(C)O)ccn2)cc1Nc1cccc(-c2cn(CCN3CCOCC3)nn2)c1OC] | 591.7 | 592.3 | 1.3 | QC-ACN-AA-XB |

Example 426
6-(cyclopropanecarboxamido)-4-((2-methoxy-3-(2-(2-((2-methoxyethyl)amino)-2-oxoethyl)-2H-1,2,3-triazol-4-yl)phenyl)amino)-N-(methyl-d3)pyridazine-3-carboxamide
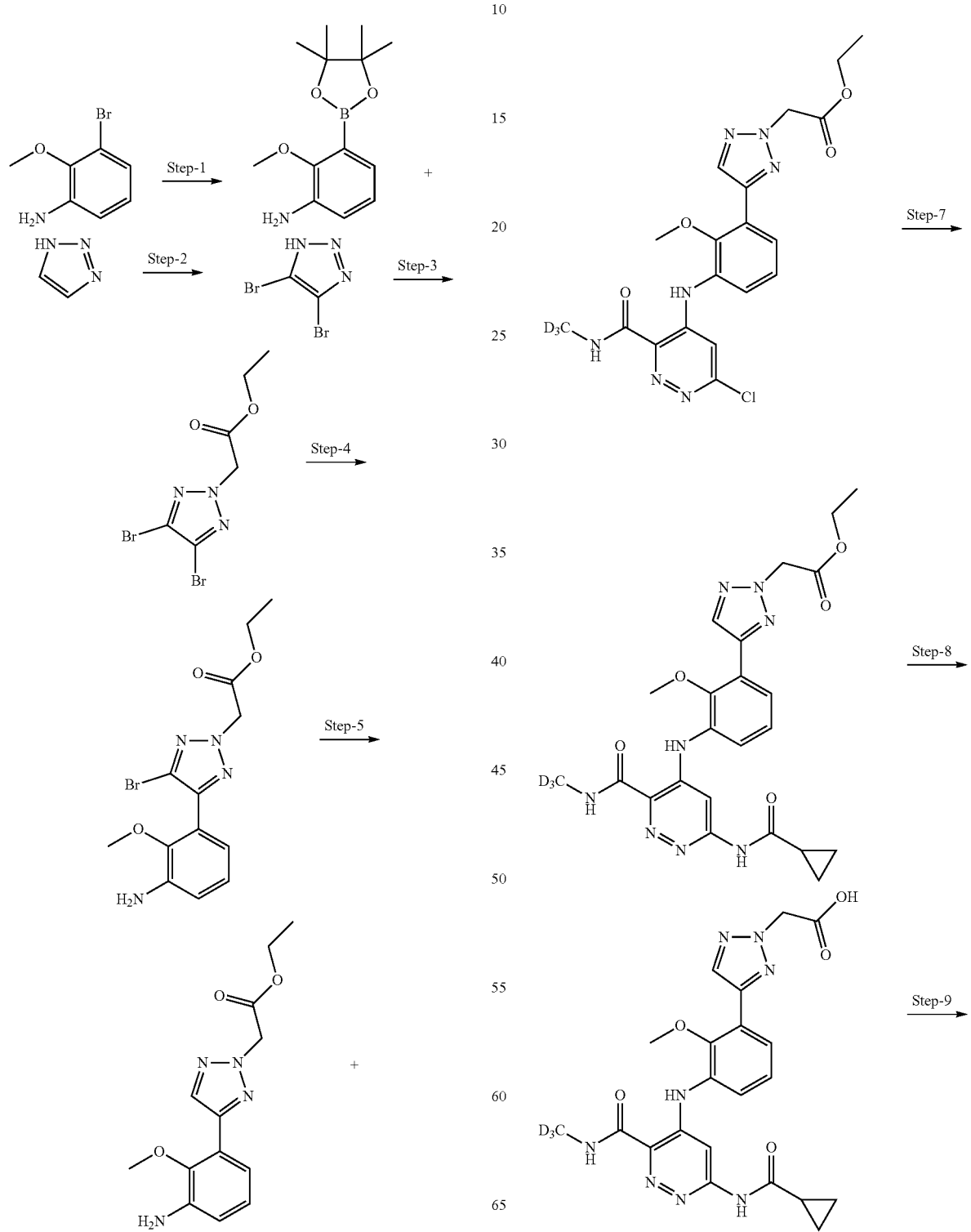

-continued

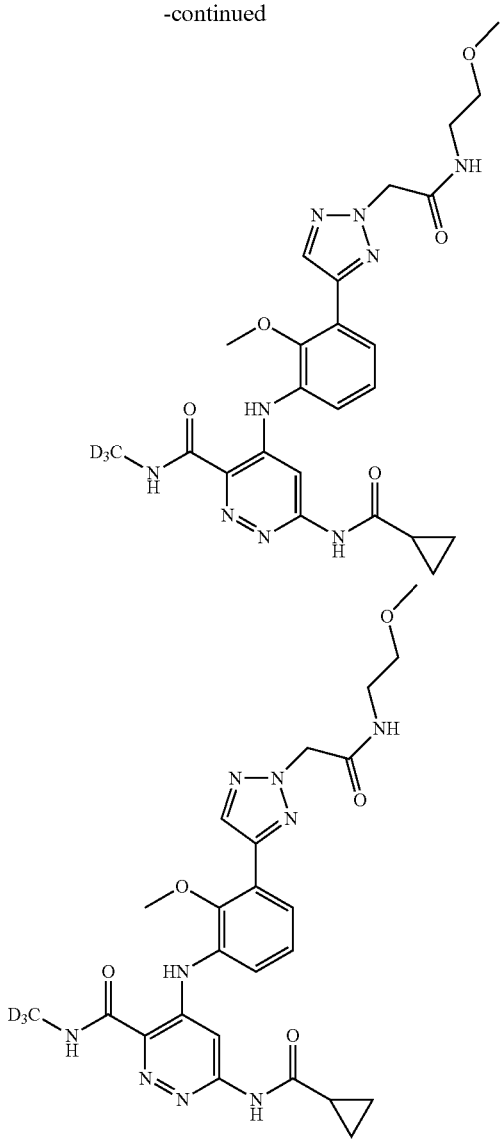

Step 1

A solution of 3-bromo-2-methoxyaniline (0.95 g, 4.70 mmol), 4,4,4',4',5,5,5',5'-octamethyl-2,2'-bi(1,3,2-dioxaborolane) (1.791 g, 7.05 mmol), PdCl$_2$(dppf)-CH$_2$Cl$_2$Adduct (0.192 g, 0.235 mmol) and potassium acetate (1.384 g, 14.11 mmol) in Dioxane (20 mL) in a flask was heated to reflux overnight. Cooled to room temperature, concentrated in vacuo on Celite. This crude product was purified by flash chromatography using an ISCO 80 g column (solid loading) eluting with 0-50% EA/hex. Appropriate fractions (25% EtOAc) were collected and concentrated in vacuo to give 2-methoxy-3-(4,4,5,5-tetramethyl-1,3,2-dioxaborolan-2-yl)aniline (0.96 g, 3.78 mmol, 80% yield) as an off-white solid. LCMS m/z 250.0 (M+H)$^+$; HPLC t$_R$ 0.70 min (analytical HPLC Method A).

Step 2

To a solution of 1H-1,2,3-triazole (0.524 mL, 9.05 mmol) in water (5 mL) at 50° C. was added bromine (0.625 mL, 12.13 mmol). The reaction was stirred at 50° C. for 90 minutes, whereupon the precipitated product was filtered off. This material was air-dried on the filter. Another aliquot of bromine (0.625 mL, 12.13 mmol) was added to the mother liquor, which was stirred at room temperature overnight. After stirring overnight, collected the solid product by filtration. Filtered off a total of 4,5-dibromo-1H-1,2,3-triazole (1.83 g, 7.91 mmol, 87% yield) as a white solid. Carried on as-is to alkylation.

Step 3

To a solution of 4,5-dibromo-1H-1,2,3-triazole (1.5 g, 6.61 mmol) in DMF (22 mL) at −10° C. (in an salt-ice-water bath) was added first potassium carbonate (1.828 g, 13.22 mmol). After stirring 15 minutes, ethyl bromoacetate (0.736 mL, 6.61 mmol) was added dropwise. After 1 h, LC-MS indicated that the reaction is complete. The reaction mixture was quenched with 10 mL water and extracted 4× with 50 mL EtOAc. The reaction mixture was washed with combined EtOac 1×10% LiCl, 1× brine and dried over sodium sulfate, filtered and concentrated. The reaction mixture was loaded onto a 40 g ISCO column for purification by flash chromatography, eluting with 0-100% EtOAc in hexanes. The reaction afforded ethyl 2-(4,5-dibromo-2H-1,2,3-triazol-2-yl)acetate (1.475 g, 4.67 mmol, 70.6% yield). Very little of the other isomer observed, none isolated. LCMS m/z 313.9/315.9 (M+H)$^+$; HPLC t$_R$ 1.00 min (analytical HPLC Method A). $^1$H NMR (400 MHz, CHLOROFORM-d) δ 5.14 (s, 2H), 4.26 (q, J=7.2 Hz, 2H), 1.29 (t, J=7.2 Hz, 3H)

Step 4

A stirred mixture of ethyl 2-(4,5-dibromo-2H-1,2,3-triazol-2-yl)acetate (1.1 g, 3.51 mmol), 2-methoxy-3-(4,4,5,5-tetramethyl-1,3,2-dioxaborolan-2-yl)aniline (0.876 g, 3.51 mmol) and PdCl$_2$(dppf)-CH$_2$Cl$_2$Adduct (0.100 g, 0.123 mmol) in Dioxane (35 mL) was degassed by bubbling nitrogen through the mixture for 5 minutes. 2M K$_3$PO$_4$ (aq) (5.27 mL, 10.54 mmol) was quickly added and the reaction mixture heated at 50° C. for 40 minutes. The reaction turned dark almost immediately. LC-MS showed complete consumption of the starting material. The reaction mixture was cooled to room temperature, then diluted with EtOAc (75 mL). This solution was then dried over sodium sulfate, filtered, concentrated and purified by flash chromatography, eluting with 0-100% EtOAc in hexanes. The reaction afforded ethyl 2-(4-(3-amino-2-methoxyphenyl)-5-bromo-2H-1,2,3-triazol-2-yl)acetate (0.595 g, 1.642 mmol, 46.7% yield) as a tan solid. LCMS m/z 355.1/357.1 (M+H)$^+$; HPLC t$_R$ 0.98 min (analytical HPLC Method A).

Step 5

Ethyl 2-(4-(3-amino-2-methoxyphenyl)-5-bromo-2H-1,2,3-triazol-2-yl)acetate (0.595 g, 1.675 mmol) was dissolved in Ethanol (12 mL), and 10% Pd on C (0.446 g, 0.419 mmol) was added. This mixture was degassed, and then flooded with hydrogen gas. This was stirred at 50° C. overnight. After stirring overnight, the reaction is complete. Diluted with EtOAc/MeOH, then filtered through Celite and concentrated to afford ethyl 2-(4-(3-amino-2-methoxyphenyl)-2H-1,2,3-triazol-2-yl)acetate, AcOH (0.575 g, 1.624 mmol, 97% yield) as a tan solid. LCMS m/z 277.1 (M+H)$^+$; HPLC t$_R$ 0.72 min (analytical HPLC Method A); $^1$H NMR (400 MHz, METHANOL-d$_4$) δ 8.12 (s, 1H), 7.19 (dd, J=7.7, 1.6

Hz, 1H), 6.96 (t, J=7.8 Hz, 1H), 6.84 (dd, J=7.9, 1.6 Hz, 1H), 5.36 (s, 2H), 4.27 (q, J=7.1 Hz, 2H), 3.68 (s, 3H), 1.30 (t, J=7.1 Hz, 3H)

Step 6

To a solution of 4,6-dichloro-N-(methyl-d3)pyridazine-3-carboxamide (155 mg, 0.741 mmol) and ethyl 2-(4-(3-amino-2-methoxyphenyl)-2H-1,2,3-triazol-2-yl)acetate, AcOH (262 mg, 0.779 mmol) in Tetrahydrofuran (6 mL) was added lithium bis(trimethylsilyl)amide (2.224 mL, 2.224 mmol) in a dropwise manner (<1 min) using a syringe and the reaction stirred until complete by LCMS (~15 min). HCl (1M aq) (0.278 mL, 1.112 mmol) was added to quench the residual base. Then the reaction was partitioned between EtOAc and water. The water layer was washed 1× ethyl acetate, and then the combined organic layer was washed 1× ammonium chloride (sat.), 1× brine. It was then dried over sodium sulfate, then filtered and concentrated to afford the crude acetylene as a tan solid. Redissolved in DCM, then loaded onto a 12 g ISCO column for purification by flash chromatography. Eluted with 0-100% EtOAc in hexanes. The reaction afforded ethyl 2-(4-(3-((6-chloro-3-(trideuteromethylcarbamoyl)pyridazin-4-yl)amino)-2-methoxyphenyl)-2H-1,2,3-triazol-2-yl)acetate (135 mg, 0.298 mmol, 40.2% yield) as an off-white solid. LCMS m/z 449.3 (M+H)$^+$; HPLC $t_R$ 0.91 min (analytical HPLC Method A).

Step 7

A mixture of ethyl 2-(4-(3-((6-chloro-3-(trideuteromethylcarbamoyl)pyridazin-4-yl)amino)-2-methoxyphenyl)-2H-1,2,3-triazol-2-yl)acetate (120 mg, 0.267 mmol), Xantphos (30.9 mg, 0.053 mmol), and cyclopropanecarboxamide (45.5 mg, 0.535 mmol) in dioxane (3 mL) was degassed by bubbling $N_2$ through it for 5 minutes. Then $Cs_2CO_3$ (348 mg, 1.069 mmol) and $Pd_2(dba)_3$ (24.48 mg, 0.027 mmol) were added, the vessel was sealed, and the reaction was stirred at 120° C. for 90 minutes. The reaction was complete by LC-MS, so the crude material was concentrated onto Celite and purified by flash chromatography, using a 24 g ISCO column and eluting with 0-100% EtOAc in hexanes to afford ethyl 2-(4-(3-((6-(cyclopropanecarboxamido)-3-((methyl-d3)carbamoyl)pyridazin-4-yl)amino)-2-methoxyphenyl)-2H-1,2,3-triazol-2-yl)acetate (61 mg, 0.120 mmol, 44.9% yield). LCMS m/z 498.4 (M+H)$^+$; HPLC $t_R$ 0.79 min (analytical HPLC Method A).

Step 8

To a solution of ethyl 2-(4-(3-((6-(cyclopropanecarboxamido)-3-((methyl-d3)carbamoyl)pyridazin-4-yl)amino)-2-methoxyphenyl)-2H-1,2,3-triazol-2-yl)acetate (61 mg, 0.123 mmol) in Tetrahydrofuran (1 mL) was added 1N NaOH (0.135 mL, 0.135 mmol) and a few drops of methanol. The solution was stirred at room temperature. After 2 h, the reaction is complete. Neutralised with 140 uL 1N HCl, then diluted with 50 mL EtOAc. Dried this mixture over sodium sulfate, then filtered and concentrated to afford crude 2-(4-(3-((6-(cyclopropanecarboxamido)-3-(trideuteromethylcarbamoyl)pyridazin-4-yl)amino)-2-methoxyphenyl)-2H-1,2,3-triazol-2-yl)acetic acid (56 mg, 0.113 mmol, 92% yield) as a yellow solid. LCMS m/z 470.2 (M+H)$^+$; HPLC $t_R$ 0.67 min (analytical HPLC Method A).

Step 9

A solution of 2-(4-(3-((6-(cyclopropanecarboxamido)-3-(trideuteromethyl carbamoyl)pyridazin-4-yl)amino)-2-methoxyphenyl)-2H-1,2,3-triazol-2-yl)acetic acid (30 mg, 0.064 mmol), BOP (42.4 mg, 0.096 mmol), 2-methoxyethanamine (14.40 mg, 0.192 mmol), and DIEA (0.056 mL, 0.320 mmol) in DMF (1 mL) was stirred for 45 minutes at room temperature. The reaction appears to be complete by LC-MS. The reaction mixture was diluted with DMF, then filtered and purified by prep HPLC to afford 6-(cyclopropanecarboxamido)-4-((2-methoxy-3-(2-(2-((2-methoxyethyl)amino)-2-oxoethyl)-2H-1,2,3-triazol-4-yl)phenyl)amino)-N-trideuteromethylpyridazine-3-carboxamide (10.6 mg, 0.020 mmol, 30.6% yield) LCMS m/z 527.3 (M+H)$^+$; HPLC $t_R$ 0.67 min (analytical HPLC Method A).

The Examples in Table 7 were prepared using a similar procedure used to prepare Example 426.

TABLE 7

| Ex. No. | Structure | MW | Obs. MS Ion | RT | QC Method |
|---|---|---|---|---|---|
| 427 | 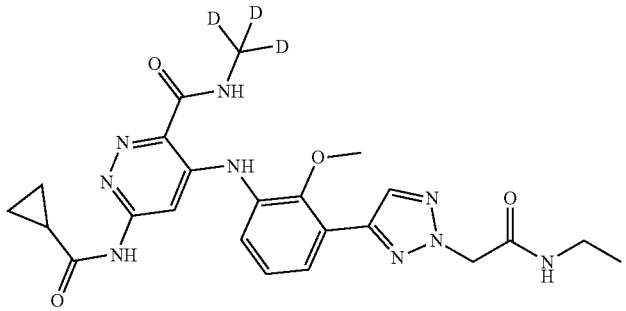 [SMILES: [2H]C([2H])([2H])NC(=O)c1nnc(NC(=O)C2CC2)cc1Nc1cccc(-c2cnn(CC(=O)NCC)n2)c1OC] | 496.5 | 497.3 | 1.42 | QC-ACN-AA-XB |

TABLE 7-continued

| Ex. No. | Structure | MW | Obs. MS Ion | RT | QC Method |
|---|---|---|---|---|---|
| 428 | 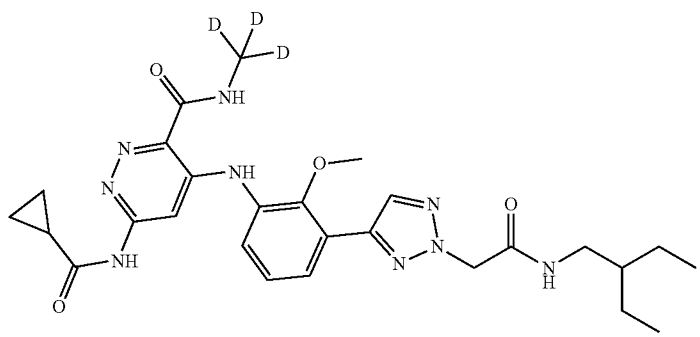 [SMILES: [2H]C([2H])([2H])NC(=O)c1nnc(NC(=O)C2CC2)cc1Nc1cccc(-c2cnn(CC(=O)NCC(CC)CC)n2)c1OC] | 552.7 | 553.2 | 1.53 | QC-ACN-TFA-XB |
| 429 | 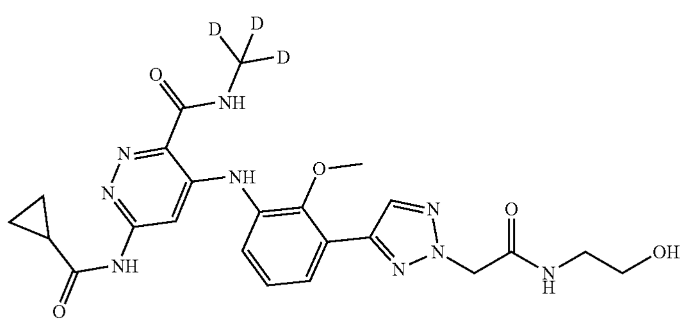 [SMILES: [2H]C([2H])([2H])NC(=O)c1nnc(NC(=O)C2CC2)cc1Nc1cccc(-c2cnn(CC(=O)NCCO)n2)c1OC] | 512.5 | 513.2 | 0.89 | QC-ACN-TFA-XB |
| 430 | 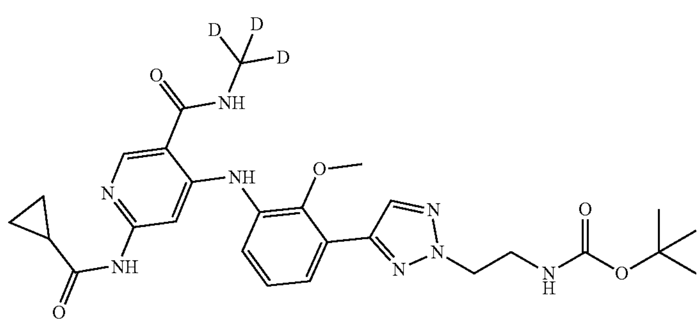 [SMILES: [2H]C([2H])([2H])NC(=O)c1cnc(NC(=O)C2CC2)cc1Nc1cccc(-c2cnn(CCNC(=O)OC(C)(C)C)n2)c1OC] | 553.6 | 554.4 | 1.6 | QC-ACN-AA-XB |
| 431 | 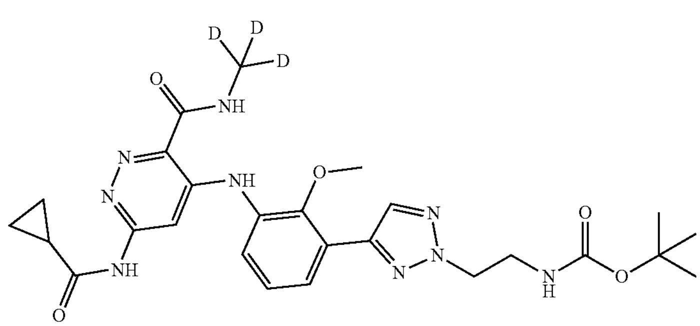 [SMILES: [2H]C([2H])([2H])NC(=O)c1nnc(NC(=O)C2CC2)cc1Nc1cccc(-c2cnn(CCNC(=O)OC(C)(C)C)n2)c1OC] | 554.6 | 555.3 | 1.77 | QC-ACN-AA-XB |

TABLE 7-continued

| Ex. No. | Structure | MW | Obs. MS Ion | RT | QC Method |
|---|---|---|---|---|---|
| 432 | 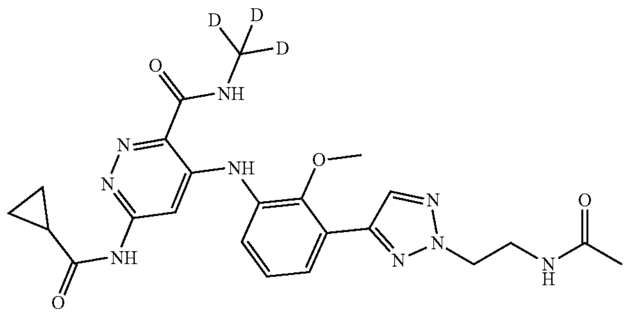 [SMILES: [2H]C([2H])([2H])NC(=O)c1nnc(NC(=O)C2CC2)cc1Nc1cccc(-c2cnn(CCNC(C)=O)n2)c1OC] | 496.5 | 497.3 | 1.27 | QC-ACN-AA-XB |
| 433 | 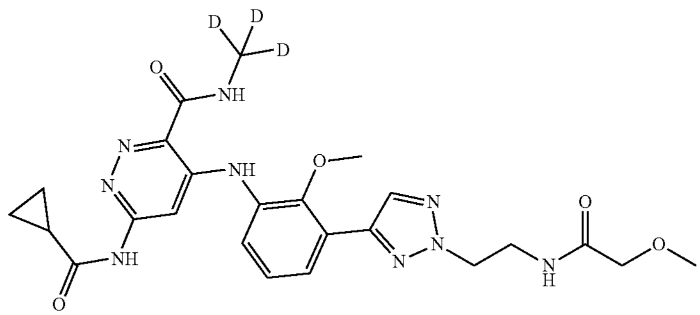 [SMILES: [2H]C([2H])([2H])NC(=O)c1nnc(NC(=O)C2CC2)cc1Nc1cccc(-c2cnn(CCNC(=O)COC)n2)c1OC] | 526.6 | 527.3 | 1.14 | QC-ACN-TFA-XB |
| 434 | 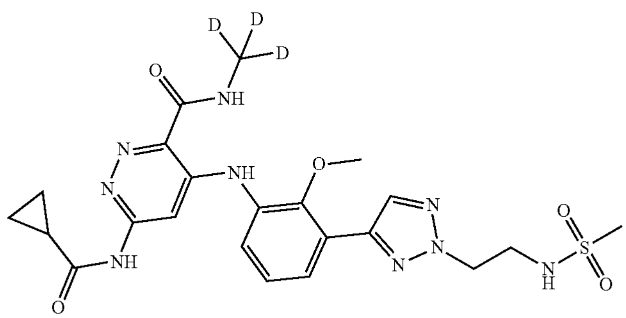 [SMILES: [2H]C([2H])([2H])NC(=O)c1nnc(NC(=O)C2CC2)cc1Nc1cccc(-c2cnn(CCNS(C)(=O)=O)n2)c1OC] | 532.6 | 533.3 | 1.36 | QC-ACN-AA-XB |
| 435 | 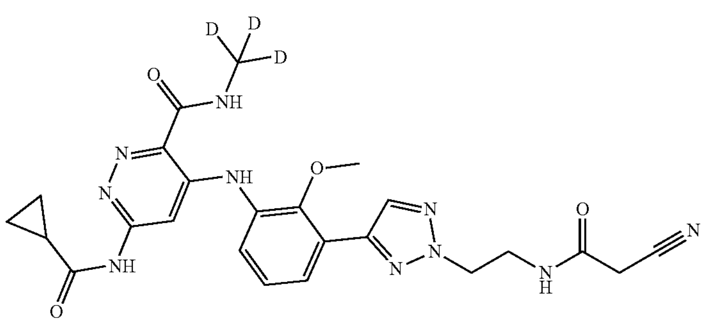 [SMILES: [2H]C([2H])([2H])NC(=O)c1nnc(NC(=O)C2CC2)cc1Nc1cccc(-c2cnn(CCNC(=O)CC#N)n2)c1OC] | 521.6 | 522.3 | 1.31 | QC-ACN-AA-XB |
| 436 | 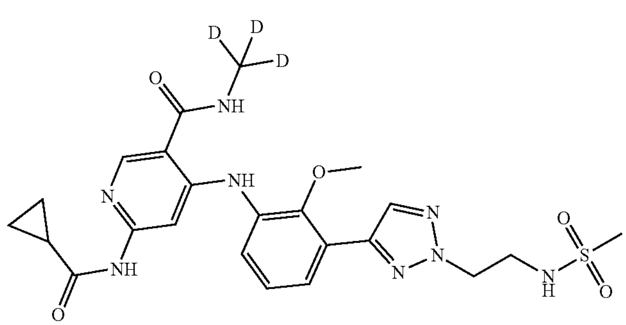 [SMILES: [2H]C([2H])([2H])NC(=O)c1cnc(NC(=O)C2CC2)cc1Nc1cccc(-c2cnn(CCNS(C)(=O)=O)n2)c1OC] | 531.6 | 532.24 | 1.18 | QC-ACN-AA-XB |

TABLE 7-continued
| Ex. No. | Structure | MW | Obs. MS Ion | RT | QC Method |
|---|---|---|---|---|---|
| 437 | 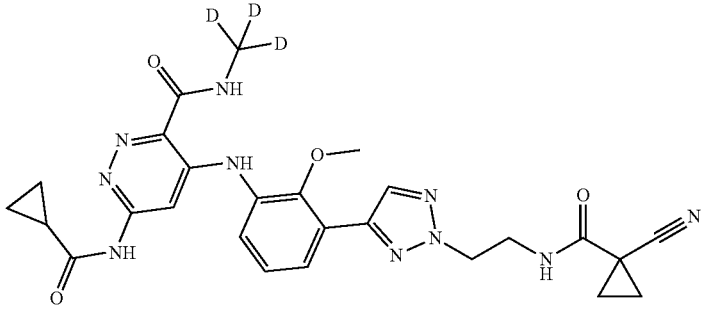 [SMILES: [2H]C([2H])([2H])NC(=O)c1nnc(NC(=O)C2CC2)cc1Nc1cccc(-c2cnn(CCNC(=O)C3(C#N)CC3)n2)c1OC] | 547.6 | 548.2 | 1.38 | QC-ACN-AA-XB |
| 438 | 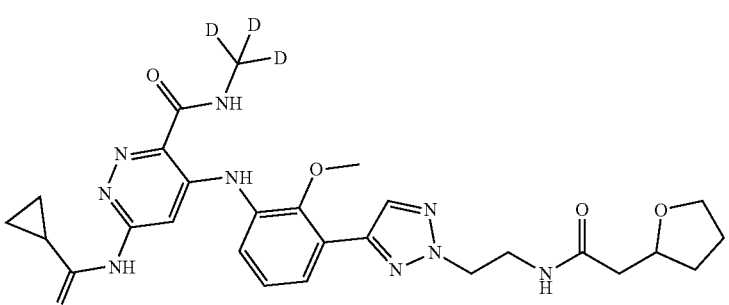 | 566.6 | 567.3 | 1.3 | QC-ACN-AA-XB |
| 439 | 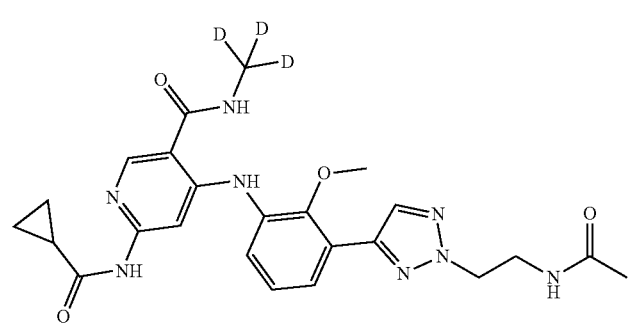 [SMILES: [2H]C([2H])([2H])NC(=O)c1cnc(NC(=O)C2CC2)cc1Nc1cccc(-c2cnn(CCNC(C)=O)n2)c1OC] | 495.6 | 496.1 | 1.1 | QC-ACN-AA-XB |
| 440 | 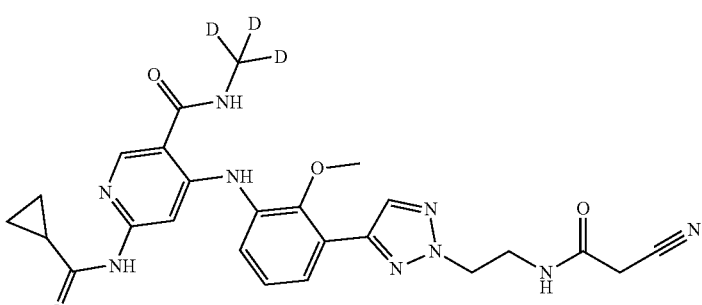 | 520.6 | 521.2 | 1.14 | QC-ACN-AA-XB |

TABLE 7-continued
| Ex. No. | Structure | MW | Obs. MS Ion | RT | QC Method |
|---|---|---|---|---|---|
| 441 | 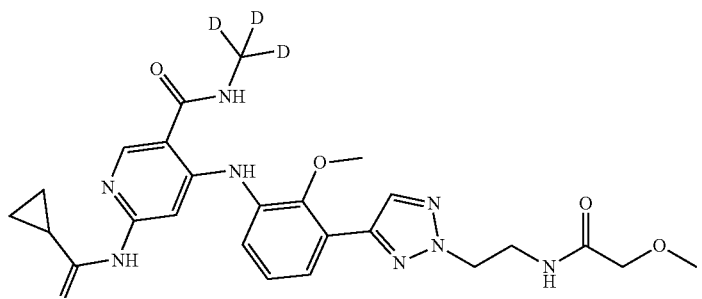 | 525.6 | 526.1 | 1.18 | QC-ACN-AA-XB |
| 442 | 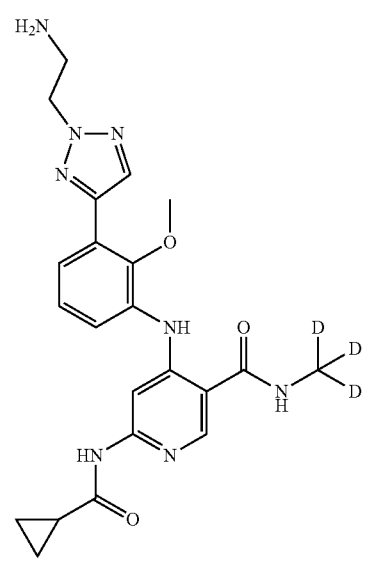 | 453.5 | 454.4 | 0.94 | QC-ACN-AA-XB |
| 443 | 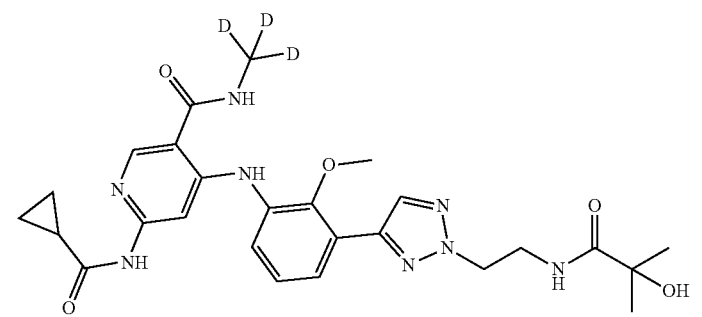 [SMILES: [2H]C([2H])([2H])NC(=O)c1cnc(NC(=O)C2CC2)cc1Nc1cccc(-c2cnn(CCNC(=O)C(C)(C)O)n2)c1OC] | 539.6 | 540.3 | 1.14 | QC-ACN-AA-XB |
| 444 | 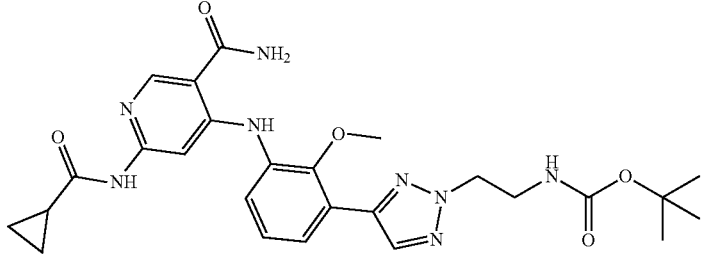 [SMILES: COc1c(Nc2cc(NC(=O)C3CC3)ncc2C(N)=O)cccc1-c1cnn(CCNC(=O)OC(C)(C)C)n1] | 536.6 | 537.1 | 1.26 | QC-ACN-TFA-XB |

TABLE 7-continued
| Ex. No. | Structure | MW | Obs. MS Ion | RT | QC Method |
|---|---|---|---|---|---|
| 445 | 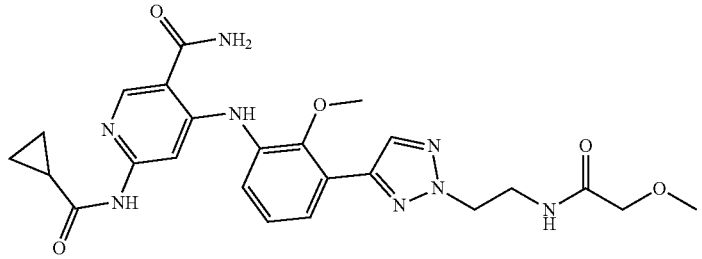 [SMILES: COCC(=O)NCCn1ncc(-c2cccc(Nc3cc(NC(=O)C4CC4)ncc3C(N)=O)c2OC)n1] | 508.5 | 509.2 | 1.16 | QC-ACN-AA-XB |
| 446 | 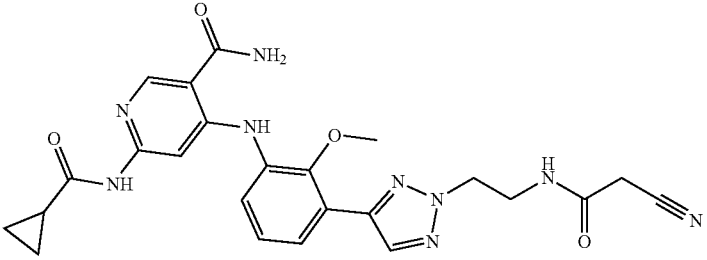 [SMILES: COc1c(Nc2cc(NC(=O)C3CC3)ncc2C(N)=O)cccc1-c1cnn(CCNC(=O)CC#N)n1] | 503.5 | 504.1 | 0.84 | QC-ACN-TFA-XB |
| 447 | 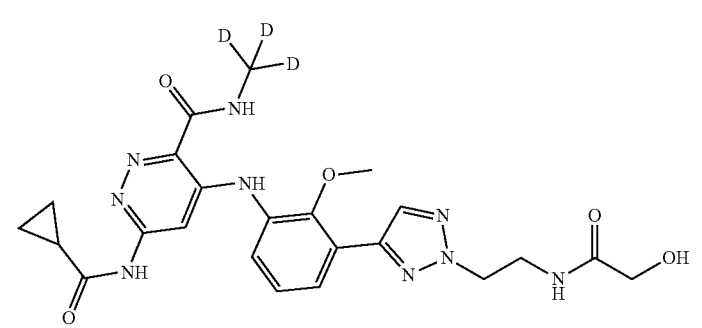 [SMILES: [2H]C([2H])([2H])NC(=O)c1nnc(NC(=O)C2CC2)cc1Nc1cccc(-c2cnn(CCNC(=O)CO)n2)c1OC] | 512.5 | 513.2 | 1.16 | QC-ACN-AA-XB |
| 448 | 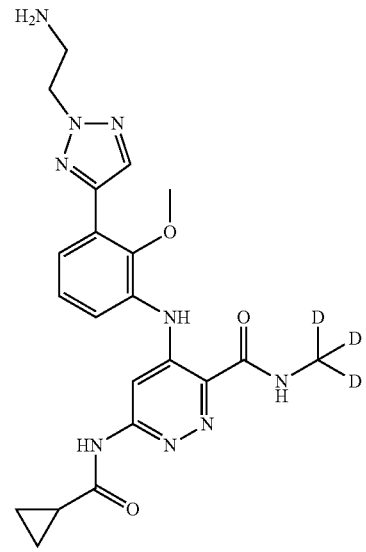 | 454.5 | 455.2 | 0.99 | QC-ACN-AA-XB |

TABLE 7-continued

| Ex. No. | Structure | MW | Obs. MS Ion | RT | QC Method |
|---|---|---|---|---|---|
| 449 | 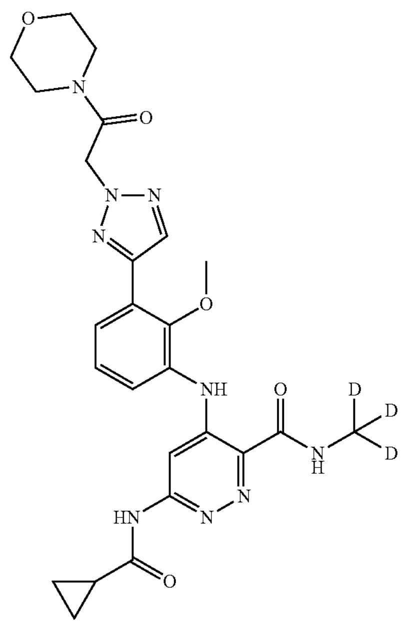 [SMILES: [2H]C([2H])([2H])NC(=O)c1nnc(NC(=O)C2CC2)cc1Nc1cccc(-c2cnn(CC(=O)N3CCOCC3)n2)c1OC] | 538.6 | 539.2 | 1.09 | QC-ACN-TFA-XB |
| 450 | 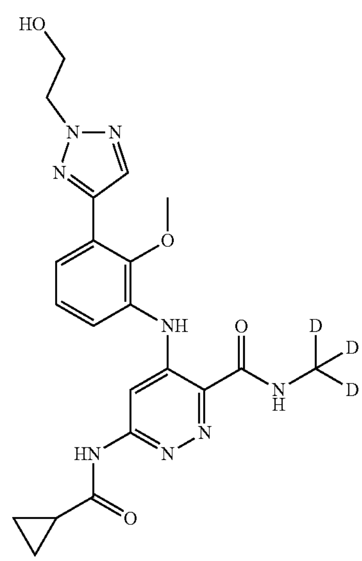 [SMILES: [2H]C([2H])([2H])NC(=O)c1nnc(NC(=O)C2CC2)cc1Nc1cccc(-c2cnn(CCO)n2)c1OC] | 455.5 | 456.3 | 1.25 | QC-ACN-AA-XB |

Example 451

4-((2-methoxy-3-(2-methyl-2H-1,2,3-triazol-4-yl)phenyl)amino)-6-((6-methoxypyridazin-3-yl)amino)-N-(methyl-d3)pyridazine-3-carboxamide

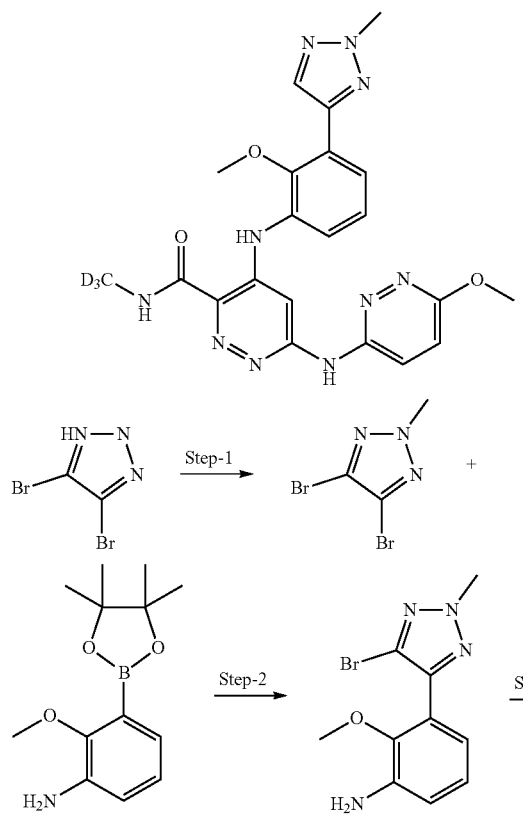

-continued

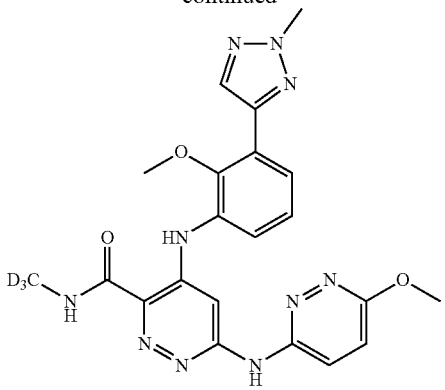

Step 1

To a solution of 4,5-dibromo-1H-1,2,3-triazole (0.401 g, 1.768 mmol) in DMF (6 mL) at 0° C. (in an ice-water bath) was added first potassium carbonate (0.366 g, 2.65 mmol) and then iodomethane (0.116 mL, 1.856 mmol) was added dropwise. After stirring 1 h, the reaction appears to be incomplete by HPLC. Added additional 50 uL iodomethane, continued stirring, now at room temp. Reaction still appears to be incomplete. Added additional 50 uL iodomethane. Quenched with 10 mL water. Extracted 2×50 mL EtOAc. Washed combined EtOac 1×10% LiCl, 1× brine. Then dried over sodium sulfate, filtered and concentrated. Loaded onto a 40 g ISCO column for purification by flash chromatography, eluting with 0-100% EtOAc in hexanes. Two peaks elute, the first eluting being larger by UV absorbance, but giving no MS signal. This is 4,5-dibromo-2-methyl-2H-1,2,3-triazole (0.266 g, 1.082 mmol, 61.2% yield), designated Isomer 2. HPLC $t_R$ 0.90 min (analytical HPLC Method A). $^1$H NMR (400 MHz, chloroform-d) δ 4.17 (s, 3H). The second peak is smaller by UV, but gives the correct mass and dibromo isotopic pattern in MS. This material is 4,5-dibromo-2-methyl-2H-1,2,3-triazole (0.101 g, 1.082 mmol, 61.2% yield) designated Isomer 1. LCMS m/z 242.0/244.0 (M+H)$^+$; HPLC $t_R$ 0.67 min (analytical HPLC Method A). $^1$H NMR (400 MHz, chloroform-d) δ 4.08 (s, 3H)

Step 2

A stirred mixture of 4,5-dibromo-2-methyl-2H-1,2,3-triazole (100 mg, 0.415 mmol), 2-methoxy-3-(4,4,5,5-tetramethyl-1,3,2-dioxaborolan-2-yl)aniline (98 mg, 0.394 mmol) and PdCl$_2$(dppf)-CH$_2$Cl$_2$Adduct (16.95 mg, 0.021 mmol) in Dioxane (3 mL) was degassed by bubbling nitrogen through the mixture for 5 minutes. 2M K$_3$PO$_4$ (aq) (0.623 mL, 1.245 mmol) was quickly added and the reaction mixture heated at 50° C. for 40 minutes. The reaction turned dark almost immediately even at this lower temperature. LC-MS showed complete consumption of the starting material. The reaction mixture was cooled to room temperature, then diluted with EtOAc (75 mL). This solution was then dried over sodium sulfate, filtered, concentrated and purified by flash chromatography, eluting with 0-100% EtOAc in hexanes. The reaction afforded 3-(5-bromo-2-methyl-2H-1,2,3-triazol-4-yl)-2-methoxyaniline (70 mg, 0.247 mmol, 59.6% yield) as a yellow oil. LCMS m/z 283.1/285.1 (M+H)$^+$; HPLC $t_R$ 1.11 min (analytical HPLC Method A).

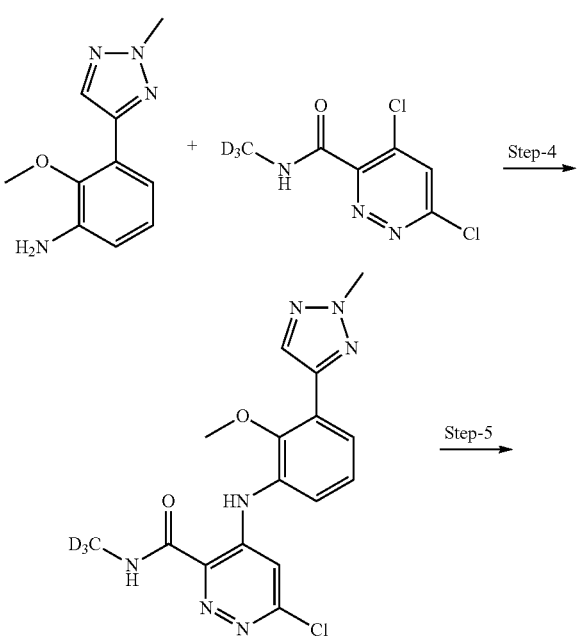

Step 3

3-(5-bromo-2-methyl-2H-1,2,3-triazol-4-yl)-2-methoxyaniline (0.145 g, 0.512 mmol) was dissolved in Ethyl acetate (5 mL), and 10% Pd on C (0.136 g, 0.128 mmol) was added. This mixture was degassed, and then flooded with hydrogen gas. This was stirred overnight at room temperature. After stirring overnight, LC-Ms indicates a clean reaction with ~30% conversion to desired product. Added additional 10% Pd on C (0.136 g, 0.128 mmol) and Ethanol (1 mL). This mixture was re-degassed, and then flooded with hydrogen gas. This was stirred at 50° C. for 3 h. After 3 h, the reaction is complete. Filtered and concentrated to afford 2-methoxy-3-(2-methyl-2H-1,2,3-triazol-4-yl)aniline (78 mg, 0.374 mmol, 73.1% yield) as a tan solid. LCMS m/z 205.1 (M+H)$^+$; HPLC $t_R$ 0.70 min (analytical HPLC Method A).

Step 4

To a solution of 4,6-dichloro-N-(methyl-d3)pyridazine-3-carboxamide (270 mg, 1.292 mmol) and 2-methoxy-3-(2-methyl-2H-1,2,3-triazol-4-yl)aniline (290 mg, 1.421 mmol) in Tetrahydrofuran (10 mL) was added lithium bis(trimethylsilyl)amide (3.23 mL, 3.23 mmol) in a dropwise manner (<5 min) using a syringe and the reaction stirred until complete by LCMS (~15 min). HCl (1M aq) (0.484 mL, 1.937 mmol) was added to quench the residual base. Then the reaction was partitioned between EtOAc and water. The water layer was washed 1× ethyl acetate, and then the combined organic layer was washed 1× ammonium chloride (sat.), 1× brine. It was then dried over sodium sulfate, then filtered and concentrated to afford the crude acetylene as a tan solid. Redissolved in DCM, then loaded onto a 24 g ISCO column for purification by flash chromatography. Eluted with 0-100% EtOAc in hexanes. The reaction afforded 6-chloro-4-((2-methoxy-3-(2-methyl-2H-1,2,3-triazol-4-yl)phenyl)amino)-N-trideuteromethylpyridazine-3-carboxamide (182 mg, 0.473 mmol, 36.6% yield) as an off-white solid. LCMS m/z 377.2 (M+H)$^+$; HPLC $t_R$ 0.87 min (analytical HPLC Method A).

Step 5

A mixture of 6-chloro-4-((2-methoxy-3-(2-methyl-2H-1,2,3-triazol-4-yl)phenyl)amino)-N-trideuteromethylpyridazine-3-carboxamide (30 mg, 0.080 mmol), Xantphos (9.21 mg, 0.016 mmol), and 6-methoxypyridazin-3-amine (19.92 mg, 0.159 mmol) in dioxane (1.5 mL) was degassed by bubbling $N_2$ through it for 5 minutes. Then $Cs_2CO_3$ (104 mg, 0.318 mmol) and $Pd_2(dba)_3$ (7.29 mg, 7.96 µmol) were added, the vessel was sealed, and the reaction was stirred at 130° C. for 45 minutes. The reaction was complete by LC-MS. The reaction was cooled to room temperature, and then was diluted with DMF. This solution was then filtered and purified by prep HPLC. The reaction afforded 4-((2-methoxy-3-(2-methyl-2H-1,2,3-triazol-4-yl)phenyl)amino)-6-((6-methoxypyridazin-3-yl)amino)-N-trideuteromethylpyridazine-3-carboxamide (22 mg, 0.046 mmol, 58.2% yield) as a yellow solid. LCMS m/z 466.2 (M+H)$^+$; HPLC $t_R$ 0.69 min (analytical HPLC Method A); $^1$H NMR (400 MHz, DMSO-$d_6$) δ 11.05 (s, 1H), 10.27 (s, 1H), 9.14 (s, 1H), 8.16 (s, 1H), 7.96 (s, 1H), 7.93 (d, J=9.5 Hz, 1H), 7.68 (dd, J=7.9, 1.5 Hz, 1H), 7.57 (dd, J=8.0, 1.4 Hz, 1H), 7.30 (t, J=7.9 Hz, 1H), 7.22 (d, J=9.5 Hz, 1H), 4.24 (s, 3H), 3.95 (s, 3H), 3.68 (s, 3H)

The Examples in Table 8 were prepared using a similar procedure used to prepare Example 451.

TABLE 8

| Ex. No. | Structure | MW | Obs. MS Ion | RT | QC Method |
|---|---|---|---|---|---|
| 452 | 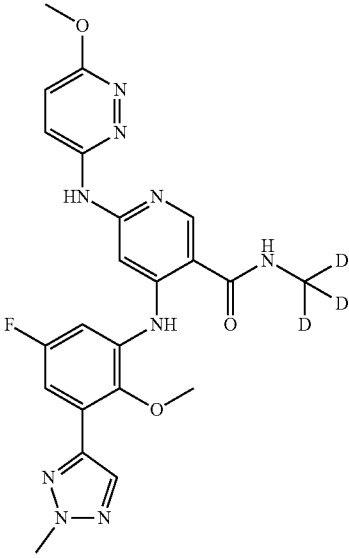 [SMILES: [2H]C([2H])([2H])NC(=O)c1cnc(Nc2ccc(OC)nn2)cc1Nc1cc(F)cc(-c2cnn(C)n2)c1OC] | 482.5 | 483.2 | 1.57 | QC-ACN-AA-XB |

TABLE 8-continued

| Ex. No. | Structure | MW | Obs. MS Ion | RT | QC Method |
|---|---|---|---|---|---|
| 453 | 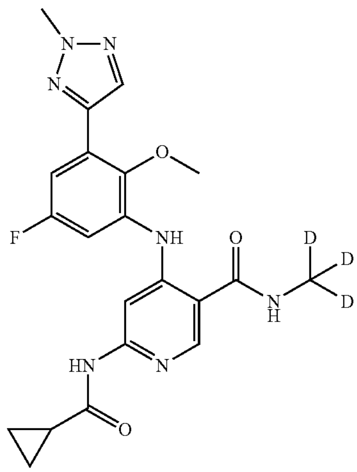 [SMILES: [2H]C([2H])([2H])NC(=O)c1cnc(NC(=O)C2CC2)cc1Nc1cc(F)cc(-c2cnn(C)n2)c1OC] | 442.5 | 443.2 | 1.57 | QC-ACN-AA-XB |
| 454 | 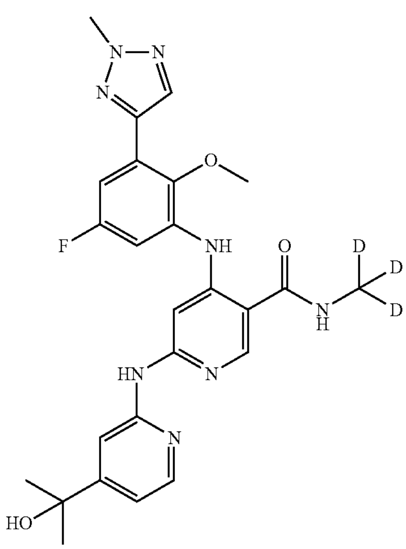 [SMILES: [2H]C([2H])([2H])NC(=O)c1cnc(Nc2cc(C(C)(C)O)ccn2)cc1Nc1cc(F)cc(-c2cnn(C)n2)c1OC] | 509.6 | 510.1 | 1.59 | QC-ACN-AA-XB |

Example 455
6-(cyclopropanecarboxamido)-4-((3-(5-(1,1-dioxido-thiomorpholine-4-carbonyl)-1-methyl-1H-pyrazol-3-yl)-2-methoxyphenyl)amino)-N-(methyl-d3) pyridazine-3-carboxamide
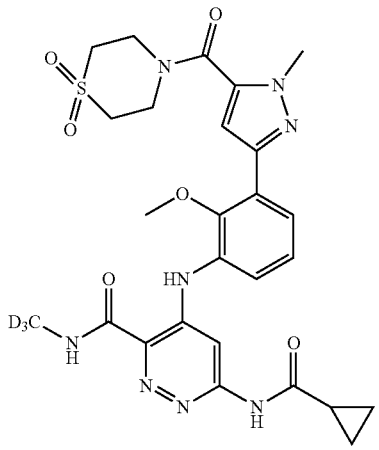
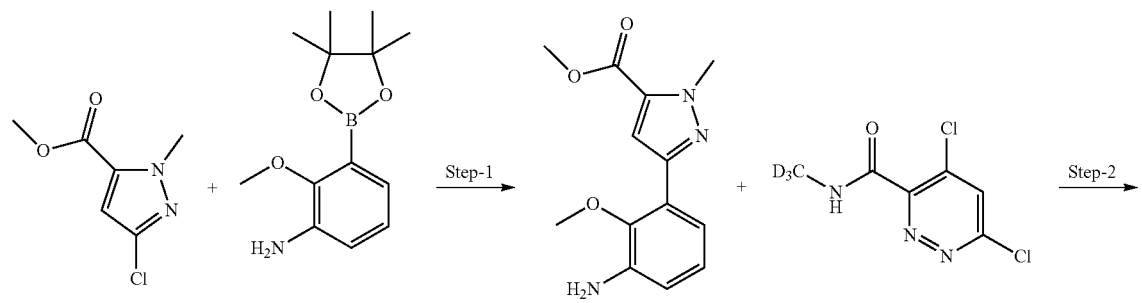
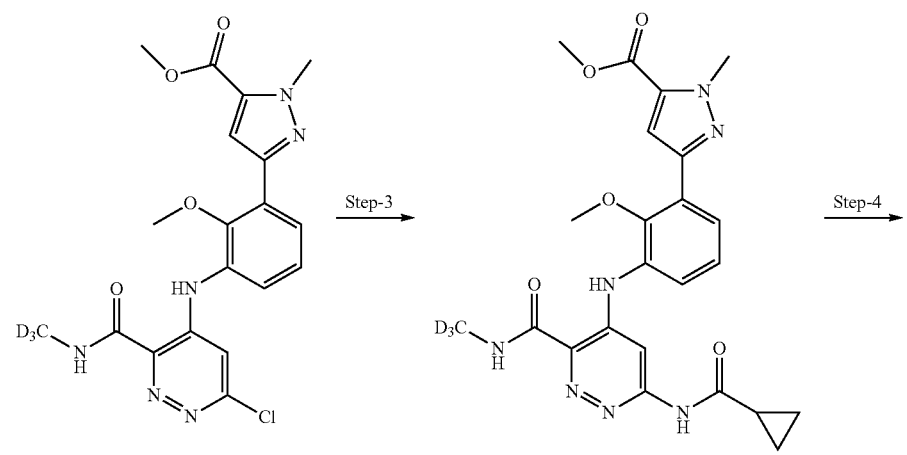

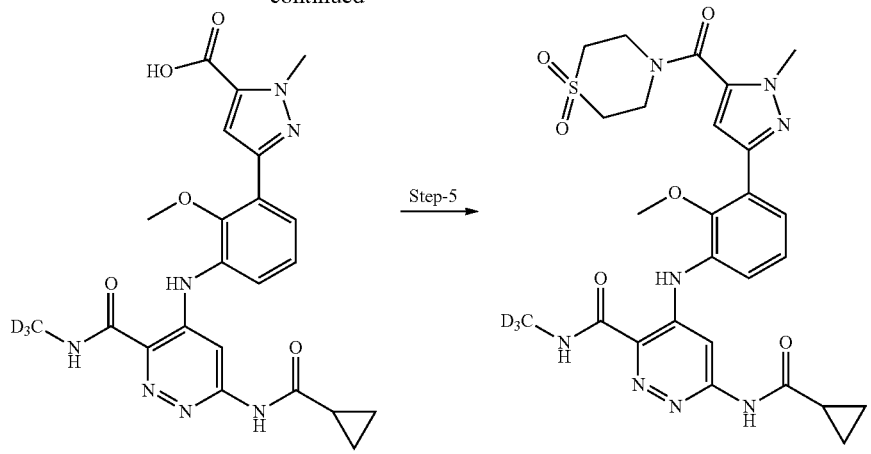

Step 1

A stirred mixture of methyl 3-chloro-1-methyl-1H-pyrazole-5-carboxylate (200 mg, 1.146 mmol), 2-methoxy-3-(4,4,5,5-tetramethyl-1,3,2-dioxaborolan-2-yl)aniline (499 mg, 2.005 mmol) and 1,1'-bis(di-tert-butylphosphino)ferrocene palladium dichloride (37.3 mg, 0.057 mmol) in Dioxane (6 ml) was degassed by bubbling nitrogen through the mixture for 5 minutes. 2M $K_3PO_4$ (aq) (1.718 ml, 3.44 mmol) was quickly added and the reaction mixture heated at 125° C. for 1 hr. The reaction mixture was partitioned between EtOAc (30 ml) and water (30 ml). The organic layer was washed with brine (30 ml), dried ($Na_2SO_4$) and concentrated to afford a brown oil that was chromatographed on a 24 gm ISCO silica gel cartridge, eluting with a 0-50% EtOAc/Hexanes gradient. The pure fractions were concentrated to afford methyl 3-(3-amino-2-methoxyphenyl)-1-methyl-1H-pyrazole-5-carboxylate (89 mg, 0.337 mmol, 29.4% yield) as a tan solid. LCMS m/z 262.2 (M+H)$^+$; HPLC $t_R$ 0.65 min (analytical HPLC Method A).

Step 2

To a solution of 4,6-dichloro-N-trideuteromethylpyridazine-3-carboxamide (72 mg, 0.344 mmol) and methyl 3-(3-amino-2-methoxyphenyl)-1-methyl-1H-pyrazole-5-carboxylate (90 mg, 0.344 mmol) in Tetrahydrofuran (3 mL) at rt was added dropwise over 5 minutes LiHMDS, 1M (0.861 mL, 0.861 mmol). The resulting solution was stirred at rt for 30 minutes. The reaction mixture was quenched with 1 ml of saturated $NH_4Cl$ solution. The resulting mixture was partitioned between EtOAc (30 ml) and saturated $NH_4Cl$ solution (30 ml). The organic layer was washed with brine (30 ml), dried ($Na_2SO_4$) and concentrated to an amber oil that was chromatographed on a 12 gm ISCO silica gel cartridge, eluting with a 0-60% EtOAc/Hex gradient. The pure fractions were concentrated to afford methyl 3-(3-((6-chloro-3-(trideuteromethylcarbamoyl)pyridazin-4-yl)amino)-2-methoxyphenyl)-1-methyl-1H-pyrazole-5-carboxylate (79 mg, 0.178 mmol, 51.8% yield) as a tan solid. LCMS m/z 434.2 (M+H)$^+$; HPLC $t_R$ 0.97 min (analytical HPLC Method A).

Step 3

A mixture of 3-(3-((6-chloro-3-(trideuteromethylcarbamoyl)pyridazin-4-yl)amino)-2-methoxyphenyl)-1-methyl-1H-pyrazole-5-carboxylate (0.141 g, 0.325 mmol), Xantphos (0.038 g, 0.065 mmol), and cyclopropanecarboxamide (0.055 g, 0.650 mmol) in dioxane (3 mL) was degassed by bubbling $N_2$ through it for 5 minutes. Then $Cs_2CO_3$ (0.424 g, 1.300 mmol) and $Pd_2(dba)_3$ (0.030 g, 0.032 mmol) were added, the vessel was sealed, and the reaction was stirred at 130° C. for 45 minutes. The reaction was complete by LC-MS. The reaction was cooled to room temperature, then concentrated and loaded directly onto a 12 g ISCO column for purification by flash chromatography, eluting with 0-15% MeOH in DCM to afford methyl 3-(3-((6-(cyclopropanecarboxamido)-3-(trideuteromethylcarbamoyl) pyridazin-4-yl)amino)-2-methoxyphenyl)-1-methyl-1H-pyrazole-5-carboxylate (99 mg, 0.203 mmol, 62.5% yield) as a pale yellow solid. LCMS m/z 483.5 (M+H)$^+$; HPLC $t_R$ 0.80 min (analytical HPLC Method A). $^1$H NMR (400 MHz, DMSO-$d_6$) δ 11.32 (s, 1H), 10.96 (s, 1H), 9.14 (s, 1H), 8.13 (s, 1H), 7.71 (dd, J=7.9, 1.6 Hz, 1H), 7.44 (dd, J=7.9, 1.5 Hz, 1H), 7.30-7.24 (m, 2H), 4.18 (s, 3H), 3.88 (s, 3H), 3.64-3.60 (m, 3H), 2.13-2.04 (m, 1H), 0.86-0.79 (m, 4H)

Step 4

A mixture of methyl 3-(3-((6-(cyclopropanecarboxamido)-3-(trideuteromethylcarbamoyl)pyridazin-4-yl)amino)-2-methoxyphenyl)-1-methyl-1H-pyrazole-5-carboxylate (99 mg, 0.205 mmol) and lithium hydroxide monohydrate (10.34 mg, 0.246 mmol) in THF (2 mL) and Water (0.4 mL) was stirred at rt for 24 hr. The volatiles were removed in vacuo to afford 3-(3-((6-(cyclopropanecarboxamido)-3-(trideuteromethylcarbamoyl)pyridazin-4-yl)amino)-2-methoxyphenyl)-1-methyl-1H-pyrazole-5-carboxylic acid, lithium salt (96 mg, 0.192 mmol, 93% yield) as a yellow solid. Used as is. LCMS m/z 469.4 (M+H)$^+$; HPLC $t_R$ 0.70 min (analytical HPLC Method A).

Step 5

A mixture of 3-(3-((6-(cyclopropanecarboxamido)-3-(trideuteromethylcarbamoyl)pyridazin-4-yl)amino)-2-methoxyphenyl)-1-methyl-1H-pyrazole-5-carboxylic acid, lithium salt (10 mg, 0.021 mmol), thiomorpholine 1,1-dioxide (7.11 mg, 0.053 mmol), BOP (12.09 mg, 0.027 mmol) and $Et_3N$ (0.015 mL, 0.105 mmol) in DMF (0.2 mL) was agitated at rt for 1 h. The reaction was complete by LC-MS, so the reaction was diluted to 1.5 mL with methanol, then filtered and submitted for purification. The reaction afforded 6-(cyclopropanecarboxamido)-4-((3-(5-(1,1-dioxidothiomorpholine-4-carbonyl)-1-methyl-1H-pyrazol-3-yl)-2-methoxyphenyl)amino)-N-trideuteromethylpyridazine-3-carboxamide (8.1 mg, 0.013 mmol, 60.5% yield) LCMS m/z 586.4 (M+H)⁺; HPLC $t_R$ 0.68 min (analytical HPLC Method A).

¹H NM/R (500 MHz, DMSO-d₆) δ 11.34 (s, 1H), 11.03 (s, 1H), 9.15 (s, 1H), 8.18 (s, 1H), 7.70 (d, J=7.7 Hz, 1H), 7.44 (d, J=7.7 Hz, 1H), 7.26 (t, J=7.7 Hz, 1H), 7.05 (s, 1H), 4.01 (br. s., 5H), 3.95 (s, 3H), 3.63 (s, 3H), 3.34 (br. s., 2H), 2.12-2.04 (m, 2H), 0.91-0.77 (m, 4H)

The Examples in Table 9 were prepared using a similar procedure used to prepare Example 455.

TABLE 9

| Ex. No. | Structure | MW | Obs. MS Ion | RT | QC Method |
|---|---|---|---|---|---|
| 456 | 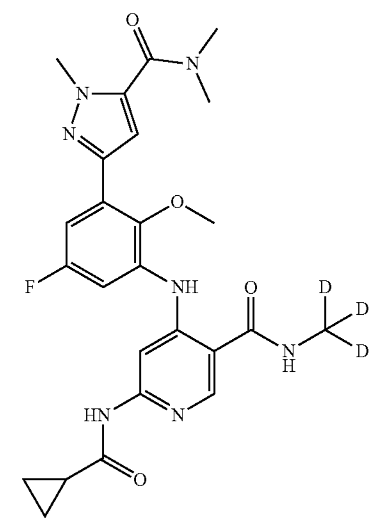 [SMILES: [2H]C([2H])([2H])NC(=O)c1cnc(NC(=O)C2CC2)cc1Nc1cc(F)cc(-c2cc(C(=O)N(C)C)n(C)n2)c1OC] | 512.6 | 513.2 | 1.35 | QC-ACN-AA-XB |
| 457 | 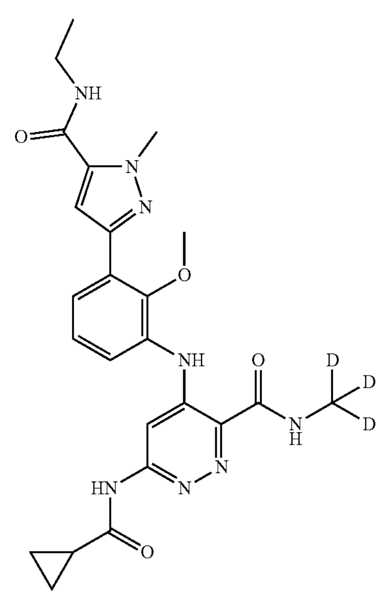 [SMILES: [2H]C([2H])([2H])NC(=O)c1nnc(NC(=O)C2CC2)cc1Nc1cccc(-c2cc(C(=O)NCC)n(C)n2)c1OC] | 495.6 | 496.2 | 1.49 | QC-ACN-AA-XB |

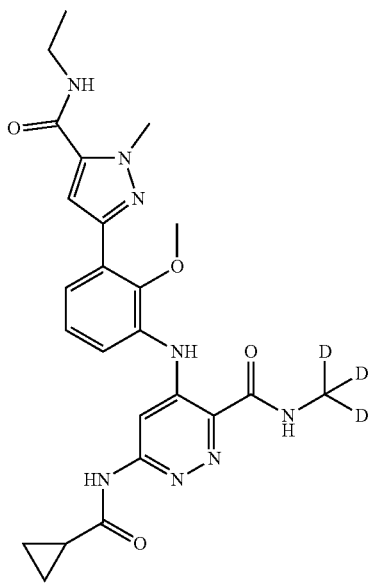

TABLE 9-continued
| Ex. No. | Structure | MW | Obs. MS Ion | RT | QC Method |
|---|---|---|---|---|---|
| 458 | 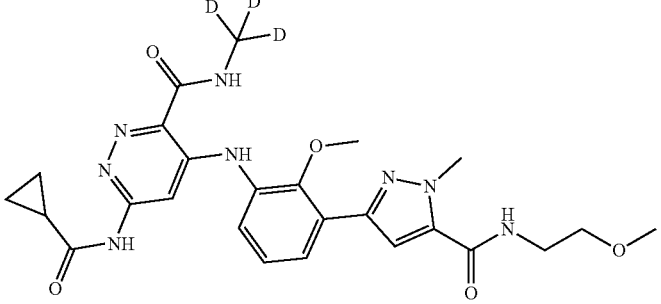 | 525.6 | 526.4 | 1.43 | QC-ACN-AA-XB |
| 459 | 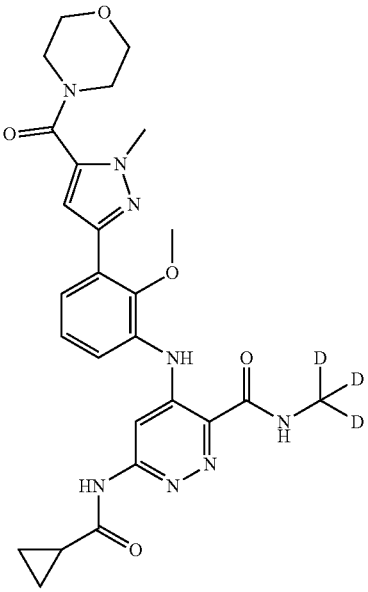 [SMILES: [2H]C([2H])([2H])NC(=O)c1nnc(NC(=O)C2CC2)cc1Nc1cccc(-c2cc(C(=O)N3CCOCC3)n(C)n2)c1OC] | 537.6 | 538.4 | 1.35 | QC-ACN-AA-XB |
| 460 | 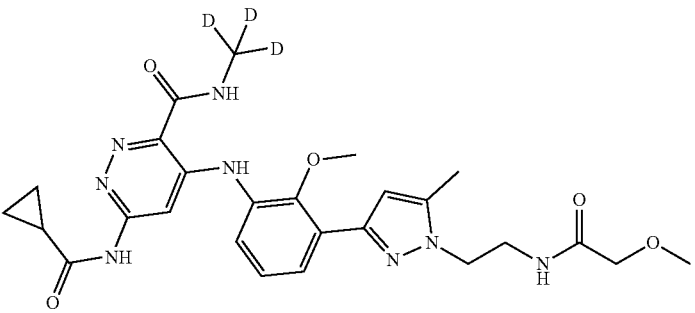 [SMILES: [2H]C([2H])([2H])NC(=O)c1nnc(NC(=O)C2CC2)cc1Nc1cccc(-c2cc(C)n(CCNC(=O)COC)n2)c1OC] | 539.6 | 540.3 | 1.41 | QC-ACN-AA-XB |

TABLE 9-continued

| Ex. No. | Structure | MW | Obs. MS Ion | RT | QC Method |
|---|---|---|---|---|---|
| 461 | 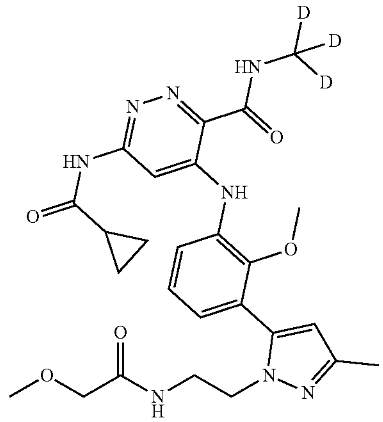 | 539.6 | 540.3 | 1.36 | QC-ACN-AA-XB |
| 462 | 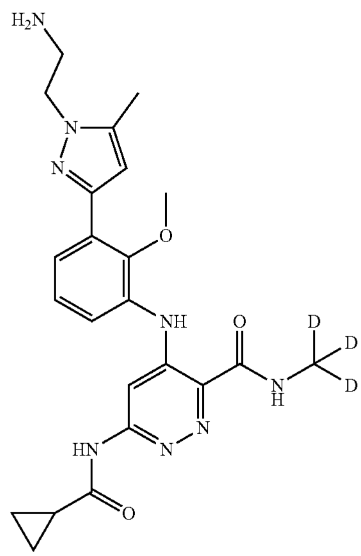 [SMILES: [2H]C([2H])([2H])NC(=O)c1nnc(NC(=O)C2CC2)cc1Nc1cccc(-c2cc(C)n(CCN)n2)c1OC] | 467.5 | 468.3 | 1.34 | QC-ACN-AA-XB |
| 463 | 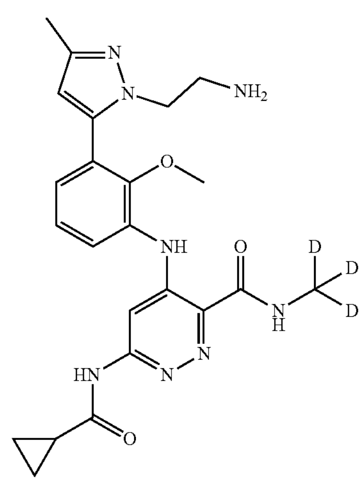 [SMILES: [2H]C([2H])([2H])NC(=O)c1nnc(NC(=O)C2CC2)cc1Nc1cccc(-c2cc(C)nn2CCN)c1OC] | 467.5 | 468.2 | 1.28 | QC-ACN-AA-XB |

TABLE 9-continued
| Ex. No. | Structure | MW | Obs. MS Ion | RT | QC Method |
|---|---|---|---|---|---|
| 464 | 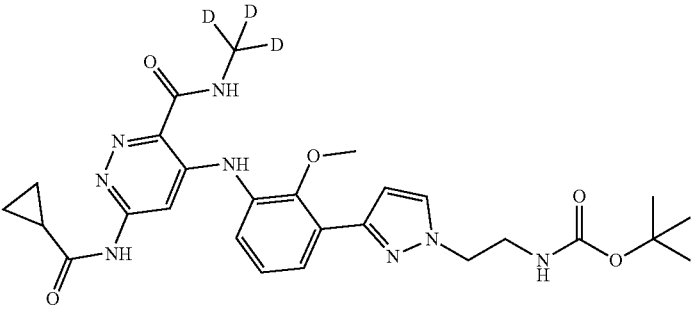 [SMILES: [2H]C([2H])([2H])NC(=O)c1nnc(NC(=O)C2CC2)cc1Nc1cccc(-c2ccn(CCNC(=O)OC(C)(C)C)n2)c1OC] | 553.6 | 554.3 | 1.69 | QC-ACN-AA-XB |
| 465 | 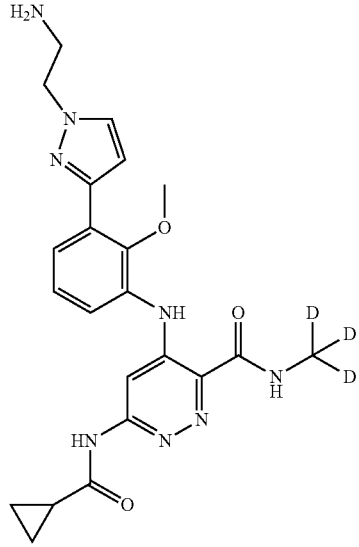 [SMILES: [2H]C([2H])([2H])NC(=O)c1nnc(NC(=O)C2CC2)cc1Nc1cccc(-c2ccn(CCN)n2)c1OC] | 453.5 | 454.3 | 1.21 | QC-ACN-AA-XB |
| 466 | 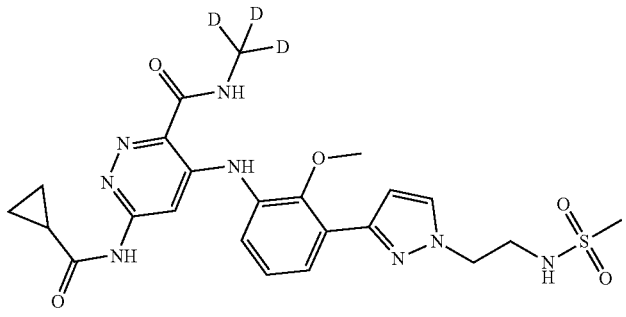 [SMILES: [2H]C([2H])([2H])NC(=O)c1nnc(NC(=O)C2CC2)cc1Nc1cccc(-c2ccn(CCNS(C)(=O)=O)n2)c1OC] | 531.6 | 532.2 | 1.24 | QC-ACN-AA-XB |
| 467 | 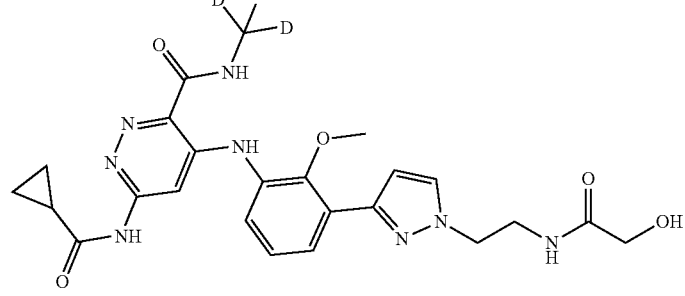 | 511.6 | 512.2 | 0.92 | QC-ACN-TFA-XB |

TABLE 9-continued

| Ex. No. | Structure | MW | Obs. MS Ion | RT | QC Method |
|---|---|---|---|---|---|
| 468 | 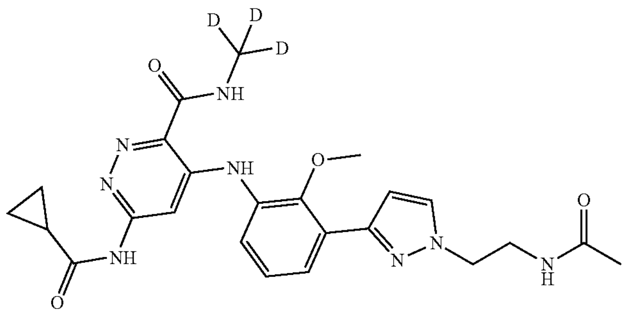 [SMILES: [2H]C([2H])([2H])NC(=O)c1nnc(NC(=O)C2CC2)cc1Nc1cccc(-c2ccn(CCNC(C)=O)n2)c1OC] | 495.6 | 496.4 | 1.16 | QC-ACN-AA-XB |
| 469 | 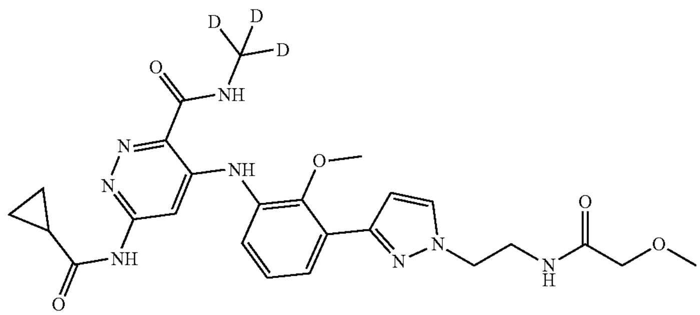 [SMILES: [2H]C([2H])([2H])NC(=O)c1nnc(NC(=O)C2CC2)cc1Nc1cccc(-c2ccn(CCNC(=O)COC)n2)c1OC] | 525.6 | 526.2 | 1.23 | QC-ACN-AA-XB |
| 470 | 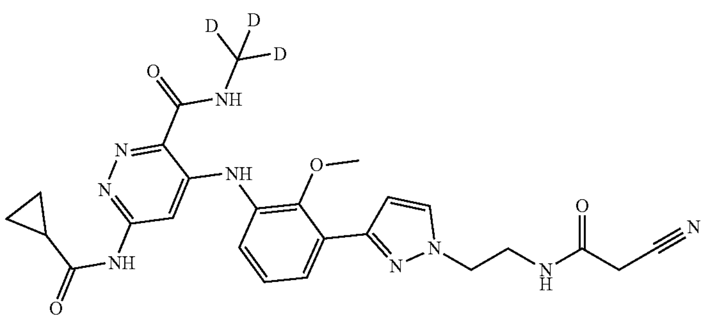 [SMILES: [2H]C([2H])([2H])NC(=O)c1nnc(NC(=O)C2CC2)cc1Nc1cccc(-c2ccn(CCNC(=O)CC#N)n2)c1OC] | 520.6 | 521.4 | 1.21 | QC-ACN-AA-XB |
| 471 | 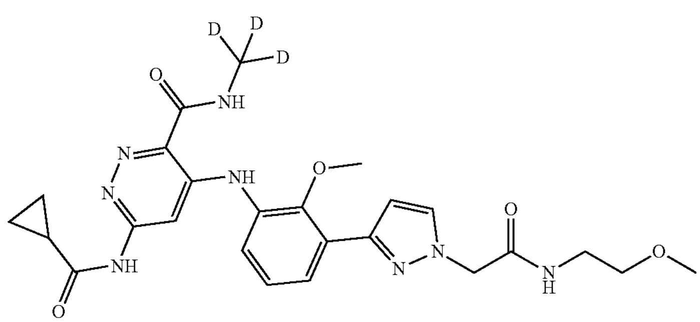 [SMILES: [2H]C([2H])([2H])NC(=O)c1nnc(NC(=O)C2CC2)cc1Nc1cccc(-c2ccn(CC(=O)NCCOC)n2)c1OC] | 525.6 | 526.4 | 1.23 | QC-ACN-AA-XB |
| 472 | 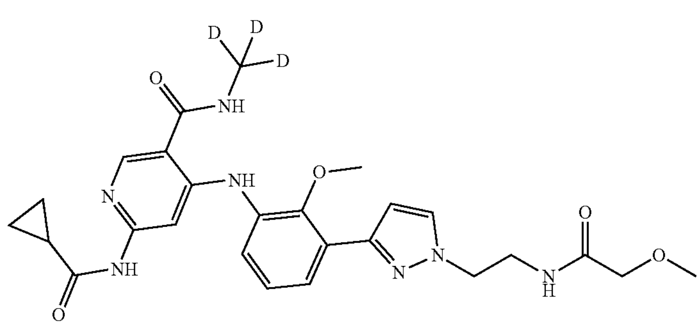 [SMILES: [2H]C([2H])([2H])NC(=O)c1cnc(NC(=O)C2CC2)cc1Nc1cccc(-c2ccn(CCNC(=O)COC)n2)c1OC] | 524.6 | 525.0 | 1.03 | QC-ACN-TFA-XB |

TABLE 9-continued

| Ex. No. | Structure | MW | Obs. MS Ion | RT | QC Method |
|---|---|---|---|---|---|
| 473 | 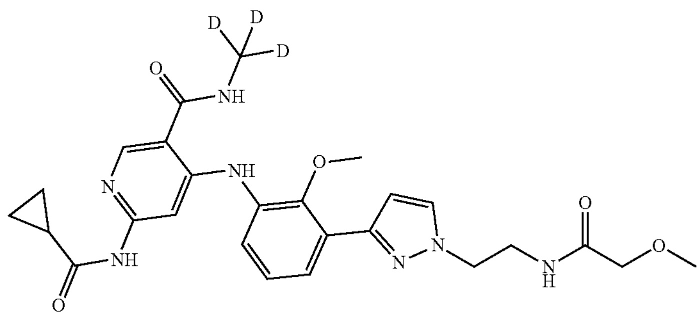 [SMILES: [2H]C([2H])([2H])NC(=O)c1cnc(NC(=O)C2CC2)cc1Nc1cccc(-c2ccn(CCNC(=O)COC)n2)c1OC] | 524.6 | 525.4 | 1.09 | QC-ACN-TFA-XB |
| 474 | 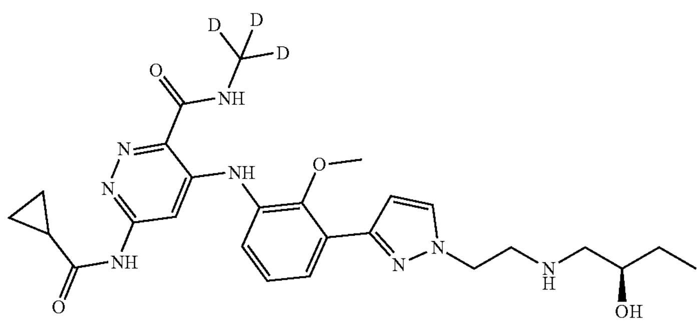 [SMILES: [2H]C([2H])([2H])NC(=O)c1nnc(NC(=O)C2CC2)cc1Nc1cccc(-c2ccn(CCNC[C@H](O)CC)n2)c1OC] | 525.6 | 526.4 | 1.1 | QC-ACN-AA-XB |
| 475 | 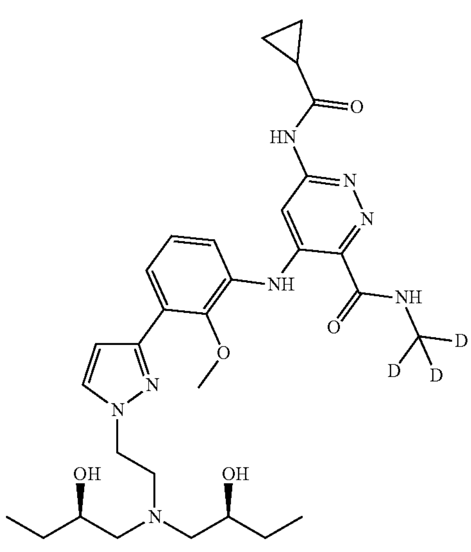 [SMILES: [2H]C([2H])([2H])NC(=O)c1nnc(NC(=O)C2CC2)cc1Nc1cccc(-c2ccn(CCN(C[C@H](O)CC)C[C@@H](O)CC)n2)c1OC] | 597.7 | 598.3 | 1.63 | QC-ACN-AA-XB |

TABLE 9-continued
| Ex. No. | Structure | MW | Obs. MS Ion | RT | QC Method |
|---|---|---|---|---|---|
| 476 | 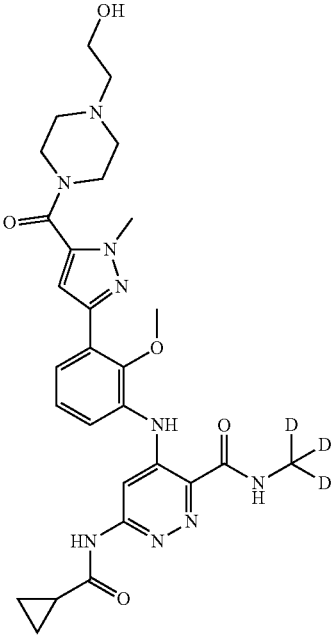 [SMILES: [2H]C([2H])([2H])NC(=O)c1nnc(NC(=O)C2CC2)cc1Nc1cccc(-c2cc(C(=O)N3CCN(CCO)CC3)n(C)n2)c1OC] | 580.7 | 581.2 | 1.26 | QC-ACN-AA-XB |
| 477 | 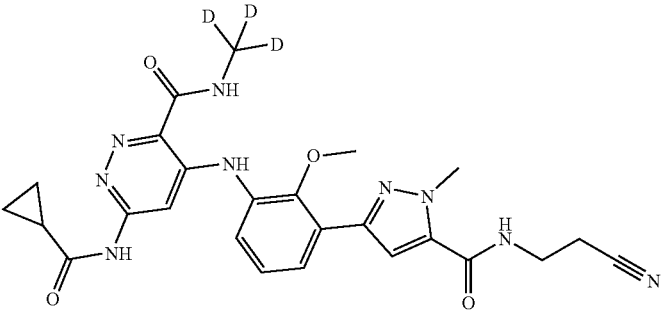 [SMILES: [2H]C([2H])([2H])NC(=O)c1nnc(NC(=O)C2CC2)cc1Nc1cccc(-c2cc(C(=O)NCCC#N)n(C)n2)c1OC] | 520.6 | 521.2 | 1.4 | QC-ACN-AA-XB |
| 478 | 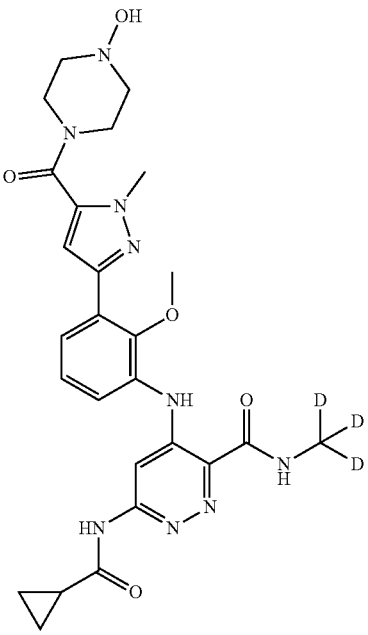 [SMILES: [2H]C([2H])([2H])NC(=O)c1nnc(NC(=O)C2CC2)cc1Nc1cccc(-c2cc(C(=O)N3CCN(O)CC3)n(C)n2)c1OC] | 551.6 | 552.4 | 1.2 | QC-ACN-AA-XB |

TABLE 9-continued

| Ex. No. | Structure | MW | Obs. MS Ion | RT | QC Method |
|---|---|---|---|---|---|
| 479 | 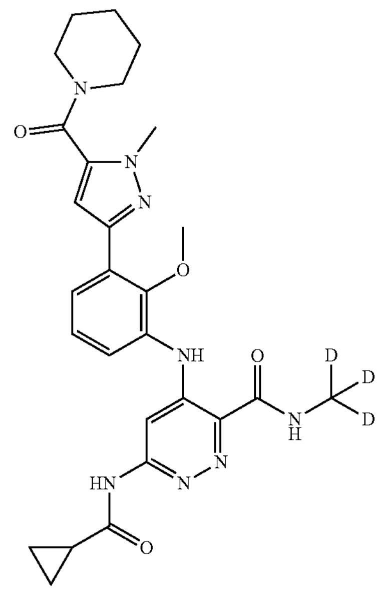 [SMILES: [2H]C([2H])([2H])NC(=O)c1nnc(NC(=O)C2CC2)cc1Nc1cccc(-c2cc(C(=O)N3CCCCC3)n(C)n2)c1OC] | 535.6 | 536.2 | 1.57 | QC-ACN-AA-XB |
| 480 | 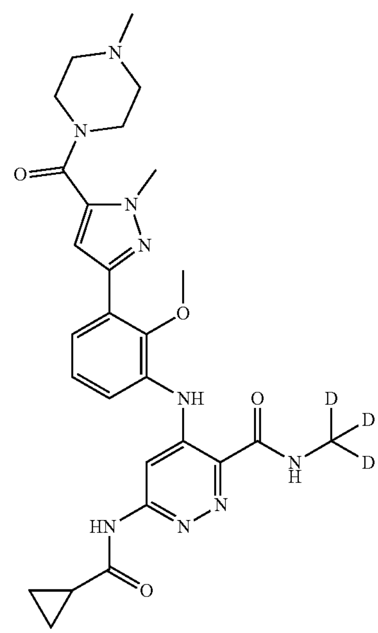 [SMILES: [2H]C([2H])([2H])NC(=O)c1nnc(NC(=O)C2CC2)cc1Nc1cccc(-c2cc(C(=O)N3CCN(C)CC3)n(C)n2)c1OC] | 550.6 | 551.2 | 1.32 | QC-ACN-AA-XB |
| 481 | 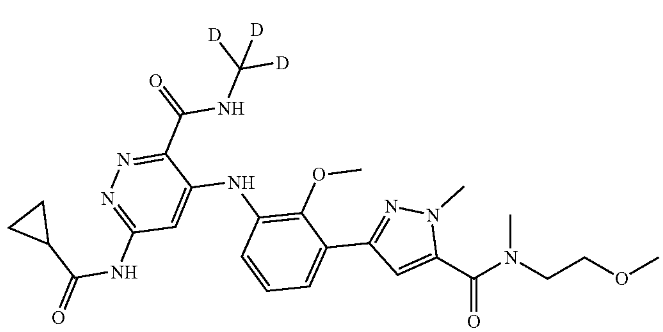 [SMILES: [2H]C([2H])([2H])NC(=O)c1nnc(NC(=O)C2CC2)cc1Nc1cccc(-c2cc(C(=O)N(C)CCOC)n(C)n2)c1OC] | 539.6 | 540.2 | 1.44 | QC-ACN-AA-XB |

TABLE 9-continued
| Ex. No. | Structure | Obs. MW | MS Ion | RT | QC Method |
|---|---|---|---|---|---|
| 482 | 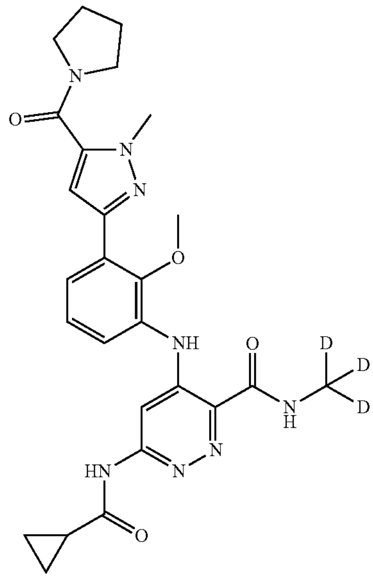 [SMILES: [2H]C([2H])([2H])NC(=O)c1nnc(NC(=O)C2CC2)cc1Nc1cccc(-c2cc(C(=O)N3CCCC3)n(C)n2)c1OC] | 521.6 | 522.2 | 1.51 | QC-ACN-AA-XB |
| 483 | 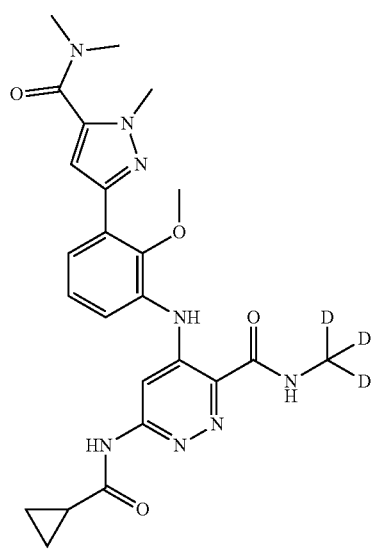 [SMILES: [2H]C([2H])([2H])NC(=O)c1nnc(NC(=O)C2CC2)cc1Nc1cccc(-c2cc(C(=O)N(C)C)n(C)n2)c1OC] | 495.6 | 496.4 | 1.32 | QC-ACN-AA-XB |

TABLE 9-continued

| Ex. No. | Structure | MW | Obs. MS Ion | RT | QC Method |
|---|---|---|---|---|---|
| 484 | 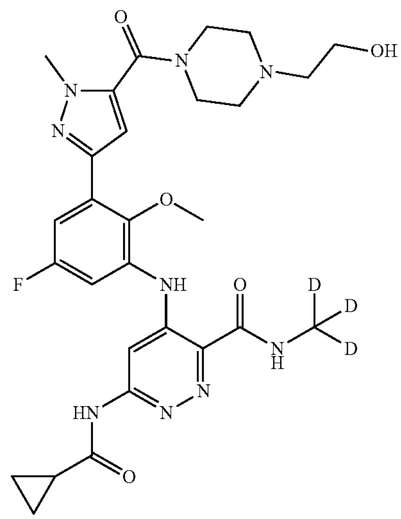 [SMILES: [2H]C([2H])([2H])NC(=O)c1nnc(NC(=O)C2CC2)cc1Nc1cc(F)cc(-c2cc(C(=O)N3CCN(CCO)CC3)n(C)n2)c1OC] | 598.7 | 599.2 | 1.29 | QC-ACN-AA-XB |
| 485 | 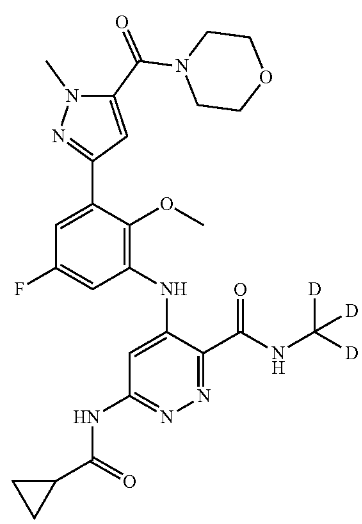 [SMILES: [2H]C([2H])([2H])NC(=O)c1nnc(NC(=O)C2CC2)cc1Nc1cc(F)cc(-c2cc(C(=O)N3CCOCC3)n(C)n2)c1OC] | 555.6 | 556.3 | 1.46 | QC-ACN-AA-XB |
| 486 | 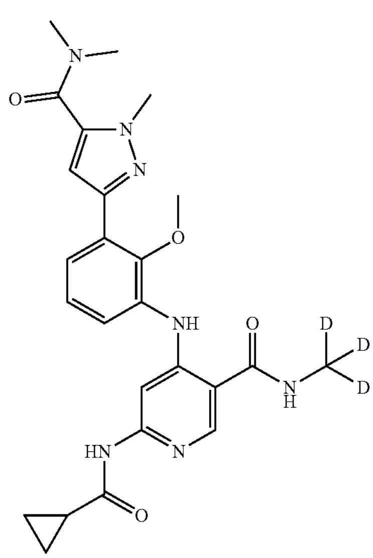 [SMILES: [2H]C([2H])([2H])NC(=O)c1cnc(NC(=O)C2CC2)cc1Nc1cccc(-c2cc(C(=O)N(C)C)n(C)n2)c1OC] | 494.6 | 495.3 | 1.21 | QC-ACN-AA-XB |

TABLE 9-continued
| Ex. No. | Structure | MW | Obs. MS Ion | RT | QC Method |
|---|---|---|---|---|---|
| 487 | 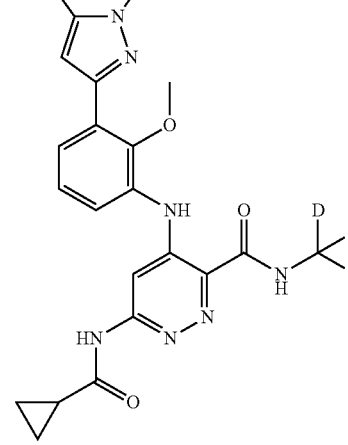 | 482.6 | 483.6 | 0.74 | A |
| 488 | 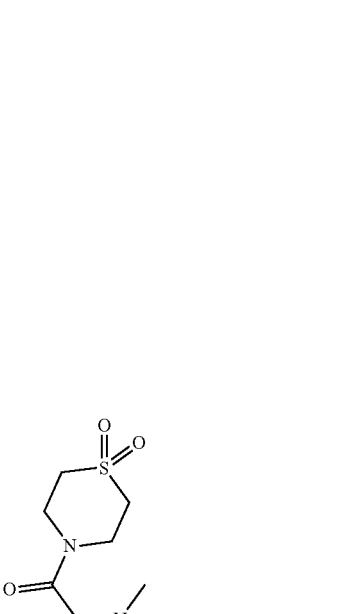 | 584.7 | 585.1 | 0.94 | QC-ACN-TFA-XB |

TABLE 9-continued
| Ex. No. | Structure | MW | Obs. MS Ion | RT | QC Method |
|---|---|---|---|---|---|
| 489 | 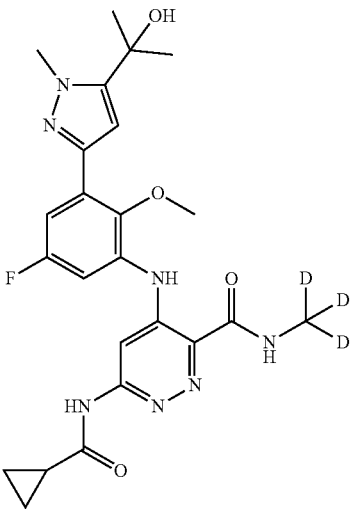 [SMILES: [2H]C([2H])([2H])NC(=O)c1nnc(NC(=O)C2CC2)cc1Nc1cc(F)cc(-c2cc(C(C)(C)O)n(C)n2)c1OC] | 500.6 | 501.2 | 1.57 | QC-ACN-AA-XB |
| 490 | 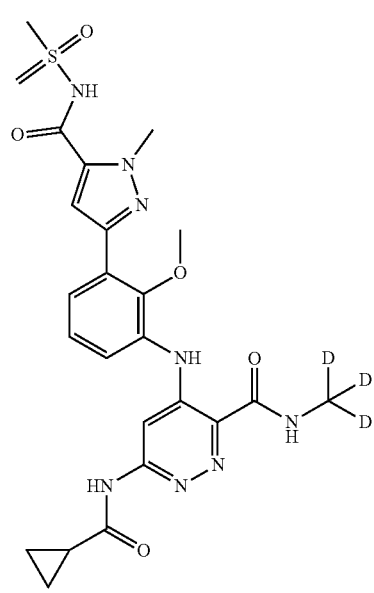 [SMILES: [2H]C([2H])([2H])NC(=O)c1nnc(NC(=O)C2CC2)cc1Nc1cccc(-c2cc(C(=O)NS(=C)(C)=O)n(C)n2)c1OC] | 545.6 | 546.4 | 1.18 | QC-ACN-TFA-XB |
| 491 | 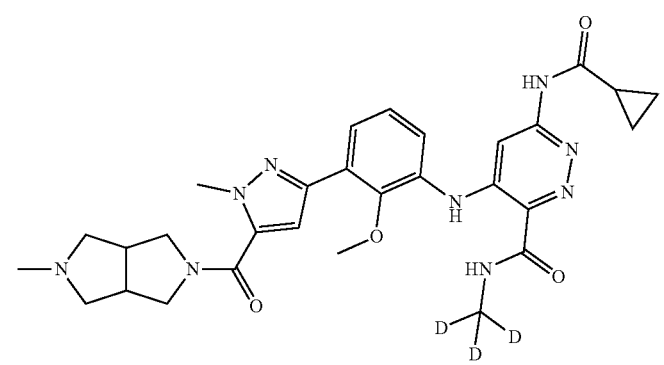 [SMILES: [2H]C([2H])([2H])NC(=O)c1nnc(NC(=O)C2CC2)cc1Nc1cccc(-c2cc(C(=O)N3CC4CN(C)CC4C3)n(C)n2)c1OC] | 576.7 | 577.2 | 0.86 | QC-ACN-TFA-XB |

TABLE 9-continued
| Ex. No. | Structure | MW | Obs. MS Ion | RT | QC Method |
|---|---|---|---|---|---|
| 492 | 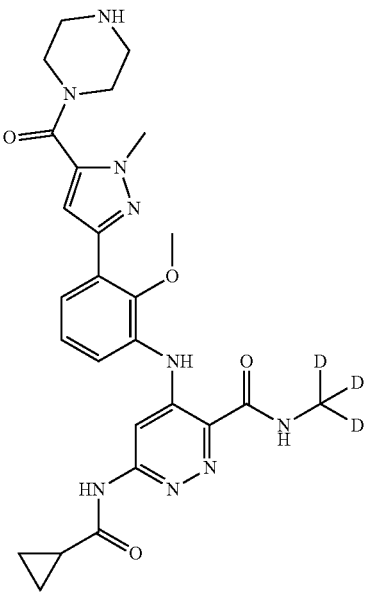 [SMILES: [2H]C([2H])([2H])NC(=O)c1nnc(NC(=O)C2CC2)cc1Nc1cccc(-c2cc(C(=O)N3CCNCC3)n(C)n2)c1OC] | 536.6 | 537.2 | 0.83 | QC-ACN-TFA-XB |
| 493 | 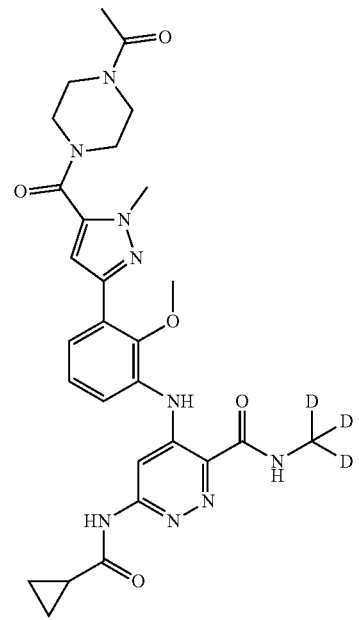 [SMILES: [2H]C([2H])([2H])NC(=O)c1nnc(NC(=O)C2CC2)cc1Nc1cccc(-c2cc(C(=O)N3CCN(C(C)=O)CC3)n(C)n2)c1OC] | 578.6 | 579.4 | 1.02 | QC-ACN-TFA-XB |

TABLE 9-continued

| Ex. No. | Structure | MW | Obs. MS Ion | RT | QC Method |
|---|---|---|---|---|---|
| 494 | 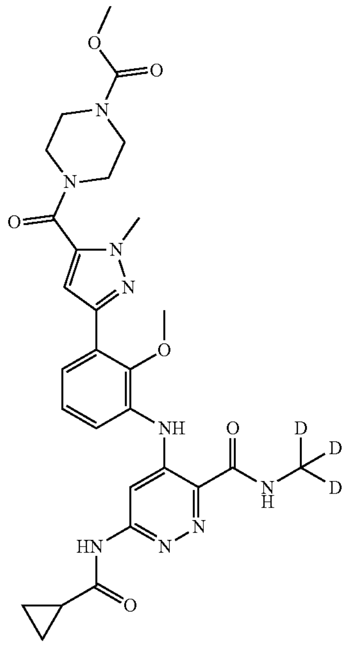 [SMILES: [2H]C([2H])([2H])NC(=O)c1nnc(NC(=O)C2CC2)cc1Nc1cccc(-c2cc(C(=O)N3CCN(C(=O)OC)CC3)n(C)n2)c1OC] | 594.6 | 595.4 | 1.42 | QC-ACN-AA-XB |
| 495 | 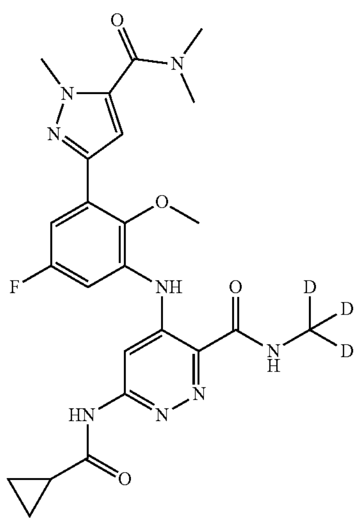 [SMILES: [2H]C([2H])([2H])NC(=O)c1nnc(NC(=O)C2CC2)cc1Nc1cc(F)cc(-c2cc(C(=O)N(C)C)n(C)n2)c1OC] | 513.5 | 514.1 | 1.49 | QC-ACN-AA-XB |
| 496 | 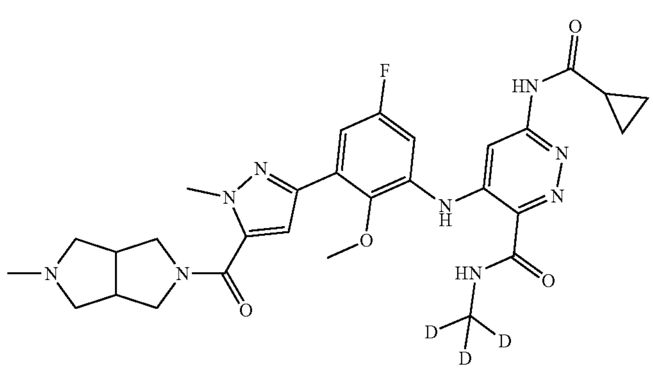 [SMILES: [2H]C([2H])([2H])NC(=O)c1nnc(NC(=O)C2CC2)cc1Nc1cc(F)cc(-c2cc(C(=O)N3CC4CN(C)CC4C3)n(C)n2)c1OC] | 594.7 | 595.2 | 1.32 | QC-ACN-AA-XB |

TABLE 9-continued

| Ex. No. | Structure | MW | Obs. MS Ion | RT | QC Method |
|---|---|---|---|---|---|
| 497 | 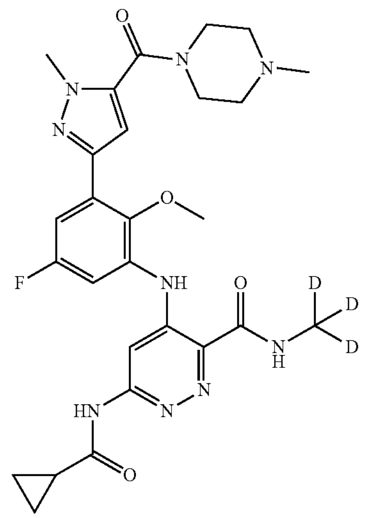 [SMILES: [2H]C([2H])([2H])NC(=O)c1nnc(NC(=O)C2CC2)cc1Nc1cc(F)cc(-c2cc(C(=O)N3CCN(C)CC3)n(C)n2)c1OC] | 568.6 | 569.3 | 1.44 | QC-ACN-AA-XB |
| 498 | 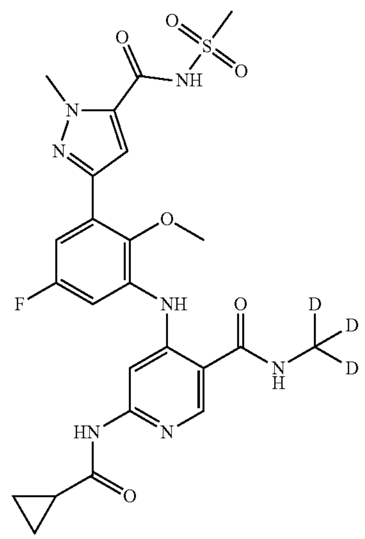 [SMILES: [2H]C([2H])([2H])NC(=O)c1cnc(NC(=O)C2CC2)cc1Nc1cc(F)cc(-c2cc(C(=O)NS(C)(=O)=O)n(C)n2)c1OC] | 562.6 | 563.3 | 1.14 | QC-ACN-TFA-XB |
| 499 | 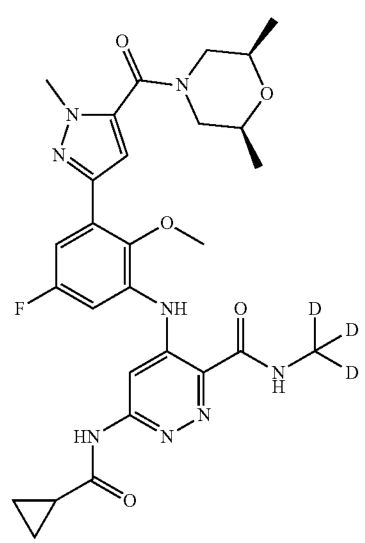 [SMILES: [2H]C([2H])([2H])NC(=O)c1nnc(NC(=O)C2CC2)cc1Nc1cc(F)cc(-c2cc(C(=O)N3C[C@@H](C)O[C@@H](C)C3)n(C)n2)c1OC] | 583.6 | 584.3 | 1.72 | QC-ACN-AA-XB |

| Ex. No. | Structure | Obs. MW | MS Ion | RT | QC Method |
|---|---|---|---|---|---|
| 500 | 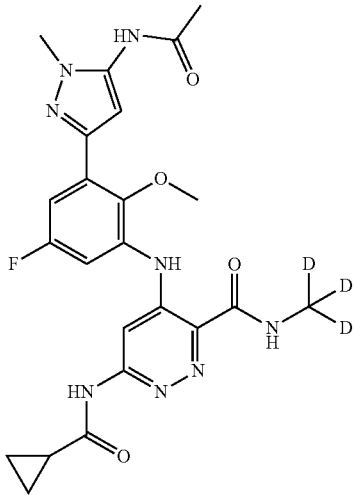 [SMILES: [2H]C([2H])([2H])NC(=O)c1nnc(NC(=O)C2CC2)cc1Nc1cc(F)cc(-c2cc(NC(C)=O)n(C)n2)c1OC] | 499.5 | 500.4 | 1.33 | QC-ACN-AA-XB |
| 501 | 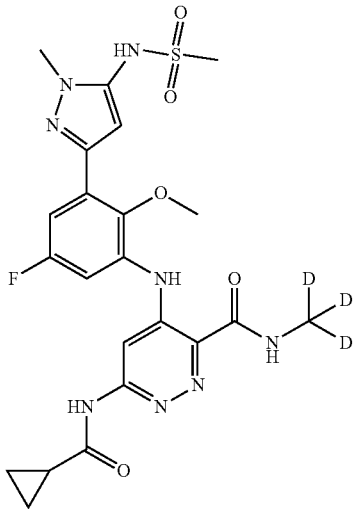 [SMILES: [2H]C([2H])([2H])NC(=O)c1nnc(NC(=O)C2CC2)cc1Nc1cc(F)cc(-c2cc(NS(C)(=O)=O)n(C)n2)c1OC] | 535.6 | 536.2 | 1.25 | QC-ACN-AA-XB |

TABLE 9-continued

| Ex. No. | Structure | Obs. MW | MS Ion | RT | QC Method |
|---|---|---|---|---|---|
| 502 | 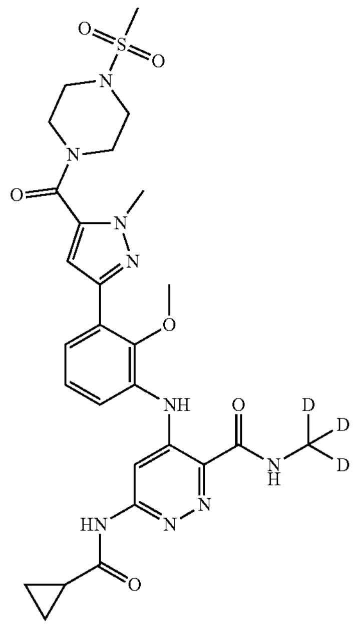 [SMILES: [2H]C([2H])([2H])NC(=O)c1nnc(NC(=O)C2CC2)cc1Nc1cccc(-c2cc(C(=O)N3CCN(S(C)(=O)=O)CC3)n(C)n2)c1OC] | 614.7 | 615.2 | 1.39 | QC-ACN-AA-XB |
| 503 | 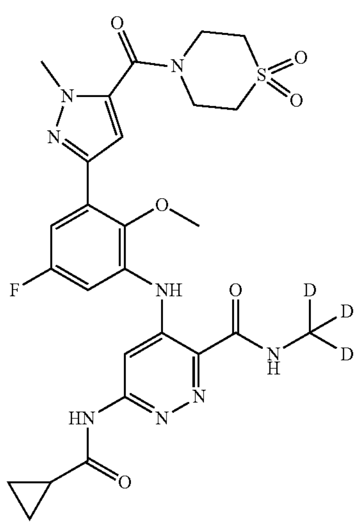 [SMILES: [2H]C([2H])([2H])NC(=O)c1nnc(NC(=O)C2CC2)cc1Nc1cc(F)cc(-c2cc(C(=O)N3CCS(=O)(=O)CC3)n(C)n2)c1OC] | 603.6 | 604.2 | 1.47 | QC-ACN-AA-XB |
| 504 | 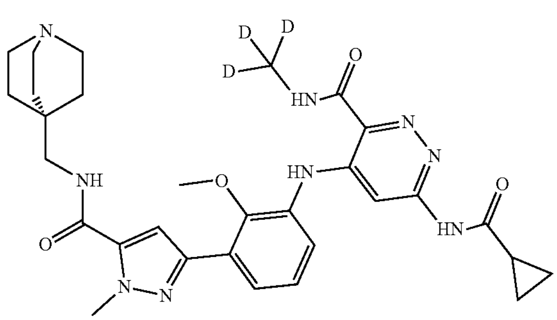 | 590.7 | 591.4 | 0.93 | QC-ACN-TFA-XB |

TABLE 9-continued
| Ex. No. | Structure | MW | Obs. MS Ion | RT | QC Method |
|---|---|---|---|---|---|
| 505 | 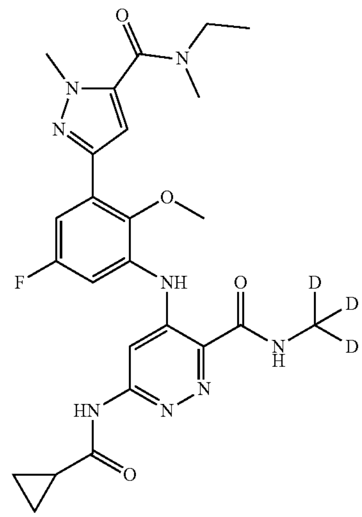 [SMILES: [2H]C([2H])([2H])NC(=O)c1nnc(NC(=O)C2CC2)cc1Nc1cc(F)cc(-c2cc(C(=O)N(C)CC)n(C)n2)c1OC] | 527.6 | 528.3 | 1.62 | QC-ACN-AA-XB |
| 506 | 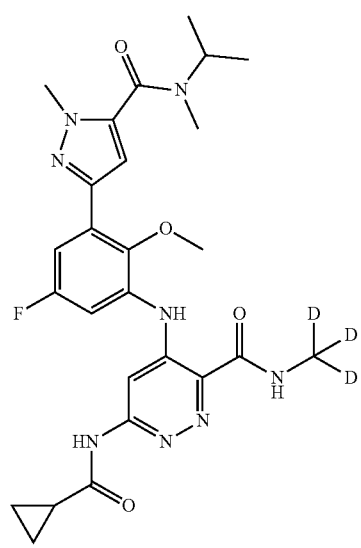 [SMILES: [2H]C([2H])([2H])NC(=O)c1nnc(NC(=O)C2CC2)cc1Nc1cc(F)cc(-c2cc(C(=O)N(C)C(C)C)n(C)n2)c1OC] | 541.6 | 542.3 | 1.53 | QC-ACN-TFA-XB |

TABLE 9-continued
| Ex. No. | Structure | MW | Obs. MS Ion | RT | QC Method |
|---|---|---|---|---|---|
| 507 | 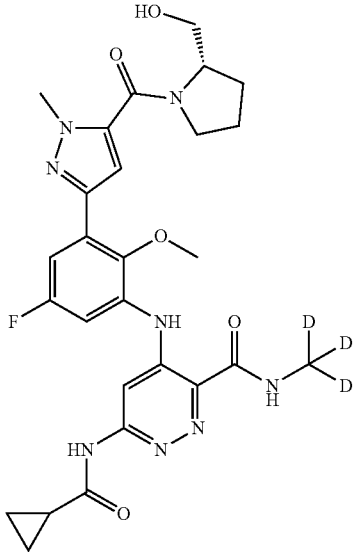 [SMILES: [2H]C([2H])([2H])NC(=O)c1nnc(NC(=O)C2CC2)cc1Nc1cc(F)cc(-c2cc(C(=O)N3CCC[C@H]3CO)n(C)n2)c1OC] | 569.6 | 570.1 | 1.31 | QC-ACN-TFA-XB |
| 508 | 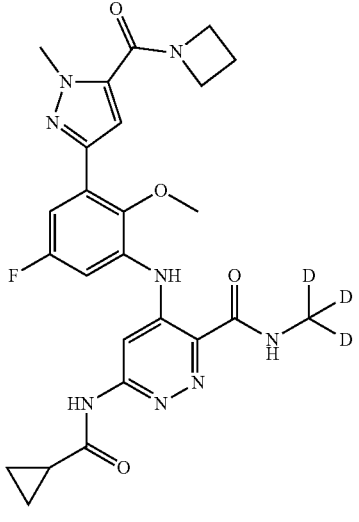 [SMILES: [2H]C([2H])([2H])NC(=O)c1nnc(NC(=O)C2CC2)cc1Nc1cc(F)cc(-c2cc(C(=O)N3CCC3)n(C)n2)c1OC] | 525.6 | 526.2 | 1.6 | QC-ACN-AA-XB |
| 509 | 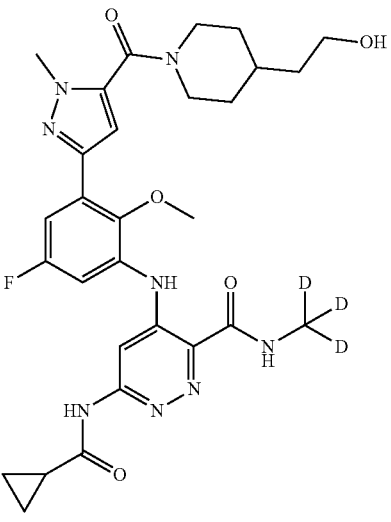 [SMILES: [2H]C([2H])([2H])NC(=O)c1nnc(NC(=O)C2CC2)cc1Nc1cc(F)cc(-c2cc(C(=O)N3CCC(CCO)CC3)n(C)n2)c1OC] | 597.7 | 598.3 | 1.27 | QC-ACN-TFA-XB |

TABLE 9-continued

| Ex. No. | Structure | MW | Obs. MS Ion | RT | QC Method |
|---|---|---|---|---|---|
| 510 | 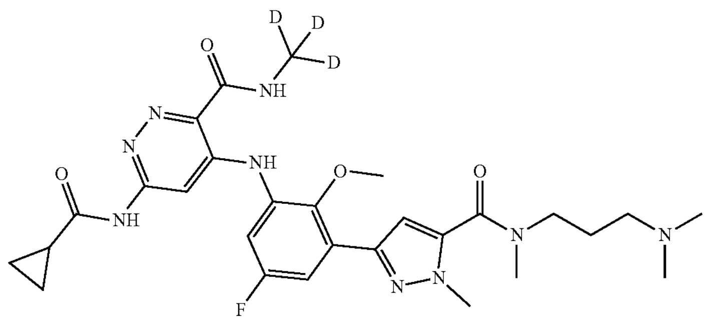 [SMILES: [2H]C([2H])([2H])NC(=O)c1nnc(NC(=O)C2CC2)cc1Nc1cc(F)cc(-c2cc(C(=O)N(C)CCCN(C)C)n(C)n2)c1OC] | 584.7 | 585.5 | 1 | QC-ACN-TFA-XB |
| 511 | 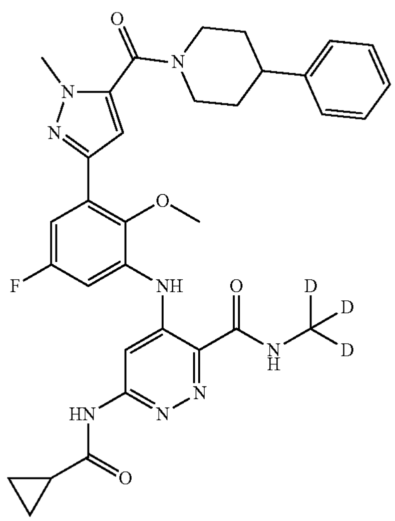 [SMILES: [2H]C([2H])([2H])NC(=O)c1nnc(NC(=O)C2CC2)cc1Nc1cc(F)cc(-c2cc(C(=O)N3CCC(c4ccccc4)CC3)n(C)n2)c1OC] | 629.7 | 630.4 | 1.9 | QC-ACN-TFA-XB |
| 512 | 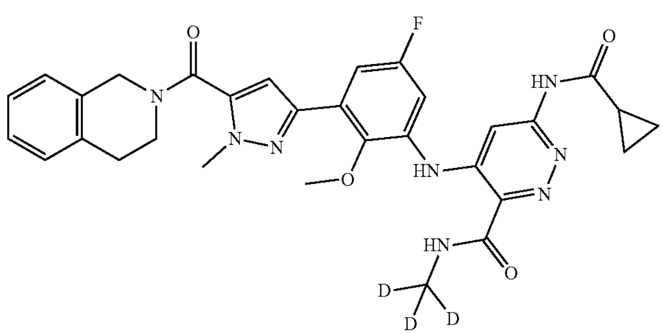 [SMILES: [2H]C([2H])([2H])NC(=O)c1nnc(NC(=O)C2CC2)cc1Nc1cc(F)cc(-c2cc(C(=O)N3CCc4ccccc4C3)n(C)n2)c1OC] | 601.7 | 602.4 | 1.78 | QC-ACN-TFA-XB |
| 513 | 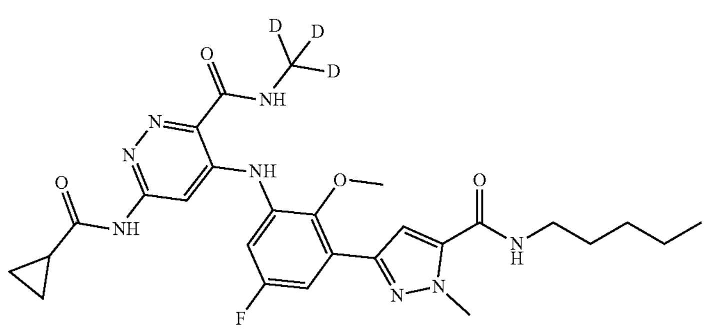 [SMILES: [2H]C([2H])([2H])NC(=O)c1nnc(NC(=O)C2CC2)cc1Nc1cc(F)cc(-c2cc(C(=O)NCCCCC)n(C)n2)c1OC] | 555.6 | 556.2 | 2.08 | QC-ACN-AA-XB |

TABLE 9-continued

| Ex. No. | Structure | Obs. MW | MS Ion | RT | QC Method |
|---|---|---|---|---|---|
| 514 | 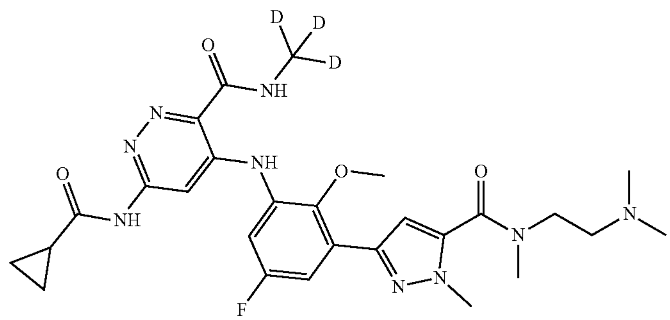 [SMILES: [2H]C([2H])([2H])NC(=O)c1nnc(NC(=O)C2CC2)cc1Nc1cc(F)cc(-c2cc(C(=O)N(C)CCN(C)C)n(C)n2)c1OC] | 570.6 | 571.4 | 1.29 | QC-ACN-AA-XB |
| 515 | 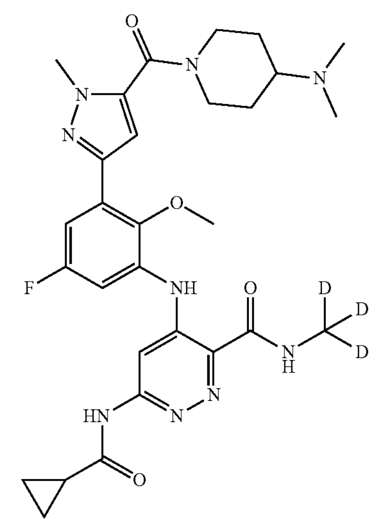 [SMILES: [2H]C([2H])([2H])NC(=O)c1nnc(NC(=O)C2CC2)cc1Nc1cc(F)cc(-c2cc(C(=O)N3CCC(N(C)C)CC3)n(C)n2)c1OC] | 596.7 | 597.3 | 1.24 | QC-ACN-AA-XB |
| 516 | 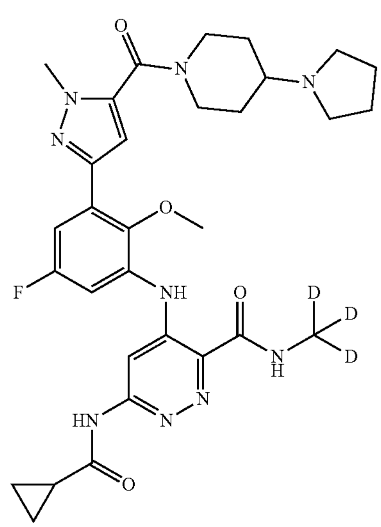 [SMILES: [2H]C([2H])([2H])NC(=O)c1nnc(NC(=O)C2CC2)cc1Nc1cc(F)cc(-c2cc(C(=O)N3CCC(N4CCCC4)CC3)n(C)n2)c1OC] | 622.7 | 623.5 | 1.25 | QC-ACN-AA-XB |

TABLE 9-continued

| Ex. No. | Structure | MW | Obs. MS Ion | RT | QC Method |
|---|---|---|---|---|---|
| 517 | 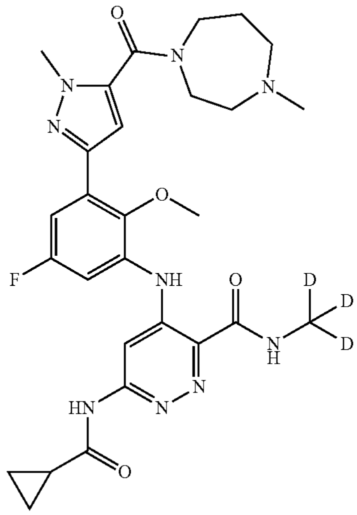 [SMILES: [2H]C([2H])([2H])NC(=O)c1nnc(NC(=O)C2CC2)cc1Nc1cc(F)cc(-c2cc(C(=O)N3CCCN(C)CC3)n(C)n2)c1OC] | 582.7 | 583.3 | 1.11 | QC-ACN-TFA-XB |
| 518 | 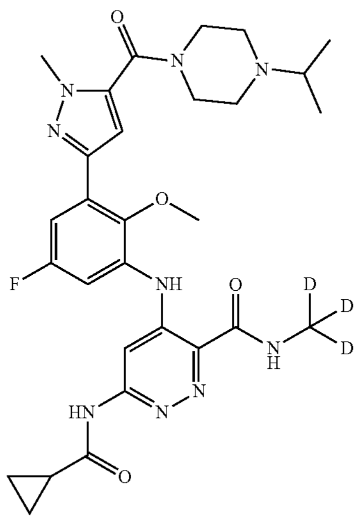 [SMILES: [2H]C([2H])([2H])NC(=O)c1nnc(NC(=O)C2CC2)cc1Nc1cc(F)cc(-c2cc(C(=O)N3CCN(C(C)C)CC3)n(C)n2)c1OC] | 596.7 | 597.5 | 1.56 | QC-ACN-AA-XB |
| 519 | 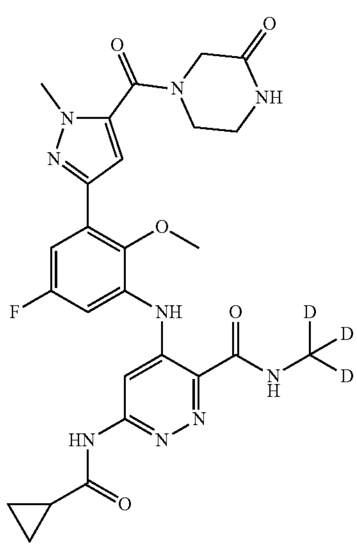 [SMILES: [2H]C([2H])([2H])NC(=O)c1nnc(NC(=O)C2CC2)cc1Nc1cc(F)cc(-c2cc(C(=O)N3CCNC(=O)C3)n(C)n2)c1OC] | 568.6 | 569.3 | 1.31 | QC-ACN-AA-XB |

TABLE 9-continued

| Ex. No. | Structure | MW | Obs. MS Ion | RT | QC Method |
|---|---|---|---|---|---|
| 520 | 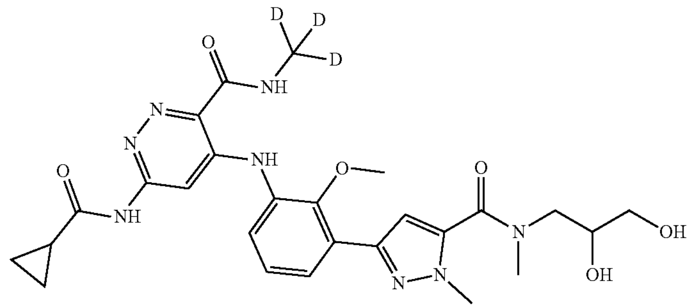 [SMILES: [2H]C([2H])([2H])NC(=O)c1nnc(NC(=O)C2CC2)cc1Nc1cccc(-c2cc(C(=O)N(C)CC(O)CO)n(C)n2)c1OC] | 555.6 | 556.3 | 1.15 | QC-ACN-AA-XB |
| 521 | 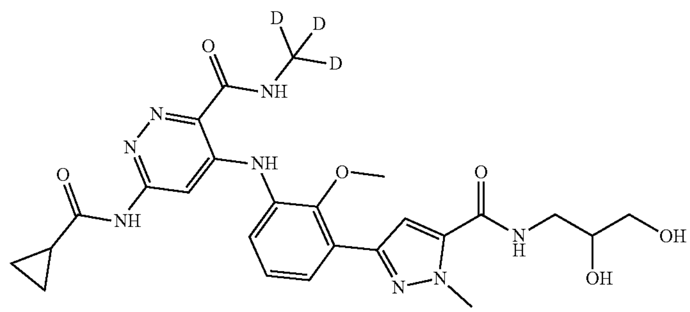 [SMILES: [2H]C([2H])([2H])NC(=O)c1nnc(NC(=O)C2CC2)cc1Nc1cccc(-c2cc(C(=O)NCC(O)CO)n(C)n2)c1OC] | 541.6 | 542.3 | 1.2 | QC-ACN-AA-XB |
| 522 | 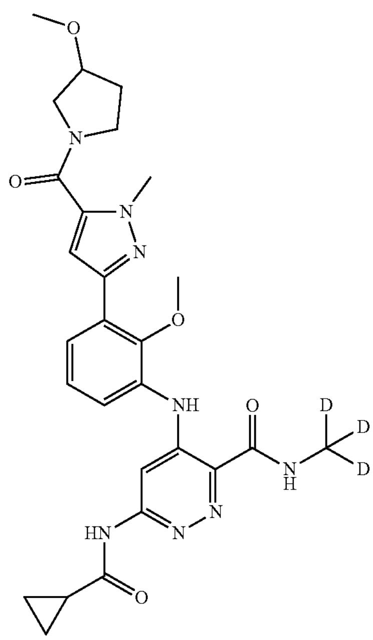 [SMILES: [2H]C([2H])([2H])NC(=O)c1nnc(NC(=O)C2CC2)cc1Nc1cccc(-c2cc(C(=O)N3CCC(OC)C3)n(C)n2)c1OC] | 551.6 | 552.3 | 1.44 | QC-ACN-AA-XB |
| 523 | 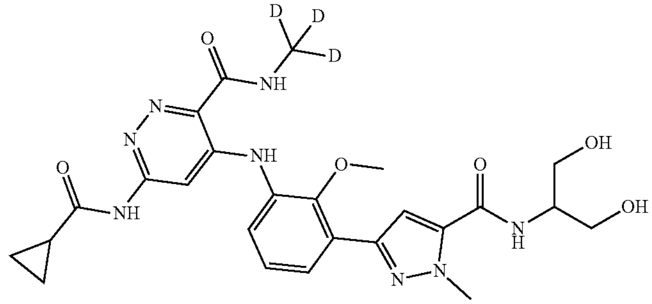 [SMILES: [2H]C([2H])([2H])NC(=O)c1nnc(NC(=O)C2CC2)cc1Nc1cccc(-c2cc(C(=O)NC(CO)CO)n(C)n2)c1OC] | 541.6 | 542.3 | 0.92 | QC-ACN-TFA-XB |

| Ex. No. | Structure | MW | Obs. MS Ion | RT | QC Method |
|---|---|---|---|---|---|
| 524 | 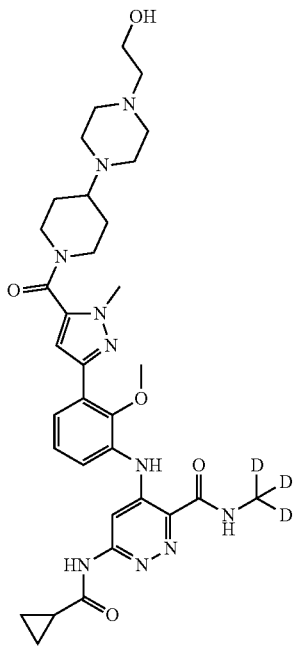 [SMILES: [2H]C([2H])([2H])NC(=O)c1nnc(NC(=O)C2CC2)cc1Nc1cccc(-c2cc(C(=O)N3CCC(N4CCN(CCO)CC4)CC3)n(C)n2)c1OC] | 663.8 | 664.4 | 0.79 | QC-ACN-TFA-XB |
| 525 | 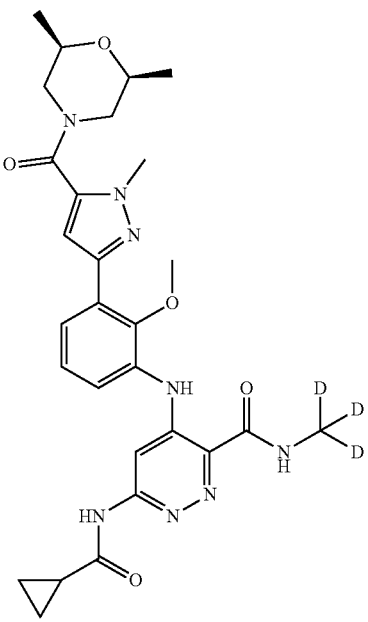 [SMILES: [2H]C([2H])([2H])NC(=O)c1nnc(NC(=O)C2CC2)cc1Nc1cccc(-c2cc(C(=O)N3C[C@@H](C)O[C@@H](C)C3)n(C)n2)c1OC] | 565.6 | 566.3 | 1.6 | QC-ACN-AA-XB |

TABLE 9-continued

| Ex. No. | Structure | Obs. MW | MS Ion | RT | QC Method |
|---|---|---|---|---|---|
| 526 | 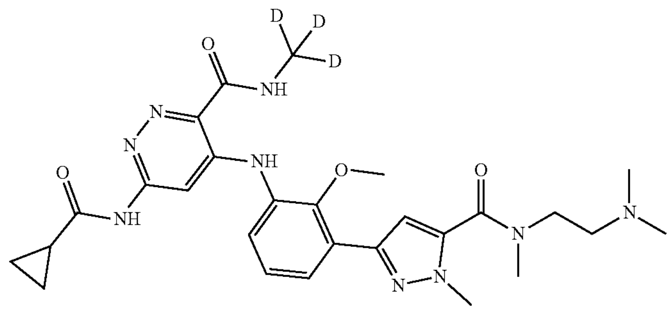 [SMILES: [2H]C([2H])([2H])NC(=O)c1nnc(NC(=O)C2CC2)cc1Nc1cccc(-c2cc(C(=O)N(C)CCN(C)C)n(C)n2)c1OC] | 552.7 | 553.4 | 0.99 | QC-ACN-TFA-XB |
| 527 | 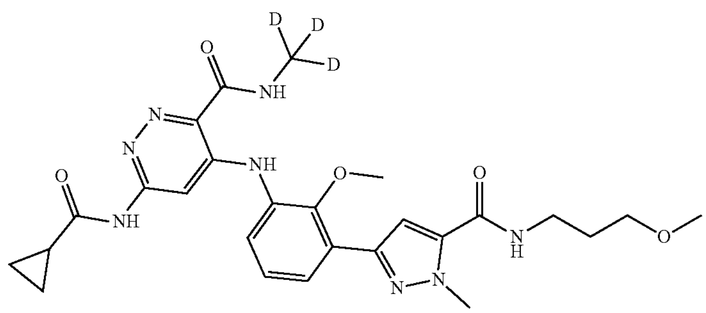 [SMILES: [2H]C([2H])([2H])NC(=O)c1nnc(NC(=O)C2CC2)cc1Nc1cccc(-c2cc(C(=O)NCCCOC)n(C)n2)c1OC] | 539.6 | 540.2 | 1.22 | QC-ACN-TFA-XB |
| 528 | 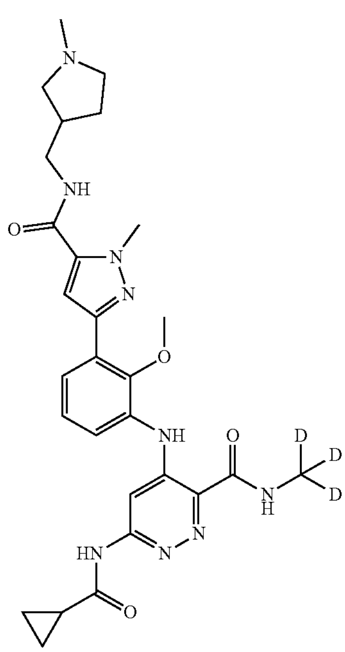 [SMILES: [2H]C([2H])([2H])NC(=O)c1nnc(NC(=O)C2CC2)cc1Nc1cccc(-c2cc(C(=O)NCC3CCN(C)C3)n(C)n2)c1OC] | 564.7 | 565.2 | 1.21 | QC-ACN-AA-XB |

TABLE 9-continued
| Ex. No. | Structure | MW | Obs. MS Ion | RT | QC Method |
|---|---|---|---|---|---|
| 529 | 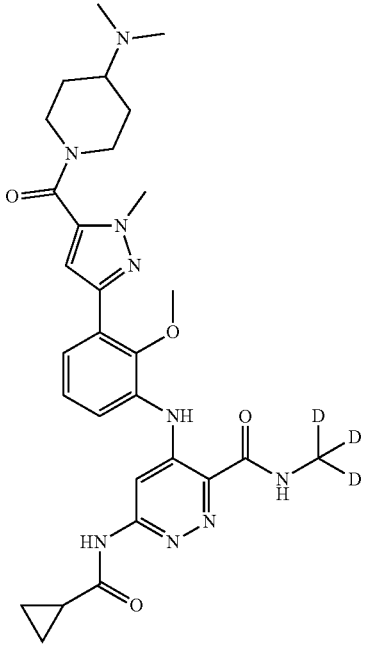 [SMILES: [2H]C([2H])([2H])NC(=O)c1nnc(NC(=O)C2CC2)cc1Nc1cccc(-c2cc(C(=O)N3CCC(N(C)C)CC3)n(C)n2)c1OC] | 578.7 | 579.4 | 1.16 | QC-ACN-AA-XB |
| 530 | 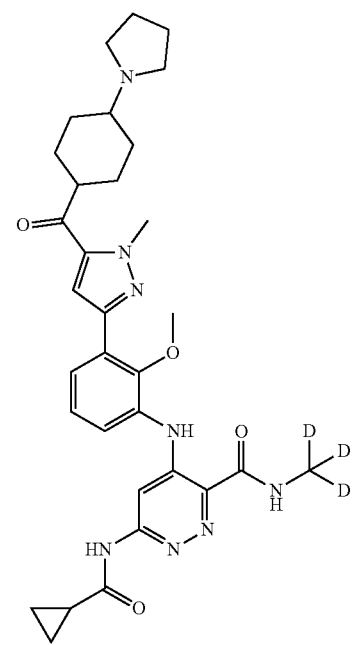 [SMILES: [2H]C([2H])([2H])NC(=O)c1nnc(NC(=O)C2CC2)cc1Nc1cccc(-c2cc(C(=O)C3CCC(N4CCCC4)CC3)n(C)n2)c1OC] | 604.7 | 605.4 | 1.19 | QC-ACN-AA-XB |

TABLE 9-continued
| Ex. No. | Structure | MW | Obs. MS Ion | RT | QC Method |
|---|---|---|---|---|---|
| 531 | 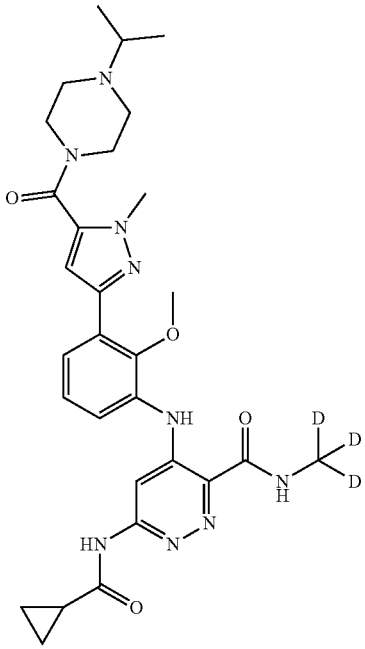 [SMILES: [2H]C([2H])([2H])NC(=O)c1nnc(NC(=O)C2CC2)cc1Nc1cccc(-c2cc(C(=O)N3CCN(C(C)C)CC3)n(C)n2)c1OC] | 578.7 | 579.2 | 1.49 | QC-ACN-AA-XB |
| 532 | 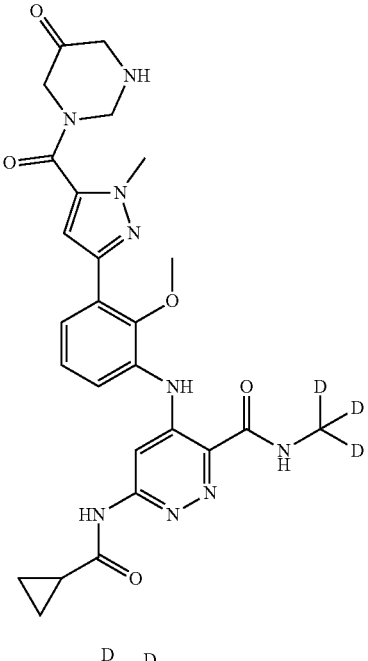 | 550.6 | 551.3 | 1.19 | QC-ACN-AA-XB |
| 533 | 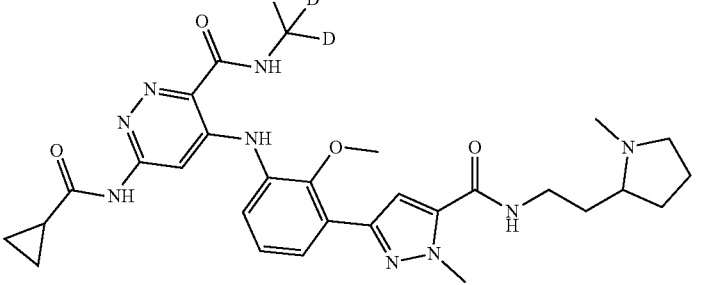 | 578.7 | 579.2 | 1.24 | QC-ACN-AA-XB |

TABLE 9-continued
| Ex. No. | Structure | MW | Obs. MS Ion | RT | QC Method |
|---|---|---|---|---|---|
| 534 | 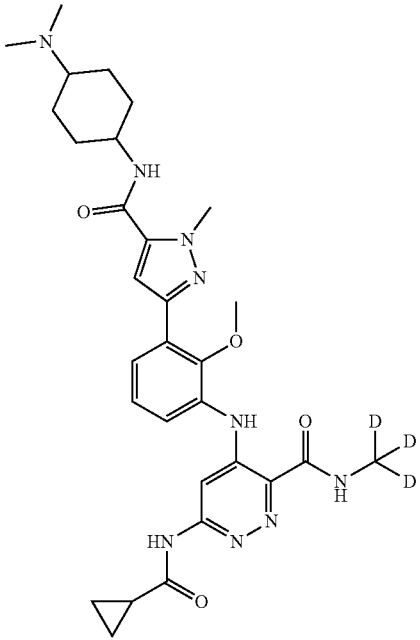 [SMILES: [2H]C([2H])([2H])NC(=O)c1nnc(NC(=O)C2CC2)cc1Nc1cccc(-c2cc(C(=O)NC3CCC(N(C)C)CC3)n(C)n2)c1OC] | 592.7 | 593.4 | 1.26 | QC-ACN-AA-XB |
| 535 | 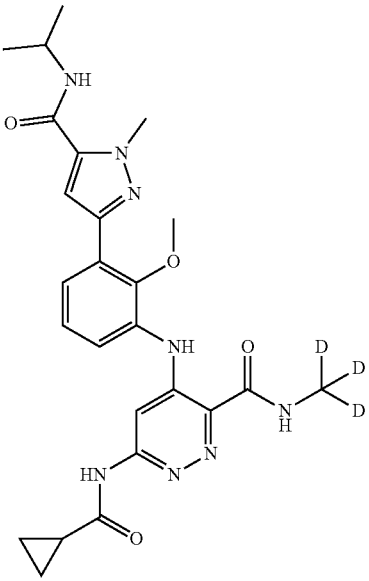 [SMILES: [2H]C([2H])([2H])NC(=O)c1nnc(NC(=O)C2CC2)cc1Nc1cccc(-c2cc(C(=O)NC(C)C)n(C)n2)c1OC] | 509.6 | 510.3 | 1.64 | QC-ACN-AA-XB |
| 536 | 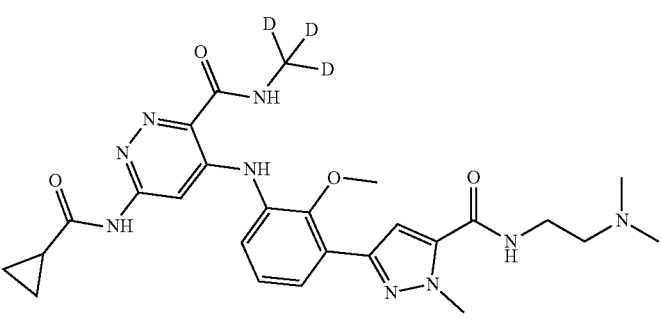 [SMILES: [2H]C([2H])([2H])NC(=O)c1nnc(NC(=O)C2CC2)cc1Nc1cccc(-c2cc(C(=O)NCCN(C)C)n(C)n2)c1OC] | 538.6 | 539.3 | 1.21 | QC-ACN-AA-XB |

TABLE 9-continued
| Ex. No. | Structure | Obs. MW | MS Ion | RT | QC Method |
|---|---|---|---|---|---|
| 537 | 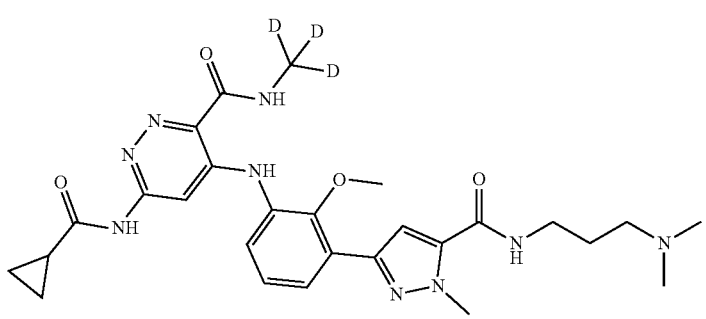 [SMILES: [2H]C([2H])([2H])NC(=O)c1nnc(NC(=O)C2CC2)cc1Nc1cccc(-c2cc(C(=O)NCCCN(C)C)n(C)n2)c1OC] | 552.7 | 553.3 | 1.19 | QC-ACN-AA-XB |
| 538 | 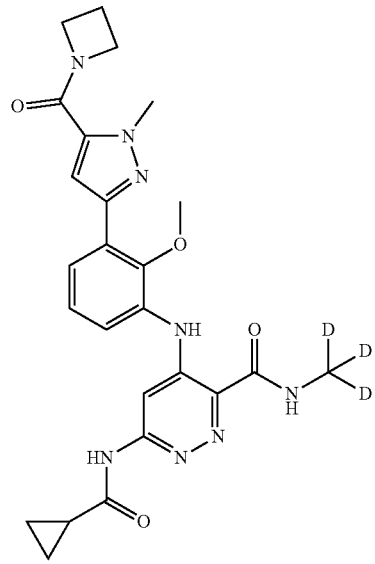 [SMILES: [2H]C([2H])([2H])NC(=O)c1nnc(NC(=O)C2CC2)cc1Nc1cccc(-c2cc(C(=O)N3CCC3)n(C)n2)c1OC] | 507.6 | 508.2 | 1.26 | QC-ACN-TFA-XB |
| 539 | 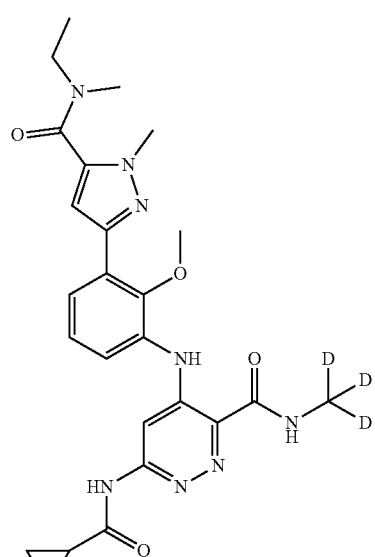 | 509.6 | 510.3 | 1.48 | QC-ACN-AA-XB |

TABLE 9-continued

| Ex. No. | Structure | Obs. MW | MS Ion | RT | QC Method |
|---|---|---|---|---|---|
| 540 | 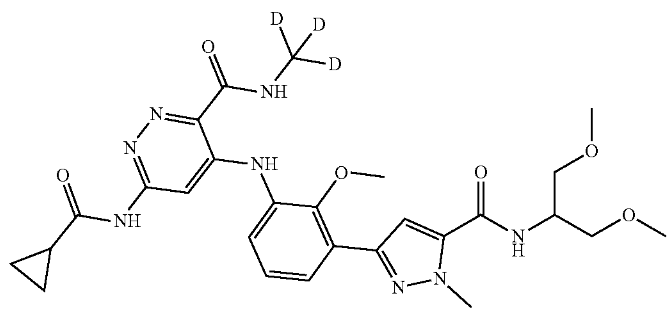 [SMILES: [2H]C([2H])([2H])NC(=O)c1nnc(NC(=O)C2CC2)cc1Nc1cccc(-c2cc(C(=O)NC(COC)COC)n(C)n2)c1OC] | 569.6 | 570.2 | 1.23 | QC-ACN-TFA-XB |
| 541 | 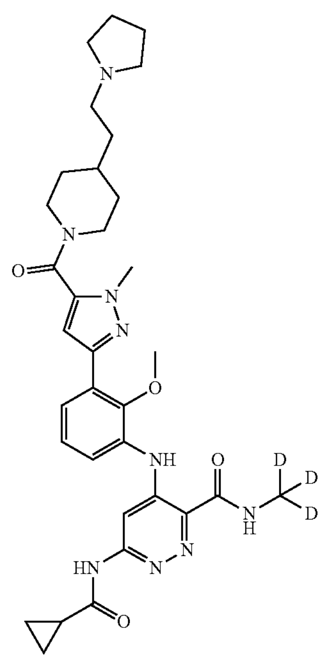 [SMILES: [2H]C([2H])([2H])NC(=O)c1nnc(NC(=O)C2CC2)cc1Nc1cccc(-c2cc(C(=O)N3CCC(CCN4CCCC4)CC3)n(C)n2)c1OC] | 632.8 | 633.4 | 1.22 | QC-ACN-AA-XB |
| 542 | 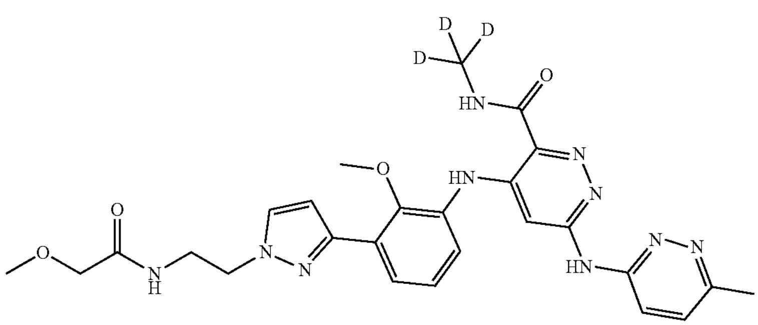 | 549.6 | 550.3 | 0.61 | A |

TABLE 9-continued
| Ex. No. | Structure | MW | Obs. MS Ion | RT | QC Method |
|---|---|---|---|---|---|
| 543 | 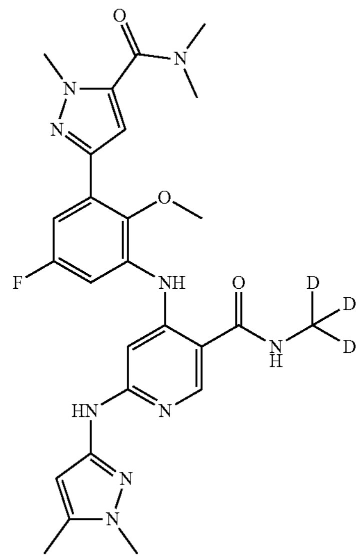 [SMILES: [2H]C([2H])([2H])NC(=O)c1cnc(Nc2cc(C)n(C)n2)cc1Nc1cc(F)cc(-c2cc(C(=O)N(C)C)n(C)n2)c1OC] | 538.6 | 539.3 | 1.39 | QC-ACN-AA-XB |
| 544 | 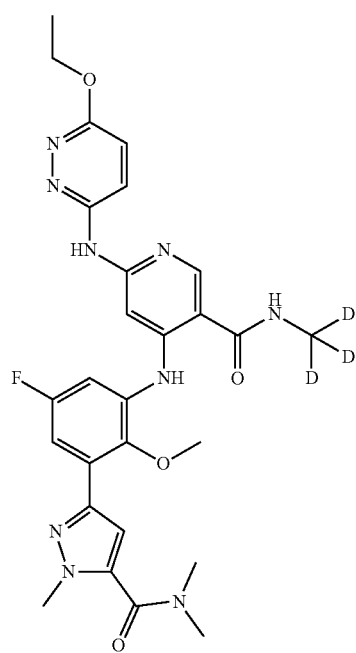 [SMILES: [2H]C([2H])([2H])NC(=O)c1cnc(Nc2ccc(OCC)nn2)cc1Nc1cc(F)cc(-c2cc(C(=O)N(C)C)n(C)n2)c1OC] | 566.6 | 567.0 | 1.61 | QC-ACN-AA-XB |

TABLE 9-continued

| Ex. No. | Structure | MW | Obs. MS Ion | RT | QC Method |
|---|---|---|---|---|---|
| 545 | 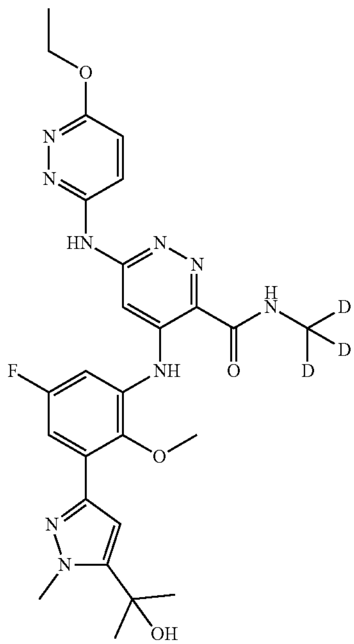 [SMILES: [2H]C([2H])([2H])NC(=O)c1nnc(Nc2ccc(OCC)nn2)cc1Nc1cc(F)cc(-c2cc(C(C)(C)O)n(C)n2)c1OC] | 554.6 | 555.1 | 1.24 | QC-ACN-TFA-XB |
| 546 | 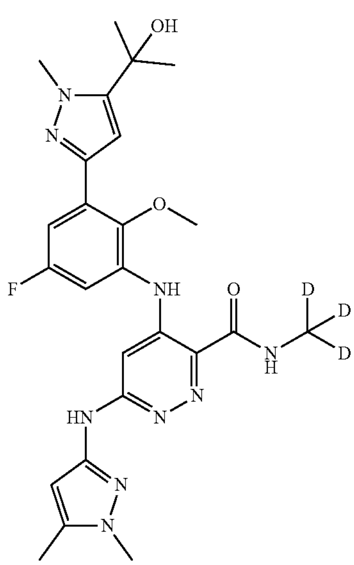 [SMILES: [2H]C([2H])([2H])NC(=O)c1nnc(Nc2cc(C)n(C)n2)cc1Nc1cc(F)cc(-c2cc(C(C)(C)O)n(C)n2)c1OC] | 526.6 | 527.2 | 1.23 | QC-ACN-TFA-XB |

TABLE 9-continued
| Ex. No. | Structure | MW | Obs. MS Ion | RT | QC Method |
|---|---|---|---|---|---|
| 547 | 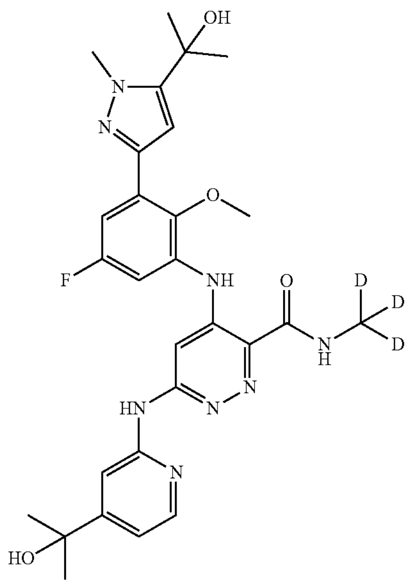 [SMILES: [2H]C([2H])([2H])NC(=O)c1nnc(Nc2cc(C(C)(C)O)ccn2)cc1Nc1cc(F)cc(-c2cc(C(C)(C)O)n(C)n2)c1OC] | 567.6 | 568.4 | 1.59 | QC-ACN-AA-XB |
| 548 | 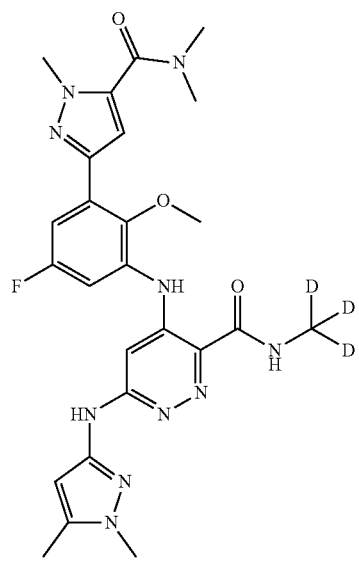 | 539.6 | 540.2 | 1.51 | QC-ACN-AA-XB |

… TABLE 9-continued
| Ex. No. | Structure | MW | Obs. MS Ion | RT | QC Method |
|---|---|---|---|---|---|
| 549 | 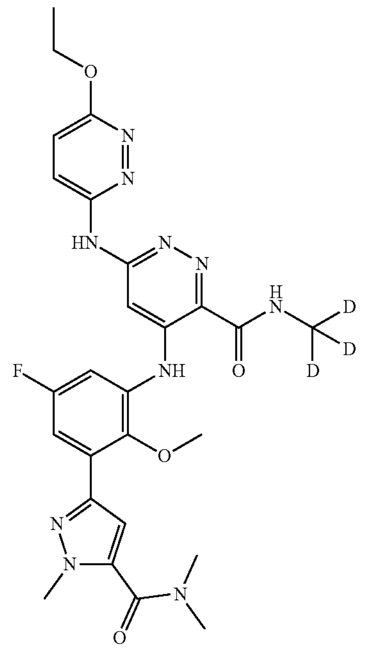 [SMILES: [2H]C([2H])([2H])NC(=O)c1nnc(Nc2ccc(OCC)nn2)cc1Nc1cc(F)cc(-c2cc(C(=O)N(C)C)n(C)n2)c1OC] | 567.6 | 568.1 | 1.18 | QC-ACN-TFA-XB |
| 550 | 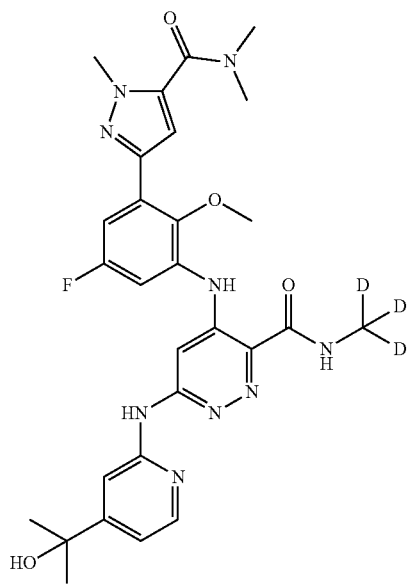 [SMILES: [2H]C([2H])([2H])NC(=O)c1nnc(Nc2cc(C(C)(C)O)ccn2)cc1Nc1cc(F)cc(-c2cc(C(=O)N(C)C)n(C)n2)c1OC] | 580.6 | 581.3 | 1.54 | QC-ACN-AA-XB |

TABLE 9-continued
| Ex. No. | Structure | Obs. MW | MS Ion | RT | QC Method |
|---|---|---|---|---|---|
| 551 | 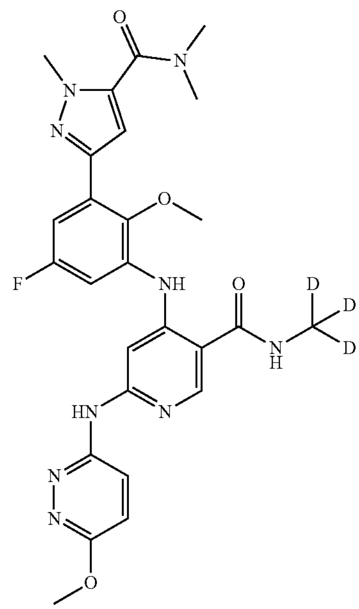 [SMILES: [2H]C([2H])([2H])NC(=O)c1cnc(Nc2ccc(OC)nn2)cc1Nc1cc(F)cc(-c2cc(C(=O)N(C)C)n(C)n2)c1OC] | 552.6 | 553.2 | 1.43 | QC-ACN-AA-XB |
| 552 | 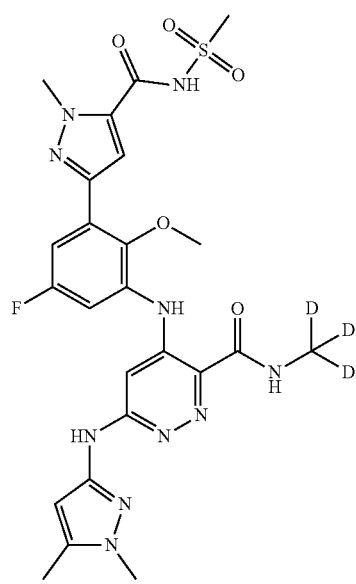 [SMILES: [2H]C([2H])([2H])NC(=O)c1nnc(Nc2cc(C)n(C)n2)cc1Nc1cc(F)cc(-c2cc(C(=O)NS(C)(=O)=O)n(C)n2)c1OC] | 588.6 | 589.1 | 1.25 | QC-ACN-TFA-XB |

TABLE 9-continued
| Ex. No. | Structure | Obs. MW | MS Ion | RT | QC Method |
|---|---|---|---|---|---|
| 553 | 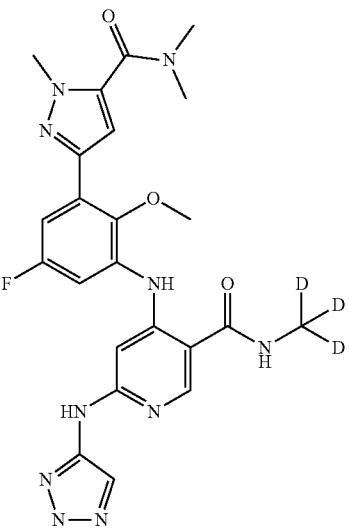 | 525.6 | 526.3 | 1.42 | QC-ACN-AA-XB |
| 554 | 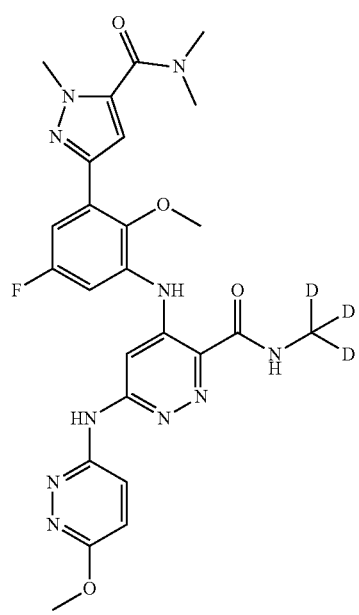 [SMILES: [2H]C([2H])([2H])NC(=O)c1nnc(Nc2ccc(OC)nn2)cc1Nc1cc(F)cc(-c2cc(C(=O)N(C)C)n(C)n2)c1OC] | 553.6 | 554.1 | 1.51 | QC-ACN-AA-XB |

TABLE 9-continued
| Ex. No. | Structure | MW | Obs. MS Ion | RT | QC Method |
|---|---|---|---|---|---|
| 555 | 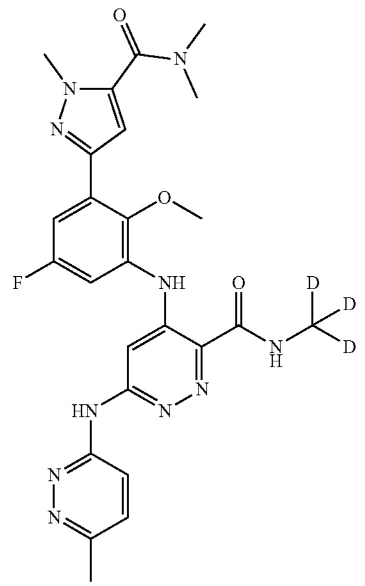 [SMILES: [2H]C([2H])([2H])NC(=O)c1nnc(Nc2ccc(C)nn2)cc1Nc1cc(F)cc(-c2cc(C(=O)N(C)C)n(C)n2)c1OC] | 537.6 | 538.3 | 1.15 | QC-ACN-TFA-XB |
Example 556
4-((3-(1-(2-acetamidoethyl)-1H-pyrazol-4-yl)-2-methoxyphenyl)amino)-6-(cyclopropanecarboxamido)-N-(methyl-d3)pyridazine-3-carboxamide
35
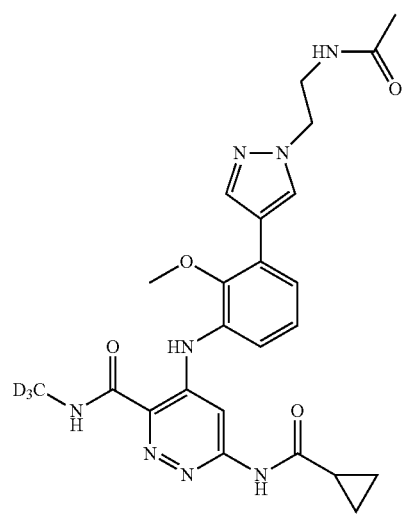

-continued
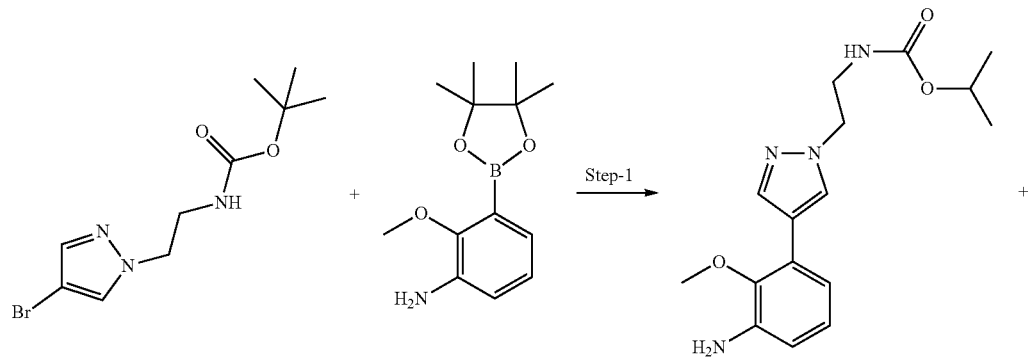
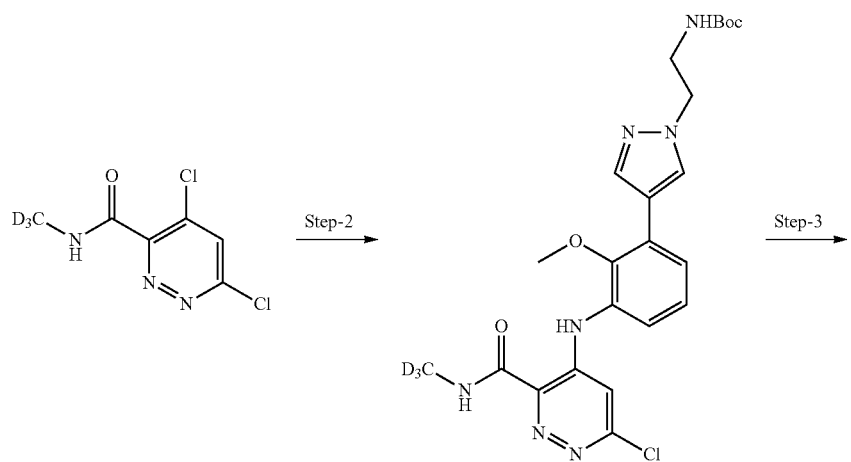
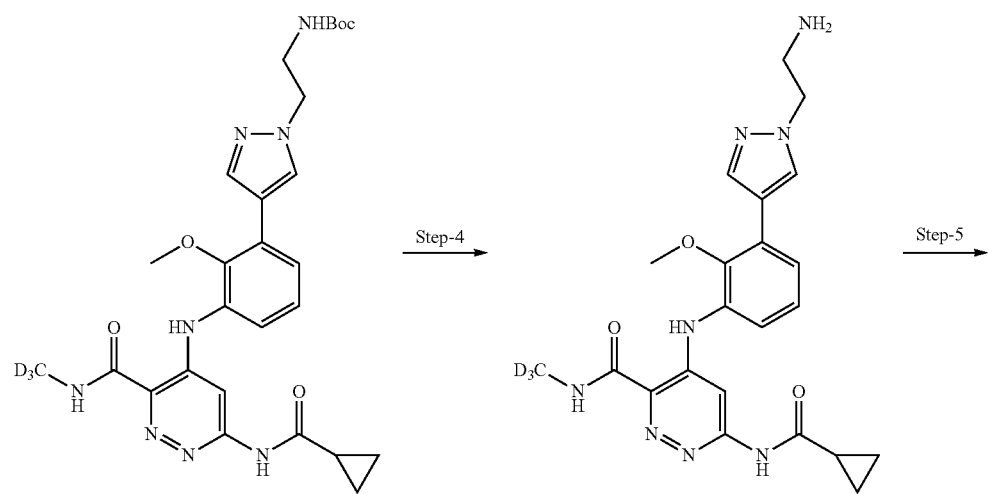

-continued

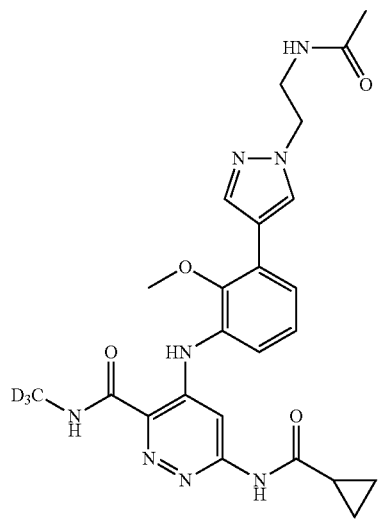

Step 1

A solution of tert-butyl (2-(4-bromo-1H-pyrazol-1-yl)ethyl)carbamate (0.18 g, 0.620 mmol), 2-methoxy-3-(4,4,5,5-tetramethyl-1,3,2-dioxaborolan-2-yl)aniline (0.170 g, 0.682 mmol), and 1,1'-bis(di-tert-butylphosphino)ferrocene palladium dichloride (0.020 g, 0.031 mmol) was degassed by bubbling $N_2$ through the solution for 5 minutes. Then 2M $K_3PO_4$ (aq) (0.931 mL, 1.861 mmol) was added and the mixture was stirred at 100° C. for 1 h. LC-MS showed complete conversion to the desired product mass. The reaction mixture was cooled to room temperature, then diluted with EtOAc (75 mL). This solution was then dried over sodium sulfate, filtered, concentrated and purified by flash chromatography, eluting with 0-100% EtOAc in hexanes to afford tert-butyl (2-(4-(3-amino-2-methoxyphenyl)-1H-pyrazol-1-yl)ethyl)carbamate (177 mg, 0.532 mmol, 86% yield) in total, a yellow solid.

LCMS m/z 333.2 (M+H)$^+$; HPLC $t_R$ 0.68 min (analytical HPLC Method A).

Step 2

To a solution of 4,6-dichloro-N-trideuteromethylpyridazine-3-carboxamide (122 mg, 0.586 mmol) and tert-butyl (2-(4-(3-amino-2-methoxyphenyl)-1H-pyrazol-1-yl)ethyl)carbamate (177 mg, 0.532 mmol) in THF (5 mL) was added LiHMDS, 1M in THF (2.130 mL, 2.130 mmol) and the reaction stirred at room temperature for a total of 20 minutes. The crude reaction was quenched with sat. aqueous ammonium chloride, then diluted with EtOAc. The aqueous layer was washed 2× EtOAc, and the combined EtOAc layers were washed 1× brine. This solution was then dried over sodium sulfate, then filtered and concentrated. The crude material was then loaded onto a 24 g ISCO column for purification by flash chromatography. Eluted with 0-100% EtOAc in hexanes. The reaction afforded tert-butyl (2-(4-(3-((6-chloro-3-(trideuteromethylcarbamoyl) pyridazin-4-yl)amino)-2-methoxyphenyl)-1H-pyrazol-1-yl)ethyl)carbamate (184 mg, 0.353 mmol, 66.4% yield) as an off-white solid. LCMS m/z 505.4 (M+H)$^+$; HPLC $t_R$ 0.93 min (analytical HPLC Method A); $^1$H NMR (400 MHz, DMSO-d$_6$) δ 11.10 (s, 1H), 9.37 (s, 1H), 8.16 (s, 1H), 7.96 (s, 1H), 7.52 (dd, J=7.8, 1.2 Hz, 1H), 7.37 (dd, J=7.9, 1.4 Hz, 1H), 7.25-7.19 (m, 1H), 7.17 (s, 1H), 6.95 (t, J=5.6 Hz, 1H), 4.24-4.15 (m, 2H), 3.60 (s, 3H), 3.39-3.34 (m, 2H), 1.38-1.33 (m, 9H)

Step 3

A mixture of tert-butyl (2-(4-(3-((6-chloro-3-(trideuteromethylcarbamoyl)pyridazin-4-yl)amino)-2-methoxyphenyl)-1H-pyrazol-1-yl)ethyl)carbamate (182 mg, 0.360 mmol), Xantphos (41.7 mg, 0.072 mmol), and cyclopropanecarboxamide (92 mg, 1.081 mmol) in dioxane (3.5 mL) was degassed by bubbling $N_2$ through it for 5 minutes. Then $Cs_2CO_3$ (470 mg, 1.442 mmol) and Pd$_2$(dba)$_3$ (33.0 mg, 0.036 mmol) were added, the vessel was sealed, and the reaction was stirred at 130° C. for 1 h. The reaction was complete by LC-MS, so the crude material was concentrated diluted with EtOAc (75 mL), then dried over sodium sulfate. The reaction mixture was filtered and concentrated, then loaded onto a 24 g ISCO column for purification by flash chromatography, eluting with 0-15% MeOH in DCM to afford tert-butyl (2-(4-(3-((6-(cyclopropanecarboxamido)-3-(trideuteromethylcarbamoyl)pyridazin-4-yl)amino)-2-methoxyphenyl)-1H-pyrazol-1-yl)ethyl)carbamate (155 mg, 0.266 mmol, 73.8% yield). LCMS m/z 554.6 (M+H)$^+$; HPLC $t_R$ 0.81 min (analytical HPLC Method A)

Step 4

A solution of tert-butyl (2-(4-(3-((6-(cyclopropanecarboxamido)-3-(trideuteromethylcarbamoyl)pyridazin-4-yl)amino)-2-methoxyphenyl)-1H-pyrazol-1-yl)ethyl)carbamate (155 mg, 0.280 mmol) in DCM (3 mL) and HCl, 4M in 1,4-dioxane (0.700 mL, 2.80 mmol) was stirred at room temperature overnight. After stirring overnight, the reaction is complete. Concentrated to a yellow solid, used as-is in the next step. (4-((3-(1-(2-aminoethyl)-1H-pyrazol-4-yl)-2-methoxyphenyl)amino)-6-(cyclopropanecarboxamido)-N-trideuteromethylpyridazine-3-carboxamide (125 mg, 0.255 mmol, 91% yield). LCMS m/z 454.3 (M+H)$^+$; HPLC $t_R$ 0.61 min (analytical HPLC Method A).

Step 5

To a solution of 4-((3-(1-(2-aminoethyl)-1H-pyrazol-4-yl)-2-methoxyphenyl)amino)-6-(cyclopropanecarboxamido)-N-trideuteromethylpyridazine-3-carboxamide (12 mg, 0.026 mmol) in DMF (0.5 mL) and triethylamine (0.011 mL, 0.079 mmol) was added acetic anhydride (3.74 μl, 0.040 mmol). The reaction was stirred at room temperature for 30 minutes, whereupon the reaction was complete by LC-MS. Quenched the excess acetic anhydride with methanol, then concentrated to a solid. Redissolved in 2 mL methanol, filtered and submitted for purification. The reaction afforded 4-((3-(1-(2-acetamidoethyl)-1H-pyrazol-4-yl)-2-methoxyphenyl)amino)-6-(cyclopropanecarboxamido)-N-trideuteromethylpyridazine-3-carboxamide (7.5 mg, 0.015 mmol, 56.6% yield) LCMS m/z 496.2 (M+H)+; HPLC t$_R$ 0.64 min (analytical HPLC Method A); $^1$H NM/R (500 MHz, DMSO-d$_6$) δ 11.33 (s, 1H), 10.97 (s, 1H), 9.15 (s, 1H), 8.18 (s, 1H), 8.15 (s, 1H), 8.02 (t, J=5.4 Hz, 1H), 7.98 (s, 1H), 7.46 (d, J=7.7 Hz, 1H), 7.29 (d, J=7.4 Hz, 1H), 7.23-7.17 (m, 1H), 4.22 (t, J=6.1 Hz, 2H), 3.60 (s, 3H), 3.47 (q, J=5.8 Hz, 1H), 2.12-2.04 (m, 2H), 1.80 (s, 3H), 0.88-0.77 (m, 4H)

The Examples in Table 10 were prepared using a similar procedure used to prepare Example 556.

TABLE 10

| Ex. No. | Structure | MW | Obs. MS Ion | RT | QC Method |
|---|---|---|---|---|---|
| 557 | 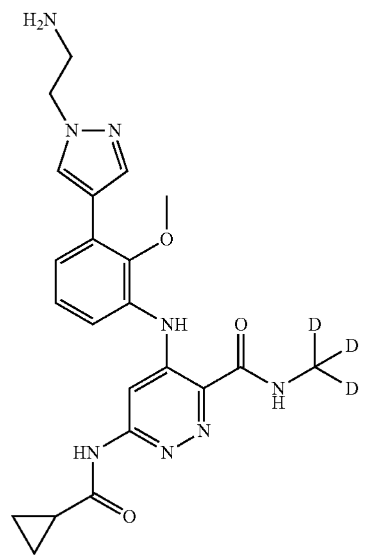 [SMILES: [2H]C([2H])([2H])NC(=O)c1nnc(NC(=O)C2CC2)cc1Nc1cccc(-c2cnn(CCN)c2)c1OC] | 453.5 | 454.3 | 0.98 | QC-ACN-AA-XB |
| 558 | 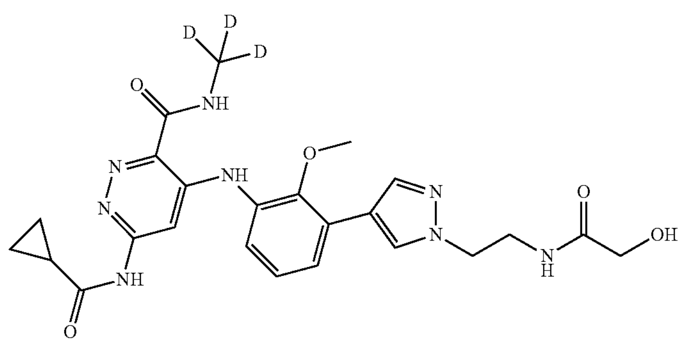 [SMILES: [2H]C([2H])([2H])NC(=O)c1nnc(NC(=O)C2CC2)cc1Nc1cccc(-c2cnn(CCNC(=O)CO)c2)c1OC] | 511.6 | 512.2 | 1.1 | QC-ACN-AA-XB |
| 559 | 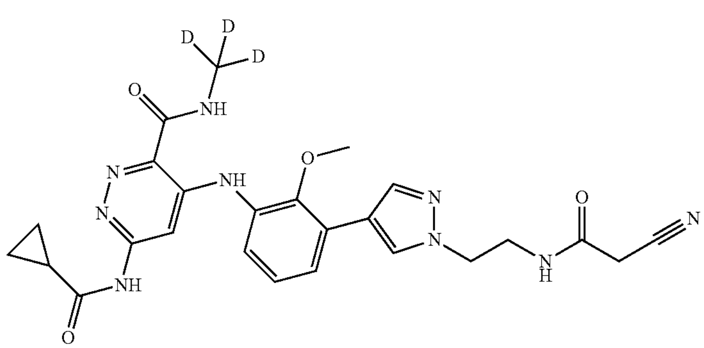 [SMILES: [2H]C([2H])([2H])NC(=O)c1nnc(NC(=O)C2CC2)cc1Nc1cccc(-c2cnn(CCNC(=O)CC#N)c2)c1OC] | 520.6 | 521.3 | 1.25 | QC-ACN-AA-XB |

TABLE 10-continued
| Ex. No. | Structure | MW | Obs. MS Ion | RT | QC Method |
|---|---|---|---|---|---|
| 560 | 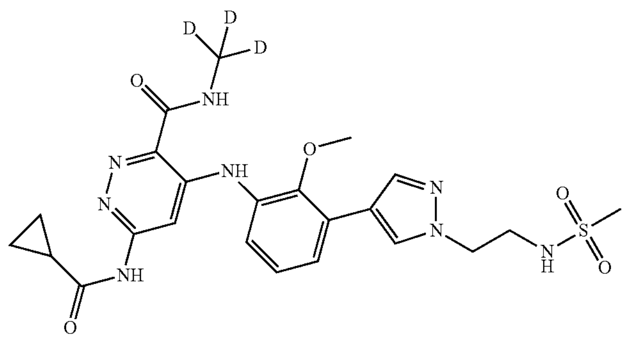 [SMILES: [2H]C([2H])([2H])NC(=O)c1nnc(NC(=O)C2CC2)cc1Nc1cccc(-c2cnn(CCNS(C)(=O)=O)c2)c1OC] | 531.6 | 532.2 | 1.24 | QC-ACN-AA-XB |
| 561 | 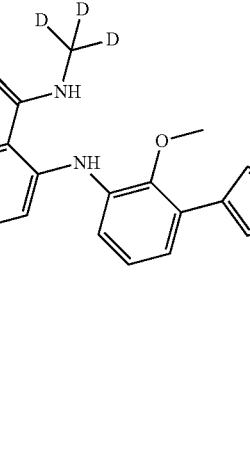 | 563.6 | 554.3 | 1.6 | QC-ACN-AA-XB |
| 562 | 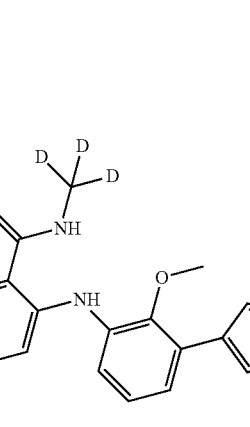 | 525.6 | 526.4 | 1.23 | QC-ACN-AA-XB |

Example 563
4-((3-(1-(2-acetamidoethyl)-1H-pyrazol-4-yl)-2-methoxyphenyl)amino)-6-(cyclopropanecarboxamido)-N-(methyl-d3)pyridazine-3-carboxamide
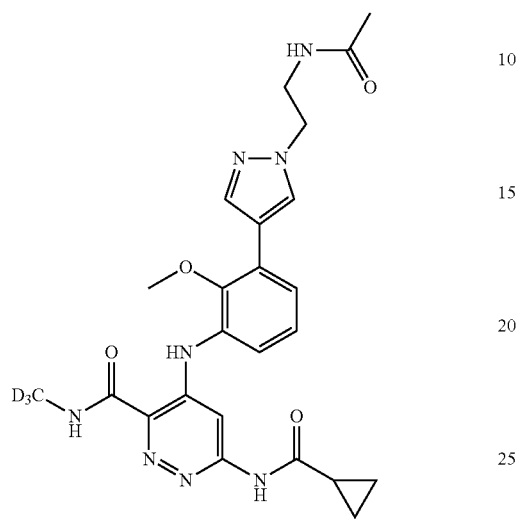
The Examples in Table 11 were prepared using a similar procedure used to prepare Example 563.
TABLE 11
| Ex. No. | Structure | MW | Obs. MS Ion | RT | QC Method |
|---|---|---|---|---|---|
| 564 | 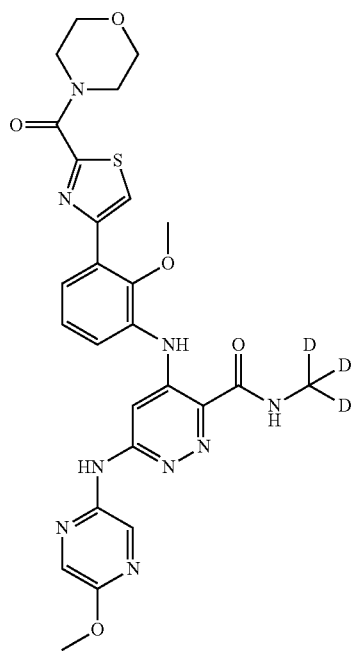 [SMILES: [2H]C([2H])([2H])NC(=O)c1nnc(Nc2cnc(OC)cn2)cc1Nc1cccc(-c2csc(C(=O)N3CCOCC3)n2)c1OC] | 580.6 | 581.2 | 1.71 | QC-ACN-AA-XB |

TABLE 11-continued

| Ex. No. | Structure | MW | Obs. MS Ion | RT | QC Method |
|---|---|---|---|---|---|
| 565 | 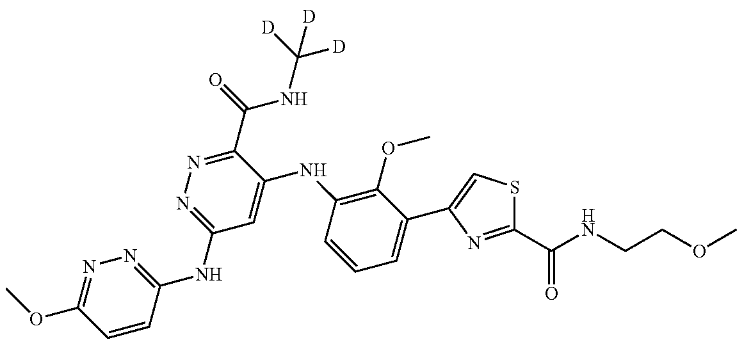 | 568.6 | 569.0 | 1.57 | QC-ACN-AA-XB |
| 566 | 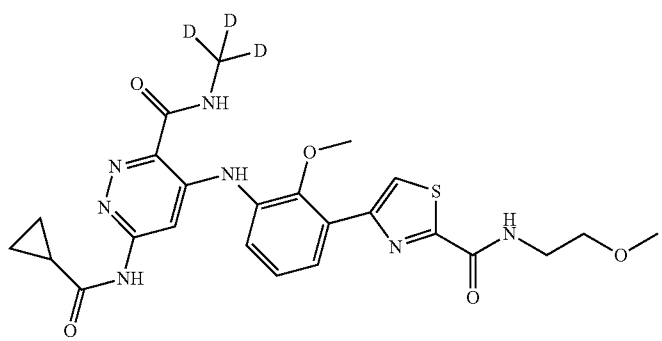 [SMILES: [2H]C([2H])([2H])NC(=O)c1nnc(NC(=O)C2CC2)cc1Nc1cccc(-c2csc(C(=O)NCCOC)n2)c1OC] | 528.6 | 529.3 | 1.5 | QC-ACN-AA-XB |
| 567 | 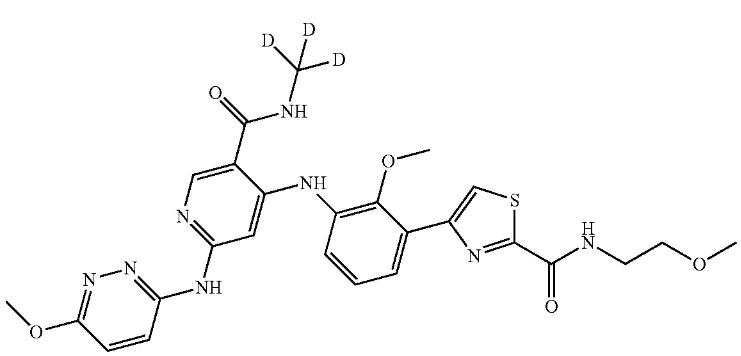 | 567.6 | 568.1 | 1.27 | QC-ACN-TFA-XB |

TABLE 11-continued

| Ex. No. | Structure | MW | Obs. MS Ion | RT | QC Method |
|---|---|---|---|---|---|
| 568 | 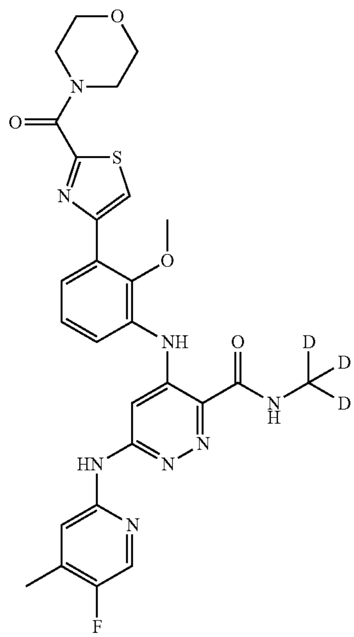 [SMILES: [2H]C([2H])([2H])NC(=O)c1nnc(Nc2cc(C)c(F)cn2)cc1Nc1cccc(-c2csc(C(=O)N3CCOCC3)n2)c1OC] | 581.6 | 582.2 | 1.82 | QC-ACN-AA-XB |
| 569 | 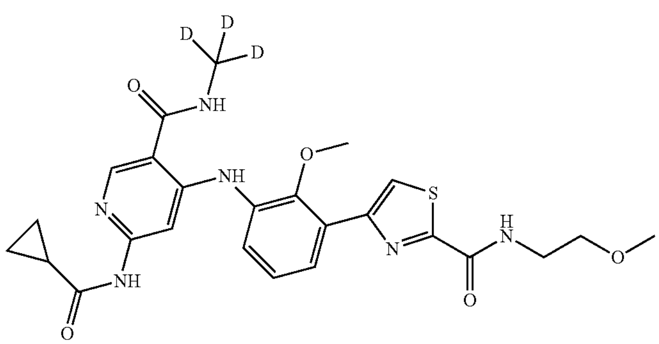 [SMILES: [2H]C([2H])([2H])NC(=O)c1cnc(NC(=O)C2CC2)cc1Nc1cccc(-c2csc(C(=O)NCCOC)n2)c1OC] | 527.6 | 528.1 | 1.24 | QC-ACN-TFA-XB |
| 570 | 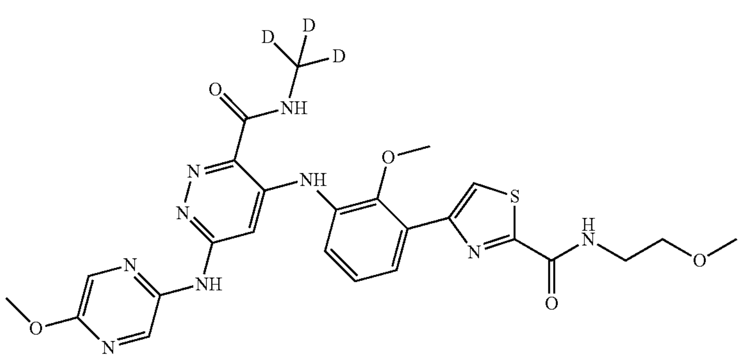 | 568.6 | 569.2 | 1.71 | QC-ACN-AA-XB |

TABLE 11-continued

| Ex. No. | Structure | MW | Obs. MS Ion | RT | QC Method |
|---|---|---|---|---|---|
| 571 | 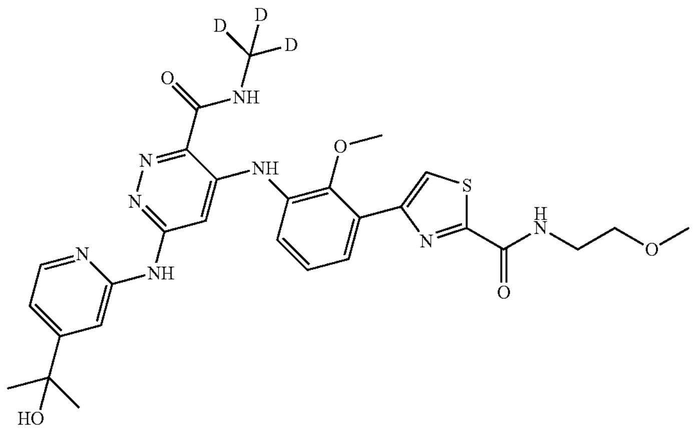 [SMILES: [2H]C([2H])([2H])NC(=O)c1nnc(Nc2cc(C(C)(C)O)ccn2)cc1Nc1cccc(-c2csc(C(=O)NCCOC)n2)c1OC] | 595.7 | 596.2 | 1.61 | QC-ACN-AA-XB |
| 572 | 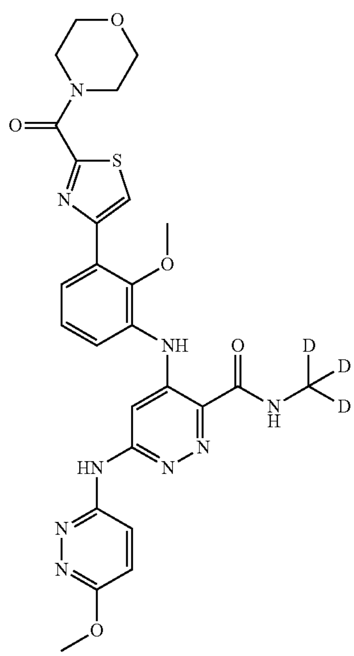 [SMILES: [2H]C([2H])([2H])NC(=O)c1nnc(Nc2ccc(OC)nn2)cc1Nc1cccc(-c2csc(C(=O)N3CCOCC3)n2)c1OC] | 580.6 | 581.2 | 1.66 | QC-ACN-AA-XB |
| 573 | 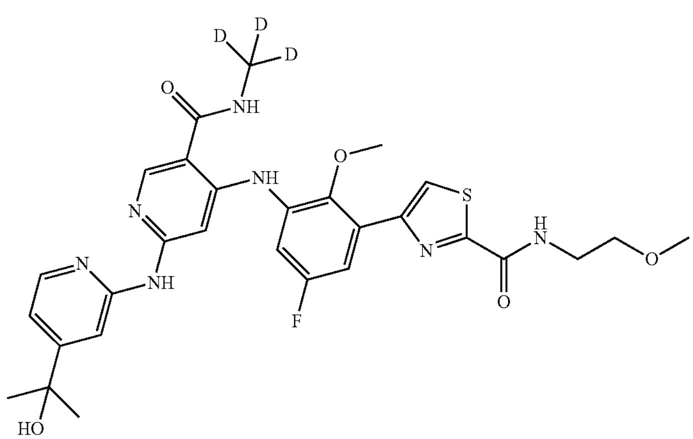 [SMILES: [2H]C([2H])([2H])NC(=O)c1cnc(Nc2cc(C(C)(C)O)ccn2)cc1Nc1cc(F)cc(-c2csc(C(=O)NCCOC)n2)c1OC] | 612.7 | 613.3 | 1.55 | QC-ACN-AA-XB |

TABLE 11-continued
| Ex. No. | Structure | MW | Obs. MS Ion | RT | QC Method |
|---|---|---|---|---|---|
| 574 | 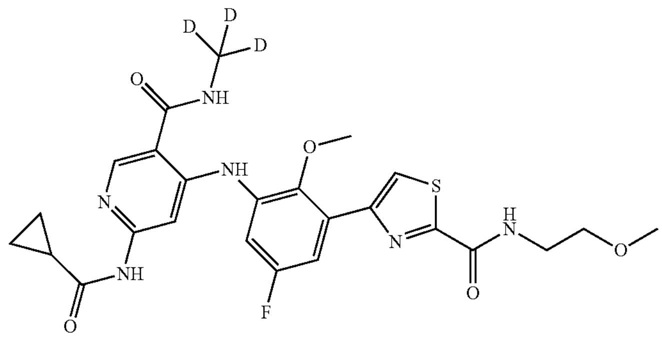 [SMILES: [2H]C([2H])([2H])NC(=O)c1cnc(NC(=O)C2CC2)cc1Nc1cc(F)cc(-c2csc(C(=O)NCCOC)n2)c1OC] | 545.6 | 546.1 | 1.66 | QC-ACN-AA-XB |
| 575 | 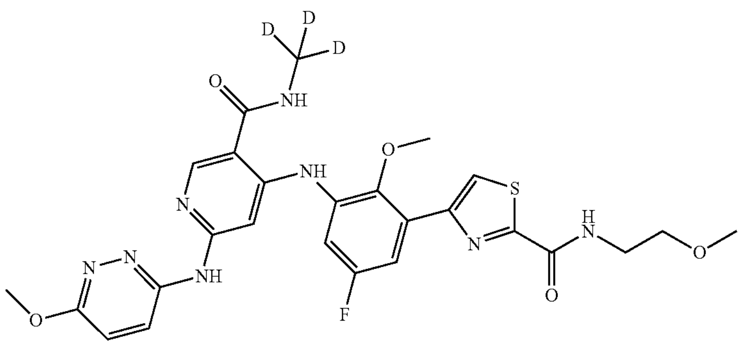 | 585.6 | 586.1 | 1.27 | QC-ACN-TFA-XB |
Example 576
6-(cyclopropanecarboxamido)-4-((2-methoxy-3-(3-(morpholinomethyl)-1,2,4-oxadiazol-5-yl)phenyl)amino)nicotinamide
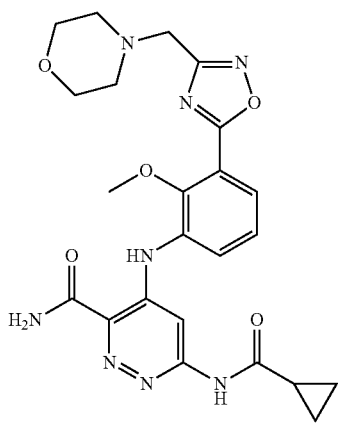

467 468
-continued
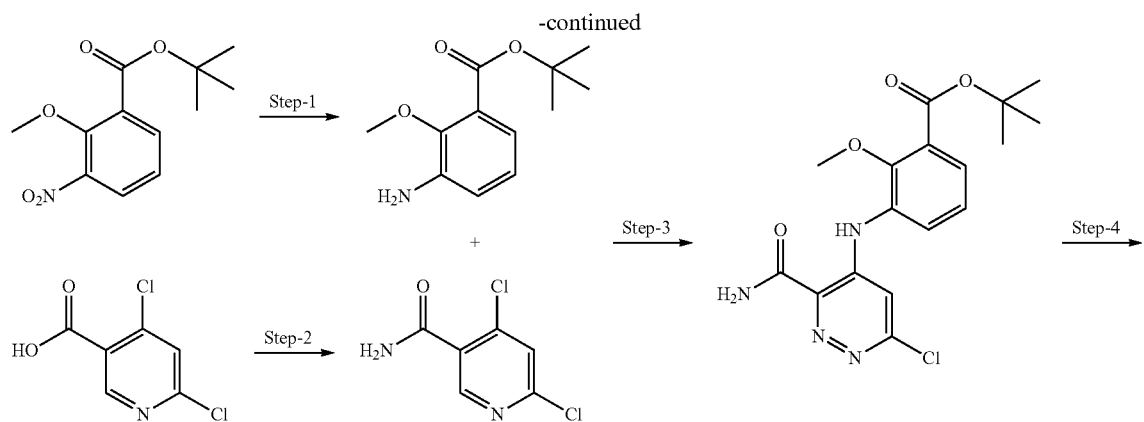
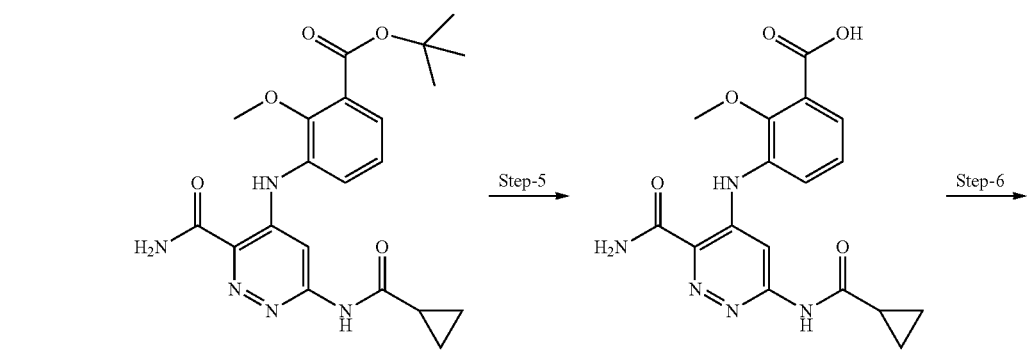
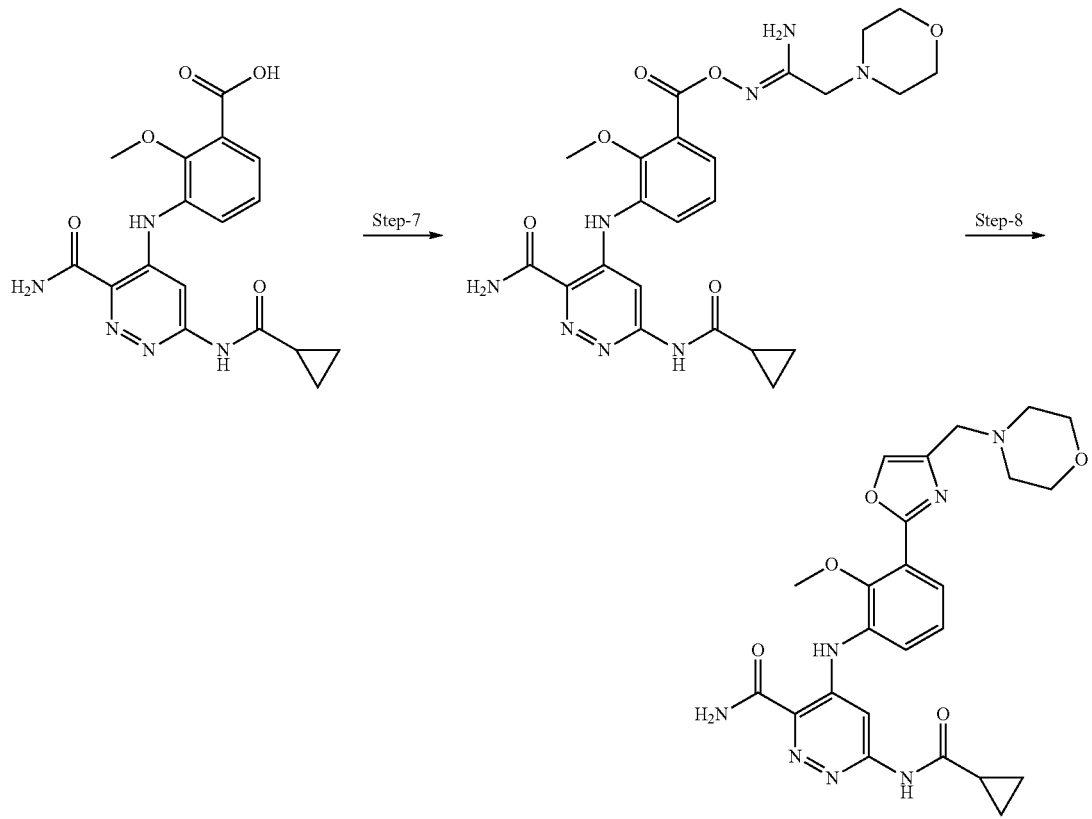

Step 1

A mixture of tert-butyl 2-methoxy-3-nitrobenzoate (200 mg, 0.790 mmol) and 10% Palladium on carbon (42.0 mg, 0.039 mmol) in ethyl acetate (8 ml) was stirred under an atmosphere of hydrogen at rt for 16 hr. Filtration through a 0.45 micron nylon filter and concentration of the filtrate afforded tert-butyl 3-amino-2-methoxybenzoate (165 mg, 0.739 mmol, 94% yield) as a yellow oil. HPLC $t_R$ 1.43 min (analytical HPLC Method A) $^1$H NMR (400 MHz, CHLOROFORM-d) δ 7.11 (dd, J=7.7, 1.8 Hz, 1H), 6.96-6.89 (m, 1H), 6.88-6.83 (m, 1H), 3.84 (s, 3H), 1.60 (s, 9H).

Step 2

To a heterogeneous, colorless solution of 4,6-dichloronicotinic acid (1 g, 5.21 mmol) in Dichloromethane (35 mL) under nitrogen was added oxalyl dichloride (0.585 mL, 6.77 mmol), followed by DMF (0.403 mL, 5.21 mmol); effervescence ensued. LCMS after 2 h of mostly homogeneous solution showed completion of reaction (quenched with ethanol, see ethyl ester M+H 219.9). The solution was concentrated in vacuo; DCE (20 mL) was added, and the solution was concentrated in vacuo. This was repeated twice to give crude 4,6-dichloronicotinoyl chloride. Poured 50 mL 28% ammonium hydroxide into a separatory funnel, extracted 3×15 mL DCM. Dried the combined DCM layers over sodium sulfate, then filtered and used this ammonia solution as is in the reaction. This solution was added to a homogeneous yellow solution of 4,6-dichloronicotinoyl chloride (1.1 g, 5.23 mmol) in 5 mL DCM at 0° C. and TEA (2.186 mL, 15.68 mmol). After 15 minutes, the reaction was complete by LC-MS. Diluted with dichloroethane (100 mL) and washed with 1 N aqueous HCl. The layers were separated, and the aqueous layer was extracted with dichloroethane (2×50 mL). The organic layers were combined, dried over sodium sulfate, filtered and concentrated in vacuo. The crude was taken up in DCM, then purified by flash chromatography using an 40 g silica gel column eluting with 0-100% ethyl acetate in hexanes. Appropriate fractions were collected and concentrated in vacuo to give 4,6-dichloronicotinamide (0.787 g, 3.91 mmol, 74.9% yield). LCMS m/z 190.9 (M+H)$^+$; HPLC $t_R$ 0.54 min (analytical HPLC Method A). $^1$H NMR (400 MHz, DMSO-$d_6$) δ 8.51-8.49 (m, 1H), 8.11 (br. s., 1H), 7.91-7.87 (m, 2H)

Step 3

To a solution of 4,6-dichloronicotinamide (192 mg, 1.008 mmol) and tert-butyl 3-amino-2-methoxybenzoate (225 mg, 1.008 mmol) in Tetrahydrofuran (6 mL) at rt was added dropwise over 1 minute LiHMDS, 1M (2.52 mL, 2.52 mmol). The resulting solution was stirred at room temperature for 1 hr. The reaction mixture was quenched with 1 ml of saturated aqueous ammonium chloride solution. The resulting mixture was partitioned between EtOAc (30 ml) and saturated NH$_4$Cl solution (30 ml). The organic layer was washed with brine (30 ml), dried (Na$_2$SO$_4$) and concentrated to an amber oil that was chromatographed on a 12 g silica gel cartridge, eluting with a 0-100% ethyl acetate in hexanes gradient. The pure fractions were concentrated to afford tert-butyl 3-((5-carbamoyl-2-chloropyridin-4-yl)amino)-2-methoxybenzoate (106 mg, 0.267 mmol, 26.4% yield) as a light yellow solid. LCMS m/z 378.2 (M+H)$^+$; HPLC $t_R$ 0.91 min (analytical HPLC Method A). $^1$H NMR (400 MHz, DMSO-$d_6$) δ 11.09 (s, 1H), 9.37 (s, 1H), 7.72 (dd, J=7.9, 1.3 Hz, 1H), 7.49 (dd, J=7.8, 1.4 Hz, 1H), 7.27 (t, J=7.9 Hz, 1H), 7.19 (s, 1H), 3.74 (s, 3H), 1.56 (s, 9H).

Step 4

A mixture of tert-butyl 3-((5-carbamoyl-2-chloropyridin-4-yl)amino)-2-methoxybenzoate (22 mg, 0.058 mmol), cyclopropanecarboxamide (49.6 mg, 0.582 mmol), Pd$_2$(dba)$_3$, Chloroform adduct (6.02 mg, 5.82 µmol), Xantphos (6.74 mg, 0.012 mmol) and Cs$_2$CO$_3$ (76 mg, 0.233 mmol) in Dioxane (1.5 mL) was degassed by bubbling N$_2$ through the mixture for 5 minutes. The reaction vessel was sealed and heated to 130° C. overnight. After cooling to rt, the reaction mixture was partitioned between EtOAc (50 ml) and water (50 ml). The aqueous layer was extracted with EtOAc (30 ml) and the combined organics were dried (Na$_2$SO$_4$) and concentrated to afford a yellow oil that was chromatographed on a 12 g silica gel cartridge, eluting with a 0-100% ethyl acetate in hexanes gradient. The pure fractions were concentrated to afford tert-butyl 3-((5-carbamoyl-2-(cyclopropanecarboxamido)pyridin-4-yl)amino)-2-methoxybenzoate (12 mg, 0.028 mmol, 48.3% yield) as a yellow solid. LCMS m/z 427.3 (M+H)$^+$; HPLC $t_R$ 0.75 min (analytical HPLC Method A).

Step 5

A mixture of tert-butyl 3-((5-carbamoyl-2-(cyclopropanecarboxamido)pyridin-4-yl)amino)-2-methoxybenzoate (35 mg, 0.082 mmol) and HCl, 4N in dioxane (0.205 mL, 0.821 mmol) in DCM (1.5 mL) was stirred at rt for 8 hr. The reaction mixture was allowed to stand at rt over the weekend in the freezer. The volatiles were removed in vacuo and the residue was dried to afford 3-((5-carbamoyl-2-(cyclopropanecarboxamido)pyridin-4-yl)amino)-2-methoxybenzoic acid, HCl (36 mg, 0.080 mmol, 97% yield) as a yellow solid.

Step 6

A mixture of 3-((5-carbamoyl-2-(cyclopropanecarboxamido)pyridin-4-yl)amino)-2-methoxybenzoic acid, HCl (35 mg, 0.089 mmol), (Z)—N'-hydroxy-2-morpholinoacetimidamide (17.00 mg, 0.107 mmol), BOP (59.0 mg, 0.133 mmol) and Et$_3$N (0.037 mL, 0.267 mmol) in DMF (1 mL) was stirred at room temperature for 1.5 hr. The reaction mixture was partitioned between EtOAc (20 ml) and saturated sodium bicarbonate solution (20 ml). The organic layer was washed with water (2×20 ml) and brine (20 ml). After drying (Na$_2$SO$_4$) and filtration the organic layer was concentrated to afford (Z)-4-((3-((((1-amino-2-morpholinoethylidene)amino)oxy)carbonyl)-2-methoxyphenyl)amino)-6-(cyclopropanecarboxamido)nicotinamide (40 mg, 0.070 mmol, 79% yield) as a light yellow oil. Used as is in the next step.). LCMS m/z 512.4 (M+H)$^+$; HPLC $t_R$ 0.51 min (analytical HPLC Method A).

Step 7

A mixture of (Z)-4-((3-((((1-amino-2-morpholinoethylidene)amino) oxy)carbonyl)-2-methoxyphenyl)amino)-6-(cyclopropanecarboxamido)nicotinamide (40 mg, 0.070 mmol) and TBAF, 1M in THF (0.106 mL, 0.106 mmol) in acetonitrile (1 mL) was stirred at rt overnight. After stirring overnight, the reaction is complete. The reaction mixture was concentrated to an oil then redissolved in 1.5 mL DMF, filtered and submitted for purification. The reaction afforded 6-(cyclopropanecarboxamido)-4-((2-methoxy-3-(3-(morpholinomethyl)-1,2,4-oxadiazol-5-yl)phenyl)amino)nicotinamide (12.4 mg, 0.024 mmol, 34.6% yield) LCMS m/z 494.4 (M+H)$^+$; HPLC $t_R$ 0.53 min (analytical HPLC Method A). $^1$H NMR (500 MHz, DMSO-$d_6$) δ 11.05 (s, 2H), 10.80 (s, 1H), 8.64 (s, 1H), 8.21 (br. s., 1H), 8.04 (s, 1H), 7.76 (d, J=8.1 Hz, 2H), 7.55 (br. s, 1H), 7.40 (t, J=7.9 Hz, 1H), 3.77 (s, 3H), 3.19-3.13 (m, 2H), 2.02-1.95 (m, 1H), 1.57 (br. s., 2H), 1.36-1.27 (m, 2H), 0.93 (t, J=7.4 Hz, 3H), 0.79 (d, J=6.1 Hz, 4H)

The Examples in Table 12 were prepared using a similar procedure used to prepare Example 576.

TABLE 12
| Ex. No. | Structure | MW | Obs. MS Ion | RT | QC Method |
|---|---|---|---|---|---|
| 577 | 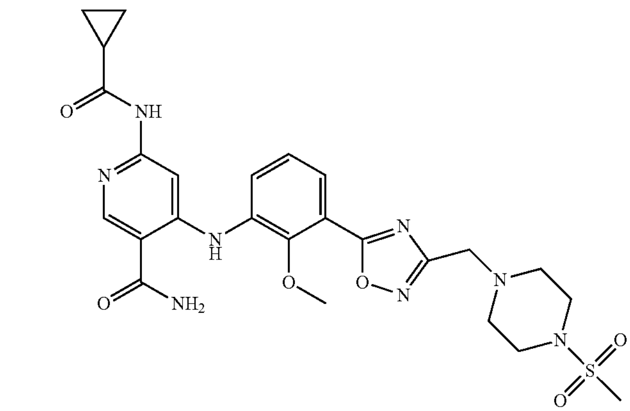 [SMILES: COc1c(Nc2cc(NC(=O)C3CC3)ncc2C(N)=O)cccc1-c1nc(CN2CCN(S(C)(=O)=O)CC2)no1] | 570.6 | 571.2 | 1.26 | QC-ACN-AA-XB |
| 578 | 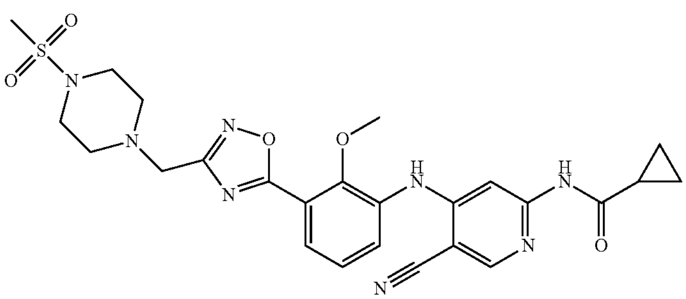 [SMILES: COc1c(Nc2cc(NC(=O)C3CC3)ncc2C#N)cccc1-c1nc(CN2CCN(S(C)(=O)=O)CC2)no1] | 552.6 | 553.0 | 1.37 | QC-ACN-AA-XB |
Example 579
N-(4-((2-methoxy-3-(3-(morpholinomethyl)-1,2,4-oxadiazol-5-yl)phenyl)amino)pyridin-2-yl)cyclopropanecarboxamide
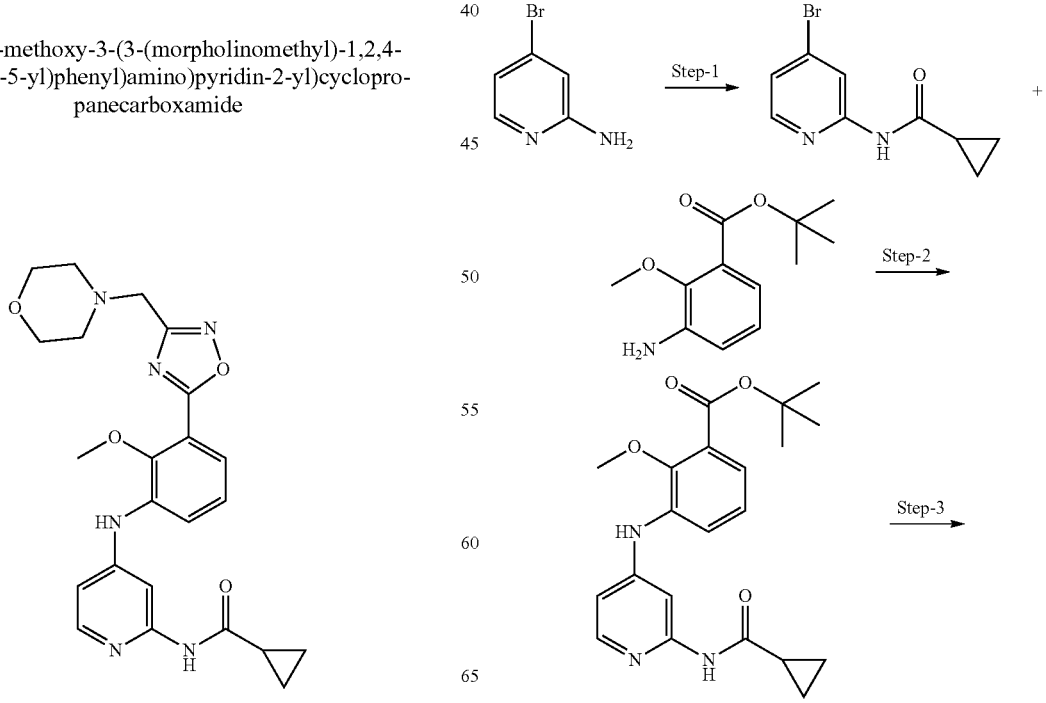

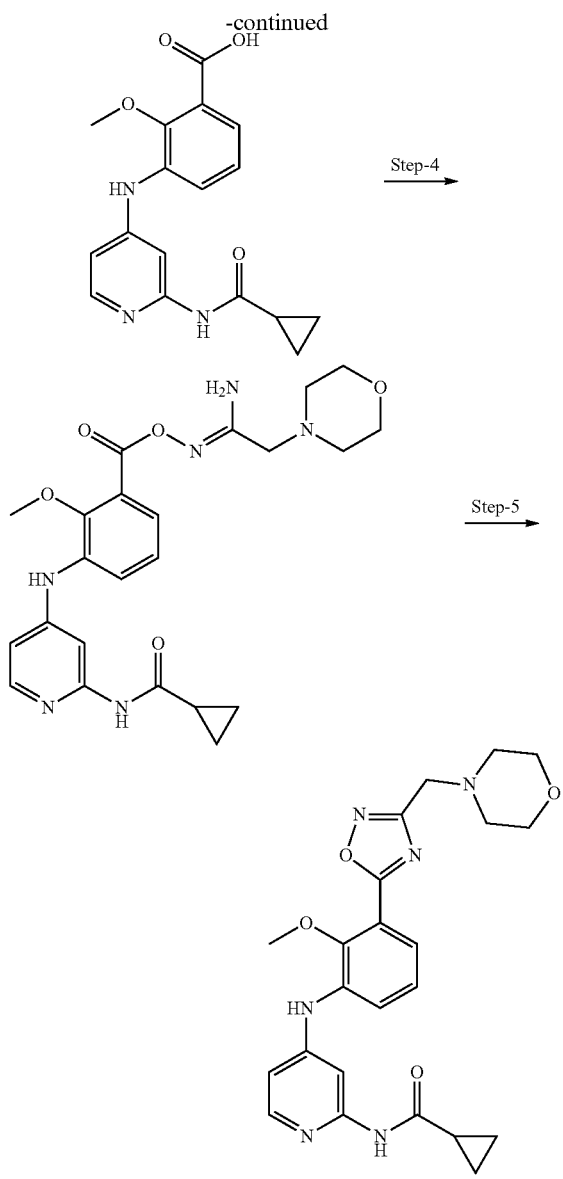

Step 1

To a solution of 4-bromopyridin-2-amine (300 mg, 1.734 mmol) and triethylamine (0.725 mL, 5.20 mmol) in DCM (15 mL) at 0° C. in an ice bath was added dropwise cyclopropanecarbonyl chloride (0.189 mL, 2.081 mmol). This solution was allowed to warm to room temperature after addition was complete. After 1 hour, the reaction is complete. Quenched with saturated aq. sodium bicarbonate, then extracted 3×50 mL DCM. Dried over sodium sulfate, then filtered and concentrated. The reaction afforded N-(4-bromopyridin-2-yl)cyclopropanecarboxamide (401 mg, 1.580 mmol, 91% yield) as a crystalline off-white solid. Carried on directly to the next step as-is. HPLC $t_R$ 0.87 min (analytical HPLC Method A).

Step 2

A mixture of N-(4-bromopyridin-2-yl)cyclopropanecarboxamide (100 mg, 0.415 mmol), Xantphos (48.0 mg, 0.083 mmol), and tert-butyl 3-amino-2-methoxybenzoate (185 mg, 0.830 mmol) in dioxane (3.5 mL) was degassed by bubbling $N_2$ through it for 5 minutes. Then $Cs_2CO_3$ (541 mg, 1.659 mmol) and $Pd_2(dba)_3$ (38.0 mg, 0.041 mmol) were added, the vessel was sealed, and the reaction was stirred at 130° C. for 45 minutes. The reaction was complete by LC-MS. The reaction was cooled to room temperature, and then concentrated, then diluted with DCM and loaded directly onto a 40 g silica gel column. Eluted with 0-15% MeOH in DCM. The reaction afforded tert-butyl 3-((2-(cyclopropanecarboxamido)pyridin-4-yl)amino)-2-methoxybenzoate (100 mg, 0.248 mmol, 59.7% yield).) LCMS m/z 384.2 $(M+H)^+$; HPLC $t_R$ 0.77 min (analytical HPLC Method A).

Step 3

A mixture of tert-butyl 3-((2-(cyclopropanecarboxamido)pyridin-4-yl)amino)-2-methoxybenzoate (108 mg, 0.282 mmol) and HCl, 4N in dioxane (0.704 mL, 2.82 mmol) in DCM (3 mL) was stirred at rt for 8 hr. The reaction mixture was allowed to stir at rt. The volatiles were removed in vacuo and the residue was dried to afford 3-((2-(cyclopropanecarboxamido)pyridin-4-yl)amino)-2-methoxybenzoic acid, HCl (100 mg, 0.261 mmol, 93% yield) as a yellow solid.) LCMS m/z 328.2 $(M+H)^+$; HPLC $t_R$ 0.55 min (analytical HPLC Method A).

Step 4

A mixture of 3-((2-(cyclopropanecarboxamido)pyridin-4-yl)amino)-2-methoxybenzoic acid, HCl (40 mg, 0.114 mmol), (Z)—N'-hydroxy-2-morpholinoacetimidamide (21.81 mg, 0.137 mmol), BOP (76 mg, 0.171 mmol) and $Et_3N$ (0.048 mL, 0.343 mmol) in DMF (1 mL) was stirred at rt for 1.5 hr. The reaction mixture was partitioned between EtOAc (20 ml) and saturated sodium bicarbonate solution (20 ml). The organic layer was washed with water (2×20 ml) and brine (20 ml). After drying ($Na_2SO_4$) and filtration the organic layer was concentrated to afford (Z)—N-(4-((3-((((1-amino-2-morpholinoethylidene)amino)oxy)carbonyl)-2-methoxyphenyl)amino)pyridin-2-yl)cyclopropanecarboxamide (44 mg, 0.094 mmol, 82% yield) as a light yellow oil. Used as is.) LCMS m/z 469.2 $(M+H)^+$; HPLC $t_R$ 0.50 min (analytical HPLC Method A).

Step 5

A mixture of (Z)—N-(4-((3-((((1-amino-2-morpholinoethylidene)amino)oxy) carbonyl)-2-methoxyphenyl)amino) pyridin-2-yl)cyclopropanecarboxamide (44 mg, 0.094 mmol) and TBAF, 1M in THF (0.141 mL, 0.141 mmol) in Acetonitrile (1 mL) was stirred at rt over the weekend. The reaction was incomplete, so another 300 uL of the TBAF solution was added, and the reaction allowed to stir another night at room temperature. the reaction is now complete by LC-MS. The reaction mixture was partitioned between EtOAc (30 ml) and brine. After drying ($Na_2SO_4$) and filtration the organic layer was concentrated to afford a yellow oil. This was dissolved in 2 mL methanol, then filtered and submitted for purification. The reaction afforded N-(4-((2-methoxy-3-(3-(morpholinomethyl)-1,2,4-oxadiazol-5-yl)phenyl)amino)pyridin-2-yl)cyclopropanecarboxamide (22.2 mg, 0.049 mmol, 51.9% yield).) LCMS m/z 451.2 $(M+H)^+$; HPLC $t_R$ 0.51 min (analytical HPLC Method A). $^1$H NMR (500 MHz, DMSO-$d_6$) δ 10.66-10.37 (m, 1H), 8.63 (s, 1H), 7.95 (br d, J=5.4 Hz, 1H), 7.78-7.74 (m, 2H), 7.63 (br d, J=7.7 Hz, 1H), 7.34 (t, J=7.9 Hz, 1H), 6.60 (br d, J=4.4 Hz, 1H), 3.76 (s, 2H), 3.71 (s, 3H), 3.63-3.60 (m, 2H), 3.19-3.14 (m, 2H), 2.60-2.53 (m, 4H), 2.00-1.95 (m, 1H), 1.57 (br s, 2H), 1.35-1.28 (m, 2H)

The Examples in Table 13 were prepared using a similar procedure used to prepare Example 579.

TABLE 13

| Ex. No. | Structure | MW | Obs. MS Ion | RT | QC Method |
|---|---|---|---|---|---|
| 580 | (structure) | 491.6 | 492.3 | 1.26 | QC-ACN-AA-XB |
| 581 | (structure) | 527.6 | 528.2 | 1.32 | QC-ACN-AA-XB |

BIOLOGICAL ASSAYS

The following assay is used to show the activity for compounds of the invention.

IFNα-Induced STAT Phosphorylation in Human Whole Blood

After an hour long incubation with compound, human whole blood (drawn with either EDTA or ACD-A as anticoagulant) was stimulated with 1000 U/mL recombinant human IFNα A/D (R&D Systems 11200-2) for 15 min. The stimulation was stopped by adding Fix/Lyse buffer (BD 558049). Cells were stained with a CD3 FITC antibody (BD 555916), washed, and permeabilized on ice using Perm III buffer (BD 558050). Cells were then stained with an Alexa-Fluor 647 pSTAT5 (pY694) antibody (BD 612599) for 30 min prior to analysis on the FACS Canto II. The amount of pSTAT5 expression was quantitated by median fluorescence intensity after gating on the CD3 positive population.

IFNα-Induced STAT Phosphorylation in Human Whole Blood Inhibition Data ND—no data available

TABLE 14

| Ex. No. | Human WB IFNα-Induced Stat Phosph. (IC$_{50}$, μM) |
|---|---|
| 1 | 2.80 |
| 2 | 0.65 |
| 3 | 0.98 |
| 4 | 0.66 |
| 5 | 3.30 |
| 6 | 0.11 |
| 7 | 0.024 |
| 8 | 0.021 |
| 9 | 0.016 |
| 10 | 0.004 |
| 11 | 0.021 |
| 12 | 0.011 |
| 13 | 0.024 |
| 14 | 0.05 |
| 15 | 0.03 |
| 16 | 0.56 |
| 17 | 0.49 |
| 18 | ND |
| 19 | 0.25 |
| 20 | 1.50 |
| 21 | 0.022 |
| 22 | ND |
| 23 | 0.06 |
| 24 | 0.24 |
| 25 | 0.43 |
| 26 | 3.90 |
| 27 | 2.01 |
| 28 | 0.21 |
| 29 | 0.13 |
| 30 | 1.38 |
| 31 | 0.38 |
| 32 | 0.08 |
| 33 | ND |
| 34 | 1.01 |
| 35 | 0.12 |
| 36 | 0.03 |
| 37 | 0.018 |
| 38 | 0.03 |
| 39 | 0.023 |
| 40 | 0.012 |
| 41 | 0.06 |
| 42 | 0.23 |
| 43 | 0.17 |
| 44 | 0.009 |
| 45 | 0.16 |
| 46 | 0.14 |
| 47 | 0.14 |
| 48 | 0.025 |
| 49 | 0.05 |
| 50 | 0.07 |
| 51 | 0.16 |
| 52 | 0.09 |
| 53 | 0.21 |
| 54 | ND |

TABLE 14-continued

| Ex. No. | Human WB IFNα-Induced Stat Phosph. (IC$_{50}$, μM) |
|---|---|
| 55 | 0.04 |
| 56 | 0.12 |
| 57 | 0.009 |
| 58 | 0.011 |
| 59 | 0.013 |
| 60 | 0.023 |
| 61 | 0.06 |
| 62 | 0.08 |
| 63 | 0.03 |
| 64 | 0.11 |
| 65 | 0.016 |
| 66 | 0.03 |
| 67 | 0.06 |
| 68 | 0.023 |
| 69 | 0.03 |
| 70 | 0.014 |
| 71 | 0.025 |
| 72 | 0.08 |
| 73 | 0.28 |
| 74 | 0.17 |
| 75 | 0.03 |
| 76 | 0.03 |
| 77 | 0.04 |
| 78 | 0.07 |
| 79 | 0.16 |
| 80 | 0.11 |
| 81 | 0.18 |
| 82 | 0.07 |
| 83 | 0.11 |
| 84 | 0.13 |
| 85 | 0.24 |
| 86 | 0.30 |
| 87 | 0.46 |
| 88 | 0.23 |
| 89 | 0.03 |
| 90 | 0.06 |
| 91 | 0.05 |
| 92 | 0.03 |
| 93 | 0.05 |
| 94 | 0.011 |
| 95 | 0.021 |
| 96 | 0.015 |
| 97 | 0.03 |
| 98 | 0.023 |
| 99 | 0.04 |
| 100 | 0.06 |
| 105 | 1.83 |
| 107 | 0.82 |
| 109 | >10.00 |
| 115 | 3.49 |
| 116 | 4.97 |
| 118 | 3.80 |
| 119 | >10.00 |
| 120 | 0.15 |
| 121 | >10.00 |
| 122 | >10.00 |
| 123 | >10.00 |
| 124 | 0.21 |
| 125 | 0.06 |
| 126 | 0.63 |
| 127 | 0.26 |
| 128 | 0.03 |
| 129 | 0.26 |
| 130 | 0.49 |
| 131 | 0.74 |
| 132 | 0.30 |
| 133 | 0.10 |
| 134 | 0.11 |
| 135 | 2.01 |
| 136 | 1.13 |
| 137 | 2.64 |
| 138 | 0.18 |
| 139 | 0.41 |
| 140 | 0.33 |
| 141 | 0.24 |
| 142 | 5.31 |
| 143 | 0.32 |
| 144 | 1.00 |
| 145 | 0.27 |
| 146 | 0.21 |
| 147 | 1.72 |
| 148 | 1.82 |
| 149 | 1.95 |
| 150 | >10.00 |
| 151 | 1.55 |
| 152 | 1.31 |
| 153 | >10.00 |
| 154 | 1.11 |
| 155 | 0.78 |
| 156 | 0.63 |
| 157 | >10.00 |
| 158 | 0.40 |
| 159 | 1.08 |
| 160 | 1.79 |
| 161 | 9.42 |
| 162 | 2.73 |
| 163 | 1.76 |
| 164 | 0.20 |
| 165 | 0.53 |
| 166 | ND |
| 167 | 2.42 |
| 168 | 0.23 |
| 169 | 0.11 |
| 170 | 0.57 |
| 171 | 0.69 |
| 172 | 1.44 |
| 173 | 0.30 |
| 174 | 0.56 |
| 175 | 0.66 |
| 176 | 0.45 |
| 177 | 1.03 |
| 178 | 0.55 |
| 179 | 0.29 |
| 180 | 0.20 |
| 181 | 0.63 |
| 182 | 2.01 |
| 183 | 1.68 |
| 184 | 0.13 |
| 185 | >10.00 |
| 186 | 0.79 |
| 187 | 1.13 |
| 188 | 1.27 |
| 189 | 0.10 |
| 190 | 2.36 |
| 191 | 0.41 |
| 192 | 0.87 |
| 193 | 7.36 |
| 194 | 0.16 |
| 195 | 0.72 |
| 196 | 1.18 |
| 197 | 6.20 |
| 198 | 1.65 |
| 199 | 1.08 |
| 200 | 0.76 |
| 201 | 0.29 |
| 202 | 1.80 |
| 203 | 0.46 |
| 204 | 0.14 |
| 205 | 0.85 |
| 206 | >10.00 |
| 207 | 0.48 |
| 208 | 1.27 |
| 209 | 1.37 |
| 210 | 0.22 |
| 211 | 0.44 |
| 212 | 0.32 |
| 213 | 4.44 |
| 214 | 0.39 |
| 215 | 0.15 |
| 216 | 0.32 |
| 217 | 0.18 |
| 218 | 0.39 |
| 219 | 5.24 |
| 220 | 0.20 |

TABLE 14-continued

| Ex. No. | Human WB IFNα-Induced Stat Phosph. (IC$_{50}$, μM) |
|---|---|
| 221 | 0.16 |
| 222 | 1.48 |
| 223 | 0.69 |
| 224 | 0.88 |
| 225 | 0.35 |
| 226 | 1.16 |
| 227 | 0.62 |
| 228 | 0.18 |
| 229 | >10.00 |
| 230 | 0.51 |
| 231 | 1.75 |
| 232 | 6.51 |
| 233 | 0.10 |
| 234 | 0.30 |
| 235 | 0.05 |
| 236 | >10.00 |
| 237 | 0.07 |
| 238 | 0.08 |
| 239 | 0.05 |
| 240 | 0.18 |
| 241 | 0.62 |
| 242 | 0.021 |
| 243 | 0.09 |
| 244 | 0.12 |
| 245 | 0.11 |
| 246 | 0.03 |
| 247 | 0.10 |
| 248 | 2.24 |
| 250 | 0.64 |
| 251 | ND |
| 252 | 3.27 |
| 253 | 0.30 |
| 254 | 5.43 |
| 255 | 0.62 |
| 256 | 0.13 |
| 257 | 0.23 |
| 258 | 0.13 |
| 259 | >10.00 |
| 260 | 0.54 |
| 261 | 0.68 |
| 262 | 2.69 |
| 263 | 0.83 |
| 264 | 1.55 |
| 265 | 0.53 |
| 266 | 2.53 |
| 267 | 0.15 |
| 268 | 0.10 |
| 269 | 0.04 |
| 270 | 0.10 |
| 271 | 0.09 |
| 272 | 0.16 |
| 273 | 0.07 |
| 274 | 0.05 |
| 275 | 0.15 |
| 276 | 0.69 |
| 277 | 0.24 |
| 278 | ND |
| 279 | 0.47 |
| 280 | ND |
| 281 | >10.00 |
| 282 | 0.18 |
| 283 | 0.36 |
| 284 | >10.00 |
| 285 | ND |
| 286 | ND |
| 287 | 1.26 |
| 288 | 0.09 |
| 289 | 0.15 |
| 290 | 0.10 |
| 291 | 0.11 |
| 292 | 0.16 |
| 293 | 0.03 |
| 294 | 0.07 |
| 295 | 0.06 |
| 296 | >10.00 |
| 297 | 0.03 |
| 298 | >10.00 |
| 299 | 0.014 |
| 300 | 0.33 |
| 301 | 0.03 |
| 302 | 0.11 |
| 303 | 0.10 |
| 304 | 0.13 |
| 305 | 0.22 |
| 306 | 0.44 |
| 307 | 0.03 |
| 309 | >10.00 |
| 310 | >10.00 |
| 311 | 0.20 |
| 312 | 0.07 |
| 313 | 0.07 |
| 314 | 0.26 |
| 315 | 0.022 |
| 316 | 0.33 |
| 317 | 0.03 |
| 318 | 0.08 |
| 319 | 0.03 |
| 320 | 0.05 |
| 321 | 0.03 |
| 322 | 0.08 |
| 324 | 0.06 |
| 325 | 0.11 |
| 326 | 0.03 |
| 327 | 0.15 |
| 328 | 0.16 |
| 329 | 0.05 |
| 330 | 0.07 |
| 331 | 0.56 |
| 332 | 0.04 |
| 334 | 0.05 |
| 335 | 0.05 |
| 336 | 0.26 |
| 337 | 0.07 |
| 338 | 0.42 |
| 339 | 0.04 |
| 340 | 0.10 |
| 341 | 0.11 |
| 342 | 0.08 |
| 343 | 0.022 |
| 344 | 0.03 |
| 345 | 0.18 |
| 346 | 0.09 |
| 347 | 0.013 |
| 348 | ND |
| 349 | 0.07 |
| 350 | 0.04 |
| 351 | 0.06 |
| 352 | 0.07 |
| 353 | 0.17 |
| 354 | 0.08 |
| 355 | 0.38 |
| 356 | 0.08 |
| 357 | 0.88 |
| 358 | 0.21 |
| 359 | 0.34 |
| 360 | 0.27 |
| 361 | 0.19 |
| 362 | 0.27 |
| 363 | 0.24 |
| 364 | 0.44 |
| 365 | 0.32 |
| 366 | 0.51 |
| 367 | 0.06 |
| 368 | 0.35 |
| 369 | 0.05 |
| 370 | 0.16 |
| 371 | 0.31 |
| 372 | 0.15 |
| 377 | 1.41 |
| 379 | 0.56 |
| 380 | ND |
| 381 | 0.13 |
| 382 | 0.10 |
| 383 | 0.03 |

TABLE 14-continued

| Ex. No. | Human WB IFNα-Induced Stat Phosph. (IC$_{50}$, µM) |
|---|---|
| 384 | 0.04 |
| 385 | 0.18 |
| 386 | 0.49 |
| 387 | 0.27 |
| 388 | >10.00 |
| 389 | 0.57 |
| 390 | 0.24 |
| 391 | 0.82 |
| 392 | 0.023 |
| 393 | 0.18 |
| 394 | 0.42 |
| 395 | 0.08 |
| 396 | 0.12 |
| 397 | 0.04 |
| 398 | ND |
| 399 | 0.18 |
| 400 | 0.03 |
| 401 | 0.18 |
| 402 | 0.04 |
| 403 | 0.19 |
| 404 | 0.11 |
| 405 | 0.09 |
| 406 | 0.18 |
| 407 | 0.16 |
| 408 | 0.11 |
| 409 | >10.00 |
| 410 | 0.26 |
| 411 | 1.80 |
| 412 | 4.62 |
| 413 | 0.17 |
| 414 | 0.31 |
| 415 | 0.04 |
| 416 | 0.46 |
| 418 | 0.13 |
| 419 | 0.20 |
| 420 | 0.22 |
| 421 | 0.29 |
| 422 | 0.59 |
| 423 | ND |
| 424 | 0.20 |
| 425 | 0.67 |
| 426 | 0.03 |
| 427 | 0.09 |
| 428 | 2.63 |
| 429 | 0.19 |
| 430 | >10.00 |
| 431 | >10.00 |
| 432 | 0.30 |
| 433 | 0.16 |
| 434 | 0.16 |
| 435 | 0.26 |
| 436 | 0.30 |
| 437 | 2.41 |
| 438 | 2.89 |
| 439 | 0.44 |
| 440 | 1.16 |
| 441 | 0.29 |
| 442 | 0.08 |
| 443 | 0.27 |
| 444 | 2.13 |
| 445 | 0.15 |
| 446 | 0.27 |
| 447 | 0.16 |
| 448 | 0.14 |
| 449 | ND |
| 450 | 0.20 |
| 451 | 0.06 |
| 452 | 0.15 |
| 453 | 0.06 |
| 454 | 0.19 |
| 455 | 0.56 |
| 456 | 0.06 |
| 457 | 0.77 |
| 458 | 1.21 |
| 459 | 0.08 |
| 461 | 0.22 |
| 462 | 4.45 |
| 463 | 0.80 |
| 464 | 1.11 |
| 465 | 0.13 |
| 466 | 0.42 |
| 467 | 0.20 |
| 468 | 0.27 |
| 469 | 0.20 |
| 470 | 0.34 |
| 471 | 1.59 |
| 472 | 0.29 |
| 473 | >10.00 |
| 474 | 3.56 |
| 475 | 2.32 |
| 476 | 0.06 |
| 477 | 1.10 |
| 478 | 0.15 |
| 479 | 0.11 |
| 480 | 0.07 |
| 481 | 0.39 |
| 482 | 0.15 |
| 483 | 0.06 |
| 484 | 0.10 |
| 485 | 0.13 |
| 486 | 0.06 |
| 487 | 0.20 |
| 488 | 0.53 |
| 489 | 0.29 |
| 491 | 0.26 |
| 492 | 0.15 |
| 493 | 0.04 |
| 494 | 0.25 |
| 495 | 0.06 |
| 496 | 0.25 |
| 497 | 0.11 |
| 499 | 0.18 |
| 500 | 0.37 |
| 501 | 1.13 |
| 502 | 0.15 |
| 503 | 0.86 |
| 504 | >10.00 |
| 505 | 0.18 |
| 506 | 0.25 |
| 507 | 0.11 |
| 508 | ND |
| 509 | 0.17 |
| 510 | 0.46 |
| 511 | 0.32 |
| 512 | 2.56 |
| 513 | >10.00 |
| 514 | 0.87 |
| 515 | 0.29 |
| 516 | 0.17 |
| 517 | 0.35 |
| 518 | 0.15 |
| 519 | 0.57 |
| 520 | 0.77 |
| 521 | 2.41 |
| 522 | 0.19 |
| 523 | 1.68 |
| 524 | 3.40 |
| 525 | 0.24 |
| 526 | 0.52 |
| 527 | 0.95 |
| 528 | 0.84 |
| 529 | 0.20 |
| 530 | 0.20 |
| 531 | 0.06 |
| 532 | 0.47 |
| 533 | 0.53 |
| 534 | 0.47 |
| 535 | 1.50 |
| 536 | 0.65 |
| 537 | 0.70 |
| 538 | 0.39 |
| 539 | 0.12 |
| 540 | 0.46 |
| 541 | 1.39 |

TABLE 14-continued

| Ex. No. | Human WB IFNα-Induced Stat Phosph. (IC$_{50}$, μM) |
|---|---|
| 542 | 0.89 |
| 543 | ND |
| 544 | ND |
| 545 | 0.22 |
| 546 | 0.11 |
| 547 | 0.40 |
| 548 | 0.17 |
| 549 | ND |
| 550 | 0.24 |
| 551 | 0.05 |
| 552 | 3.60 |
| 553 | 0.12 |
| 554 | ND |
| 555 | 0.04 |
| 556 | 1.07 |
| 557 | 0.72 |
| 558 | 1.30 |
| 559 | 0.83 |
| 560 | 2.21 |
| 561 | 4.36 |
| 562 | 0.65 |
| 563 | 3.12 |
| 564 | >10.00 |
| 565 | 0.25 |
| 566 | 0.68 |
| 567 | 0.70 |
| 568 | ND |
| 569 | 0.59 |
| 570 | 0.93 |
| 571 | 1.76 |
| 573 | 2.00 |
| 574 | 0.70 |
| 575 | ND |
| 576 | 0.013 |
| 577 | 0.019 |
| 578 | 4.34 |
| 581 | ND |

We claim:

1. A compound which is
6-cyclopropaneamido-4-{[2-methoxy-3-(5-{1-[(2-methoxyethyl)carbamoyl]propyl}-1,2,4-oxadiazol-3-yl)phenyl]amino}-N-(2H3)methylpyridazine-3-carboxamide,
6-cyclopropaneamido-4-[(2-methoxy-3-{5-[1-(morpholin-4-yl)-1-oxopentan-2-yl]-1,2,4-oxadiazol-3-yl}phenyl)amino]-N-(2H3)methylpyridazine-3-carboxamide,
6-cyclopropaneamido-4-{[2-methoxy-3-(5-{1-[(2-methoxyethyl) carbamoyl]butyl}-1,2,4-oxadiazol-3-yl)phenyl]amino}-N-(2H3)methylpyridazine-3-carboxamide,
tert-butyl N-[(1R,2R)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}propyl]carbamate,
6-cyclopropaneamido-4-[(3-{3-[(1R,2R)-1-acetamido-2-hydroxypropyl]-1,2,4-oxadiazol-5-yl}-2-methoxyphenyl)amino]-N-(2H3)methylpyridazine-3-carboxamide,
methyl N-[(1R,2R)-1-{5-[3-({6-cyclopropaneamido-3-[(2H3)methylcarbamoyl]pyridazin-4-yl}amino)-2-methoxyphenyl]-1,2,4-oxadiazol-3-yl}-2-hydroxypropyl]carbamate,
6-cyclopropaneamido-4-[(3-{3-[(1R,2R)-2-hydroxy-1-propanamidopropyl]-1,2,4-oxadiazol-5-yl}-2-methoxyphenyl)amino]-N-(2H3)methylpyridazine-3-carboxamide,
tert-butyl N-[(1R)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}ethyl]carbamate,
6-cyclopropaneamido-4-[(3-{3-[(1R)-2-hydroxy-1-propanamidoethyl]-1,2,4-oxadiazol-5-yl}-2-methoxyphenyl)amino]-N-(2H3)methylpyridazine-3-carboxamide,
6-cyclopropaneamido-4-[(3-{3-[(1R)-1-acetamido-2-hydroxyethyl]-1,2,4-oxadiazol-5-yl}-2-methoxyphenyl)amino]-N-(2H3)methylpyridazine-3-carboxamide,
(2R)-2-{5-[3-({6-cyclopropaneamido-3-[(2H3)methylcarbamoyl]pyridazin-4-yl}amino)-2-methoxyphenyl]-1,2,4-oxadiazol-3-yl}-2-acetamidoethyl acetate,
6-cyclopropaneamido-4-[(3-{3-[(1R)-2-hydroxy-1-(2-methoxyacetamido)ethyl]-1,2,4-oxadiazol-5-yl}-2-methoxyphenyl)amino]-N-(2H3)methylpyridazine-3-carboxamide,
6-cyclopropaneamido-4-[(3-{3-[(1S,2S)-1-acetamido-2-hydroxypropyl]-1,2,4-oxadiazol-5-yl}-2-methoxyphenyl)amino]-N-(2H3)methylpyridazine-3-carboxamide,
6-cyclopropaneamido-4-[(3-{3-[(1S,2S)-2-hydroxy-1-(2-methoxyacetamido)propyl]-1,2,4-oxadiazol-5-yl}-2-methoxyphenyl)amino]-N-(2H3)methylpyridazine-3-carboxamide,
tert-butyl N-[(1S,2S)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}propyl]carbamate,
6-cyclopropaneamido-4-[(3-{3-[(1S,2S)-2-hydroxy-1-propanamidopropyl]-1,2,4-oxadiazol-5-yl}-2-methoxyphenyl)amino]-N-(2H3)methylpyridazine-3-carboxamide,
tert-butyl N-[(1S)-2-(tert-butoxy)-1-{5-[3-({6-cyclopropaneamido-3-[(2H3)methylcarbamoyl]pyridazin-4-yl}amino)-2-methoxyphenyl]-1,2,4-oxadiazol-3-yl}ethyl]carbamate, or
6-cyclopropaneamido-4-[(3-{3-[(1S)-1-acetamido-2-hydroxyethyl]-1,2,4-oxadiazol-5-yl}-2-methoxyphenyl)amino]-N-(2H3)methylpyridazine-3-carboxamide,
or a pharmaceutically acceptable salt thereof.

2. A pharmaceutical composition comprising one or more compounds according to claim 1 and a pharmaceutically acceptable carrier or diluent.

* * * * *